United States Patent
Franano et al.

(10) Patent No.: US 11,484,318 B2
(45) Date of Patent: Nov. 1, 2022

(54) EXPANDABLE BODY DEVICE AND METHOD OF USE

(71) Applicant: Artio Medical, Inc., Fairway, KS (US)

(72) Inventors: F. Nicholas Franano, Olathe, KS (US); Howard M. Loree, II, Olathe, KS (US); Stephen Brunell, Olathe, KS (US); Katherine Stephenson, Olathe, KS (US)

(73) Assignee: Artio Medical, Inc., Prairie Village, KS (US)

( * ) Notice: Subject to any disclaimer, the term of this patent is extended or adjusted under 35 U.S.C. 154(b) by 343 days.

(21) Appl. No.: 14/777,412

(22) PCT Filed: Mar. 17, 2014

(86) PCT No.: PCT/US2014/030869
§ 371 (c)(1),
(2) Date: Sep. 15, 2015

(87) PCT Pub. No.: WO2014/146001
PCT Pub. Date: Sep. 18, 2014

(65) Prior Publication Data
US 2016/0030050 A1 Feb. 4, 2016

Related U.S. Application Data

(63) Continuation-in-part of application No. PCT/US2012/047072, filed on Jul. 17, 2012, which is
(Continued)

(51) Int. Cl.
*A61B 17/12* (2006.01)
*A61B 17/00* (2006.01)
*A61B 90/00* (2016.01)

(52) U.S. Cl.
CPC .... *A61B 17/12113* (2013.01); *A61B 17/1214* (2013.01); *A61B 17/12031* (2013.01);
(Continued)

(58) Field of Classification Search
CPC ........ A61B 17/12031; A61B 17/12113; A61B 17/1214; A61B 17/12172;
(Continued)

(56) References Cited

U.S. PATENT DOCUMENTS 3,794,268 A 2/1974 McNeill
4,311,146 A 1/1982 Wonder
(Continued)

FOREIGN PATENT DOCUMENTS

CN 1342056 A 3/2002
CN 1813638 A 8/2006
(Continued)

OTHER PUBLICATIONS

Office Action from related U.S. Appl. No. 13/980,278, dated Nov. 2, 2017; 37 pgs.
(Continued)

*Primary Examiner* — Todd J Scherbel
(74) *Attorney, Agent, or Firm* — Polsinelli PC

(57) ABSTRACT

Disclosed herein are medical devices comprising a single-lobed, thin-walled, expandable body and a flexible, elongated delivery device for treating saccular vascular aneurysms and occluding segments of blood vessels and other biological conduits. The expandable bodies may include gold and other metals that can be compressed, positioned in the lumen of an aneurysm, or other biological conduit and expanded. The external surface of the expandable bodies can be configured to promote local thrombosis and to promote the growth of tissue into and around the surface in order to reduce migration of the expandable body and to occlude and
(Continued)

seal the aneurysm or biological conduit. For the treatment of saccular aneurysms, the expandable body may be deployed in combination with one or more coiled wires that contact both the wall of the aneurysm and the expandable body and exert force on the expandable body to aid in sealing the aneurysm neck.

36 Claims, 57 Drawing Sheets

Related U.S. Application Data a continuation of application No. PCT/US2012/021621, filed on Jan. 17, 2012, and a continuation of application No. PCT/US2012/021620, filed on Jan. 17, 2012, and a continuation of application No. PCT/US2012/000030, filed on Jan. 17, 2012, application No. 14/777,412, which is a continuation-in-part of application No. 13/980,278, filed as application No. PCT/US2012/021620 on Jan. 17, 2012, now Pat. No. 11,090,176, application No. 14/777,412, which is a continuation-in-part of application No. 13/980,274, filed as application No. PCT/US2012/000030 on Jan. 17, 2012, now Pat. No. 9,572,697, application No. 14/777,412, which is a continuation-in-part of application No. 13/980,276, filed as application No. PCT/US2012/021621 on Jan. 17, 2012, now Pat. No. 9,572,698.

(60) Provisional application No. 61/793,737, filed on Mar. 15, 2013, provisional application No. 61/433,305, filed on Jan. 17, 2011.

(52) U.S. Cl.
CPC .. *A61B 17/12136* (2013.01); *A61B 17/12172* (2013.01); *A61B 17/12186* (2013.01); *A61B 2017/00526* (2013.01); *A61B 2017/00853* (2013.01); *A61B 2017/00867* (2013.01); *A61B 2017/00876* (2013.01); *A61B 2017/00893* (2013.01); *A61B 2017/00929* (2013.01); *A61B 2017/1205* (2013.01); *A61B 2017/12063* (2013.01); *A61B 2090/376* (2016.02); *A61B 2090/3966* (2016.02)

(58) Field of Classification Search
CPC .... A61B 2017/12063; A61B 2090/376; A61B 17/12136; A61B 2017/00853
USPC ........................................................ 606/195
See application file for complete search history.

(56) References Cited

U.S. PATENT DOCUMENTS

| | | |
|---|---|---|
| 4,341,218 A | 7/1982 | Ü |
| 4,364,392 A | 12/1982 | Strother et al. |
| 4,395,806 A | 8/1983 | Wonder et al. |
| 4,402,319 A | 9/1983 | Handa et al. |
| 4,416,028 A | 11/1983 | Eriksson et al. |
| 4,471,779 A | 9/1984 | Antoshkiw et al. |
| 4,517,979 A | 5/1985 | Pecenka |
| 4,638,803 A | 1/1987 | Rand |
| 4,770,067 A | 9/1988 | Liu et al. |
| 4,819,637 A | 4/1989 | Dormandy, Jr. et al. |
| 5,041,090 A | 8/1991 | Scheglov et al. |
| 5,167,627 A | 12/1992 | Clegg et al. |
| 5,181,921 A | 1/1993 | Makita et al. |
| 5,222,970 A | 6/1993 | Reeves |
| 5,250,059 A | 10/1993 | Andreas et al. |
| 5,282,847 A | 2/1994 | Trescony et al. |
| 5,327,885 A | 7/1994 | Griffith |
| 5,344,401 A | 9/1994 | Radisch et al. |
| 5,354,295 A | 10/1994 | Guglielmi et al. |
| 5,370,691 A | 12/1994 | Samson |
| 5,382,261 A | 1/1995 | Palmaz |
| 5,522,836 A | 6/1996 | Palermo |
| 5,527,337 A | 6/1996 | Stack et al. |
| 5,609,606 A | 3/1997 | O'Boyle |
| 5,769,817 A | 6/1998 | Burgmeier |
| 5,833,671 A | 11/1998 | Macoviak et al. |
| 5,902,308 A | 5/1999 | Murphy |
| 5,980,530 A | 11/1999 | Willard et al. |
| 6,022,359 A | 2/2000 | Frantzen |
| 6,063,070 A | 5/2000 | Eder |
| 6,096,021 A | 8/2000 | Helm et al. |
| 6,146,372 A | 11/2000 | Leschinsky et al. |
| 6,156,005 A | 12/2000 | Theron |
| 6,186,978 B1 | 2/2001 | Samson et al. |
| 6,187,034 B1 | 2/2001 | Frantzen |
| 6,293,960 B1 | 9/2001 | Ken |
| 6,293,968 B1 | 9/2001 | Taheri |
| 6,312,405 B1 | 11/2001 | Meyer et al. |
| 6,344,041 B1 | 2/2002 | Kupiecki et al. |
| 6,346,117 B1 | 2/2002 | Greenhalgh |
| 6,375,668 B1 | 4/2002 | Gifford et al. |
| 6,395,008 B1 | 5/2002 | Ellis et al. |
| 6,409,754 B1 | 6/2002 | Smith et al. |
| 6,425,893 B1 | 7/2002 | Guglielmi |
| 6,454,780 B1 | 9/2002 | Wallace |
| 6,463,317 B1 | 10/2002 | Kucharczyk et al. |
| 6,676,667 B2 | 1/2004 | Mareiro et al. |
| 6,706,064 B1 | 3/2004 | Anson |
| 6,733,513 B2 | 5/2004 | Boyle et al. |
| 6,976,950 B2 | 12/2005 | Connors et al. |
| 6,976,951 B2 | 12/2005 | Connors et al. |
| 7,252,677 B2 | 8/2007 | Burwell et al. |
| 7,329,236 B2 | 2/2008 | Kesten et al. |
| 7,410,482 B2 | 8/2008 | Murphy et al. |
| 7,527,622 B2 | 5/2009 | Lane et al. |
| 7,632,291 B2 | 12/2009 | Stephens et al. |
| 7,632,301 B2 | 12/2009 | Alt |
| 7,713,297 B2 | 5/2010 | Alt |
| 7,955,246 B2 | 6/2011 | Lubock et al. |
| 3,007,674 A1 | 8/2011 | Johnson |
| 8,016,853 B2 | 9/2011 | Griffen et al. |
| 8,333,798 B2 | 12/2012 | Gandhi et al. |
| 8,372,114 B2 | 2/2013 | Hines |
| 8,574,146 B2 | 11/2013 | Gillespie, Jr. et al. |
| 8,668,717 B2 | 3/2014 | Hines |
| 9,283,100 B2 | 3/2016 | Wang et al. |
| 9,572,697 B2 | 2/2017 | Franano et al. |
| 9,572,698 B2 | 2/2017 | Franano et al. |
| 2002/0016624 A1 | 2/2002 | Patterson et al. |
| 2002/0026210 A1* | 2/2002 | Abdel-Gawwad ......................... A61B 17/12136 606/194 |
| 2002/0029035 A1 | 3/2002 | Lee et al. |
| 2002/0052638 A1 | 5/2002 | Zadno-Azizi |
| 2002/0052639 A1 | 5/2002 | Fischell et al. |
| 2002/0082638 A1 | 6/2002 | Porter et al. |
| 2002/0143383 A1 | 10/2002 | Parodi |
| 2002/0165572 A1 | 11/2002 | Saadat |
| 2002/0169473 A1 | 11/2002 | Sepetka et al. |
| 2003/0028210 A1 | 2/2003 | Boyle et al. |
| 2003/0074039 A1 | 4/2003 | Puskas |
| 2003/0083732 A1 | 5/2003 | Stinson |
| 2003/0135265 A1 | 7/2003 | Stinson |
| 2003/0171739 A1 | 9/2003 | Murphy et al. |
| 2003/0187492 A1 | 10/2003 | McHale |
| 2003/0212419 A1 | 11/2003 | West |
| 2003/0220666 A1 | 11/2003 | Mirigian et al. |
| 2003/0236494 A1 | 12/2003 | Seward |
| 2004/0019322 A1 | 1/2004 | Hoffmann |
| 2004/0093014 A1 | 5/2004 | Ho et al. |
| 2004/0138733 A1 | 7/2004 | Weber et al. |
| 2004/0193177 A1 | 9/2004 | Houghton et al. |
| 2004/0220610 A1 | 11/2004 | Kreidler et al. |
| 2004/0236278 A1 | 11/2004 | Herweck et al. |

(56) References Cited

U.S. PATENT DOCUMENTS

| | | |
|---|---|---|
| 2004/0243119 A1 | 12/2004 | Lane et al. |
| 2004/0254625 A1 | 12/2004 | Stephens et al. |
| 2005/0033408 A1 | 2/2005 | Jones et al. |
| 2005/0090888 A1 | 4/2005 | Hines et al. |
| 2005/0136090 A1 | 6/2005 | Falotico et al. |
| 2005/0171593 A1 | 8/2005 | Whirley et al. |
| 2006/0015169 A1 | 1/2006 | Letort |
| 2006/0079923 A1 | 4/2006 | Chhabra et al. |
| 2006/0085070 A1 | 4/2006 | Kim |
| 2006/0135947 A1 | 6/2006 | Soltesz et al. |
| 2006/0155296 A1 | 7/2006 | Richter |
| 2006/0155364 A1 | 7/2006 | Holloway et al. |
| 2006/0155367 A1 | 7/2006 | Hines |
| 2006/0200191 A1 | 9/2006 | Zadno-Azizi |
| 2006/0206199 A1 | 9/2006 | Churchwell et al. |
| 2006/0224229 A1 | 10/2006 | Goto |
| 2007/0032854 A1 | 2/2007 | Schmid et al. |
| 2007/0067009 A1 | 3/2007 | Gandhi et al. |
| 2007/0112370 A1 | 5/2007 | Andrews et al. |
| 2007/0129746 A1 | 6/2007 | Mische |
| 2007/0150041 A1 | 6/2007 | Evans et al. |
| 2007/0239191 A1 | 10/2007 | Ramzipoor |
| 2007/0244431 A1 | 10/2007 | Limon |
| 2007/0265656 A1 | 11/2007 | Amplatz et al. |
| 2007/0267780 A1 | 11/2007 | Schewe et al. |
| 2007/0288083 A1 | 12/2007 | Hines |
| 2007/0299422 A1 | 12/2007 | Inganas et al. |
| 2007/0299460 A9 | 12/2007 | Boucher et al. |
| 2008/0140177 A1 | 6/2008 | Hines |
| 2008/0188825 A1 | 8/2008 | Atanasoska et al. |
| 2008/0188923 A1 | 8/2008 | Chu |
| 2008/0195112 A1 | 8/2008 | Liu et al. |
| 2008/0281350 A1 | 11/2008 | Sepetka et al. |
| 2008/0294205 A1 | 11/2008 | Greenhalgh et al. |
| 2009/0062726 A1* | 3/2009 | Ford ............... A61B 17/12113 604/57 |
| 2009/0088829 A1 | 4/2009 | Wang et al. |
| 2009/0287297 A1 | 11/2009 | Cox |
| 2009/0297582 A1 | 12/2009 | Meyer et al. |
| 2009/0299327 A1 | 12/2009 | Tilson et al. |
| 2010/0096320 A1 | 4/2010 | Opperman |
| 2010/0114299 A1 | 5/2010 | Ben Muvhar et al. |
| 2010/0160949 A1 | 6/2010 | Takuma |
| 2010/0174353 A1 | 7/2010 | Kantor |
| 2010/0198336 A1 | 8/2010 | Weber et al. |
| 2010/0222803 A1 | 9/2010 | Seifert et al. |
| 2010/0241178 A1 | 9/2010 | Tilson et al. |
| 2010/0268260 A1 | 10/2010 | Riina et al. |
| 2010/0312179 A1 | 12/2010 | Nikolchev et al. |
| 2010/0324649 A1 | 12/2010 | Mattsson et al. |
| 2011/0046658 A1 | 2/2011 | Connor et al. |
| 2011/0190776 A1 | 8/2011 | Palmaz |
| 2011/0213403 A1 | 9/2011 | Aboytes |
| 2011/0264185 A1 | 10/2011 | Haslinger |
| 2011/0270383 A1 | 11/2011 | Jow et al. |
| 2012/0009325 A1 | 1/2012 | Storment |
| 2012/0283768 A1* | 11/2012 | Cox ............... A61B 17/12113 606/198 |
| 2012/0296407 A1 | 11/2012 | Caselnova |
| 2012/0330348 A1* | 12/2012 | Strauss ............ A61B 17/12154 606/200 |
| 2013/0317409 A1 | 11/2013 | Cully et al. |
| 2014/0012307 A1 | 1/2014 | Franano et al. |
| 2014/0012363 A1 | 1/2014 | Franano et al. |
| 2014/0018838 A1 | 1/2014 | Franano et al. |
| 2014/0081314 A1 | 3/2014 | Zaver et al. |
| 2014/0135812 A1 | 5/2014 | Divino et al. |
| 2014/0163601 A1 | 6/2014 | Stamberg |
| 2014/0364895 A1 | 12/2014 | Hines |
| 2015/0005804 A1 | 1/2015 | Franano et al. |
| 2015/0133994 A1 | 5/2015 | Amplatz et al. |
| 2016/0206321 A1 | 7/2016 | Connor |
| 2017/0245864 A1 | 8/2017 | Franano et al. |
| 2017/0258612 A1 | 9/2017 | Franano et al. |
| 2017/0258613 A1 | 9/2017 | Franano et al. |
| 2020/0155333 A1 | 5/2020 | Franano et al. |
| 2020/0163784 A1 | 5/2020 | Franano et al. |

FOREIGN PATENT DOCUMENTS

| | | |
|---|---|---|
| CN | 101843949 A | 9/2010 |
| CN | 101945624 A | 1/2011 |
| CN | 102770091 A | 11/2012 |
| CN | 103476349 A | 12/2013 |
| DE | 10302241 A1 | 8/2004 |
| EP | 0101012 A2 | 2/1984 |
| EP | 1 982 655 A1 | 10/2008 |
| EP | 2055343 A2 | 5/2009 |
| JP | 2007236472 A | 9/2007 |
| JP | 2012-512718 A | 6/2012 |
| WO | 97/17911 A1 | 5/1997 |
| WO | 99/03404 A1 | 1/1999 |
| WO | 99/05977 A1 | 2/1999 |
| WO | 99/07294 A1 | 2/1999 |
| WO | 99/60932 A1 | 12/1999 |
| WO | 00/27292 A1 | 5/2000 |
| WO | 01/52752 A1 | 7/2001 |
| WO | 02/38038 A2 | 5/2002 |
| WO | 02/051320 A2 | 7/2002 |
| WO | 92/080782 A1 | 10/2002 |
| WO | 02/87449 A1 | 11/2002 |
| WO | 03/011363 A2 | 2/2003 |
| WO | 03/061528 A1 | 7/2003 |
| WO | 2004/030518 A2 | 4/2004 |
| WO | 2004/091712 A2 | 10/2004 |
| WO | 2004/112656 A2 | 12/2004 |
| WO | 2006/074410 A2 | 7/2006 |
| WO | 2007/006139 A1 | 1/2007 |
| WO | 2007/092103 A2 | 8/2007 |
| WO | 2008/063455 A1 | 5/2008 |
| WO | 2009/027530 A1 | 3/2009 |
| WO | 2009/045764 A1 | 4/2009 |
| WO | 2009/134337 A1 | 11/2009 |
| WO | 2009/135166 A2 | 11/2009 |
| WO | 2010/028310 A2 | 3/2010 |
| WO | 2012/099704 A2 | 7/2012 |
| WO | 2012/099909 A2 | 7/2012 |
| WO | WO2012099910 A2 * | 7/2012 ............ A61M 25/10 |
| WO | 2013/109309 A1 | 7/2013 |
| WO | 2014/146001 A2 | 9/2014 |
| WO | 2016/044647 A2 | 3/2016 |

OTHER PUBLICATIONS

Office Action from related U.S. Appl. No. 13/980,278, dated Jan. 23, 2017; 35 pgs.

Office Action from related U.S. Appl. No. 13/980,278, dated Aug. 5, 2016; 33 pgs.

Office Action from related U.S. Appl. No. 13/980,278, dated Oct. 23, 2015; 27 pgs.

Notice of Allowance from related U.S. Appl. No. 13/980,276, dated Dec. 7, 2016; 10 pgs.

Office Action from related U.S. Appl. No. 13/980,276, dated Feb. 25, 2016; 22 pgs.

Office Action from related U.S. Appl. No. 13/980,276, dated Jun. 1, 2015; 17 pgs.

Office Action from related U.S. Appl. No. 13/980,276, dated Sep. 5, 2014; 10 pgs.

Office Action from related U.S. Appl. No. 14/372,967, dated Aug. 9, 2017; 24 pgs.

Office Action from related U.S. Appl. No. 14/372,967, dated Nov. 14, 2016; 19 pgs.

Office Action from related Israeli Patent Application No. 227465, dated Oct. 25, 2016; 4 pgs.

Office Action from related Israeli Patent Application No. 227439, dated Oct. 11, 2016; 4 pgs.

Office Action from related Israeli Patent Application No. 227439, dated Nov. 28, 2017; 4 pgs.

Office Action from related Israeli Patent Application No. 227440, dated Oct. 6, 2016; 4 pgs.

(56) References Cited

OTHER PUBLICATIONS

Office Action from related Israeli Patent Application No. 227440, dated Jan. 8, 2018; 4 pgs.
Office Action from related New Zealand Patent Application No. 711474, dated Jun. 27, 2017; 7 pgs.
Office Action from related Russian Patent Application No. 2013138347, dated Dec. 30, 2015; 15 pgs.
Office Action from related Russian Patent Application No. 2013138347, dated Apr. 5, 2016; 25 pgs.
Office Action from related Russian Patent Application No. 2013138347, dated Jun. 2, 2017; 55 pgs.
Office Action from related Russian Patent Application No. 2013138406, dated Jan. 13, 2016; 15 pgs.
Office Action from related Russian Patent Application No. 2013138406, dated May 12, 2016; 24 pgs.
Office Action from related Russian Patent Application No. 2013138406, dated Sep. 5, 2017; 21 pgs.
Office Action from related Russian Patent Application No. 2013128987, dated Feb. 17, 2016; 13 pgs.
Office Action from related Russian Patent Application No. 2013128987, dated May 25, 2016; 6 pgs.
Office Action from related Russian Patent Application No. 2013128987, dated Jul. 25, 2017; 7 pgs.
Decision on Grant from related Russian Patent Application No. 2013128987, dated Dec. 1, 2017; 18 pgs.
Office Action from related Russian Patent Application No. 2014133717, dated Jun. 27, 2016; 5 pgs.
Office Action from related Russian Patent Application No. 2014133717, dated Aug. 17, 2017; 8 pgs.
Decision on Grant from related Russian Patent Application No. 2014133717, dated Dec. 5, 2017; 14 pgs.
Office Action from related Russian Patent Application No. 2015144196, dated Jun. 15, 2016; 1 pg.
Office Action from related Russian Patent Application No. 2017112929, dated May 26, 2017; 4 pgs.
Office Action and Search Report from related Taiwan Patent Application No. 103110016, dated Jun. 30, 2017; 12 pgs.
Office Action from related Australian Patent Application No. 2012207618, dated Jan. 22, 2016; 2 pgs.
Office Action from related Australian Patent Application No. 2012207386, dated Nov. 14, 2015; 3 pgs.
Office Action from related Australian Patent Application No. 2012207387, dated Jan. 21, 2016; 2 pgs.
Office Action from related Australian Patent Application No. 2012366236, dated Oct. 12, 2016; 2 pgs.
Office Action from related Australian Patent Application No. 2012366236, dated Sep. 22, 2017; 3 pgs.
Office Action from related Australian Patent Application No. 2014232323, dated Feb. 6, 2018; 5 pgs.
Office Action from related Australian Patent Application No. 2016256789, dated Aug. 7, 2017; 2 pgs.
Office Action and Search Report from related Canadian Patent Application No. 2,823,378, dated Oct. 30, 2017; 4 pgs.
Office Action and Search Report from related Canadian Patent Application No. 2,822,311, dated Sep. 7, 2017; 4 pgs.
Office Action and Search Report from related Canadian Patent Application No. 2,824,284, dated Sep. 6, 2017; 6 pgs.
Office Action from related European Patent Application No. 12736401.6, dated Nov. 21, 2017; 4 pgs.
Office Action from related European Patent Application No. 12865636.0, dated Apr. 3, 2017; 6 pgs.
Office Action from related European Patent Application No. 14762932.3, dated Aug. 30, 2017; 4 pgs.
Office Action from related Japanese Application No. 2013-549436, dated Nov. 17, 2015; 13 pgs.
Office Action from related Japanese Application No. 2013-549436, dated Nov. 8, 2016; 10 pgs.
Decision of Refusal from related Japanese Application No. 2013-549436, dated Jun. 27, 2017; 4 pgs.
Pre-appeal report from related Japanese Application No. 2013-549436, dated Nov. 28, 2017; 6 pgs.
Office Action from related Japanese Application No. 2013-549618, dated Nov. 17, 2015; 12 pgs.
Office Action from related Japanese Application No. 2013-549618, dated Nov. 8, 2016; 9 pgs.
Decision of Refusal from related Japanese Application No. 2013-549618, dated Jun. 27, 2017; 4 pgs.
Pre-appeal report from related Japanese Application No. 2013-549618, dated Nov. 28, 2017; 7 pgs.
Office Action from related Japanese Application No. 2013-549617, dated Nov. 17, 2015; 7 pgs.
Office Action from related Japanese Application No. 2013-549617, dated Nov. 8, 2016; 8 pgs.
Decision of Refusal from related Japanese Application No. 2013-549617, dated Jun. 27, 2017; 5 pgs.
Pre-appeal report from related Japanese Application No. 2013-549617, dated Nov. 28, 2017; 7 pgs.
Office Action from related Japanese Application No. 2014-552181, dated Jul. 5, 2016; 4 pgs.
Final Office Action from related Japanese Application No. 2014-552181, dated Jun. 20, 2017; 5 pgs.
First Office Action and Search Report from related Chinese Patent Application No. 201280008971.X, dated Aug. 21, 2015; 16 pgs.
Second Office Action from related Chinese Patent Application No. 201280008971.X, dated Jul. 5, 2016; 3 pgs.
Third Office Action from related Chinese Patent Application No. 201280008971.X, dated Feb. 27, 2017; 8 pgs.
First Office Action from related Chinese Patent Application No. 201280005574.7, dated Nov. 21, 2014; 8 pgs.
Second Office Action and Search Report from related Chinese Patent Application No. 201280005574.7, dated Jun. 30, 2015; 21 pgs.
Third Office Action from related Chinese Patent Application No. 201280005574.7, dated Jan. 19, 2016; 7 pgs.
Fourth Office Action from related Chinese Patent Application No. 201280005574.7, dated May 25, 2016; 3 pgs.
First Office Action and Search Report from related Chinese Patent Application No. 201280005586.X, dated Dec. 2, 2015; 13 pgs.
Second Office Action from related Chinese Patent Application No. 201280005586.X, dated Oct. 19, 2016; 7 pgs.
Third Office Action and Search Report from related Chinese Patent Application No. 201280005586.X, dated May 9, 2017; 12 pgs.
First Office Action and Search Report from related Chinese Patent Application No. 201280067371.0, dated Mar. 1, 2016; 23 pgs.
Second Office Action from related Chinese Patent Application No. 201280067371.0, dated Jan. 12, 2017; 14 pgs.
Third Office Action from related Chinese Patent Application No. 201280067371.0, dated Sep. 13, 2017; 14 pgs.
First Office Action and Search Report from related Chinese Patent Application No. 201480027636.3, dated Oct. 17, 2016; 19 pgs.
Notice of Amendment from related Chinese Patent Application No. 201580062443.6, dated Jul. 20, 2017; 3 pgs.
Notice of Amendment from related Chinese Patent Application No. 201710994867.7, dated Dec. 11, 2017; 3 pgs.
Notice of Allowance from related U.S. Appl. No. 13/980,274, dated Dec. 6, 2016; 12 pgs.
Office Action from related U.S. Appl. No. 13/980,274, dated Feb. 22, 2016; 20 pgs.
Office Action from related U.S. Appl. No. 13/980,274, dated Jun. 2, 2015; 18 pgs.
Office Action from related U.S. Appl. No. 13/980,274, dated Sep. 5, 2014; 10 pgs.
Extended European Search Report from related European Application 12737004.7, dated Oct. 2, 2014; 12 pgs.
Extended European Search Report from related European Application 12736799.3, dated Oct. 2, 2014; 12 pgs.
Extended European Search Report from related European Application 12736401.6, dated Oct. 2, 2014; 11 pgs.
Extended European Search Report from related European Application 12865636.0, dated Aug. 6, 2015; 10 pgs.
Extended European Search Report from related European Application 14762932.3, dated Sep. 16, 2016; 10 pgs.

(56) References Cited

OTHER PUBLICATIONS

International Search Report and Written Opinion from related International Application No. PCT/US2012/021620, dated Aug. 3, 2012; 19 pgs.

International Search Report and Written Opinion from related International Application No. PCT/US2012/021621, dated Aug. 16, 2012; 27 pgs.

International Search Report and Written Opinion from related International Application No. PCT/US2012/000030, dated Aug. 7, 2012; 27 pgs.

International Search Report and Written Opinion from related International Application No. PCT/US2012/047072, dated Dec. 20, 2012; 26 pgs.

International Search Report and Written Opinion from related International Application No. PCT/US2014/030869, dated Nov. 7, 2014; 26 pgs.

International Search Report and Written Opinion from related International Application No. PCT/US2015/050783, dated Apr. 11, 2016; 15 pgs.

\* cited by examiner

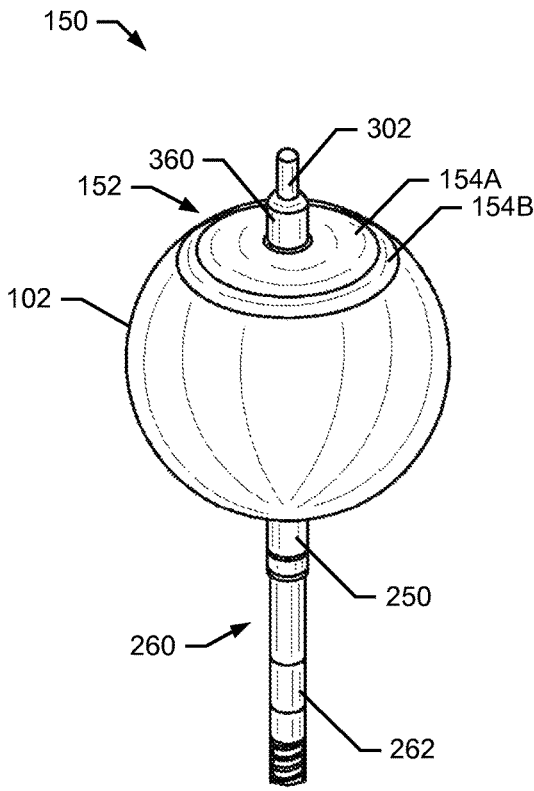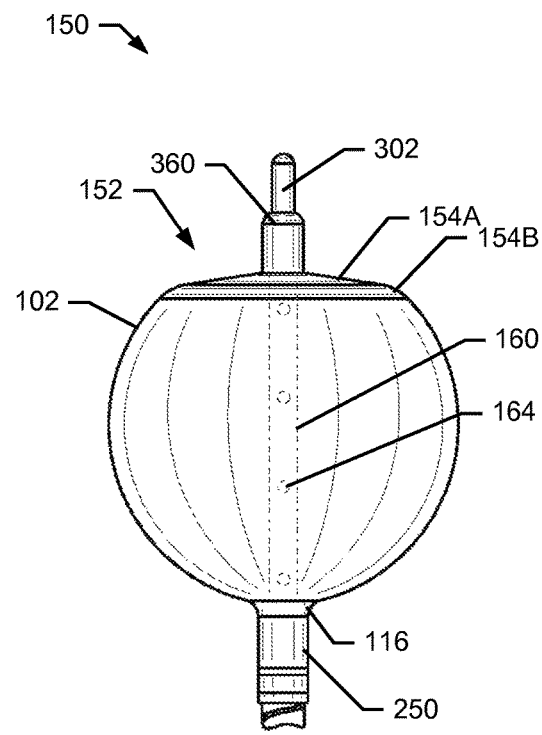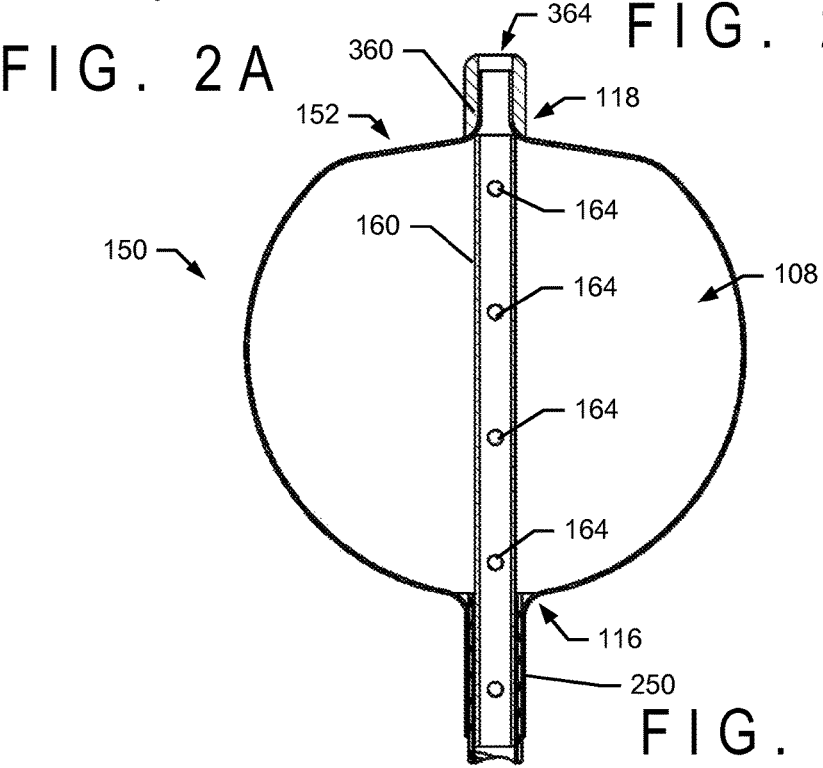

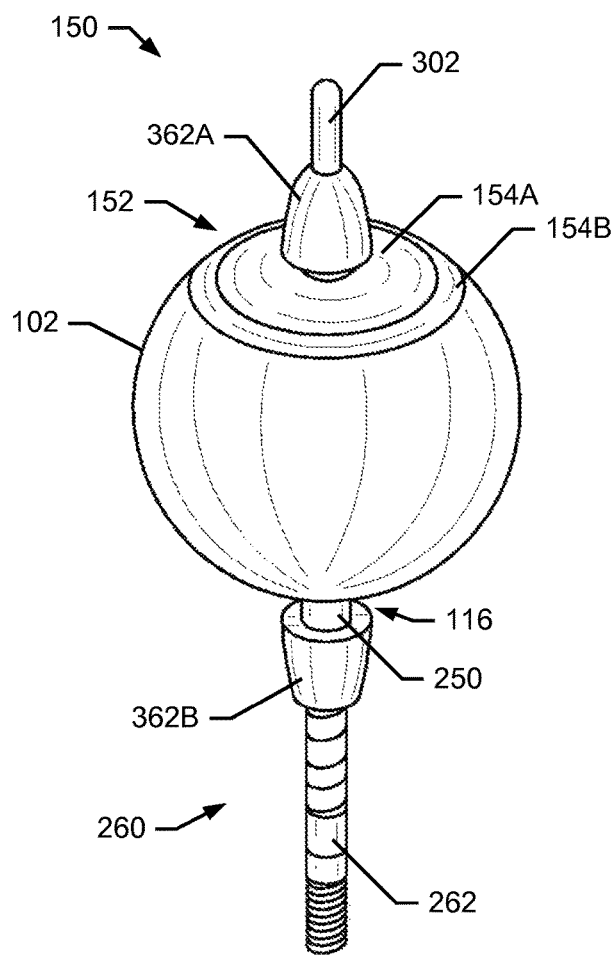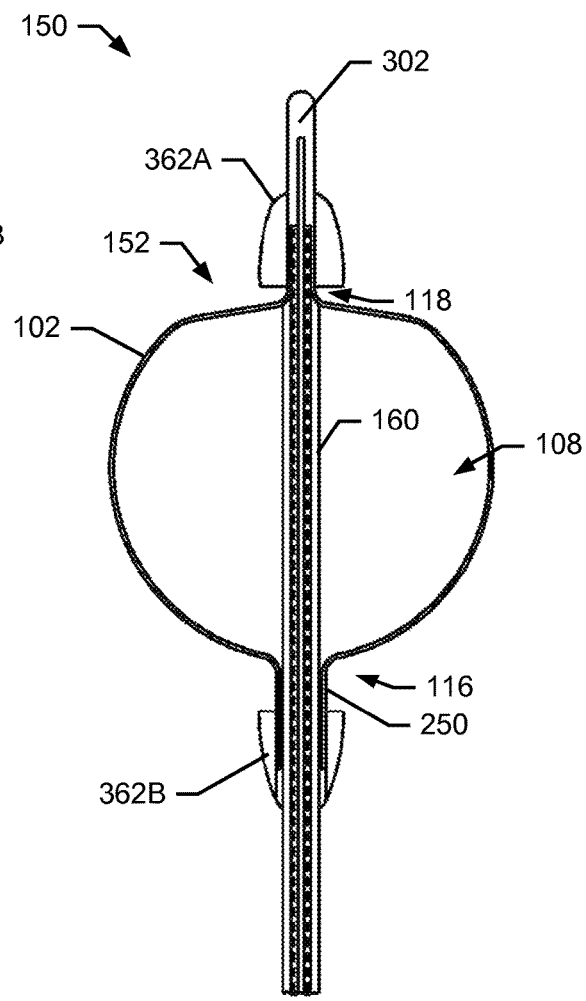
FIG. 2D
FIG. 2E

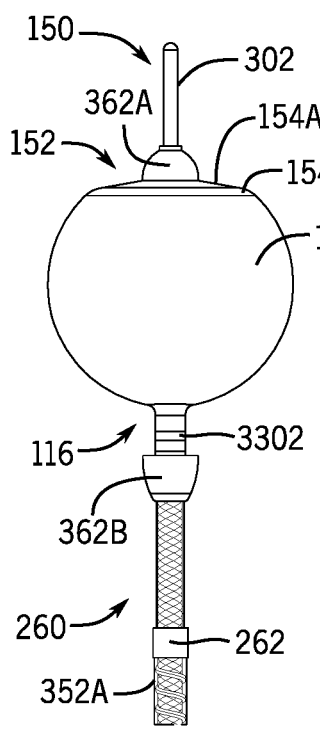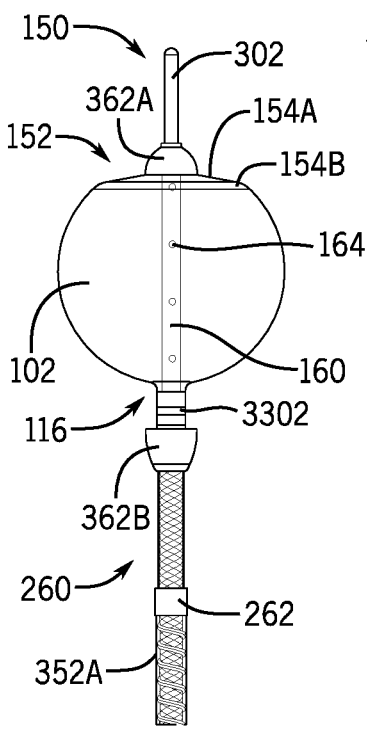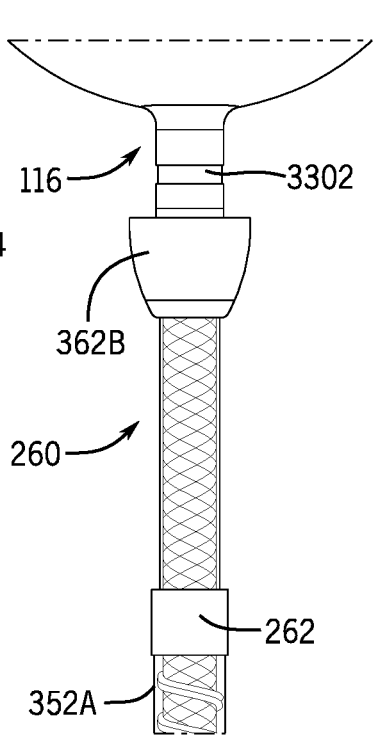
FIG. 2F　　　FIG. 2G　　　FIG. 2H
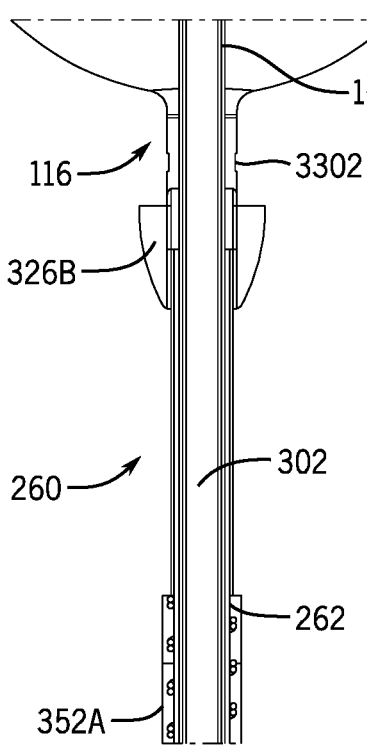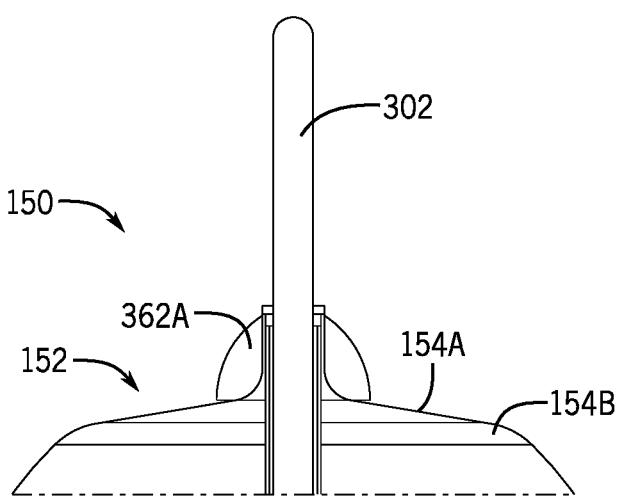
FIG. 2I　　　FIG. 2J

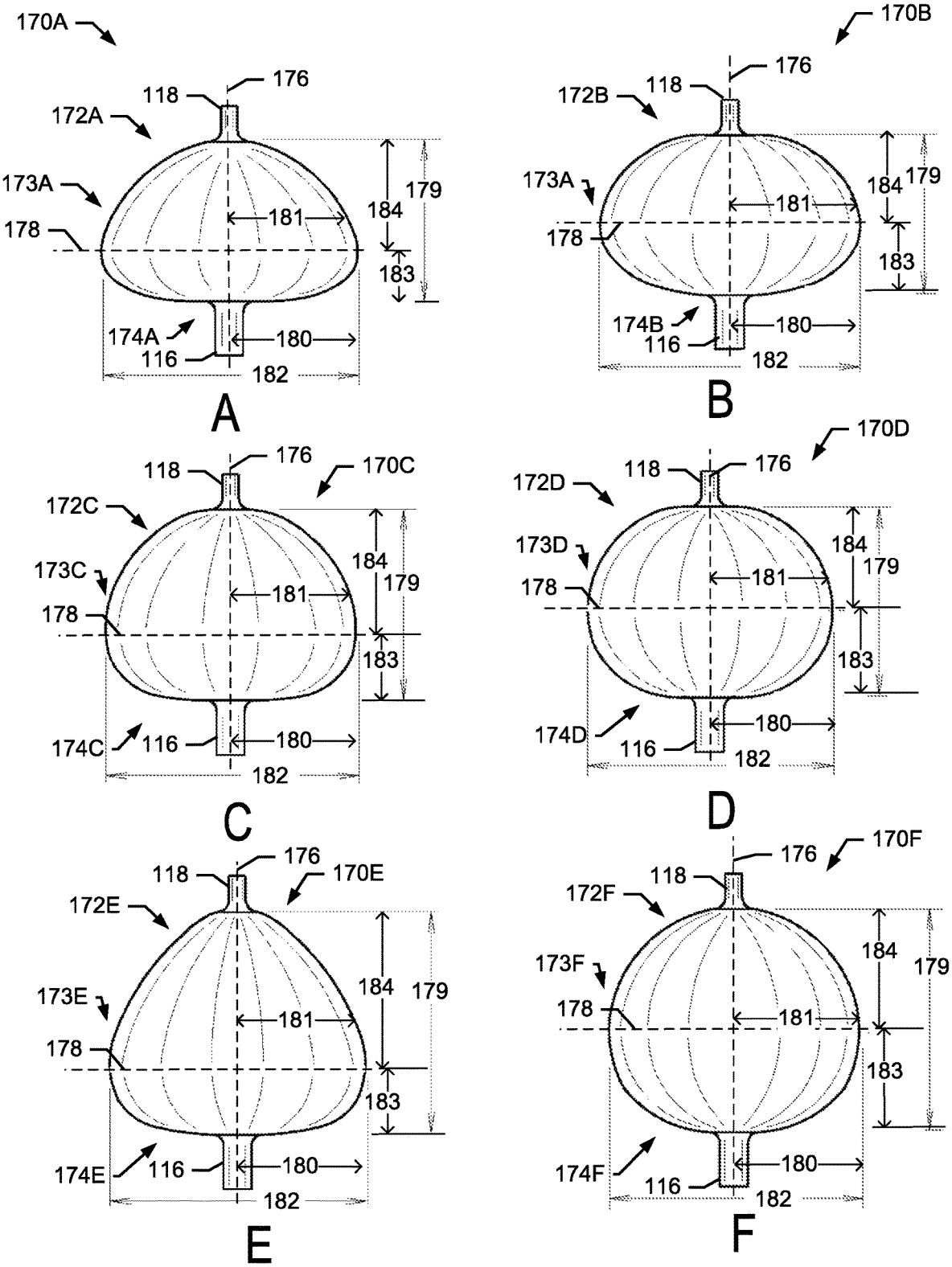
FIGS. 8A-F

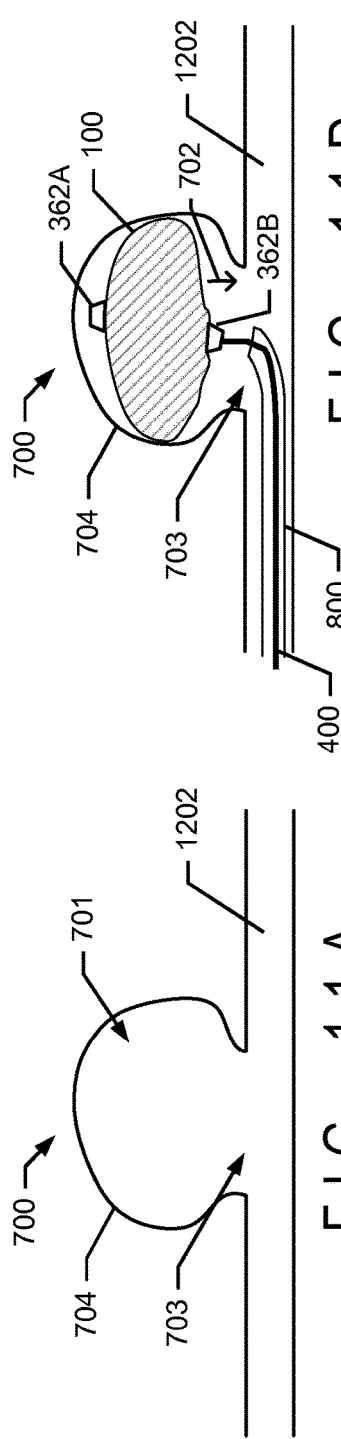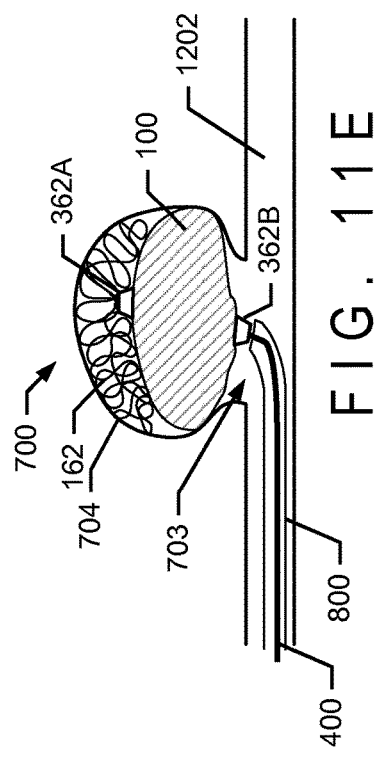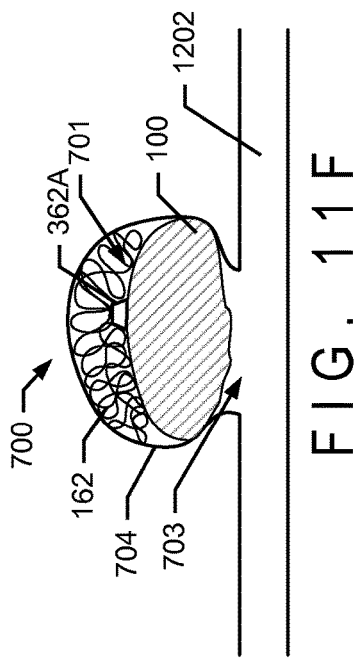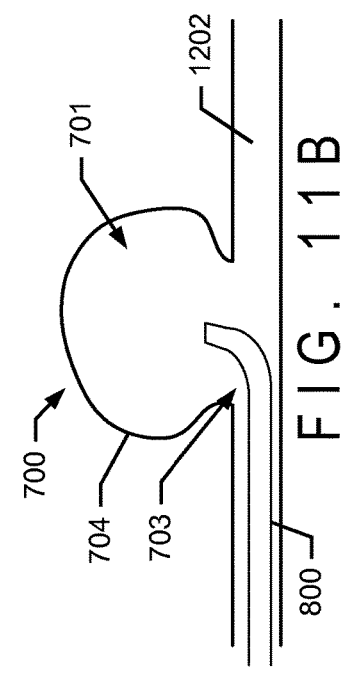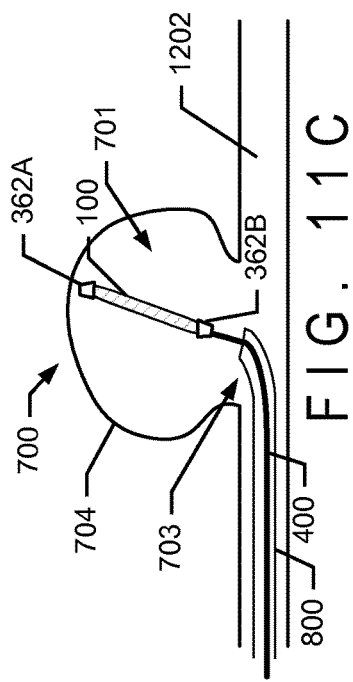

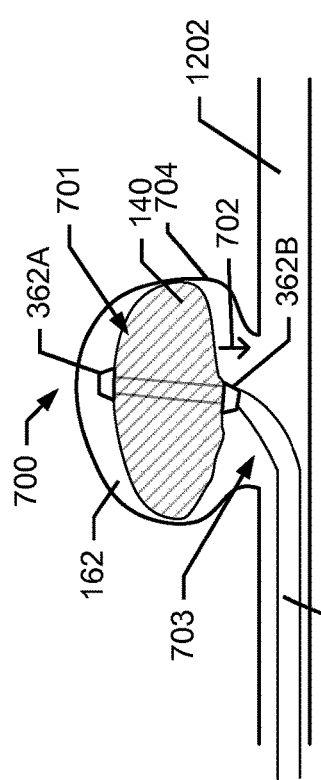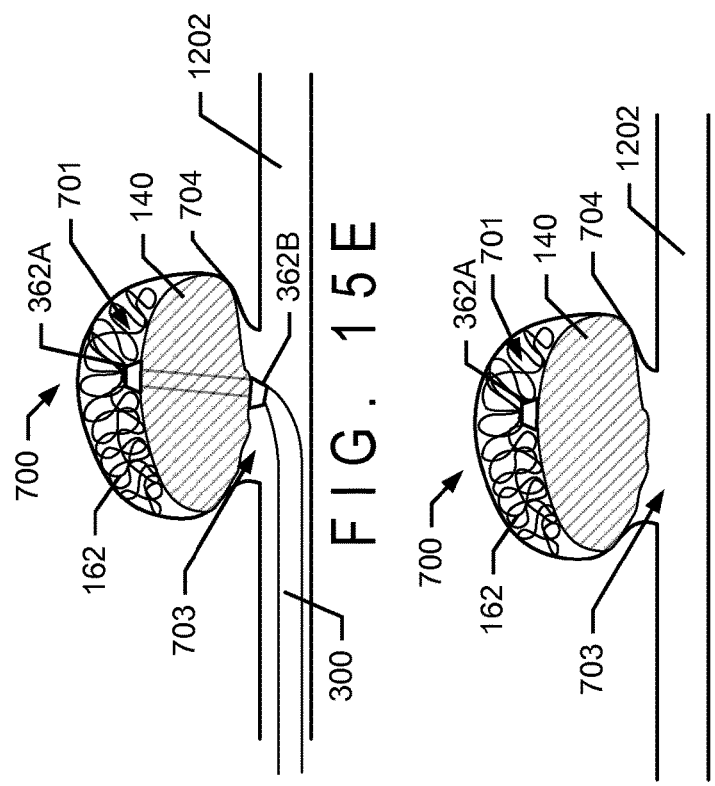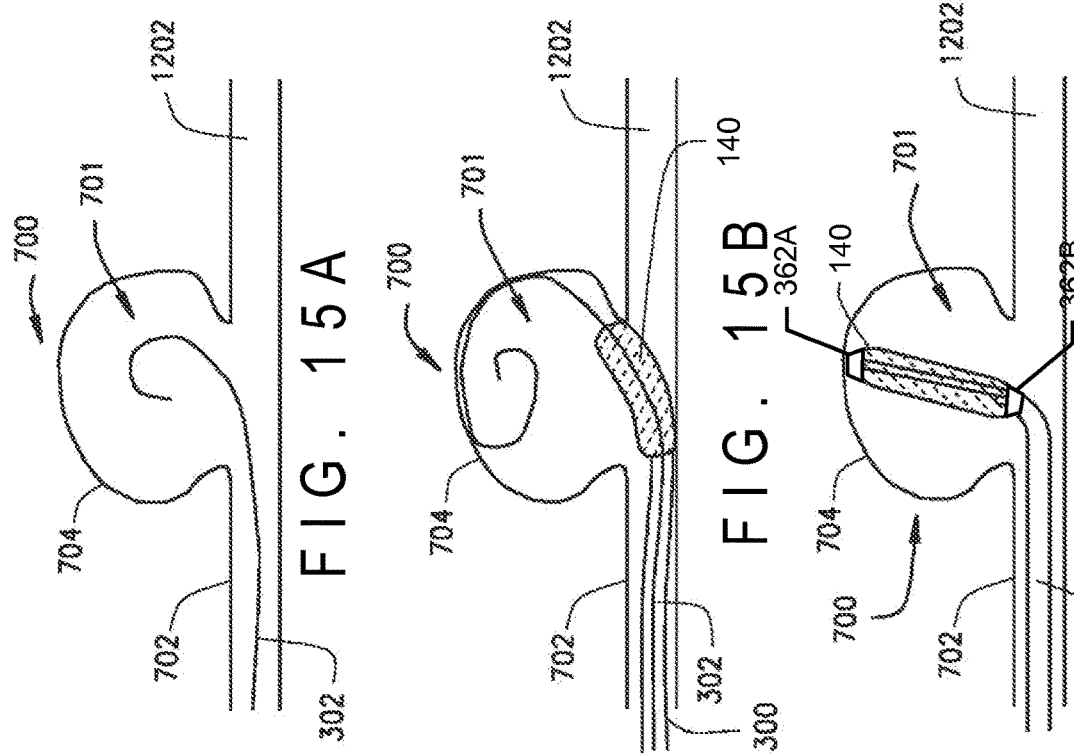

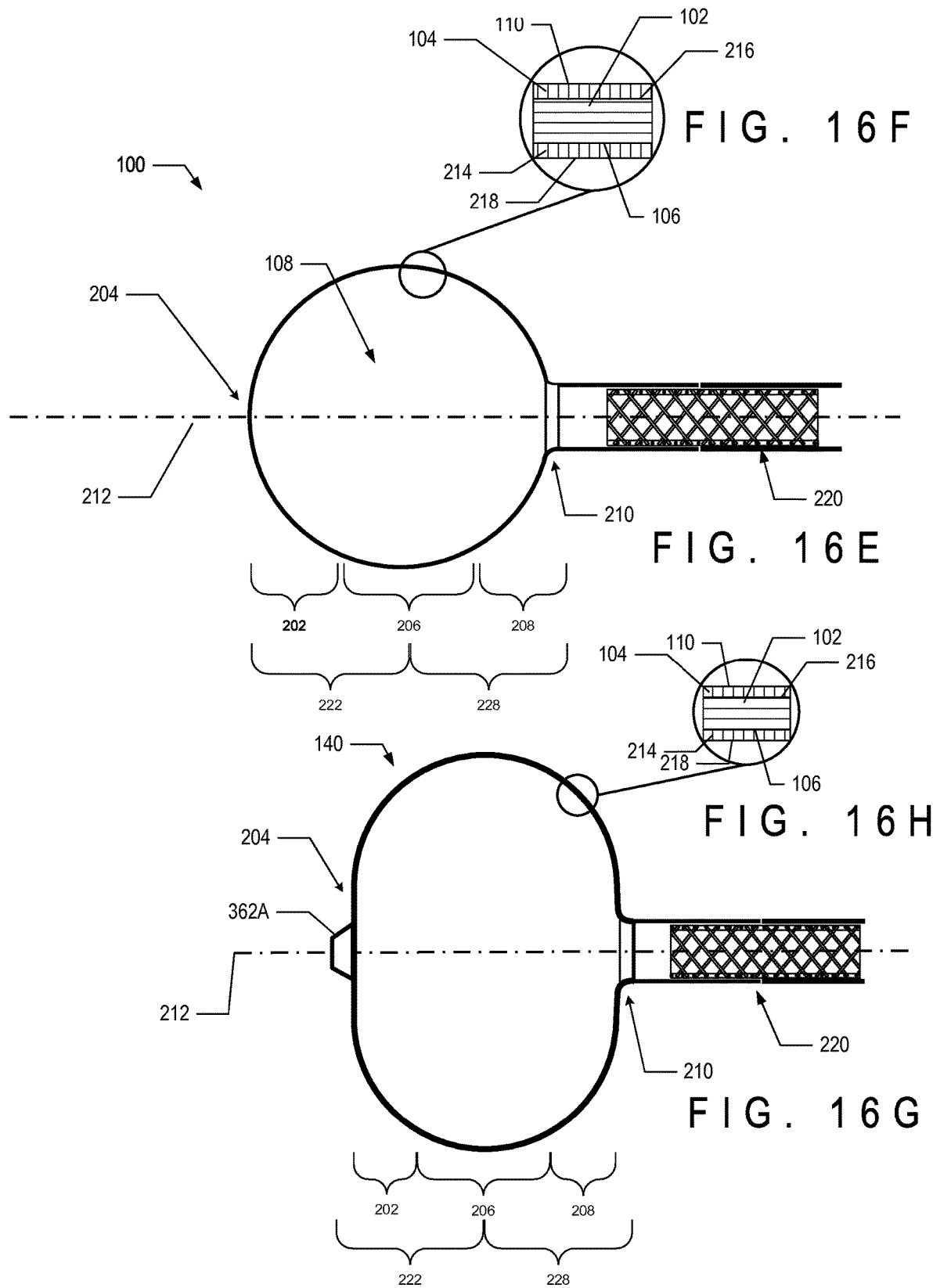

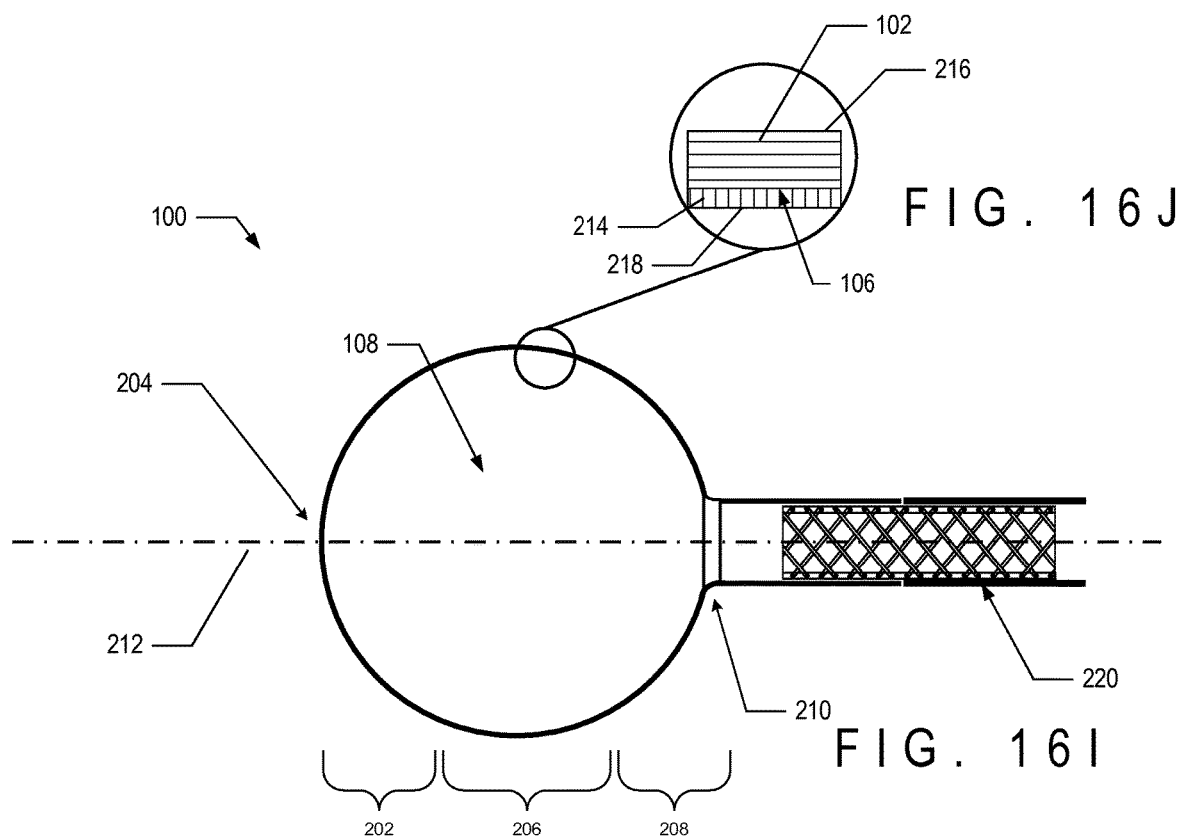
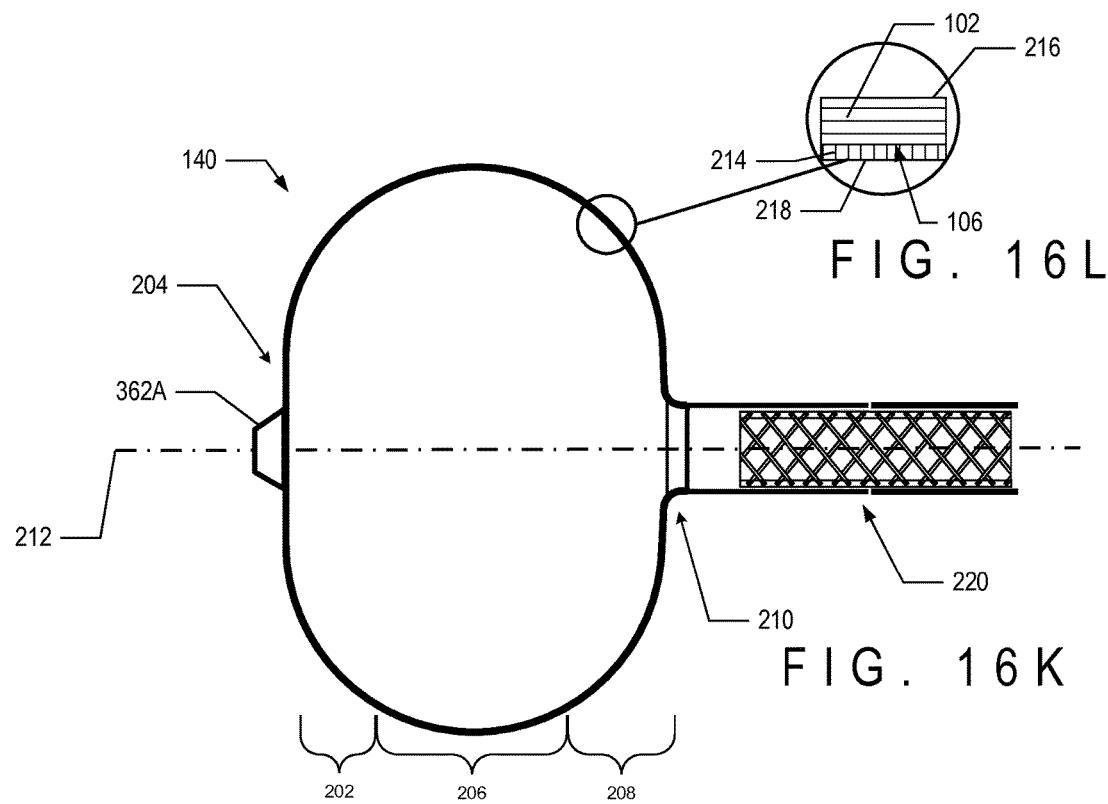

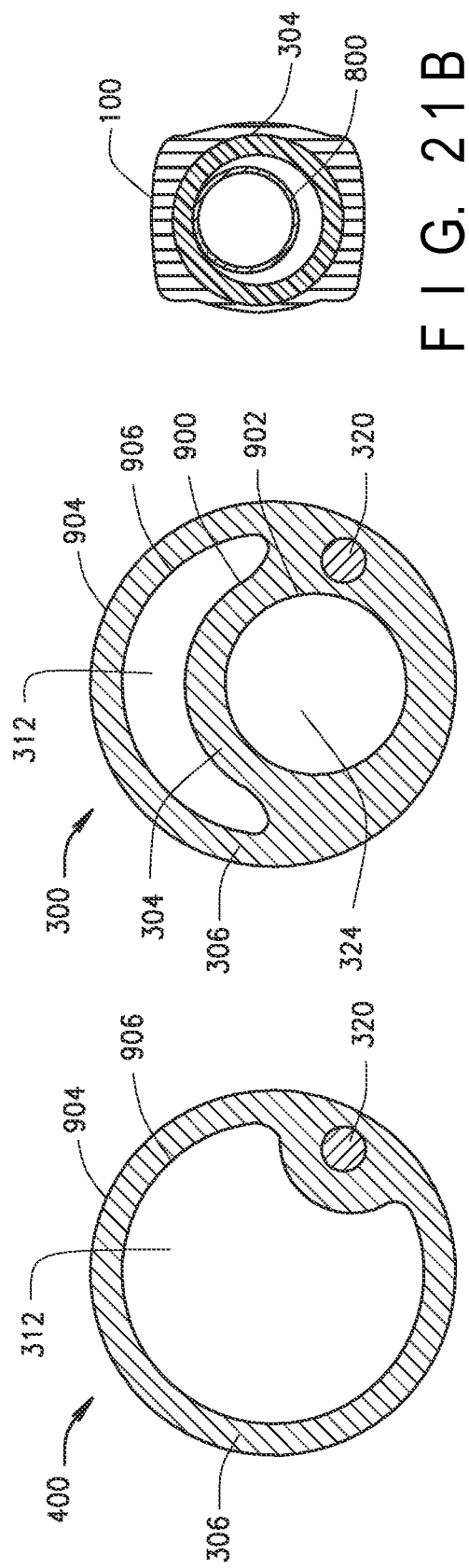
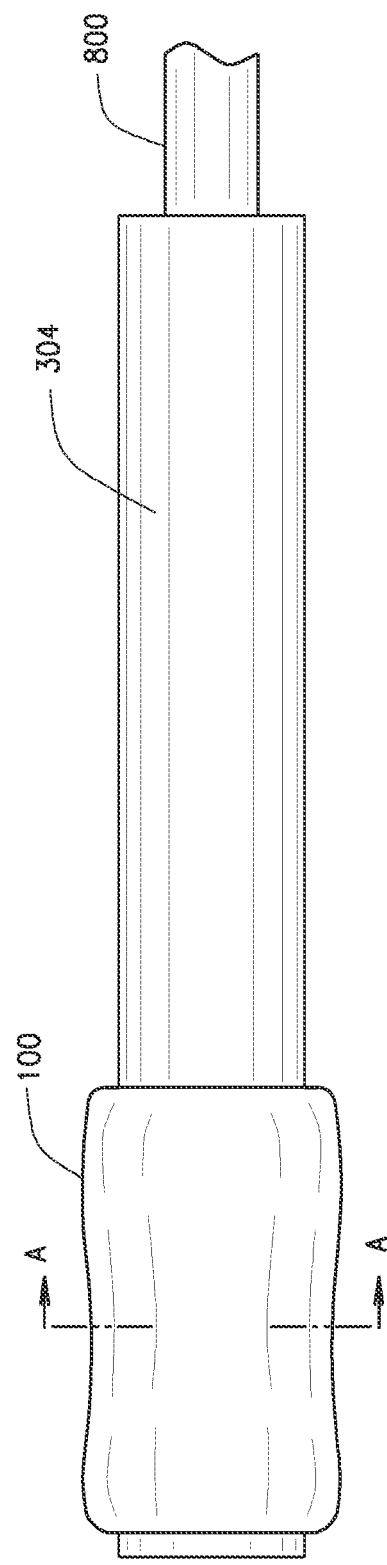
FIG. 20A
FIG. 20B
FIG. 21A
FIG. 21B

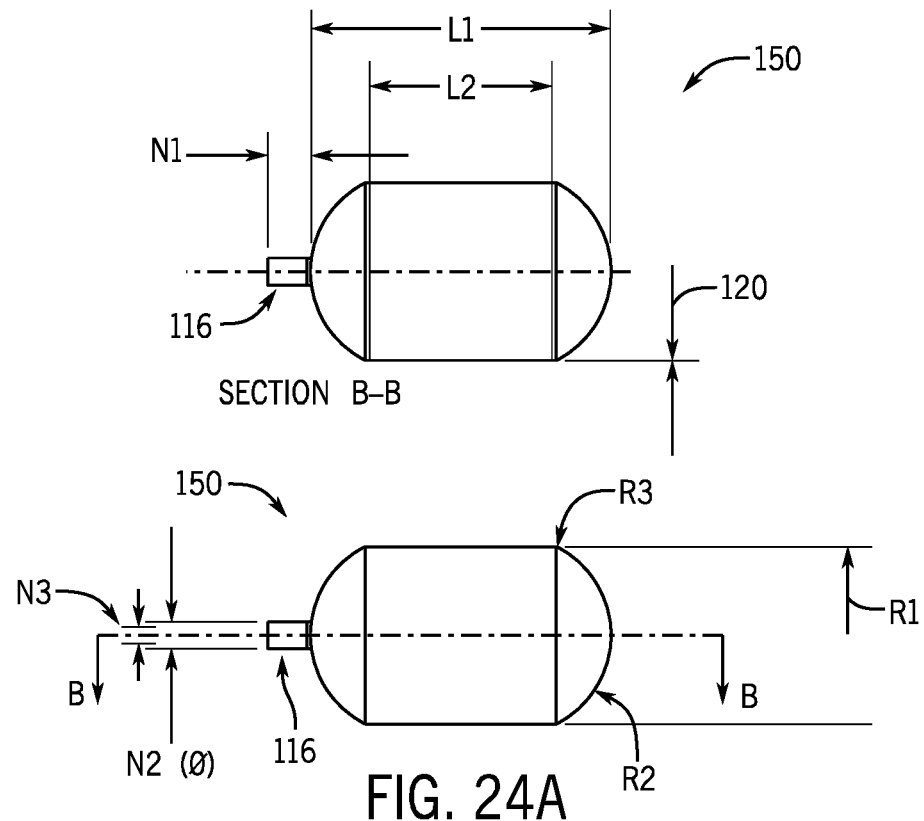
FIG. 24A
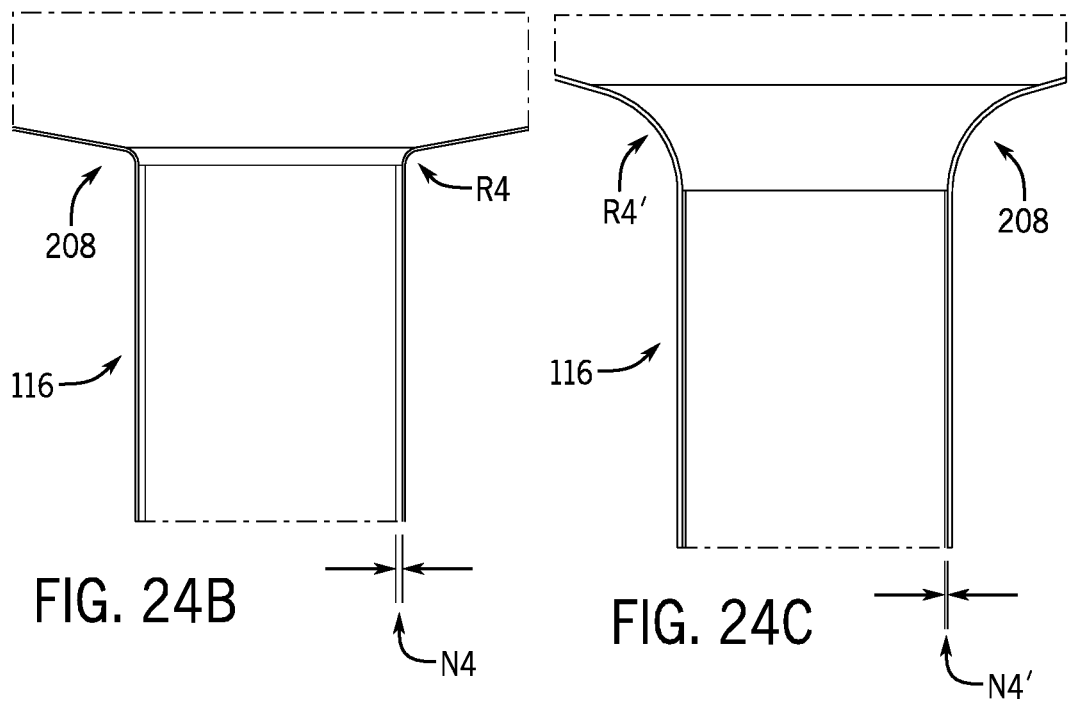
FIG. 24B
FIG. 24C

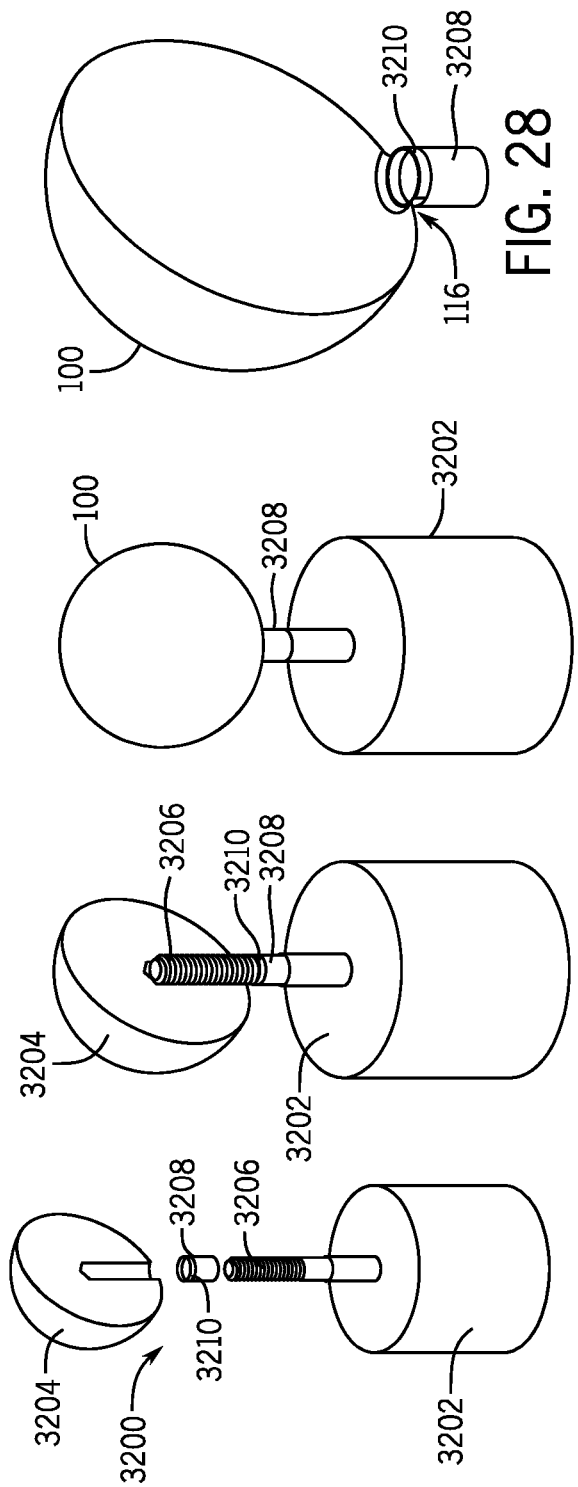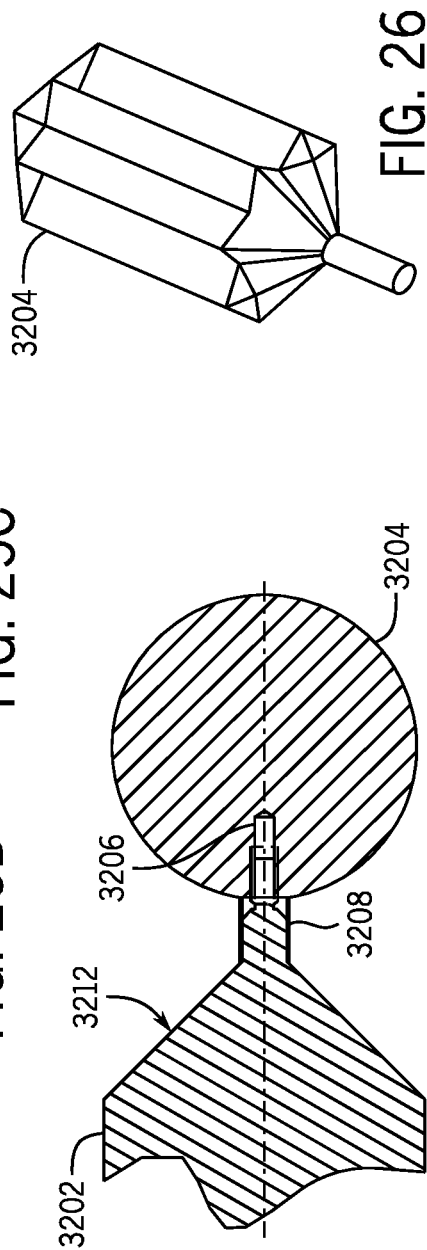

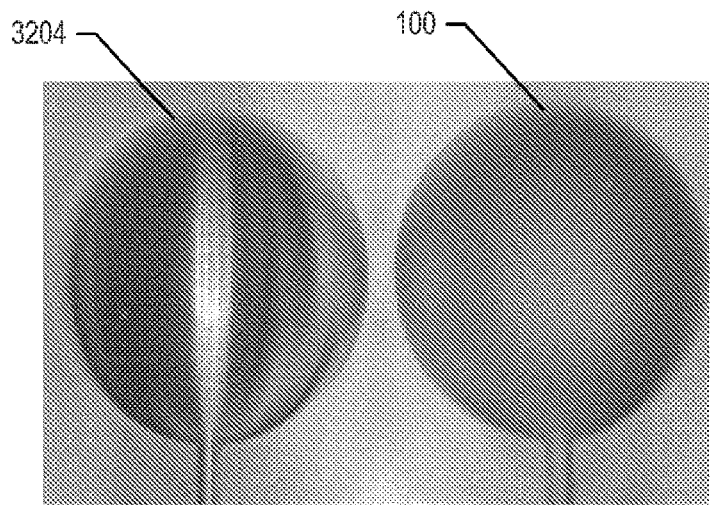
F I G. 29A    F I G. 29B
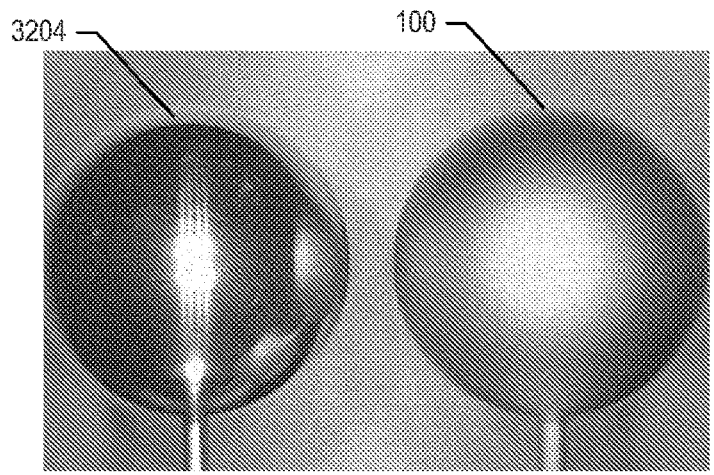
F I G. 29C    F I G. 29D
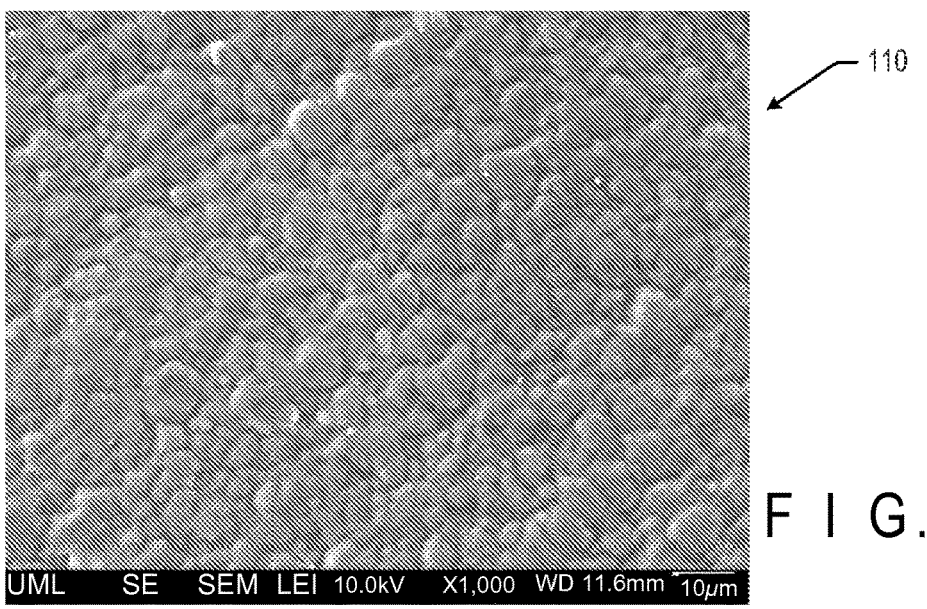
F I G. 29E

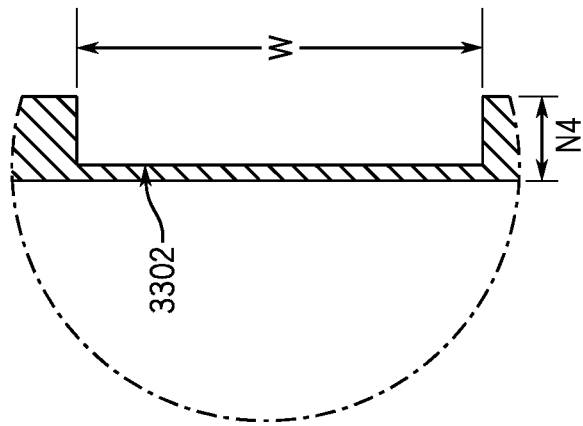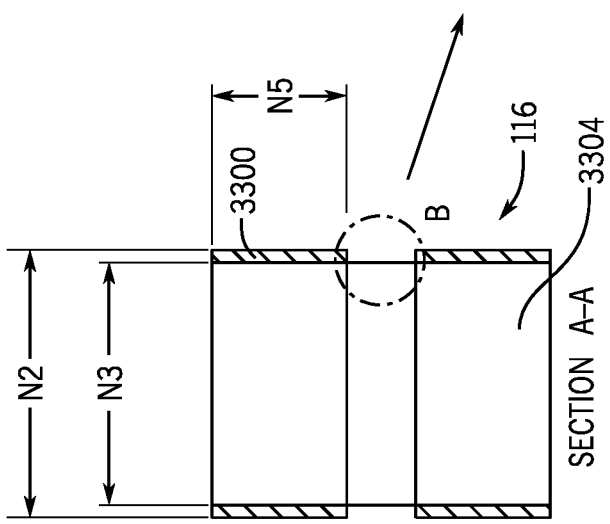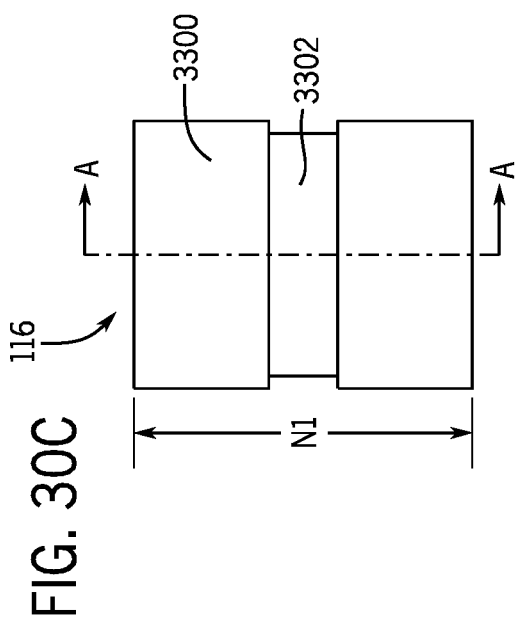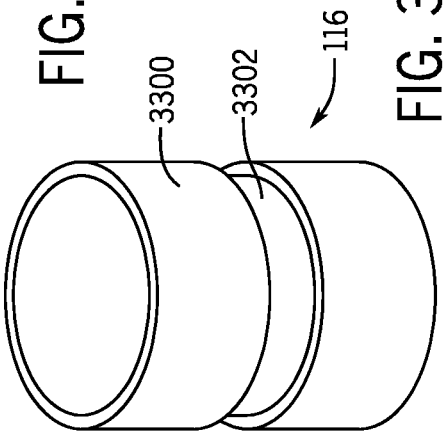

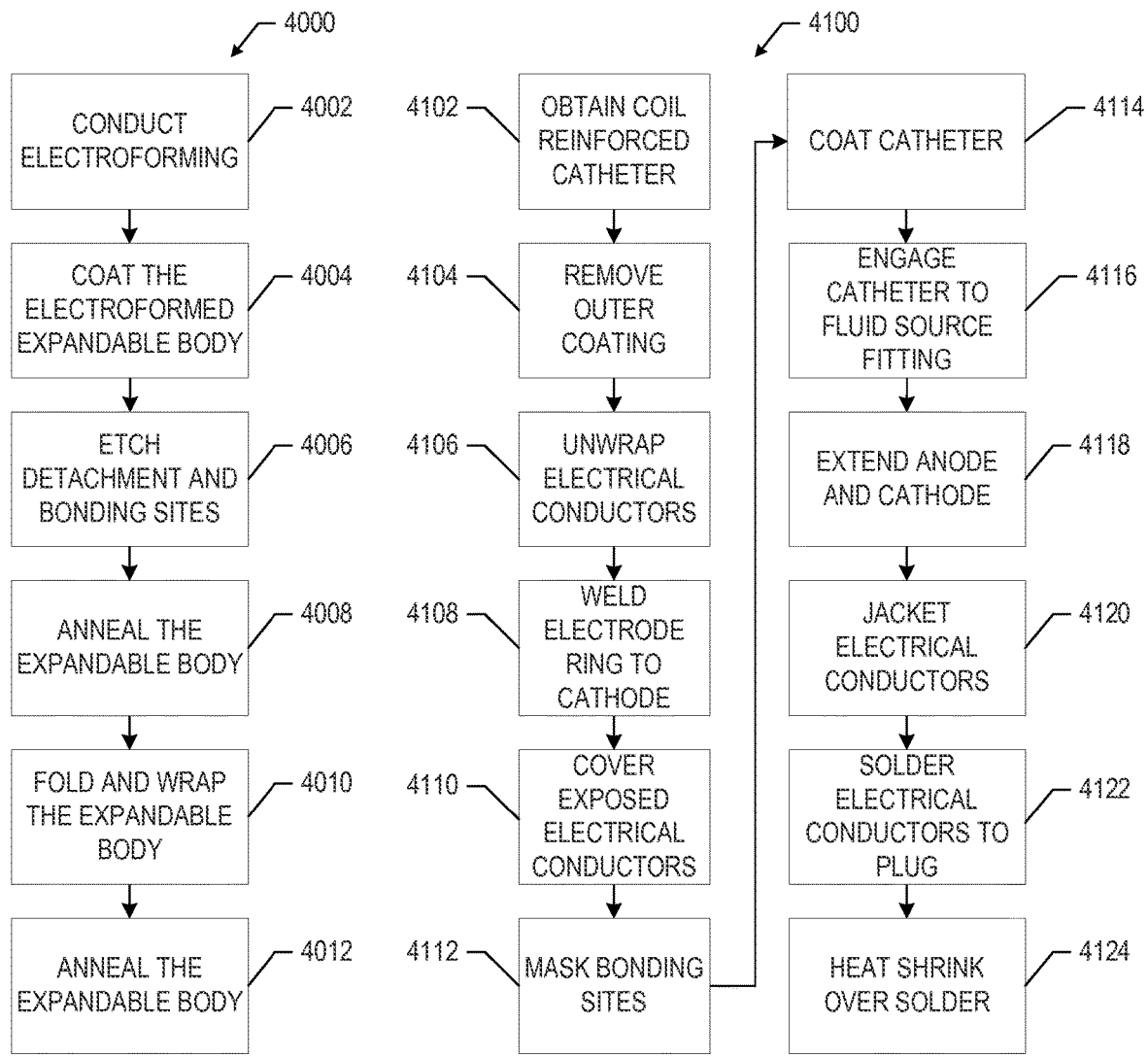

Figure 6: Histopathology Results of Nonclinical Pilot Study of Blockstent Microcatheter vs. Amplatzer Vascular Plug II (AVP2), 29 Days
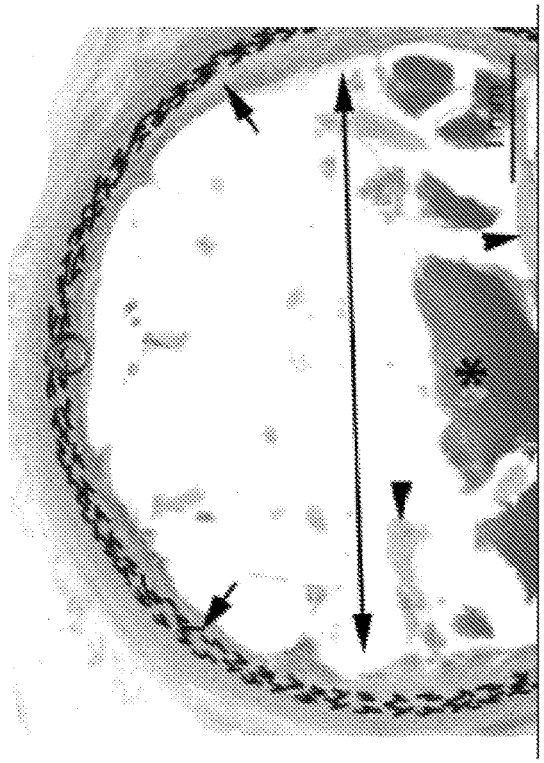
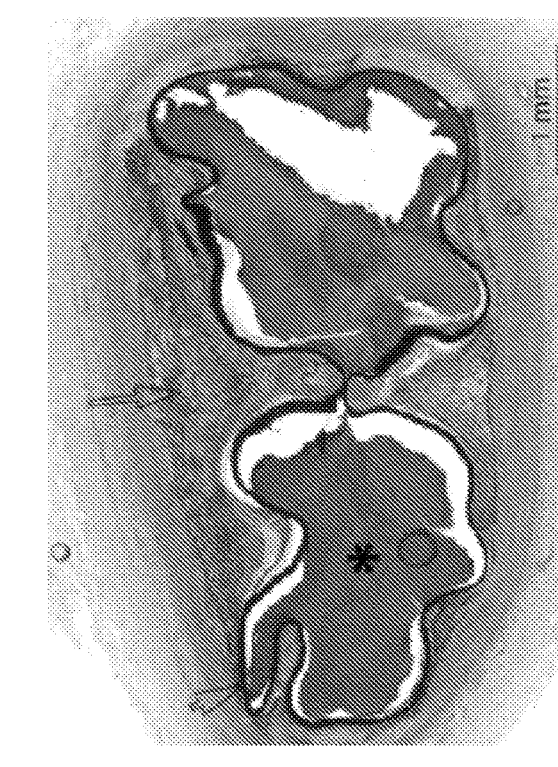
FIG. 42

EXPANDABLE BODY DEVICE AND METHOD OF USE

CROSS REFERENCE TO RELATED APPLICATIONS

The present application claims priority to: U.S. Provisional Patent application 61/793,737, which was filed on Mar. 15, 2013, entitled "Expandable Body Device and Method of Use," the entire contents of which are incorporated herein by reference in its entirety.

FIELD OF THE PRESENT DISCLOSURE

The present disclosure relates to devices and systems including an expandable body and a delivery catheter for the treatment of saccular aneurysms of the vascular system or the occlusion of blood vessel segments or other biological conduits, where the expandable body ultimately remains in the aneurysm, blood vessel segment, or biological conduit segment in an expanded state. Further, the present disclosure relates to methods and systems for delivering and positioning various embodiments of the expandable body, which are dimensioned and configured to fill and/or seal at least a portion of the saccular aneurysm, blood vessel segment, or biological conduit segment such that the expandable body remains in place in an expanded state while the delivery catheter is removed from the patient's body. The present disclosure also relates to devices, systems, and methods for treating saccular aneurysms wherein the expandable body may be deployed in combination with one or more coiled wires that contact both the wall of the aneurysm and the expandable body and exert force on the expandable body to aid in sealing the aneurysm neck.

BACKGROUND OF THE PRESENT DISCLOSURE

An aneurysm is an abnormal outward bulging of a blood vessel that can occur anywhere in the body. This bulge weakens the blood vessel wall, making it susceptible to rupture, which can result in bleeding or hemorrhage. Aneurysms are common in the arterial circulation of the brain, where they are known as cerebral or intracranial aneurysms. When cerebral aneurysms rupture, this often leads to a hemorrhagic stroke, brain damage, and sometimes death. Cerebral aneurysms are a common condition, affecting an estimated 2% of the adult population. Approximately 90% of cerebral aneurysms are saccular with a rounded, sac, or pouch-like shape. Invasive surgery is the traditional mode of treatment, with the surgery involving opening the skull and sealing the aneurysms by placing a small surgical clip on the outside of the neck or body of the aneurysm, thereby limiting blood flow into the aneurysm sac.

Alternatively, minimally invasive, catheter-based, endovascular treatments have been used wherein a series of small metal coiled wires ("coils") are used to fill aneurysm sacs, blood vessel segments, or biological conduit segments to effect occlusion. In order to occlude an aneurysm or blood vessel with coils, a physician inserts a catheter into a lumen of the vascular system and maneuvers the catheter tip to the location where occlusion is desired. With the catheter tip in position, the physician passes the coils through the catheter into the lumen or inner cavity of the aneurysm, blood vessel segment, or biological conduit segment.

Although effective, coiling of saccular cerebral aneurysms has drawbacks. First, coil placement is difficult to control, often resulting in coil protrusion into the parent vessel or coil migration to non-target locations. Second, coils only partially fill and occlude the aneurysm sac. The accumulation of thrombus and fibrous tissue is required to seal the aneurysm, a process that often takes weeks to months to occur and is sometimes incomplete, which can reduce the effectiveness of coils in the treatment of acute aneurysm rupture with subarachnoid hemorrhage. Even when the use of coils is initially effective, recanalization of the aneurysm, blood vessel, or biological conduit is a common occurrence, resulting in a return of blood flow to the aneurysm and increasing the risk rupture over time. Incomplete filling of saccular aneurysms with coils is especially common in the neck region of saccular aneurysms, where coil density can be low and blood flow rates high. Third, numerous coils are usually required to treat the aneurysm, resulting in high costs and long treatment times. Fourth, coils are susceptible to compaction, further exposing the aneurysm neck and thereby contributing to the high rate of aneurysm recurrence.

More recently, traditional tubular stents have been adapted for the treatment of cerebral aneurysms. These stents are placed on catheter delivery devices and positioned in the parent vessel adjacent to the aneurysm. These stents are then expanded in the parent vessel with the delivery device, followed by removal of the delivery device. The expanded metal stent acts to reduce blood flow into the aneurysm sac and promote aneurysm thrombosis. Although effective, the use of these "flow diverting" stents has drawbacks. First, the stents may cover and divert blood flow away from important arterial branches adjacent to the aneurysm, sometimes resulting in ischemia and stroke—a problem especially seen with the treatment of bifurcation aneurysms. Second, these stents are a source of thrombus and intimal hyperplasia formation in the parent vessel, which can result in narrowing in the parent vessel lumen, ischemia, and stroke.

In other clinical situations, patients can benefit from the occlusion of certain artery or vein segments. Clinical settings where endovascular vessel occlusion is beneficial include reducing bleeding from an injured vessel, reducing blood flow to tumors, and rerouting the path of blood in the vascular system for other purposes such as to reduce blood flow to vascular anomalies and malformations. Minimally invasive, catheter-based, endovascular treatments have been developed to occlude blood vessel segments. Endovascular medical devices for blood vessel occlusion include balloon catheters wherein the balloon can be inflated to fill the lumen of a blood vessel segment and detached from the catheter. There are two major drawbacks to the use of detachable balloon catheters for blood vessel occlusion. First, the balloons are made of polymers that generally resist tissue incorporation. This limits fixation of the devices where they are placed and increases the risk of migration. Second, the balloons are configured with elastic walls, which are expanded with pressurization, and valves designed to maintain that pressure after detachment. Unfortunately, there is a substantial rate of balloon and valve failure, resulting in deflation. Without tissue incorporation, balloon deflation can lead to blood vessel or biological conduit recanalization or balloon migration and occlusion of non-target vessel segments.

More recently, endovascular medical devices for blood vessel occlusion have been developed that include basket vessel structures that are used to fill a portion of the lumen of a blood vessel segment to induce thrombosis and occlusion of the blood vessel segment. Although only a single basket structure is usually required to occlude a blood vessel segment, and the devices are generally easier to control, these devices only partially fill the blood vessel and require the accumulation of thrombus and fibrous tissue to occlude the blood vessel. As with coils, this process takes weeks to occur and is sometimes incomplete, often resulting in incomplete occlusion or recanalization and a failed treatment.

Therefore, there remains a need for medical devices, systems, and methods for treating saccular aneurysms, including cerebral aneurysms, which result in a more effective and complete reduction of blood flow to saccular aneurysms that is more effective in sealing the neck, and more durable and permanent. It is further desired to have medical devices, systems, and methods that reduce the flow of blood into saccular aneurysms and seals the aneurysm neck more quickly. Finally, it is desired to have medical devices, systems, and methods for treating saccular aneurysms that can be used more easily and in less time, with a lower risk of complications, and at a lower cost when compared with existing treatments.

There also remains a need for catheter-based medical devices, systems, and methods for the occlusion of segments of blood vessel segments and other biological conduits that are simple to perform, result in a rapid, controlled, and complete occlusion, have a low risk of recanalization, device migration, or other complications, and can be purchased at a reasonable cost.

SUMMARY OF THE PRESENT DISCLOSURE

Disclosed herein are medical systems and devices for the treatment of saccular aneurysms using an expandable body or structure or one or more expandable bodies or structures in combination to occlude saccular aneurysms. Also disclosed are medical systems and devices for the occlusion or blockage of blood vessel segments, including arteries, veins, other vascular conduits, and other biological conduits using an expandable body or structure, or one or more expandable bodies or structures in combination. The expandable body or bodies may be configured for use as a balloon, a ballstent, a blockstent, a self-expanding coil of wire, or other expandable construction. The terms "expandable body", "expandable structure", "expandable balloon", "ballstent", and "blockstent", as used herein, refer to an expandable body having a single-layered or multi-layered construction and wherein the expandable body may be first introduced in a non-expanded state into a patient using a delivery device; second, negotiated in the non-expanded state through the cardiovascular system of the patient to a target treatment site (i.e., implantation site); third, expanded at the target treatment site into an expanded state; and, fourth, detached from the delivery device to remain in the patient's body in an expanded configuration at the target or treatment site. Also disclosed herein are methods of manufacturing and methods of using the medical devices and medical systems.

A medical system disclosed herein may be used to fill a biological space of a patient. Such a medical system includes a single-lobed metallic expandable body and delivery device. Such a medical system may also include one or more additional expandable bodies, including coiled wires that can be placed immediately adjacent to the single-lobed expandable body. Filling of a biological space includes occlusion of at least a portion of a lumen of a ruptured or non-ruptured saccular aneurysm or a lumen of a blood vessel segment, including arteries and veins, or a lumen of another type of biological conduit.

The single-lobed metallic expandable body includes a distal region, a proximal region generally opposite the distal region, and optionally an intermediate region transitioning from the distal region to the proximal region. A center axis extends proximal-distal between the proximal region and distal region of the single-lobed metallic expandable body. A wall of the single-lobed metallic expandable body extends generally continuously through from the proximal region, optionally through the intermediate region, to the distal region to define an exterior surface of the expandable body and an interior surface of the expandable body. The interior surface defines an interior volume of the expandable body. The expandable body is configured to expand from a deliverable (i.e., collapsed or non-expanded) configuration to an expanded configuration.

In various embodiments, the expandable body includes a proximal region and distal region separated by an intermediate region that forms the unitary construct of the expandable body. The expandable body may further be defined by a first axis and a second axis transverse to the first axis. The first axis extends between a proximal neck and a distal neck of the expandable body. In one aspect, the shape of the intermediate region may be described and defined by an arc parallel to the first axis. In various embodiments, the width or length of the expandable body along the second axis is greater than the height or length of the expandable body along the first axis. In some embodiments, when expanded, a maximum radius of the distal region, parallel to the second axis, is less than or equal to a maximum radius of the proximal region parallel to the second axis. In some embodiments, when expanded, a maximum radius of the distal region, parallel to the first axis, is less than or equal to a maximum radius of the proximal region parallel to the first axis.

In various other embodiments, the expandable bodies may also be defined and described as having a generally hemispherical proximal region affixed to a generally hemispherical distal region. Hemispheroids formed by each region may be further defined by a semi-major axis and semi-minor axis that align with the first axis or the second axis. Each region has a corresponding neck and may independently define an oblate hemispheroid, a prolate hemispheroid, or a hemisphere.

The delivery device has a longitudinally extending body that includes a proximal end and a distal end generally opposite the proximal end. The distal end of the delivery device is operably coupled to the proximal neck of the expandable body. In some embodiments, the distal end of the delivery device is also operably coupled to the distal neck of the expandable body. In one embodiment, when the expandable body is in the deliverable configuration, the wall assumes a pleated configuration having a plurality of pleats folded over in a clockwise direction relative to the first or center axis, or, alternately, in a counter-clockwise direction relative to the first or center axis to form a folded-over region of the expandable body. Conversely, when the expandable body is in the expanded configuration, the plurality of pleats is not folded over and the pleated configuration substantially ceases to exist.

In one embodiment, the system or medical system includes a detachment system having an electrical circuit partially supported on the delivery device and configured to decouple an expandable body from a distal end of the delivery device by electrolysis.

Methods for filling at least a portion of a biological space of a patient are also disclosed herein. One method includes providing a single-lobed metallic expandable body configured to expand from a deliverable configuration to an expanded configuration. The expandable body is introduced to the biological space of the patient in a deliverable configuration via a delivery device having a distal end operably engaged to a proximal neck, proximal region, or distal neck of the expandable body. A fluid medium can be delivered into the interior volume of the expandable body via the delivery device to inflate or expand the expandable body, causing it to assume an expanded configuration. After expansion, the expandable body is detached from the delivery device. In some embodiments, the method includes using a detachment system having an electrical circuit partially supported on the delivery device to decouple the expandable body from a distal end of the delivery device by electrolysis. In some embodiment a portion of the delivery device, including a portion of the proximal neck, undergoes electrolysis prior to detachment. In some embodiments, the portion of the proximal neck that undergoes electrolysis is ring shaped.

Methods for manufacturing a device or system for filling a biological space of a patient are also disclosed herein. One method includes manufacturing a single-lobed metallic expandable body having a distal region, a proximal region generally opposite the distal region, and an optional intermediate region transitioning from the distal region to the proximal region. A center or first axis extends between the proximal neck and the distal neck of the single lobed metallic expandable body. A wall of the single-lobed metallic expandable body extends generally continuously from the proximal region through the intermediate region, and to the proximal region to define an exterior surface of the expandable body and an interior surface of the expandable body. The interior surface defines an interior volume of the expandable body. The method also includes welding or joining all or a portion of one or two neck segments to the expandable body. The neck segments may be joined during an electroforming process to form the expandable body.

The methods also include manufacturing a delivery device having a longitudinally extending body that includes a proximal end and a distal end generally opposite the proximal end, operably coupling the distal end of the delivery device to the expandable body, including to the proximal neck or proximal region of the expandable body. The methods of manufacturing also include forming the wall of the expandable body into a pleated configuration. The pleated configuration includes a plurality of pleats folded over in a clockwise direction relative to the first or center axis, or alternately, a counter-clockwise direction relative to the first or center axis to form a folded-over region of the expandable body.

Another method of manufacturing a system for filling a biological space of a patient includes coupling a stainless steel ring to a proximal end of a sacrificial mandrel, depositing a metal layer over the sacrificial mandrel and at least over a portion of the stainless steel ring or tube, and eliminating the sacrificial mandrel to leave behind the metal layer in the form of a hollow body having the shape of the sacrificial mandrel, which can be fashioned into an expandable body. This embodiment of a method of manufacturing includes a method wherein the metal is deposited by electroforming, and a method wherein the metal deposited is gold. The stainless steel ring is therefore joined to and extending from a proximal region of the hollow body, forming a neck, including forming a proximal neck. The stainless steel ring may also be added by welding a separate segment to the neck or main body of the expandable body, the main body defined as comprising the proximal region and the distal region, and optionally the intermediate region. In certain embodiments, a stainless steel ring or tube is coupled to a delivery device, and configured wherein the ring or tube can be severed by electrolysis.

The method can include applying an electrical insulation material to an exterior surface and an interior surface of the expandable body and an exterior surface or interior surface of the stainless steel ring and creating an anode by rendering a portion of the exterior surface of the region of the neck composed of the stainless steel ring free of the electrical insulation material. The method further includes coupling at least a portion of the stainless steel ring to a distal end of a delivery device and electrically coupling an electrolysis system to the stainless steel ring to form a potential anode through a conduction path that travels through the delivery device. The method also includes affixing one or more end caps or nose cones to the necks of the expandable body, or to the distal end of the delivery catheter. The end caps or nose cones may comprise a polymeric material. In addition, a polymer sheath or coating may be attached to the expandable body and end caps or nose cones, such that the polymer sheath encapsulates the expandable body when in a folded, wrapped, or compressed delivery configuration.

In the various embodiments of the devices, systems and methods described above, the walls of the expandable body can include at least one metal layer having a thickness ranging between approximately 5 and 50 µm. In one example, the metal layer of the proximal, intermediate, and distal regions may include gold or platinum. The wall of the expandable body may also include an inner layer of a non-metallic coating extending over an inner surface of the metal layer and/or an outer layer of a non-metallic coating extending over an outer surface of the metal layer. The non-metallic coating may be an electrical insulation material, including, for example, Parylene. For example, an inner layer and outer layer of Parylene may coat the gold or platinum metal layer.

A surface of the metal layer may include rounded, pebbled, or granular surface structures that have a surface height of approximately 0.1 µm to approximately 10 µm. The outer surface of the metal layer may include generally tubular protrusions. In one embodiment, some of the generally tubular protrusions are branched. In another embodiment, some are joined on both ends to the metal layer to form loops.

The metal layer of the expandable body may be produced by electroforming on a mandrel, wherein optionally all or a portion of the mandrel is sacrificial. Portions of the mandrel may be formed of sacrificial aluminum components, as well as non-sacrificial components made of other metals, such as stainless steel, zinc, magnesium, or copper. The mandrel may have a surface finish of no more than approximately 0.1 µm $R_t$ (i.e. maximum peak-to-valley height).

Alternately, the mandrel may have a pleated outer surface that generally replicates a pleated configuration of the expandable body that is intermediate in shape between the deliverable configuration and the expanded configuration. A non-sacrificial stainless steel mandrel component may include a surface layer of gold or platinum that extends over at least a portion of one of an inner surface or an outer surface of the non-sacrificial mandrel component.

In various embodiments, the expandable body may undergo one or more annealing processes. The expandable body may be annealed before and after being folded into the deliverable configuration. Further, the expandable body may undergo an annealing process while comprising a non-metallic coating.

The wall of the expandable body may include pores that may extend completely through the thickness of the wall from the interior to the exterior surface. The pores range from 0.1 to 500 μm in diameter. As such, the expandable body may be inflated by a fluid supply device in fluid communication with the interior volume of the expandable body via the delivery device. The fluid supply device is configured to provide a supply fluid flow rate to the interior volume that exceeds an escape fluid flow rate from a plurality of pores at a fluid delivery pressure. In one embodiment, at the time of expansion of the expandable body the pores are filled with a material that is biodegradable or bioerodible, such that the pores open some period of time after expansion in vivo.

When in the delivery or deliverable configuration, the folded-over region of the expandable body may define a wire-receiving channel. In one embodiment, no portion of the delivery device or delivery catheter is found within the folded-over region of the expandable body. In another embodiment, a portion of the delivery device or delivery catheter is found within the folded-over region of the expandable body. Each pleat includes a ridge line extending proximal-distal and radially away from the center axis and each pleat is separated from any immediately adjacent pleat by an interposed trough extending proximal-distal, such that the pleated configuration has an alternating ridge-trough arrangement. When folded, each pleat is folded over an immediately adjacent pleat in a clockwise direction relative to the first or center axis, or in a counter-clockwise direction relative to the first or center axis. In one embodiment, no portion of the delivery device is found within the folded-over region of the expandable body. In another embodiment, the folded-over region of the expandable body may define a channel for receiving a guide wire. In another embodiment, a portion of the delivery device or delivery catheter is found within the folded-over region of the expandable body.

In various embodiments, the expandable body is inflated or expanded to achieve the expanded configuration. The expandable body is inflated or expanded via the delivery of a fluid medium to the interior volume of the expandable body. The fluid medium typically includes a liquid or gas. In various embodiments, during expansion, pressure within the expandable body is 5 atmospheres (atm) or less. Other suitable pressures include 3 atm or less, 2 atm or less, and 1 atm or less.

During expansion or inflation, the pleated configuration and the plurality of pleats of the expandable body that are present in the deliverable configuration are substantially eliminated. When expanded, the expandable body possesses sufficient strength to maintain itself in the expanded configuration within a biological space after detachment or separation from the delivery device.

The metallic expandable body and the delivery device are configured to allow the interior volume of the expandable body to, optionally, be at least partially filled with a solid or semi-solid support structure. The support structures include metallic or polymeric coils or wires, metallic or polymeric expansile structures, beads, balls, microspheres, a bioresorbable or bioerodible material, or combinations thereof. In one embodiment, solid or semi-solid material or members not derived from the patient are not required in the interior volume of the expandable body to cause the expandable body to assume or maintain the expanded configuration after separation of the expandable body and the delivery device.

When in the expanded configuration, the expandable body may have an overall shape that is spherical, spheroid, or ellipsoid. In various embodiments, an expandable body smaller than the biological space to be filled is selected. In various embodiments, when expanded, the expandable body has a maximal width, length, or diameter parallel to the second axis that is greater than the width of the mouth or opening into the biological space, such that the expanded form of the expandable body may reduce the flow of biological fluid into the biological space, or seal the mouth or opening into the biological space. For example, the expandable body may be used to seal a saccular aneurysm or at least reduce the flow of blood into a saccular aneurysm. To maintain contact with the mouth or opening of the aneurysm, the expandable body may be deployed in combination with a coiled wire that fills at least a portion of the remaining void in the biological space and applies force to the surface of the expandable body to maintain its position within the space and maintain continued contact with the mouth or opening of the space. In certain embodiments the coiled wire is a form of an expandable body, such as when the coiled wire comprises nitinol or another self-expanding material. In particular, the coiled wire (or "coil" or "accessory coil") is deployed within the void of an aneurysm between the expandable body and the wall of the aneurysm opposite the mouth or opening from the parent vessel and into the aneurysm lumen or sac. As used herein, a parent vessel is a vessel from which the aneurysm has formed. The accessory coil contacts both the wall of the aneurysm and the expandable body and applies a force to press or hold the expandable body against the neck or mouth of the aneurysm. The size of the expandable body is selected such that the expandable body is larger or wider than the neck or mouth of the aneurysm and cannot be pushed out of the aneurysm and into the parent vessel in a manner that would occlude more than 50% of the lumen cross-sectional area of the parent vessel. In one embodiment, the accessory coil can be made with methods and materials that impart a self-expanding quality to the coil. For example, the accessory coil may be a spherically-shaped coil comprising nitinol. In other embodiments, the accessory coil may be of various other shapes, including but not limited to spherical, spheroid, ellipsoid, or cylindrical configurations. In other embodiments the accessory coil may be coated with a polymeric material, such as PTFE, to cushion the coil and increase the lubricity of the coil in a manner that may reduce trauma to the wall of the aneurysm and may reduce the force required to push the coil through and out of a coil delivery catheter.

In various aspects, the accessory coil may have a diameter in a range between approximately 0.002 and 0.012 inches. Preferably, the accessory coil has a diameter between approximately 0.004 and 0.008 inches. Similarly, the polymer coating on the accessory coil may have a thickness in a range between approximately 0.001 and 0.003 inches. Preferably, the polymer coating has a thickness between approximately 0.0015 and 0.002 inches. The accessory coil may be delivered to the biological space, such as the lumen of the aneurysm, using a delivery catheter that may be placed through the guidewire lumen of the delivery catheter that is coupled to the expandable body. This coil delivery catheter may have an outer diameter in a range between approximately 0.014 and 0.022 inches, and preferably, an outer diameter between approximately 0.016 and 0.020 inches. Similarly, the coil delivery catheter may have an inner diameter in a range between approximately 0.008 and 0.016 inches, and preferably, an inner diameter between approximately 0.010 and 0.014 inches.

The expandable body may include a proximal and distal neck that each extends away from the expandable body. In one embodiment, both the expandable body and the neck are formed entirely from a malleable metal such as gold or platinum. In another embodiment, at least a portion of at least one neck comprises stainless steel that may be subsequently severed via electrolysis, including a stainless steel ring.

The delivery device includes a longitudinally extending body, which may have the form and function of a catheter, and may have a hydrophilic or lubricious coating. This coating may also be present on the expandable body. The distal segment of the longitudinally extending body is operably coupled to the expandable body, including to the proximal neck and the proximal region. The distal segment of the longitudinally extending body may also be operably coupled to the distal neck. For example, the distal end of the longitudinally extending body may be received in the neck at the proximal region of the expandable body, such that the outer surface of the distal segment of the longitudinally extending body is in contact with an inner surface of the proximal neck of the expandable body. In another example, the distal segment of the longitudinally extending body terminates near a proximal edge of a ring-shaped region of exposed metal in the neck of the expandable body. In another example, the distal segment of the longitudinally extending body extends through the expandable body and is in contact with an inner surface of the distal neck of the expandable body. In another example, the distal segment of the longitudinally extending body extends through the expandable body and through the distal neck of the expandable body.

The various systems and methods may include or use an electrolysis system configured to deliver an electrical current to the expandable body, including to an exposed metal surface on a neck, including the proximal neck. In various embodiments the electrical current comprises a constant current, a constant voltage, or a square-wave voltage. When the longitudinally extending body or delivery catheter is coupled to the expandable body, the delivery of the electrical current can result in separation or detachment of the delivery catheter from the expandable body. The separation can occur in a circumferential or ring-shaped non-coated or exposed metal surface region of the neck formed of stainless steel or gold and exposed by, for example, laser etching. During electrolysis, the circumferential non-coated or exposed metal surface region of the neck acts as an anode. When delivering a square-wave voltage, the voltage of the anode is modulated based on a comparison between the voltage of the anode and the voltage of a reference electrode supported on the delivery device or residing external to the delivery device, such as with a needle or electrode pad residing on or in the patient, or an electrode residing on the body of the delivery catheter.

One method of manufacturing the expandable body includes: a) providing a sacrificial mandrel comprising a pleated outer surface; b) depositing a metal layer over the sacrificial mandrel; c) removing the sacrificial mandrel and leaving behind the metal layer in the form of a hollow pleated body; d) coating with a non-metallic material an interior surface and/or an exterior surface of metal layer of the hollow pleated body; and e) folding the hollow pleated body to further increase the extent to which the hollow pleated body is pleated, the folding comprising folding over a plurality of pleats in a clockwise direction relative to a center axis of the hollow pleated body, or a counter-clockwise direction relative to the center axis.

The portion of the electrolysis system supported on the delivery device includes one or more conductors embedded on or in the wall of the delivery catheter that act as electrical conductors for the electrical system. These conductors may also simultaneously provide structural reinforcement for the wall of the delivery catheter. The conductors are wires, cables, or other electrical conductors that may be routed on or through the catheter or catheter wall in a variety of configurations including a spiral, braided, or straight configuration. One of the conductors is in electrical communication with a portion of the expandable body that can function as an anode, such as at or near a circumferential region of the neck having an exposed metal surface, while another of the conductors is in electrical communication with a structure supported on the delivery device that can function as a cathode, such as a platinum metal electrode or ring. In one embodiment, one of the conductors is in electrical communication with a structure supported on the delivery device that can function as a reference electrode.

The present application is related to PCT International Patent Application No. PCT/US12/47072, which was filed on Jul. 17, 2012, entitled "Expandable Body Device and Method of Use"; PCT International Patent Application No. PCT/US12/21620, which was filed on Jan. 17, 2012, entitled "Detachable Metal Balloon Delivery Device and Method"; PCT International Patent Application No. PCT/US12/21621, which was filed on Jan. 17, 2012, entitled "Ballstent Device and Methods of Use," PCT International Patent Application No. PCT/US12/00030, which was filed on Jan. 17, 2012, entitled "Blockstent Device and Methods of Use," and U.S. Provisional Application No. 61/433,305 ("the '305 application) entitled "Detachable Metal Balloon Delivery Device and Method," filed on Jan. 17, 2011. Each of the above-listed patent applications is commonly-owned, was commonly owned by the same inventive entity at the time of filing, and is incorporated herein by reference in its entirety.

DESCRIPTION OF FIGURES

FIG. 2A is a perspective view of an embodiment of an expandable body.

FIGS. 2B-C are a partial interior view and a cross-sectional view, respectively, of an embodiment of the expandable body of FIG. 2A.

FIGS. 2D-E are a perspective view and a cross-sectional view, respectively, of an embodiment of an expandable body.

FIG. 2F is a plan view of an embodiment of an expandable body.

FIG. 2G is a partial interior view of an embodiment of an expandable body of FIG. 2F.

FIGS. 2H-K are close-up cross-sectional views of an embodiment of the expandable body of FIG. 2F.

FIGS. 11A-F are views of an embodiment of the medical device illustrating a sequence of steps associated with the delivery of the expandable body to an aneurysm and deployment.

FIGS. 15A-F are views of an embodiment of the medical device illustrating a sequence of steps associated with the delivery of the expandable body to an aneurysm and deployment.

FIG. 16E is a longitudinal cross-section of the expandable body supported on a distal end of a delivery catheter, wherein the expandable body is spherical and may be employed as an embodiment of a ballstent.

FIG. 16F is a partial cross-section through the wall of the ballstent of FIG. 16E.

FIG. 16G is a longitudinal cross-section of the expandable body supported on a distal end of a delivery catheter, wherein the expandable body is cylindrical with hemispherical ends and may be employed as an embodiment of a ballstent or blockstent.

FIG. 16H is a partial cross-section through the wall of the expandable body of FIG. 16G.

FIG. 16I is a longitudinal cross-section of the expandable body supported on a distal end of a delivery catheter, wherein the expandable body is spherical and may be employed as an embodiment of a ballstent.

FIG. 16J is a partial cross-section through the wall of the ballstent of FIG. 16I.

FIG. 16K is a longitudinal cross-section of the expandable body supported on a distal end of a delivery catheter, wherein the expandable body is cylindrical with hemispherical ends and may be employed as an embodiment of a ballstent or blockstent.

FIG. 16L is a partial cross-section through the wall of the expandable body of FIG. 16K.

FIGS. 20A-B are transverse cross-sections of embodiments of the delivery catheter of the medical device.

FIG. 21A is a plan view of an embodiment of the medical device with a lumen configured to accept a guide catheter, rather than a guide wire.

FIG. 21B is a transverse cross section of the device as taken along section line A-A in FIG. 21A.

FIG. 24A illustrates various dimensions for an expandable body having a cylindrical intermediate portion and hemispherical ends.

FIGS. 24B-C illustrate various dimensions for a neck region of an expandable body.

FIGS. 25A-C depict a sequence for electroforming an expandable body on a mandrel.

FIG. 26 depicts an embodiment of a mandrel for electroforming a metal expandable body.

FIG. 27 depicts another embodiment of a mandrel for electroforming a metal expandable body.

FIG. 28 is a partial cross-section of metal expandable body produced by electroforming.

FIGS. 29A-D are photographs of various embodiments of mandrel models and metal expandable bodies formed thereon.

FIG. 29E shows an external surface of a metal expandable body according to one embodiment.

FIGS. 30C-F are various plan views and cross-sections depicting a region of exposed metal surface wherein the metal expanded body is detached from the delivery catheter by electrolysis.

FIGS. 34-36 are flowcharts illustrating the steps for manufacturing the expandable body, a delivery catheter, and a medical kit containing a medical device, respectively.

FIG. 42 depicts tissue samples collected during clinical testing of an embodiment of the expandable body.

DETAILED DESCRIPTION

Figure 1A:
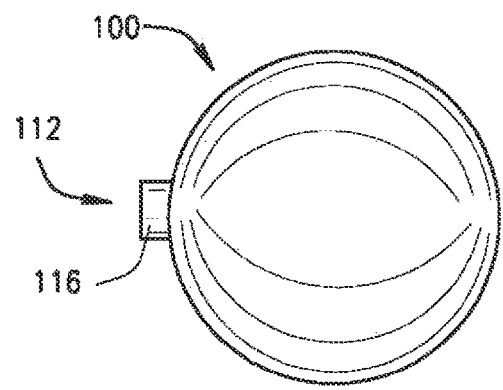
FIGS. 1A-D are planar views of embodiments of an expandable body.

The present disclosure relates to a medical device including a delivery device and an expandable structure or expandable body. The expandable body is a thin-walled, hollow metal structure that can be compressed and then expanded into a semi-rigid form that can remain in the body for an extended period. The terms "expandable body", "expanded body", "expanded expandable body", "expandable structure", "expandable balloon", "ballstent", and "blockstent" are all used to describe the hollow metal structure described herein for use in filling a biological space. The term "expanded" is generally used to describe an expandable body that is expanded, and not in the deliverable or delivery configuration. Particular embodiments of the expandable body may be referred to as a ballstent or blockstent according to structure and/or use of the body. In one example, the term "ballstent" is used at times to describe a generally rounded form of the expandable body and one that can be used for the treatment of saccular cerebral aneurysms. In another example, the term "blockstent" can be used at times to describe a generally oblong or cylindrical form the expandable body, and one that can be used to fill a portion of the lumen of an artery or vein segment, or a portion of the lumen of a segment of another form of biological conduit. Specifically, the expandable body, when acting as a ballstent, is configured for use in filling and occluding saccular aneurysms of blood vessels, especially saccular cerebral aneurysms and ruptured aneurysms. The expandable body may also be configured as a blockstent for use in blocking or occluding the lumen of segments of arteries, veins, and other biological conduits.

The delivery device is configured to deliver a ballstent to an aneurysm and to provide a pathway, through a hollow cylindrical member or lumen of a cylindrical member, for a fluid medium to move into the void of the ballstent expandable body, in order to expand it and fill at least a portion of the volume of the aneurysm sac. The delivery device can also be configured to deliver a second expandable body or other structures, such as a coiled wire or nitinol coiled wire, to an aneurysm by providing a pathway through a hollow cylindrical member or lumen of a cylindrical member for the coiled wire to pass from outside the patient into the lumen or cavity of the aneurysm. The delivery catheter also can be configured to deliver an expandable body in the form of a blockstent to a blood vessel segment and to provide a pathway, through a cylindrical member or lumen of a cylindrical member, for fluid to move into the central void of the blockstent expandable body, in order to expand it and fill at least a portion of the lumen of the blood vessel segment. Expanding the expandable body, as used herein, can refer to partial or complete expansion of the body using a fluid (i.e., a liquid, gas, gel, or combination thereof) or a solid (i.e., a solid body, a lattice, granular particles, etc., or a combination thereof).

In certain embodiments, the expandable body includes two necks positioned at opposite ends of the expandable body. For example, one neck may be located at a proximal end of the expandable body and another neck may be positioned at the distal end of the expandable body. Optionally, at least one of the necks may be joined to a ring (such as through a weld), such as a stainless steel ring, that can be severed by electrolysis after placing the expandable body in a biological space. In this instance, the main body of the expandable body may comprise a material that is less susceptible to electrolysis or galvanic corrosion, such as noble metals including but not limited to gold, while a neck may comprise a material of less relative nobility that is more susceptible to electrolysis or galvanic corrosion, such as stainless steel. Alternatively, the body and a neck may comprise materials that are more similar in their susceptibility to electrolysis or galvanic corrosion and the body and optionally a portion of the neck may be coated with a material that functions as an electrical insulator to limit the electrolysis or galvanic corrosion to the neck or the coated portion of the neck during electrolysis. Such electrical insulator could include Parylene. Alternatively, a neck may comprise a material of less relative nobility that is more susceptible to electrolysis or galvanic corrosion, such as stainless steel, and a portion of this material more susceptible to electrolysis or galvanic corrosion may be coated with additional material that is less susceptible to electrolysis or galvanic corrosion, such as noble metals including but not limited to gold, such that electrolysis will be concentrated in the portion of the neck where the material of less relative nobility that is more susceptible to electrolysis or galvanic corrosion, such as stainless steel, is exposed or uncoated.

Each of the necks may include a tip or nose cone to improve the dynamic profile of the device that reduces resistance during the advancement of the device in a forward or backward direction within an artery, vein, or other biological conduit. In this manner the tip or nose cone could reduce the risk of injury to the wall of the artery, vein, or other biological conduit. The tip or nose cone may comprise polymeric, metallic, or other materials, including materials that are biodegradable or bioerodible. The presence of a tip or nose cone on the expandable body can reduce friction, reduce trauma caused by a proximal or distal end of the body, and improve trackability of the device as it is positioned and repositioned. This is especially relevant when placing the expandable body within an aneurysm, as the dome of an aneurysm is fragile and susceptible to wall rupture when probed with a sharp or fine-pointed device. The tip or nose cone may also provide an attachment point for a polymer wrap that surrounds the folded, wrapped, or compressed expandable body as the body is positioned within the patient. The polymer wrap further increases the trackability of the body and reduces friction as the expandable body is delivered through the vascular system. The tip or nosecone may also be placed on the distal portion of a delivery catheter where it can serve a similar purpose.

The expandable body can be formed by depositing a metal layer over a mandrel using an electroforming process. During the electroforming process, a metal ring or structure may be incorporated into the metal layer to create a neck for the expandable body. This ring or structure may comprise stainless steel, zinc, copper or gold, or other material susceptible to galvanic corrosion or electrothermal separation. The mandrel may be a sacrificial mandrel that can be eliminated from the expandable body after electroforming, to leave a hollow metallic structure that is, or can be formed into, an expandable body.

The hollow metallic expandable body may undergo one or more annealing processes. The annealing process may occur before or after a neck segment that includes stainless steel is welded or otherwise joined to the expandable body. The interior and exterior surfaces of the metallic expandable body may be coated with a metallic or non-metallic material that is an electrically insulating material, including polymers such as Parylene. The interior and exterior surfaces of the metallic expandable body may be coated or partially coated with a metallic or non-metallic material that is less susceptible to electrolysis or galvanic corrosion, such as noble metals including but not limited to gold. The metallic expandable body may be annealed before and after the metallic expandable body has been caused to assume a deliverable (i.e., collapsed or non-expanded) folded or pleated configuration. The metallic body may be annealed before or after a coating is applied, including coatings of an electrically insulating material.

The metallic expandable body can be folded into a deliverable configuration for introduction into an aneurysm, an artery or vein segment, or a segment of another form of biological conduit. When folded into the deliverable configuration, the metallic expandable body can be formed into a pleated configuration, having a number of pleats, which may be wrapped around a central axis of the metallic expandable body.

When used to fill an aneurysm, the catheter delivery device and an attached ballstent expandable body are advanced into the lumen or cavity of the aneurysm sac. Similarly, when used to occlude a blood vessel or other biological conduit, the delivery device and an attached blockstent expandable body are advanced into the lumen or void of the vessel or biological conduit. The delivery device can also deliver a fluid, a solid, or a combination thereof, to the interior void of the expandable body to expand the body in the lumen of the aneurysm sac or blood vessel segment, and to help maintain the expansion of the expanded body. The expanded body may be detached from the delivery device by one or more of a variety of arrangements and methods including mechanical, electrolytic, electrothermal, chemical, hydraulic, or sonic devices, systems, arrangements and methods.

The medical device can be used as part of various systems, methods, and medical kits. These systems, methods, and medical kits can be used to treat saccular arterial aneurysms, such as a saccular cerebral aneurysm, and to occlude a segment of an artery or vein, or other biological conduit, such as a ductus arteriosus, bronchus, pancreatic duct, bile duct, ureter, or fallopian tube. These systems, methods, and medical kits can be used to treat a variety of medical conditions.

The Expandable Body

In various embodiments, an expandable body configured for the occlusion of saccular cerebral aneurysms is generally referred to as a ballstent, and can have many shapes including a spherical, spheroid, ellipsoid, or cardioid shape. In various other embodiments, the expandable body may be configured as a blockstent for the occlusion of the lumen of biological conduits, including artery and vein segments, and can have many shapes including an oblong or generally cylindrical shape, including a cylindrical shape with both flat and rounded ends.

Generally, spherical ballstents 100 and 150 are shown in FIGS. 1A-D, and 2A-4B. In particular, a spherical ballstent 100 is shown in an expanded state, in FIGS. 1A-4A. The ballstent 100 and 150 has a proximal neck 116, protruding away from the ballstent, that defines an opening 112 for the passage of fluids, liquids, gases, gels, or solids into or though the void of the ballstent. In the ballstent 100 shown in FIG. 1B, the neck 116 protrudes into the void to define the opening 112 for the passage of fluids, liquids, gases, gels, or solids into the ballstent 100.

Figure 1B:
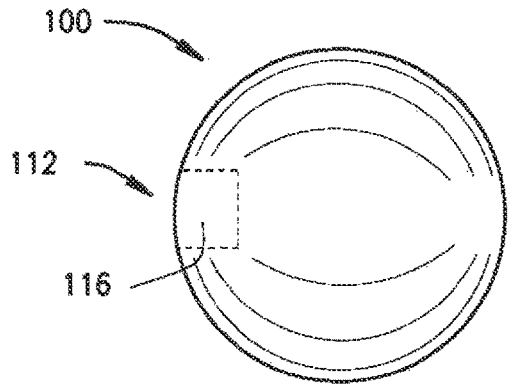
Figure 1C:
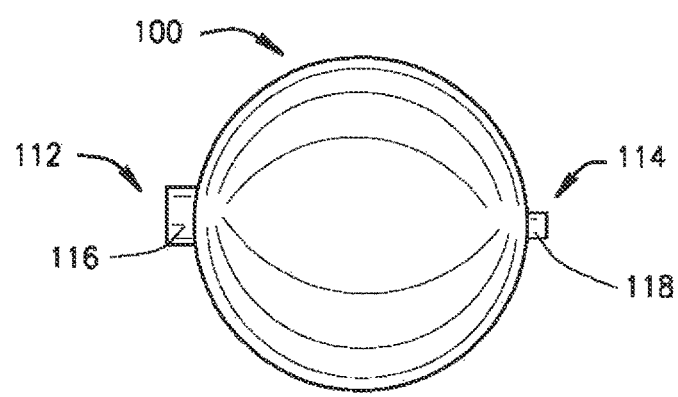
Figure 1D:
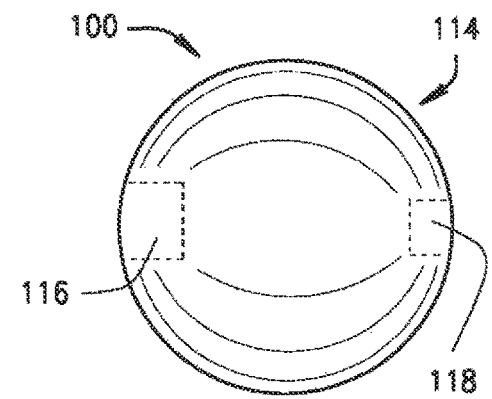

Another spherical embodiment of the ballstent 100 is shown in FIG. 1C in an expanded state. This embodiment includes a proximal neck 116 that defines an opening 112 for the passage of fluids, liquids, gases, gels, or solids, into or through the ballstent. The ballstent 100 also includes a distal neck 118, protruding away from the ballstent, that defines an opening 114 for the passage of a guide wire 302 or a coil 162, as shown in FIGS. 2A-B and 3A-B, through the ballstent or from the interior of the ballstent to the exterior of the ballstent, including distal to the distal neck. A similar spherical embodiment of the ballstent 100 is shown in FIG. 1D in an expanded state. This embodiment includes the proximal neck 116 that defines the opening 112 and the distal neck 118 that defines the opening 114, both which protrude into the interior of the ballstent 100, for the passage of fluids, liquids, gases, gels, or solids, including a guide wire 302 or a coil 162, into or through the interior of the ballstent.

Ultimately, the metallic expandable bodies disclosed herein may have a variety of configurations and any of the configurations may be employed for a variety of uses including occluding aneurysms, including saccular aneurysms, and segments of biological conduits, including arteries and veins. Generally speaking, some configurations may lend themselves more readily or effectively to one application or another. For example, the spherical expandable bodies 100 of FIGS. 1A-D may be particularly advantageous when acting as a ballstent for the filling of the lumen (or void or cavity) of a saccular aneurysm. Similarly, as explained further below, the spherical expandable bodies 100 and 150 of FIGS. 1A-D and 2A-4B and the expandable bodies 140 and 170A-F of FIGS. 6A-D, 8A-S, 16G, and 16K, for example, may be used with a coil or accessory coil 162 to fill at least a portion of the lumen (or void or cavity) of a saccular aneurysm and reduce or obstruct the flow of blood through opening from the parent vessel to the lumen of the aneurysm, or reduce or obstruct the flow of blood through the neck of a saccular aneurysm into the body of the aneurysm lumen (or void, or cavity). In various embodiments, the coil or accessory coil 162 comprises a self-expanding material, such as nitinol wire.

In some embodiments, as shown in FIGS. 8A-G and 8U, the expandable bodies 170A-G can be characterized to include a proximal region 174A-G, an intermediate region 173A-G, and a distal region 172A-G, wherein the proximal region and distal region are generally opposite each other. For each body 170A-G, proximal region 174A-G, the intermediate region 173A-G, and the distal region 172A-G form the unitary construction of the expandable body. For this characterization, the proximal region, the intermediate region, and the distal region together form a "main body" of the expandable body, which excludes the necks. The expandable bodies 170A-G may further be defined by a first axis 176 and a second axis 178 transverse to the first axis. In one aspect, the first axis 176 extends between the necks 116 and 118.

In one embodiment, the shape of the intermediate region 173A-G of the expandable bodies 170A-G may be defined by the rotation, about the first axis 176, of a variable radius arc formed along the first axis, where the maximum radius for the variable arc is equal to either the maximum radius 181 of the distal region 172 or the maximum radius 180 of the proximal region 174, as measured along the second axis 178. For some embodiments, the expanded expandable body 170A-G has a total length 179 along the first axis 176 that is less than or equal to the maximum diameter 182 of the expanded expandable body along the second axis 178.

In some embodiments without an intermediate region, as shown in FIGS. 8A-G and 8U, the expandable bodies 170A-G can be characterized to include a proximal region 174 and a distal region 172, wherein the proximal region and distal region are generally opposite each other. For each body 170A-G, proximal region 174 and the distal region 172 form the unitary construction of the expandable body. For this characterization, the proximal region and the distal region together form a "main body" of the expandable body, which excludes the necks. The expandable bodies 170A-G may also be further be defined by a first axis 176 and a second axis 178 transverse to the first axis. In one aspect, the first axis 176 extends between the necks 116 and 118. For some embodiments, the expanded expandable body 170A-G has a total length 179 along the first axis 176 that is greater than or equal to the maximum diameter 182 of the expanded expandable body along the second axis 178.

In various other embodiments, the expandable bodies may be defined and described by the proximal region 174 and the distal region 172, where each region is generally a hemispheroid. The hemispheroid formed by each region 172 and 174 is further defined by a semi-major axis and semi-minor axis that may be parallel with the first axis 176 or the second axis 178, depending upon the lengths of each axis. In various embodiments, the hemispheroid of the proximal region 174 has a semi-major axis and semi-minor axis different from that of the distal region 172. In other embodiments, the hemispheroid of the proximal region 174 has a semi-major axis and semi-minor axis the same as that in the distal region 176. Similarly, for each of the distal and proximal regions 172 and 174, respectively, the semi-major and semi-minor axis may differ from one another or be identical so that the corresponding region may have a generally shape of an oblate hemispheroid, a prolate hemispheroid, or a hemisphere. As shown, the expandable bodies 170A-G may also be fabricated in a variety of other configurations that have generally spheroid or ellipsoid shapes. The expandable bodies 170A-G may also include a proximal neck 116 and a distal neck 118.

In some embodiments, the expanded expandable bodies 170A-G have a length 179 from the proximal neck 116 to the distal neck 118 of approximately 4 mm to approximately 16 mm or larger and a maximum diameter 182 of approximately 4 mm to approximately 16 mm or larger. As shown in FIGS. 8A-F and 8U, the maximum radius length for the proximal regions 174A-G and distal regions 172A-G are equal, such that the expandable bodies 170A-G have a generally circular cross-section when viewed in cross-section along the first axis 176. As shown in FIGS. 8A-E and 8U, the radius length at any equivalent location for the proximal regions 174A-G and distal regions 172A-G may not be equal, such that the expandable bodies 170A-G may not have a generally circular cross-section when viewed in cross-section along the second axis 176. In other embodiments, as shown in FIG. 8F, the radius length at any equivalent location for the proximal regions 174A-G and distal regions 172A-G may be equal, such that the expandable bodies 170A-G may have a generally circular cross-section when viewed in cross-section along the second axis 176.

In one aspect, the different configurations of the expandable bodies 170A-G may be obtained by varying the maximum length ("height") along the first axis 176 for the proximal region 174A-G and the distal region 172A-G, independently. For example as shown in FIGS. 8A, C, and E, the height 183 for the proximal region 174A may be smaller than the height 184 for the distal region 172A. In other examples as shown in FIGS. 8B, D, and F, the height 183 for the proximal region 174A may be equal to the height 184 for the distal region 172A. In other examples, the height 183 for the proximal region 174A may be larger than the height 184 for the distal region 172A. While both expandable bodies 170A and 170B have the same maximum diameter, the difference in the heights for the proximal and distal regions of each expandable body results in different overall shapes for the expandable body. As shown, the expandable body 170A is generally heart-shaped, while the expandable body 170B has a spheroid shape.

In other examples shown in FIGS. 8A-F and 8U, the heights 183 and 184 of the proximal portion 174A-F and distal portion 173A-F, respectively, may be varied independently to produce a wide variety of configurations of the expandable bodies 170A-G. The height 183 for the proximal region 174C may be approximately 2 mm, while the height for the distal region 172C is approximately 4 mm. Similarly, the height 183 for the proximal region 174D may be approximately 3 mm, while the height for the distal region 172D is also approximately 3 mm. For the expandable body 170E, the height 183 for the proximal region 174E may be approximately 2 mm, while the height 184 for the distal region 172E is approximately 3.5 mm, while for the expandable body 170F, the height 183 for the proximal region 174F may be approximately 3 mm, while the height 184 for the distal region 172F is approximately 4 mm. As shown, the expandable bodies 170A-G may have a number of configurations that may be generally spheroid, generally spherical, or generally heart-shaped.

Figure 16A:
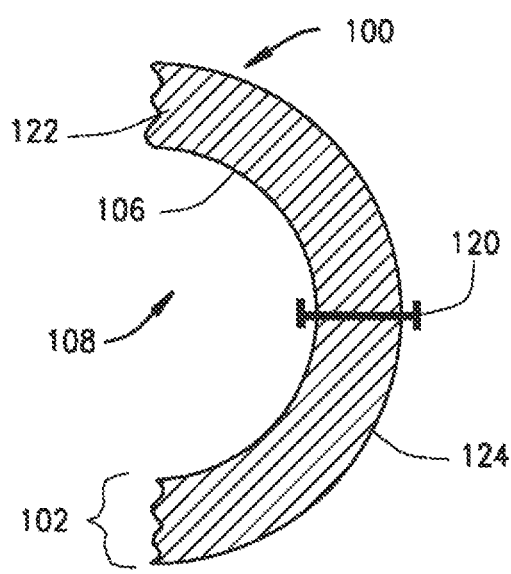
FIGS. 16A-D are hemispherical cross-sectional views taken along a diameter of embodiments of the expandable body.

The metallic expandable body, such as the expanded spherical ballstents 100 and 150 of FIGS. 1A-D and 2A-4B and the expanded expandable bodies 140 and 170A-G of FIGS. 8A-U, 16G, and 16K, may have a wall 102 composed of a single continuous layer 122, as shown in FIG. 16A. The wall 102 includes a material, preferably a metal that is biocompatible and ductile, that can be formed into a thin wall, and can assume a variety of shapes after expansion. By way of example and not limitation, the metal can be selected from the group consisting of gold, platinum, silver, nickel, titanium, vanadium, aluminum, tantalum, zirconium, chromium, silver, magnesium, niobium, scandium, cobalt, palladium, manganese, molybdenum, alloys thereof, and combinations thereof. Preferred metals include gold, platinum, and silver, alloys thereof, and combinations thereof. Expandable bodies can also be made from alternative materials that can be formed into thin-walled structures that are sufficiently rigid or semi-rigid to tolerate compression and expansion, and can maintain an expanded state in vivo. Alternative materials include polymers or plastics that are reinforced with metal coils or braids, and other materials with similar properties. The materials forming the wall 102 and the thickness of the wall are selected such that the expandable body 100, 140, 150, or 170A-G has sufficient rigidity to remain in an expanded state in vivo under typical physiologic conditions after expansion and separation from the delivery catheter, both when the pressure inside and outside the central void or space 108 is the same or similar and when the pressure outside is greater than the pressure inside.

Further, it is desirable that the materials used to form and support the expandable body 100, 140, 150, or 170A-G have sufficiently mechanical properties of ductility, malleability, and plasticity to be compressed or folded without tearing and later expanded without rupturing. In general, ductility is a measure of a material's ability to be deformed without breaking, while the malleability of the material determines the ease of deforming without breaking when the metal is subjected to pressure or forces. The ductility and malleability of a material factor into the plasticity of the material, which generally refers to a property of the material that permits it to undergo a permanent change in shape without rupture or breakage. As such, the expandable bodies may be composed of any biocompatible materials having sufficient ductility, malleability, and plasticity to undergo one or more compressions, folding processes, and expansions.

The central layer 122 of the wall 102 has an interior surface 106 and exterior surface 124 that define a wall thickness 120. In particular, for FIGS. 16A and 16B, the distance between the interior surface 106 and the exterior surface 124 is the overall wall thickness 120 of the wall 102. Preferably, the central layer 122 of the wall 102 has a thickness 120 from about 3 μm to about 50 μm and is preferably, approximately 10 μm thick. The wall thickness 120 can be uniform. For example, the wall 102 may have a uniform thickness of 3 μm, 5 μm, 10 μm, 15 μm, 20 μm, 30 μm, 40 μm, or 50 μm. For example, the thickness 120 of the wall 102 may be selected such that the expandable body is strong enough to resist compression from blood pulsation but weak enough to yield and collapse during healing and involution of a treated saccular aneurysm or an occluded segment of artery or vein, or other form of biological conduit.

Figure 16B:
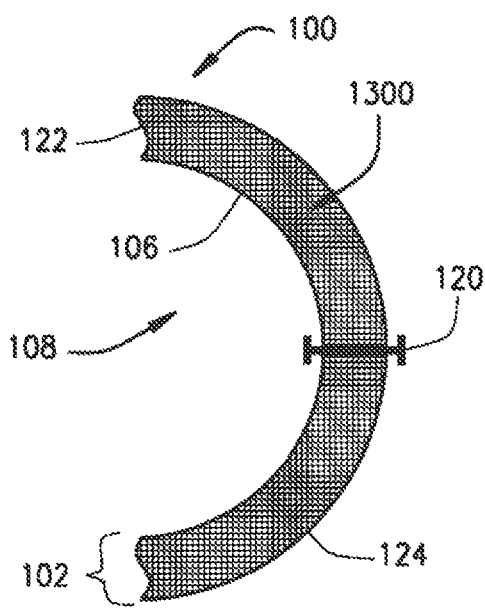

Alternatively, the thickness of the wall 102 at different locations may vary in thickness. Alternatively, the expandable body 100, 140, 150, or 170A-G may be composed of a single porous layer or wall 122, as shown in FIG. 16B, with pores or microperforations 1300 wherein at least some or all of the microperforations extend all the way from the internal surface 106 to the external surface 124. For this embodiment, the wall 102 may be of a uniform thickness or a varied thickness. During expansion of the ballstent 100 of this embodiment, the fluid medium may travel under pressure from the void or space 108, through the wall 102 and leave the ballstent at the exterior surface 124. For this embodiment, the microperforations 1300 may range from 1-500 μm in diameter. Another example range of microperforation diameters is 0.01 to 50 μm.

Figure 16C:
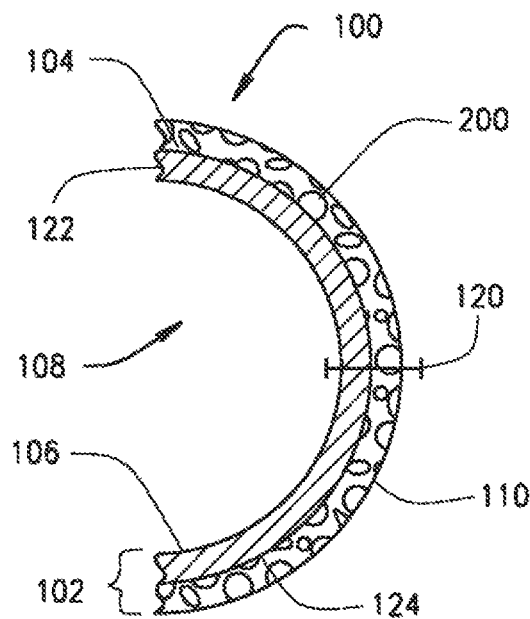
Figure 16D:
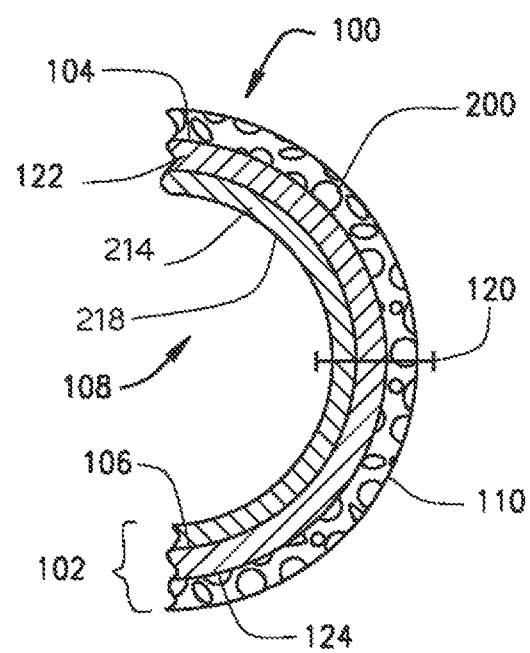

The expandable body 100, 140, 150, or 170A-G includes a central wall or layer 122, optionally with an exterior wall or layer 104, and optionally with an interior wall or layer 214, as shown in FIG. 16D. As mentioned, the construct of the central layer or wall 122 and the layers 104 and 214 can be uniform, porous, or combinations thereof. In one embodiment of the ballstent 100 used to treat a saccular aneurysm, the wall 102 includes a plurality of microperforations 1300 that extend completely through the thickness 120 of the wall 102.

In one construction, the central layer or wall 122 is continuous and formed of gold. Optionally, to this preferred construction, an exterior layer 104 formed of porous gold can be added. Optionally, an interior layer 214 formed of Parylene may be present. Optionally, an exterior layer 104 formed of Parylene may be present. In certain embodiments where electrolysis is used to separate the expanded expandable body 100, 140, 150, or 170A-G from the delivery catheter, certain portions of the ballstent or the expanded expandable body (such as the neck or body) are coated with an insulator or polymer, such as Parylene. In certain embodiments where electrolysis is used to separate the expanded expandable body 100, 140, 150, or 170A-G from the delivery catheter, certain portions of the ballstent or the expanded expandable body (such as the neck or body) are coated with a metal that is relatively resistant to electrolysis, such as gold or platinum. These portions include the external surface, the internal surface, or both the internal and external surfaces, while a portion of the neck or body remains uncoated or non-insulated. In this instance, the uncoated or non-insulated portion of the wall is electrolytically dissolved (i.e. corroded) by the passage of an electrical current from the exposed metal of the wall into the surrounding electrolyte (i.e. blood or serum). In certain embodiments, the uncoated or non-insulated portions of the wall are created by masking during the coating process. In other embodiments, the coating or insulation is removed from the uncoated or non-insulated portions of the wall or neck, as through etching or ablation, such as with laser etching or laser ablation.

One embodiment of a generally spherical ballstent 150 is shown in FIGS. 1A-4B. The generally spherical ballstent 100 or 150 includes the wall 102 that forms a spherical body when expanded. In one aspect, a distal region 152 of the wall 102 includes one or more annular portions 154A-B. The annular portions 154A-B have a radius of curvature greater than the remainder of the wall 102 such that the distal region presents a flatter surface than the remainder of the wall. The generally spherical ballstent 150 also includes a proximal neck 116 and a distal neck 118 protruding away from the distal region 152. In another embodiment, a distal neck can protrude into the interior void of the expanded expandable body.

In various embodiments, as shown in FIGS. 2B-C and 2E, a bridging catheter 160 extends through the proximal neck 116, through interior void of the expanded expandable body and into the distal neck 118. In one aspect, the bridging catheter 160 is an elongated tubular member component of the delivery catheter that provides structural support to the ballstent 150. In one embodiment, the bridging catheter 160 has an outer internal diameter in a range between approximately 0.5 and 2.0 mm and an inner diameter in a range between approximately 0.4 and 1.9 mm. In some embodiments, the bridging catheter is a component of the delivery catheter, or is operatively coupled to the delivery catheter.

In another aspect, the bridging catheter 160 provides a pathway to deliver a solid material, such as a guide wire 302 or a coil 162, as shown in FIGS. 2B-C, 2E, 2G, 2N-P, 8H, 8J-O, and 8R-S, through the interior space 108 to the exterior of the ballstent via the distal neck 118. The bridging catheter 160 may also include one or more openings 164 for the passage of fluids, liquids, gases, gels, or even solids into the interior 108 of the ballstent 150. Thus, as explained more fully below, the bridging catheter 160 may be used to inflate or expand the expandable body while also permitting a guide wire 302 or a coil 162 to pass into or through the interior 108 of the ballstent 150 and to the exterior of the distal region 152.

Figure 3A:
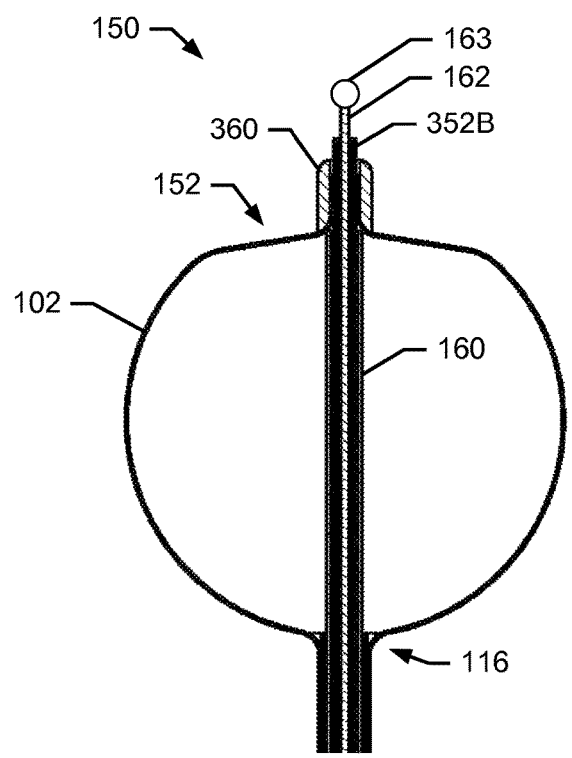
FIGS. 3A-B are a cross-sectional view and a close-up cross-sectional view, respectively, of an embodiment of an expandable body.
Figure 3B:
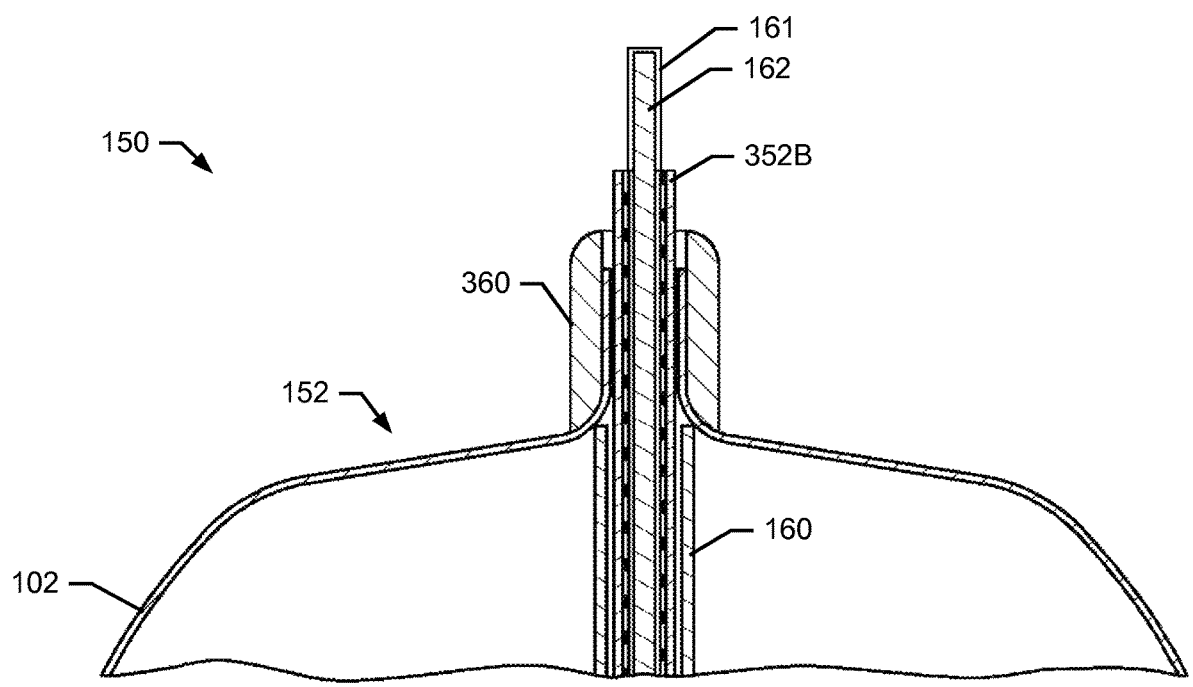
Figure 7:
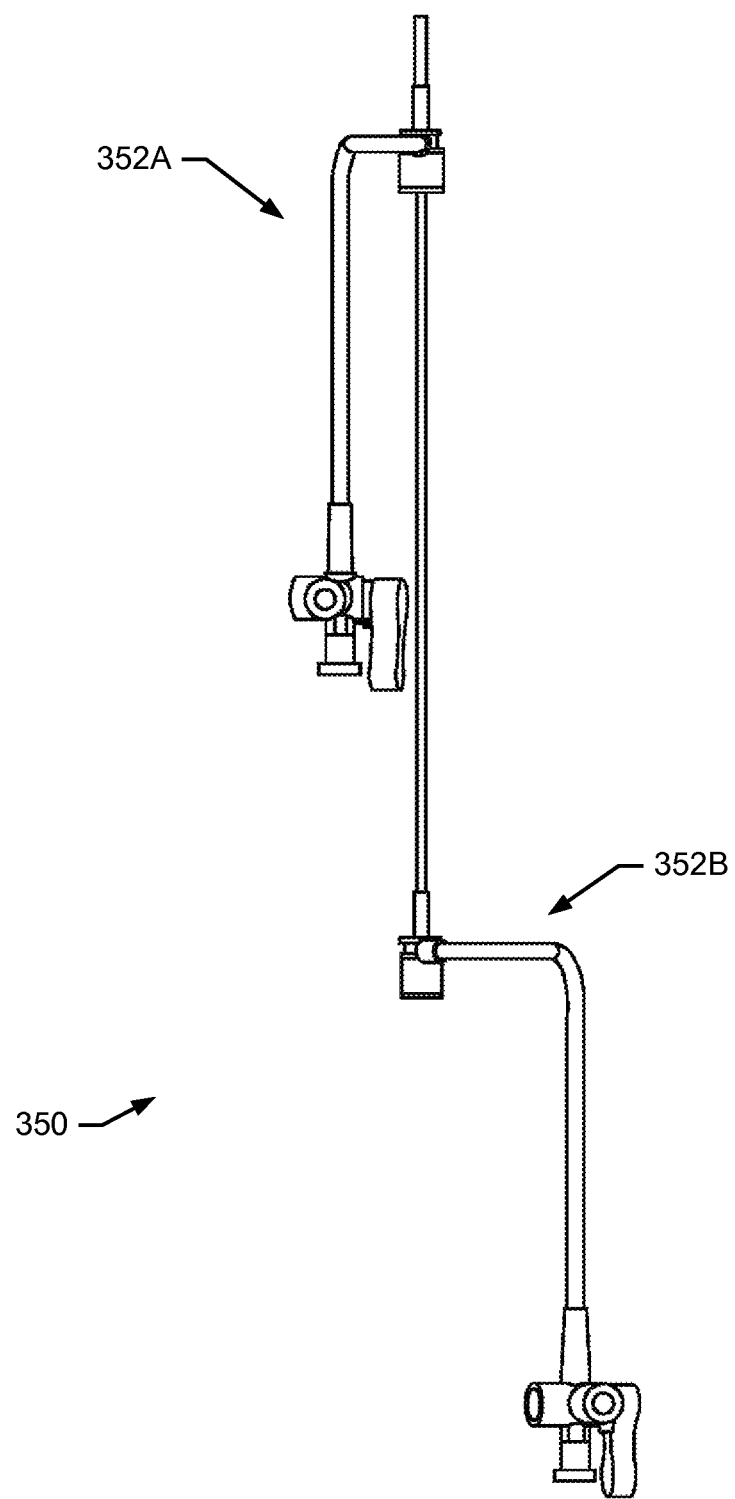
FIG. 7 is perspective view of an embodiment of a dual catheter delivery device.

In various embodiments, the openings 164 within the bridging catheter 160 may have a diameter in a range between approximately 200 µm and 1 mm. As shown in FIGS. 3A-3B, the bridging catheter 160 may be dimensioned such that it can receive a coil or accessory coil 162. The coil or accessory coil 162 may be fed directly through the lumen of the bridging catheter 160 or may be fed through a second catheter 352B (a "coil delivery catheter") that is passed through the bridging catheter 160, as shown in FIG. 7, and in this way comprises a dual catheter delivery system.

The bridging catheter 160 may also permit the passage of a catheter such as the catheter, or coil delivery catheter, 352B to pass through the interior of the expandable body 100, 140, 150, or 170A-G, to deliver the coil or accessory coil 162 to the lumen, cavity, or void of a saccular aneurysm. As shown, in FIGS. 2L-Q, the catheter 352B may be fed through the expandable body and the accessory coil 162 may be simultaneously or subsequently fed through the catheter 352B.

The Expandable Body Exterior

As discussed, the expandable body 100, 140, 150, or 170A-G may have one or more additional coating or layer(s) 104 on the exterior surface 124 of the central layer 122, as shown in FIG. 16C-D. The wall 102 and any additional exterior layers define an exterior surface 110 that, when expanded, contacts the internal wall of the aneurysm or blood vessel. The exterior layer 104 can be of a uniform or varied thickness, preferably between about 1 µm and about 59 µm. In one embodiment, the exterior layer 124 has a thickness between 0.1 and 10 µm. In a specific embodiment, the exterior layer 124 has a thickness of about 1 µm.

The exterior layer 124 can be formed of polymers, latex, elastomers, or metals. The exterior layer 124 may be an electrical insulator, and in a preferred embodiment, the exterior layer 124 is formed of a Parylene coating. The exterior layer 124 may be a metallic or non-metallic material that is less susceptible to electrolysis or galvanic corrosion, such as noble metals, and in preferred embodiments gold or platinum. The exterior coating or layer 104 of the expandable body 100, 140, 150, or 170A-G may be porous and contain a plurality of pores 200, as shown in FIGS. 16C and 16D. Alternatively, the exterior layer 104 can be smooth, with limited porosity or protrusions. For example, the exterior layer 104 may be a polished metal surface. In one embodiment, portions of the exterior layer 104 can be smooth, while other portions can be porous or contain protrusions. In one embodiment, the surface variations can include a pattern. FIG. 29E depicts structures of the exterior surface 110 after electroforming and Parylene coating. As shown, the exterior surface 110 of the wall 102 may have rounded, pebbled, or granular structures. In various embodiments, the rounded, pebbled, or granular surface structures have a height of approximately 0.1 µm to approximately 10 µm.

When configured as a porous or spongy layer, the exterior layer 104 can contain (or be configured to contain) solutions that include pharmaceutical drugs, pharmacologically active molecules, or pharmaceutical compositions within the pores 200. As such, solutions such as pharmaceutical drugs, pharmacologically active molecules, or pharmaceutical compositions can be delivered to the treatment site. Drugs, pharmacologically active molecules, or pharmaceutical compositions that promote thrombosis, stimulate cell proliferation or extracellular matrix production, or tissue growth are examples of agents that can be placed in the pores 200 of the exterior layer 104. The pharmaceutical drugs, pharmacologically active molecules, or pharmaceutical compositions are incorporated into the pores 200 of the wall or the exterior layer 104 prior to positioning the expandable body 100, 140, 150, or 170A-G at the desired location. The drug compositions may be delivered into the pores 200 via capillary or wicking action. The pores 200 range from about 0.01 µm to about 500 µm in diameter. Pore diameters for each expandable body may vary according to the specific drugs, pharmacologically active molecules, or pharmaceutical compositions to be incorporated and the desired rate of release in vivo. By way of example and not limitation, the expandable body 100, 140, 150, or 170A-G may have a porous exterior layer 104 where the pore diameter averages from about 0.01 µm to about 0.05 µm, about 0.05 µm to about 0.5 µm, 0.5 µm to about 5 µm, about 5 µm to about 25 µm, about 25 µm to about 500 µm, about 0.05 µm to about 500 µm, or about 0.01 µm to about 500 µm.

The pharmaceutical drugs, pharmacologically active molecules, or pharmaceutical compositions may include thrombin, platelet-derived growth factor, Ethiodol®, Sotradecol®, or combinations thereof. Other pharmaceutical compounds and compositions that promote thrombosis, stimulate cell proliferation, stimulate the synthesis of extracellular matrix, or the growth of tissue into the porous external wall of the expandable body 100, 140, 150, or 170A-G may also be used. Such drugs or pharmaceutical compositions may include molecules to promote cell proliferation, extracellular matrix production, or tissue growth, such that the expanded expandable body 100, 140, 150, or 170A-G will become more firmly attached to the tissue at the treatment location. The dosages and manner in which the pharmaceutical drugs, pharmacologically active molecules, or pharmaceutical compositions are incorporated into the wall 102 or exterior layer 104 are a matter of choice depending upon the treatment performed. Other compounds may be used to promote blood clotting or thrombosis around the expandable body. In various aspects, the pores 200 may be filled with a biodegradable or bioerodible material, such that the volume of material in the pores decreases over time and the pores are opened in vivo at a point in time subsequent to placement of the expandable body. For embodiments of the expandable body 100, 140, 150, or 170A-G with a porous layer 104, over time, the ballstent, blockstent, or the expandable body remains expanded with the expanded body eventually becoming affixed to the surrounding tissue.

Figure 18A:
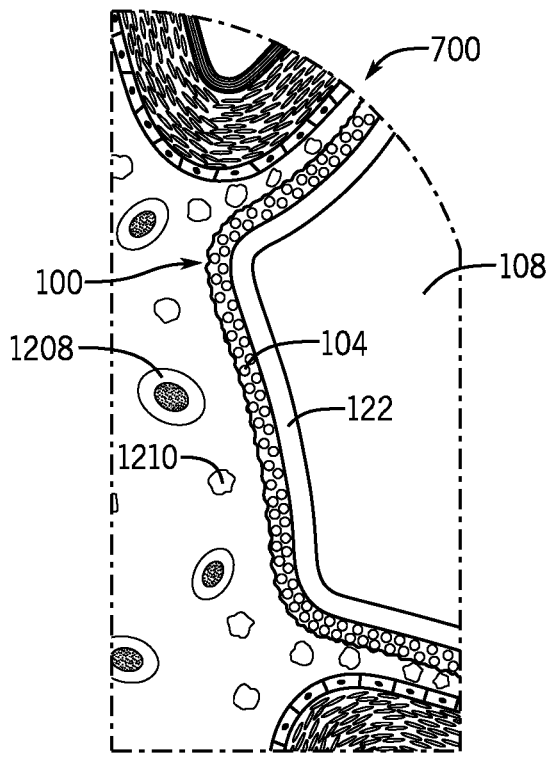
FIGS. 18A-E are plan views of embodiments of an expandable body with a porous surface layer facilitating tissue ingrowths in an aneurysm.
Figure 18B:
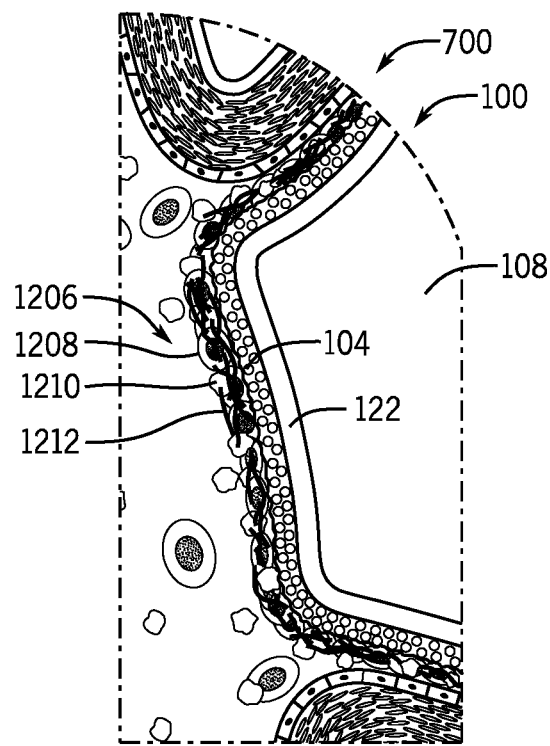
Figure 18C:
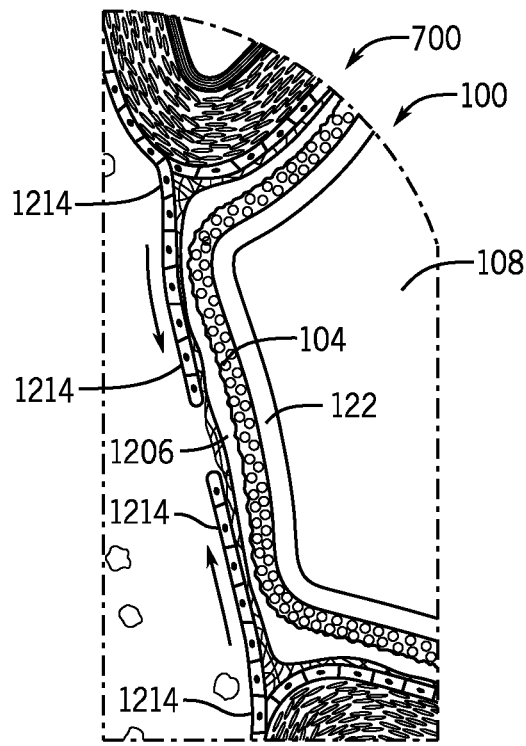
Figure 18D:
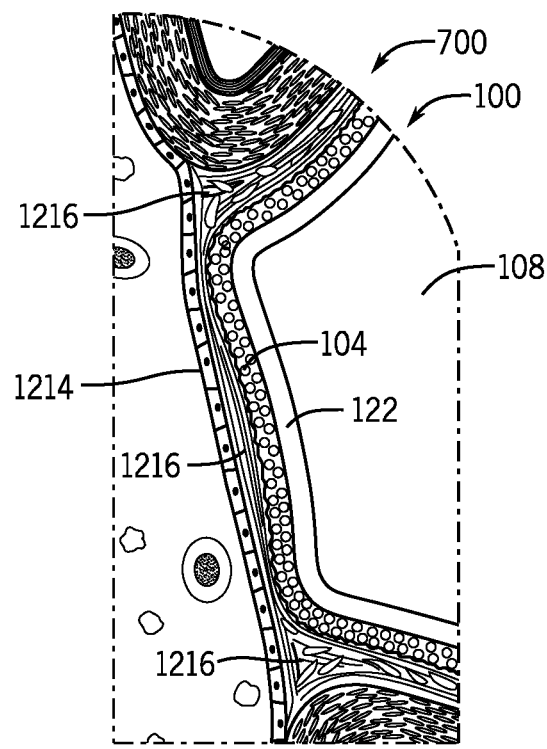
Figure 18E:
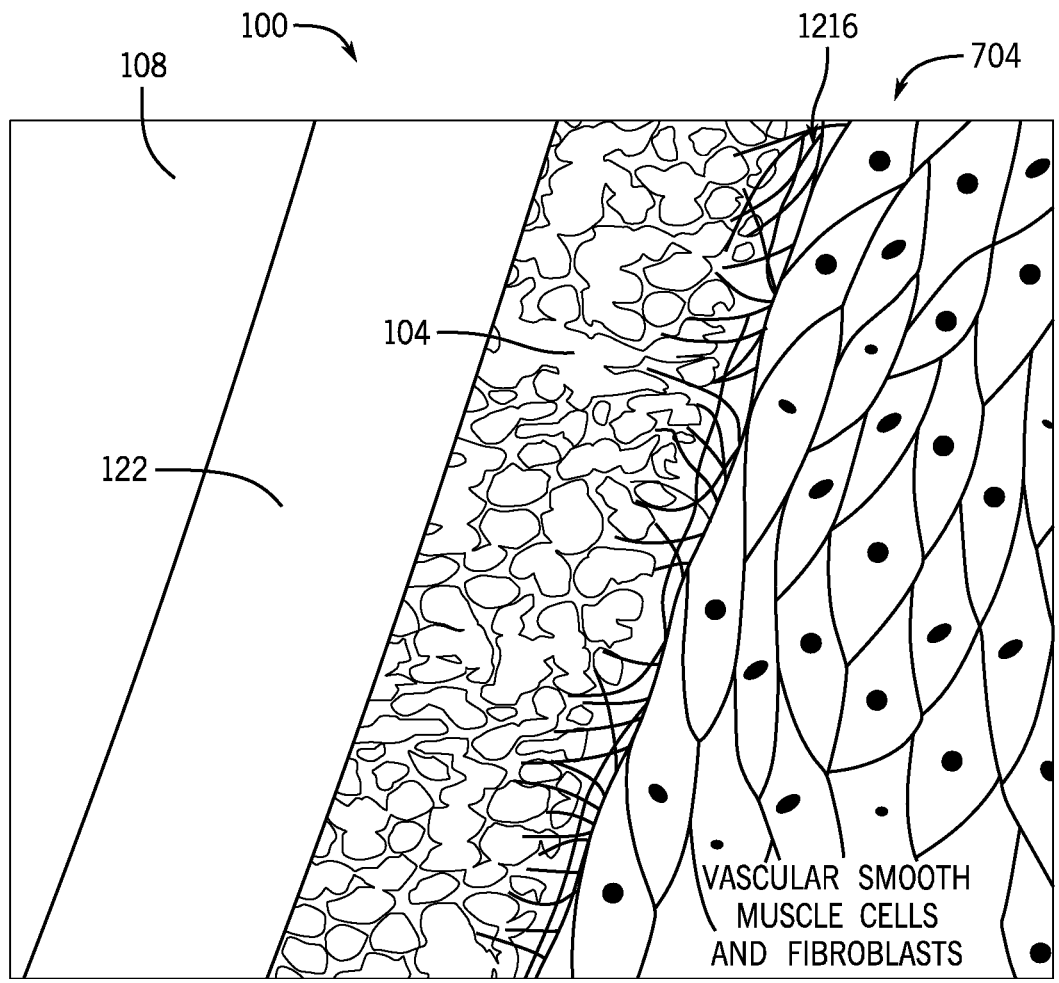
Figure 18F:
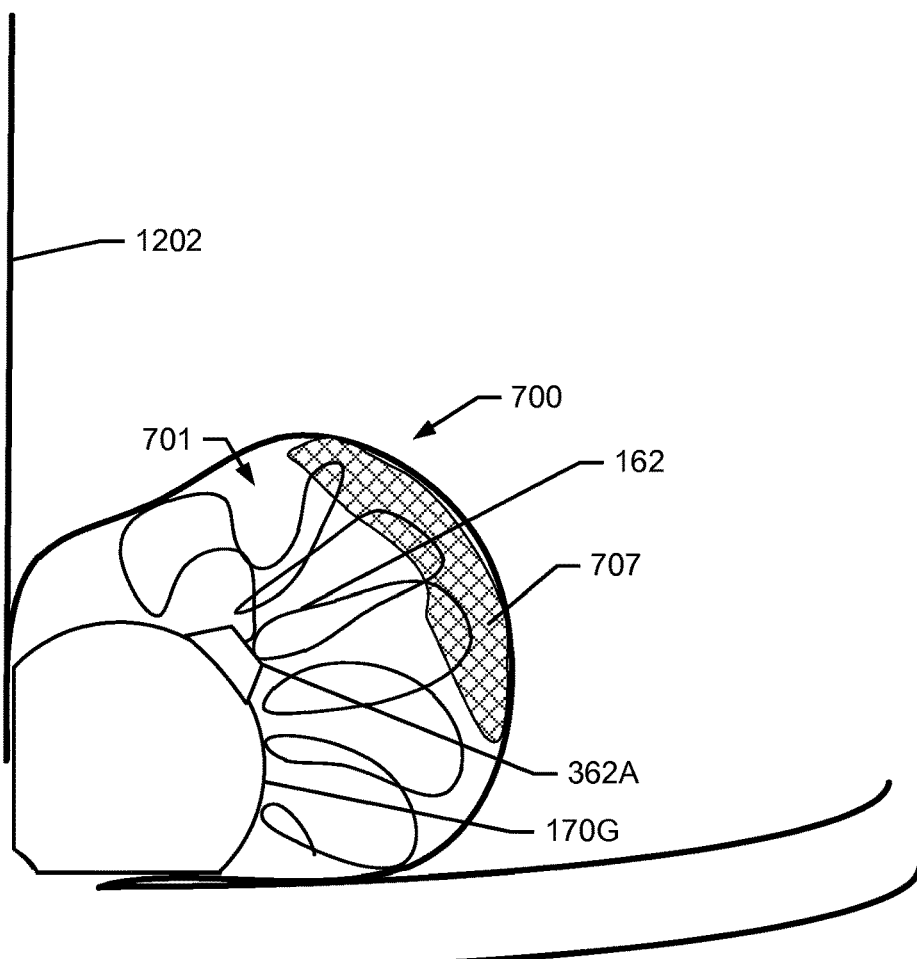
FIG. 18F is a plan view of the expandable body after the insertion of an accessory coil that contacts and secures a thrombus within a bifurcation aneurysm.
Figure 18G:
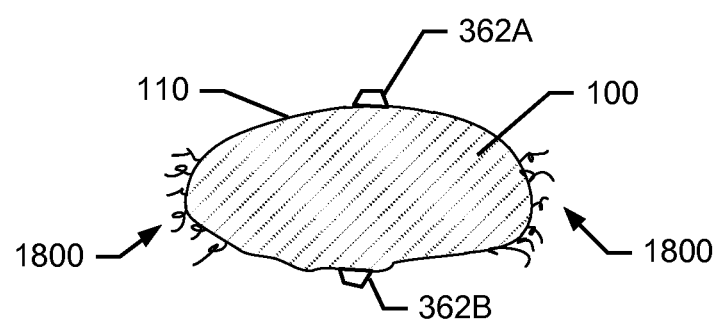
FIGS. 18G-H are plan views of embodiments of an expandable body with external surface projections for anchoring the expanded body to the surrounding tissues.
Figure 18H:
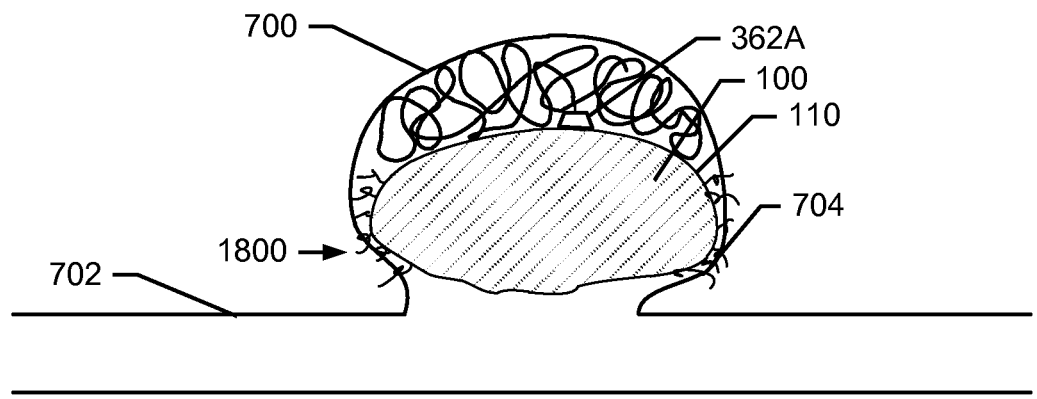

As can be understood from FIGS. 18G-H, the exterior surface 110 of the expandable body 100, 140, 150, or 170A-G may also include one or more protrusions or projections 1800 (which may be generally tubular or have other configurations) that can increase the strength of the attachment of the expanded body to the adjacent tissue, and thereby reduce the risk of movement or migration. The protrusions may have a length that ranges between about 0.01 µm to about 167 µm. Some protrusions can have a branched construction, while others may be joined on both ends to the exterior surface 110 to form loops. In some embodiments, the protrusions are rigid, or semi-rigid. In other embodiments, the protrusions are flexible and hair-like, and may further comprise globular ends, similar to the protrusions on the surface of the footpad of the gecko. The protrusions may be attached to the expandable body 100, 140, 150, or 170A-G after formation. Alternatively or additionally, the protrusions may be incorporated into the expandable body during electroforming.

In another embodiment, the ballstent 100 may comprise a porous external layer or wall 104 or a wall with external protrusions 1800 to promote thrombus formation on the external surface 110 or in the pores 200 and promote cell proliferation, extracellular matrix production, or tissue growth into or around the wall 102 of the ballstent 100 such that the ballstent 100 will, over time, become more strongly attached to the tissue in the adjacent aneurysm wall.

As shown in FIGS. 18A-D, the central layer 122 and the porous exterior layer 104 of the ballstent 100 placed into the aneurysm 700 may be configured to promote thrombus 1206 formation on the exterior layer. The thrombus may be comprised of red blood cells 1208, platelets 1210, and fibrin 1212. Over time, the thrombus 1206 may be partially absorbed into the exterior layer 104, as new endothelial cells 1214 are formed over the thrombus. The new endothelial cells may form a seal of connective tissue 1216 across the opening of aneurysm 700. In addition to sealing the opening of the aneurysm 700, connective tissue 1216 from the wall 704 of the aneurysm may grow into the porous exterior layer 104 of the ballstent 100 to adhere the ballstent to the wall of the aneurysm, as shown in FIG. 18E.

In other embodiments, the projections or protrusions 1800 may be generally tubular, straight, curved, hook-shaped, or configured as pigtail hooks as shown in FIGS. 18G-H. In a macroscopic form, the projections may be composed of nitinol or any other suitable biocompatible material.

FIG. 18H depicts an expanded ballstent 100 that is anchored to the wall 704 of an aneurysm 700. The size and shape of the protrusions may be selected based upon the condition being treated, and may be designed and dimensioned to provide sufficient anchoring support without causing excessive damage to the wall of the aneurysm or the surrounding tissue. Alternatively, microscopic protrusions or filaments may be used to anchor the ballstent. For some embodiments, these microscopic protrusions range in length from 0.01 µm to about 57 µm, and can be straight or branching. In various embodiments, both ends of one or more of the protrusions may be joined to the exterior surface 110 of the ballstent 100 and/or the exterior surface 216 of the wall 102 to form a loop.

The ballstent or expandable body 100, 140, 150, or 170A-G may also be used to contain or trap a thrombus, such as a mural thrombus, that has formed within an aneurysm or other biological space. As shown in FIG. 18F, an expandable body 170G may be placed within an aneurysm 700 having one or more thrombi, including a mural thrombus 707, within the cavity 701 or dome of the aneurysm. In one aspect, an expandable body 170G having an expanded volume smaller than the volume of the aneurysm cavity 701 is selected. The expandable body is delivered to the aneurysm, inflated or expanded, and contacted by an inserted accessory coil 162, as previously described. In this aspect, the accessory coil 162 simultaneously contacts the expandable body 170G, the thrombus 707, and the wall of the aneurysm. The expandable body 170G in conjunction with the accessory coil 162 acts to trap the thrombus 707 within the aneurysm holding it in places until absorption by the patient.

In various embodiments, an expandable body that does not completely fill the cavity 701 of an aneurysm 700 that may potentially contain a blood clot is preferred. As such, a larger expandable body that more fully fills the cavity 701, is less desirable as it may force thrombus within the aneurysm 700 out into the parent blood vessel 1202 or 1203, where the thrombus may embolize, travel through the vascular system, and cause a stroke.

In various embodiments, the expandable body 100 may include a thin polymer sheath that is wrapped around the entire body of the expandable body when in the delivery or deliverable configuration. The sheath may be added to the exterior of the expandable body 100 during fabrication of the expandable body. The sheath may be affixed to a proximal nose cone 3628, a distal nose cone 360 or 362A, or both, such as those shown in FIGS. 2A-Q. The polymer sheath increases trackability of the expandable body 100 and reduces friction with the lining of blood vessels as the expandable body is delivered through the vascular system. During inflation or expansion of the expandable body 100, the polymer sheath opens while remaining affixed to the expandable body, the delivery catheter, the proximal nose cone 362B, or the distal nose cone 360 or 362A. In one embodiment, the sheath may be perforated or partially scored before deployment to allow for easier expansion of the expandable body 100.

The Expandable Body Interior

In some embodiments, the expandable body 100, 140, 150, or 170A-G may include an additional layer or liner 214 on the interior surface 106 of the central layer 122, as shown in FIGS. 16D, 16F, 16H, 16J, and 16L. The interior layer may be made from the same materials as the central layer, or can be made of different materials. The interior layer may be formed of gold, platinum, silver, alloys thereof, or combinations thereof. The additional layer 214 on the interior surface 106 of the central layer 122 of the expandable body 100, 140, 150, or 170A-G may also be formed of a polymer, plastic, latex, rubber, woven or knitted fiber material, metal, or another material, or combinations thereof. Preferably, the interior layer 214 is an elastomeric coating that is bonded to the interior surface 106 of the central layer 122. The interior layer 214 can be a variety of thicknesses, preferably ranging between about 0.1 µm and about 59 µm. In one embodiment, the interior layer 214 has a thickness between about 0.1 µm and about 10 µm. The total thickness of the wall 102, including the central layer 122, the exterior layer 104, and the interior layer 214 is preferably between about 2 µm and about 50 µm, regardless if the wall contains one, two, three, or more layers. The interior layer 214 can comprise polymers, latex, or elastomers. In a preferred embodiment, the interior layer 214 comprises Parylene. The interior layer 214 also adds mechanical properties (such as strength) to the wall 102. Further, the interior layer 214, optionally, can form a seal that prevents the escape of a fluid medium from the expandable body 100, 140, 150, or 170A-G, should the central layer 122 contain a defect or hole. The central layer 122 and any additional layers define an interior surface 106 or 218, respectively, such that when the ballstent or the expandable body is expanded, with a fluid, liquid, gas, or solid, a central void or space 108 is defined. As shown in FIG. 16D, the distance between the interior surface 218 and the exterior surface 110 is the overall wall thickness 120 of the wall 102.

The Expandable Body Neck(s) and Opening(s)

As illustrated in FIGS. 1A-D, 2A-4B, 8A-S, 8U, 16A-D, 16G, and 16K, the expandable bodies 140, 150, or 170A-G have one or more openings 112 and 114 defined by the wall 102 or by the proximal neck 116 or the distal neck 118. In various embodiments, the ballstent, blockstent or expandable body has one or more openings 112 and 114 defined by necks 116 or 118, respectively. In all embodiments, a fluid medium can enter the opening 112 and move into the central void or space 108 defined by the interior surface 106 or 218, thereby inflating or expanding the expandable body. In various embodiments, one or both of the necks 116 and 118 may extend outwardly from its respective end region (proximal region or distal region) of the expandable bodies 100, 140, 150, or 170 A-G as shown in FIGS. 1A, 1C, 2A-4B, 8A-S, 8U, 16G and 16K. Alternately, one or both of the necks 116 and 118 may extend inwardly from its respective end region and into the interior void 108, as illustrated in FIGS. 1B and 1D. The proximal necks 116 can be used for attaching the expandable body 100, 140, 150, or 170A-G to the delivery catheter and may function in separating the ballstent or the expandable body from the delivery catheter. In various embodiments, the necks 116 and 118 and the wall 102 or main body may be formed from different metals. For example, in one embodiment, the neck(s) 116 and 118 and the wall 102 or main body may be formed by gold. In other embodiments, the neck 116 and 118 may comprise stainless steel, including but not limited to 304 series or 316L series stainless steel and the wall 102 or main body may be formed by gold, platinum, or another malleable metal. The neck 116 and 118 may comprise multiple metals, such as stainless steel and another metal such as gold or platinum, including embodiments wherein the various regions of the expandable bodies 100, 140, 150, or 170A-G are distinct in their metal content and embodiments wherein the different metals are formed in layers in the various regions, including an embodiment wherein a neck comprises an interior layer of stainless steel with an exterior layer of gold and an embodiment wherein a neck comprises an central layer of stainless steel with interior and exterior layers of gold, including embodiments wherein at least a portion of the surface of the exterior layer is stainless steel, including embodiments wherein a portion of the gold exterior layer is absent through masking or through etching, including laser etching.

Additionally, the necks 116 and 118 can be designed and dimensioned such that the opening 112 or 114, preferably the proximal opening 112, can be closed or partially closed before, during, or after separation of the expanded body from the delivery catheter. One or more openings 112 or 114 may remain open. Optionally, before, during, or after separation, the necks 116 and 118 may be folded, pinched, or closed to form a seal. The necks 116 and 118, or alternatively the stainless steel ring 250, may have a length N1, as shown in FIGS. 24A and 30C, ranging between about 0.5 mm and about 20 mm, preferably a length between about 0.5 mm and about 5 mm. In one embodiment, the neck length N1 is approximately 1.27 mm±0.08 mm.

In various embodiments, at least one of the necks 116 and 118 and the stainless steel ring 250, as shown in FIGS. 2A-E, 24A, and 30D, have an outer diameter N2 and an inner diameter N3 that defines the openings 112 and 114, respectively. The outer diameter N2 is in a range between about 0.25 mm and about 2 mm and the inner diameter N3 is in a range between about 0.24 mm and about 1.95 mm. In one embodiment, the neck outer diameter N2 is approximately 0.99±0.01 mm and the neck inner diameter N3 is approximately 0.89±0.01 mm.

The thickness of the walls of either or both of the necks 116 and 118 may be the same as the main body of the ballstent, blockstent, or the expandable body or may be thinner or thicker than the wall of main body. Preferably, either or both of the necks 116 and 118 have a wall thickness N4 between about 3 μm and about 60 μm, as shown in FIGS. 24B-C, 30D, and 30F. In one particular embodiment, the neck has a thickness of approximately 50 μm. In one embodiment of the ballstent 100 where the neck(s) 116 and 118 extend into the central void space 108 as indicated in FIGS. 1B and 1D, the external surface 110 of the expanded ballstent retains a more rounded surface contour, increasing the strength of the expanded ballstent and reducing the risk of damage to the aneurysm wall or the adjacent tissue during placement.

Figure 2K:
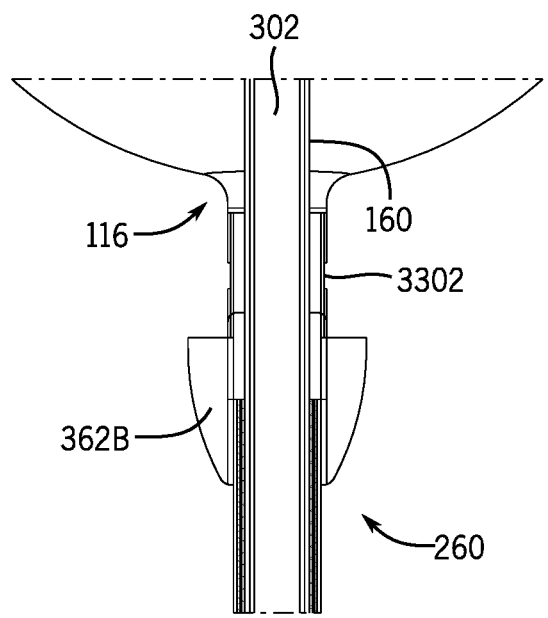
Figure 2L:
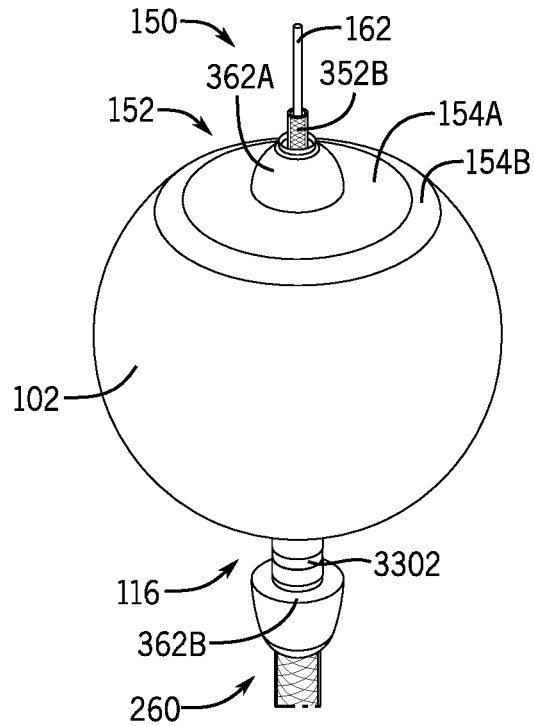
FIG. 2L is a perspective view of an embodiment of an expandable body.
Figure 2M:
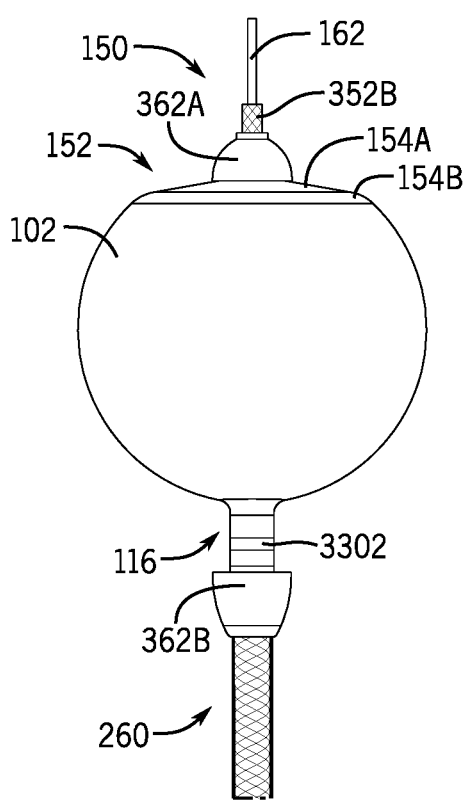
FIG. 2M is a plan view of an embodiment of the expandable body of FIG. 2L.
Figure 2N:
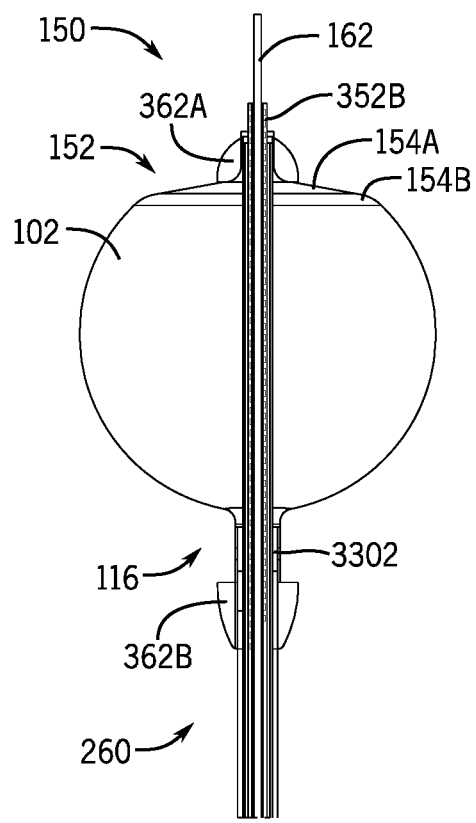
FIG. 2N is a cross-sectional view of an embodiment of the expandable body of FIG. 2L.
Figure 2O:
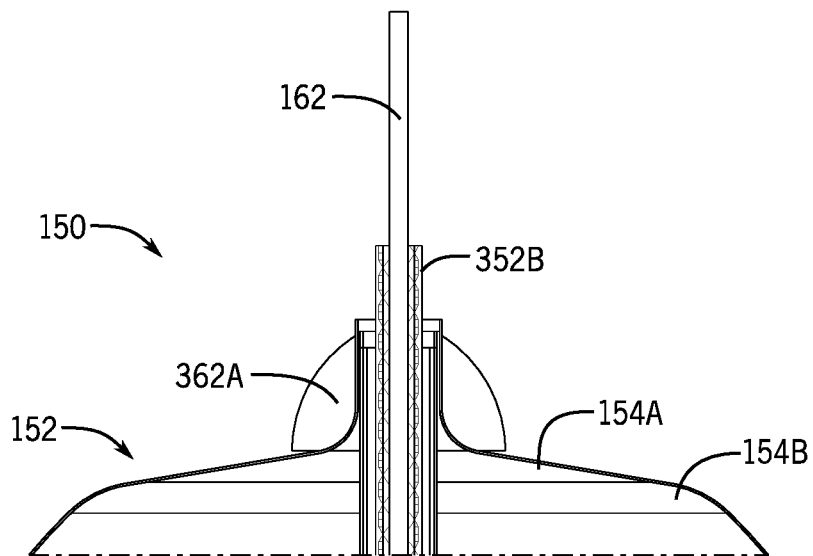
FIG. 2O is a close-up cross-sectional view of an embodiment of an embodiment of the expandable body of FIG. 2L.
Figures 2P, 2Q:
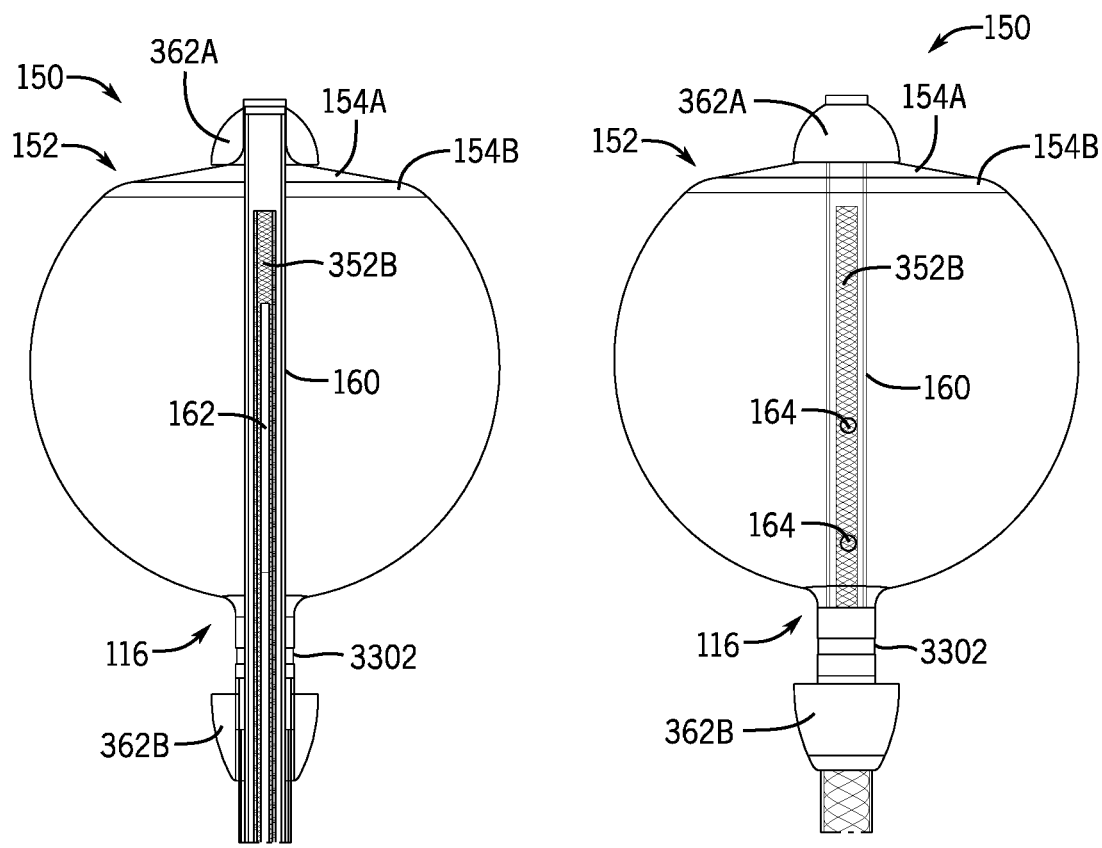
FIG. 2P is a cross-sectional view illustrating a delivery device and coil traversing the interior of the expandable body of FIG. 2L.
FIG. 2Q is a partial interior view illustrating a delivery device traversing the interior of the expandable body of FIG. 2L.

One or both of the necks 116 or 118 can be coated or insulated on the inner wall, outer wall, or both. This coating can include metals such as gold or platinum and polymers such as Parylene. In addition, the necks 116 and 118 may include one or more caps or nose cones 360, as shown in FIGS. 2A-C and 4A-B or nose cones 362A-B as shown in FIGS. 2D-Q, to improve trackability of the expandable body 100 during delivery and placement. In addition to improving the trackability of the expandable body 100 during placement, the nose cones 360 or 362A-B also serve to protect the necks 116 and 118 during positioning, as well as reducing the risk of damage to the walls or lining of any blood vessels or conduits traversed by the expandable body 100 during placement. In some embodiments, a nose cone affixed to the distal portion of the delivery catheter can serve the same purpose.

Figure 4A:
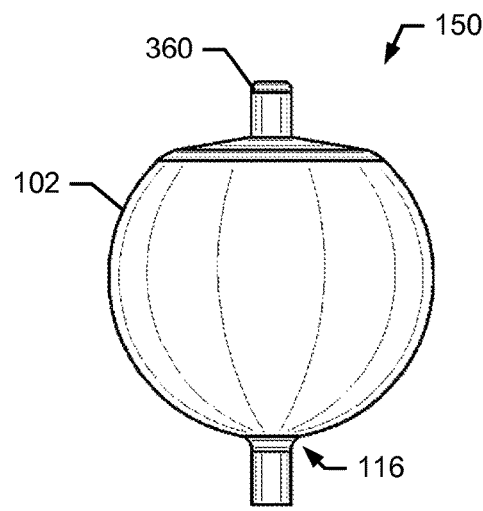
FIGS. 4A-B are a planar view and a close-up cross-sectional view, respectively, of an embodiment of an expandable body.
Figure 4B:
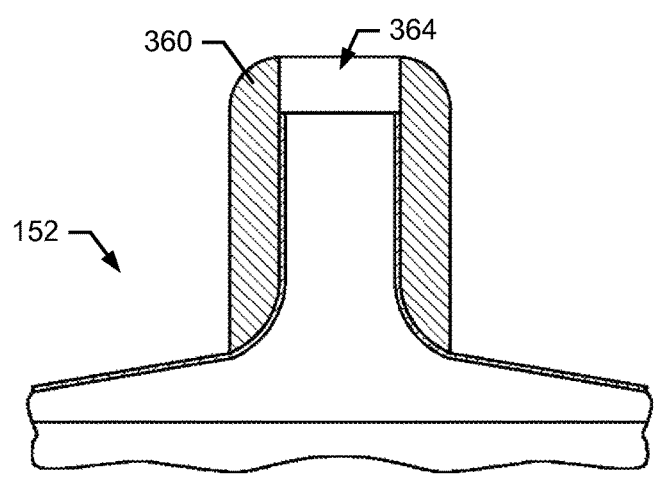
Figure 5A:
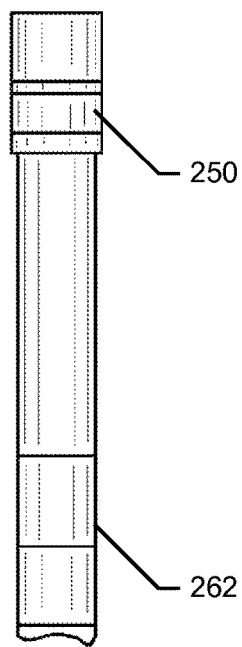
FIGS. 5A-B are a planar view and a close-up cross-sectional view, respectively, of an electrolysis neck segment for an embodiment of an expandable body.
Figure 5B:
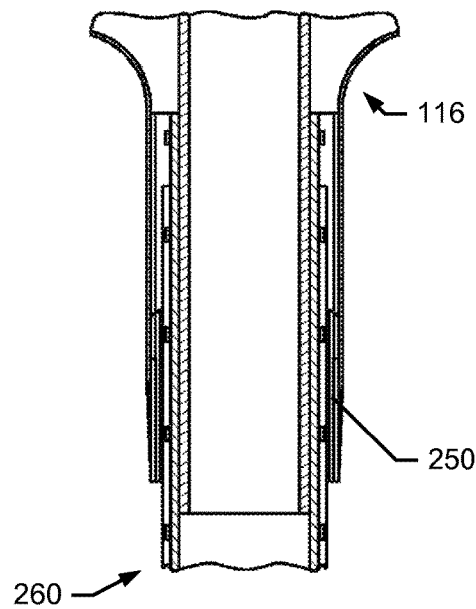
Figure 6A:
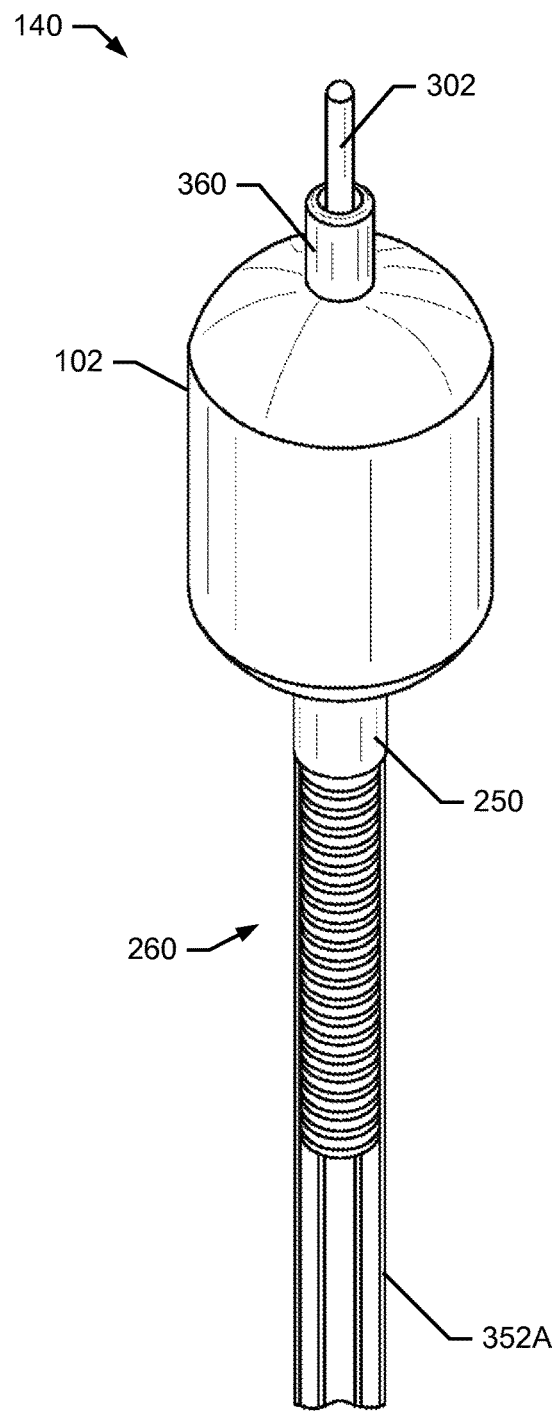
FIGS. 6A-B are a perspective view and a cross-sectional view, respectively, of an embodiment of an expandable body and delivery device.
Figure 6B:
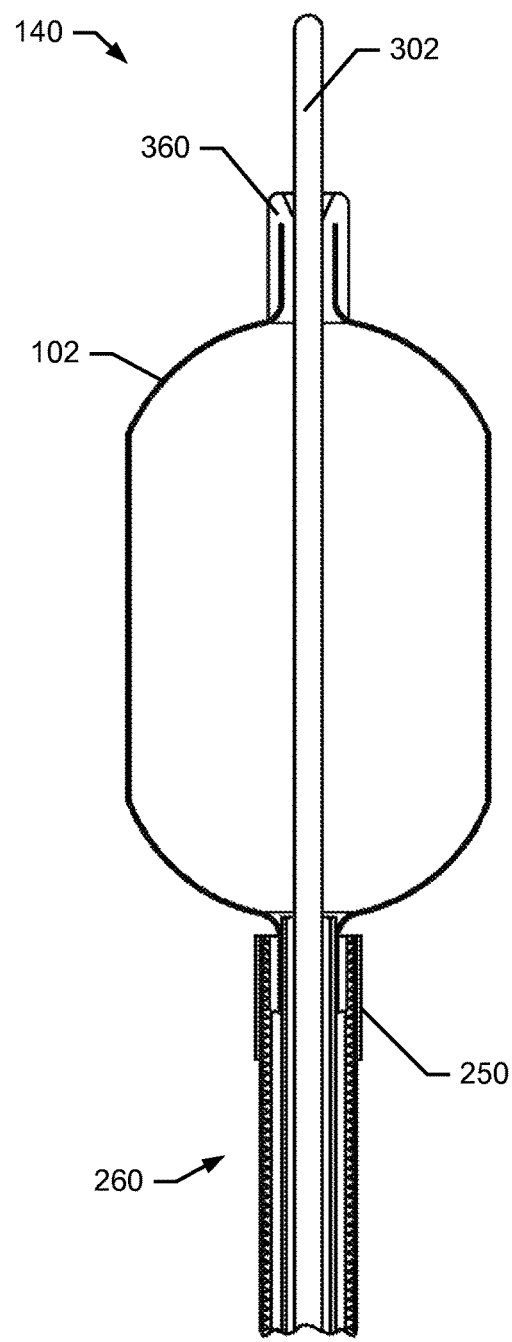
Figure 6C:
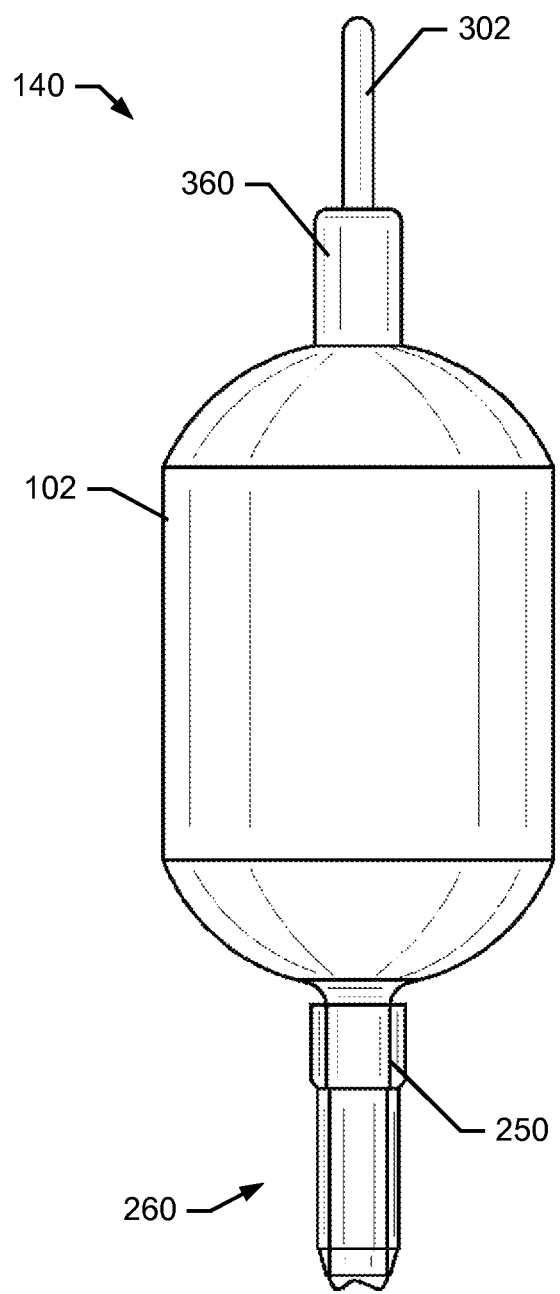
FIGS. 6C-D are a perspective view and a cross-sectional view, respectively, of an embodiment of an expandable body.
Figure 6D:
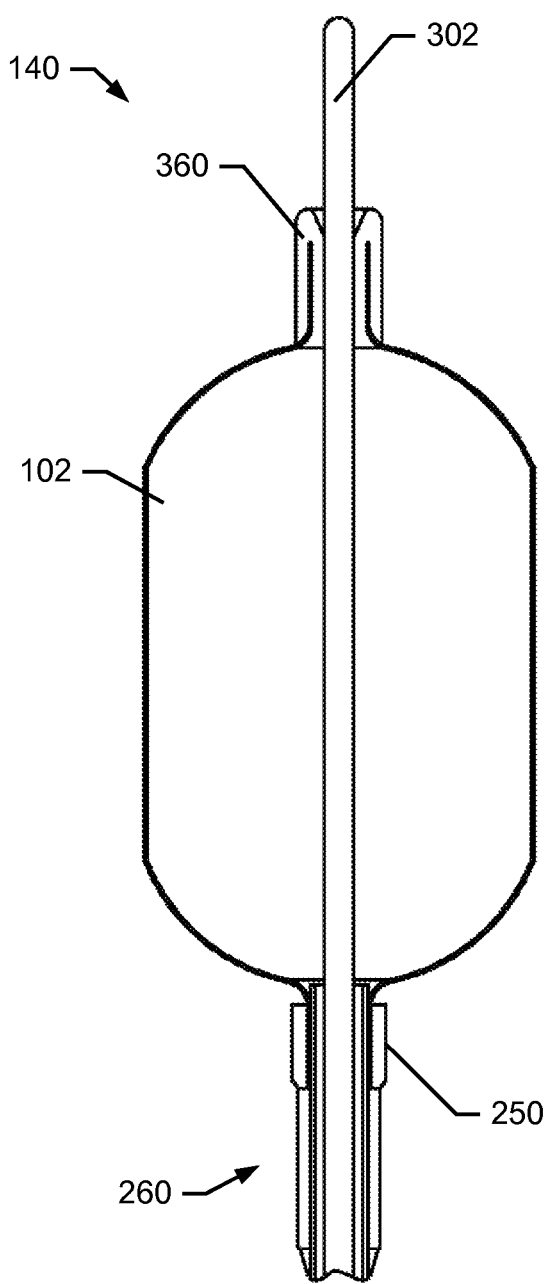

As shown in FIGS. 2C and 4B, the nose cones 360 or 362A-B include a central channel 364 that encircles and engages the necks 116 and 118. In one embodiment, the nose cone 360 is generally cylindrical as shown in FIGS. 2A-C and 4A-B, while in other embodiments, the nose cones 362A-B may have a frustoconical or "bullet-shaped" configuration, as shown in FIGS. 2D-Q. The nose cones 360 or 362A-B may be composed of any biocompatible material, including polymers and metals. In one embodiment, the nose cones 360 or 362A-B are composed of PTFE. In various embodiments, the nose cones 360 or 362A-B hay have an outer diameter in a range between approximately 0.75 and 2.5 mm, an inner diameter in a range between approximately 0.25 and 2 mm, with a length in a range between approximately 1 and 4 mm.

Figure 23A:
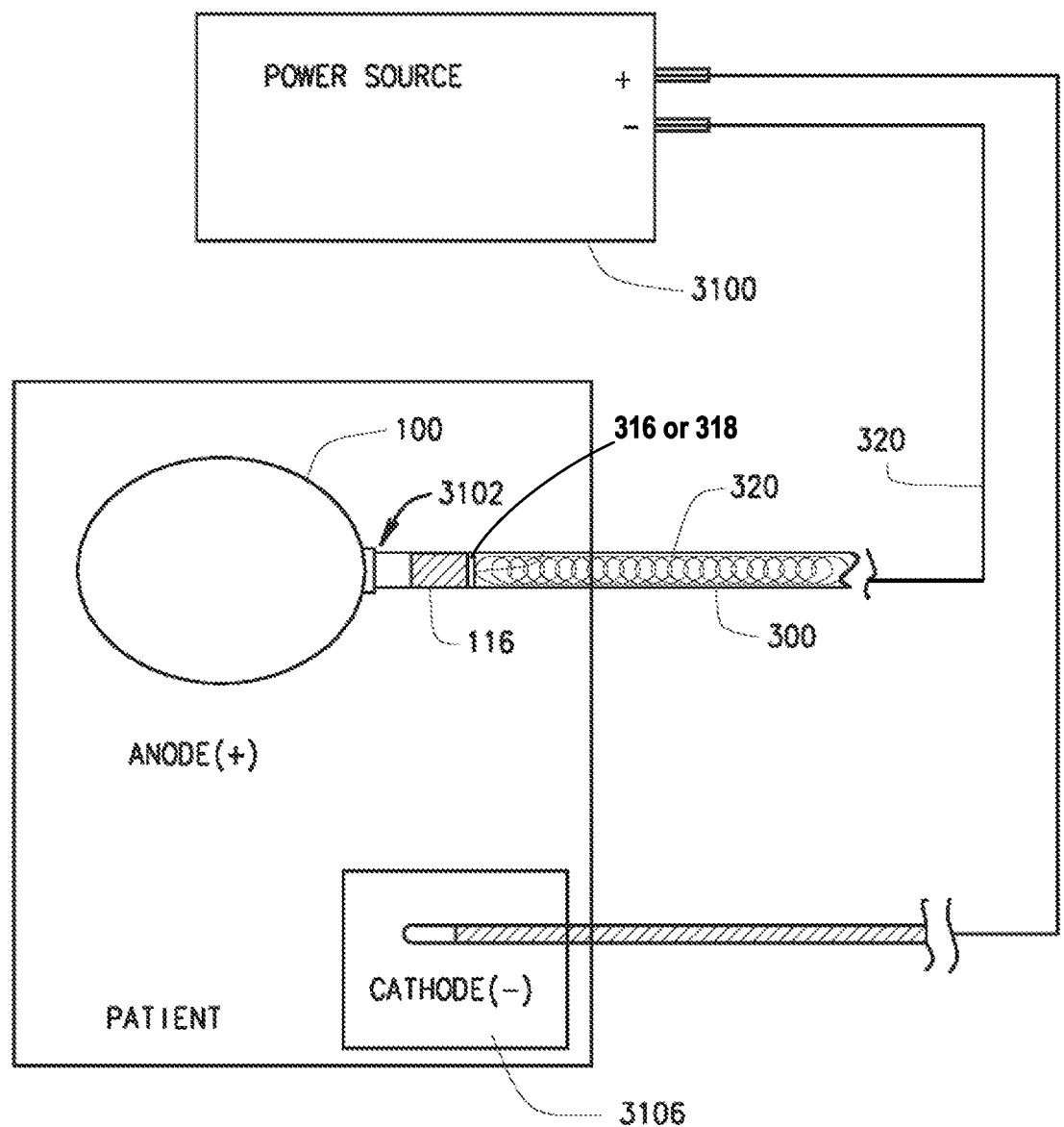
FIG. 23A is a plan view of an embodiment of the medical device wherein the expandable body is attached to the delivery catheter with an adhesive and separated from the delivery catheter by electrolysis of a portion of the neck of the expandable body.

In various embodiments, the necks 116 and 118 are further modified to provide a detachment point for detaching the expandable body 100, 140, 150, or 170 A-G from a delivery catheter. For example, a strip of electrically conductive material, including an uncoated or non-insulated section of a neck, weld, solder, or other fixation point, or a portion of the ballstent, blockstent or the expandable body itself, is left exposed, uncoated, or non-insulated or later exposed after coating, including an exposed, uncoated, or non-insulated region that in the shape of a circumferential or ring-shaped exposed surface of metal or conductive materials that can be subjected to electrolysis to achieve separation between the expanded expandable body and the distal end of the delivery device. Preferably, a stainless steel ring is affixed to the wall 102 or the main body of the expandable body, as stainless steel is highly sensitive to galvanic corrosion and electrolysis. For example, as can be understood from FIGS. 16E, 16G, 16I, 16K, 28, and 30A-B, in one embodiment, at least a portion of an inner surface of the metal layer of the neck of the metallic expandable body is electrically insulated by having an outer surface of a distal portion of the delivery device extending along the inner surface of the metal layer of the neck of the metallic expandable body. In some embodiments, on the inner surface of the proximal neck 116, a proximal boundary of the ring-shaped exposed metal surface may be defined by a distal boundary of the delivery device in the neck region and a distal boundary of the ring-shaped exposed metal surface may be defined by a boundary of the inner insulation layer in the neck region. For the outer surface of the proximal neck 116, both the proximal and distal boundary of the ring-shaped exposed metal surface may be defined by a boundary of the outer insulation layer in the neck region. In such an embodiment, the distal end of the delivery catheter 300 or 400 may distally terminate near a proximal edge of the ring-shaped exposed metal surface of the neck. As indicated in FIG. 23A, a conductive wire can be engaged in electrical contact with the uncoated or non-insulated portion of the neck or a weld or solder between a neck and the delivery catheter, or on the expandable body itself 100, 140, 150, or 170A-G to allow the uncoated or non-insulated portion to be dissolved (corroded) or removed via electrolysis.

In other embodiments, one or both necks 116 and 118 may be affixed with a metallic ring 250, as shown in FIGS. 2A, 2B, 5A, and 5B, which may be subsequently severed using electrolysis. The metallic ring 250 may be composed of stainless steel and, as explained below, may be subjected to one or more heating procedures to sensitize the steel to galvanic corrosion, thereby allowing for faster separation or severing via electrolysis.

Expandable Body Shapes and Dimensions

FIGS. 16E-F and 16I-J illustrate a ballstent 100 and a delivery catheter 220 that may be used to deliver the ballstent. In one characterization, the ballstent 100 includes a distal region 202 that includes the distal end 204 of the ballstent. Adjacent to the distal region 202 is an intermediate region 206 where the ballstent transitions from the distal region 202 to a proximal region 208 that includes a proximal end 210 of the ballstent. The proximal region 208 is generally opposite the distal region 202. A center axis 212 extends proximal-distal between the proximal region 208 and the distal region 202. The ballstent wall 102 extends generally continuously through the intermediate region 206 from the proximal region 208 to the distal region 202, and the ballstent 100 is in the form of a single-lobed metallic expandable body. In another characterization, the ballstent 100 includes a distal region 222 that is joined directly to a proximal region 228 that is generally opposite the distal region 222. A center axis 212 extends proximal-distal between the proximal region 208 and the distal region 202. The ballstent wall 102 extends generally continuously from proximal region 208 to the distal region 202 and the ballstent 100 is in the form of a single-lobed metallic expandable body.

In one embodiment, when the ballstent 100 is expanded, the intermediate region 206, the proximal region 208, and the distal region 202 combine to form a generally spherical shape. In various embodiments, the dimensions of the ballstents 100 are selected based upon the size and shape of the saccular aneurysm being treated. Preferred shapes of the ballstent 100 include round, oblong, and irregular. The diameter of the round expanded ballstent 100 ranges from about 2 mm to about 30 mm, and preferably has an expanded diameter ranging from about 2 mm to about 20 mm. The expanded length of oblong ballstent or blockstent preferably ranges between about 2 mm to about 30 mm. The ballstent 100 may have an expanded volume that ranges between about 0.001 mL to about 65 mL. In preferred embodiments, the expanded diameter of the spherical ballstent 100 ranges from about 2 mm to about 10 mm, while the preferred expanded volume ranges from about 0.004 mL to about 40 mL. In preferred embodiments, the expanded length of the oblong ballstent or blockstent 100 ranges between about 2 mm to about 30 mm.

FIGS. 16G-H and 16K-L illustrate an expandable body 140 and a catheter 220 that may be used to deliver the expandable body. In some embodiments, the expandable body 140 can include a generally cylindrical intermediate region 206 (where the longitudinal axis of the cylindrical portion is perpendicular to the central axis 212), a generally hemispherical proximal region 208 and, a generally hemispherical distal region 208, as shown in FIG. 16G. In other embodiments, the expandable body 140 can include a generally cylindrical intermediate region 206 (where the longitudinal axis of the cylindrical portion is aligned along a longitudinal axis of the neck 116), a generally hemispherical proximal region 208 and, a generally hemispherical distal region 208, as shown in FIG. 24 A. The intermediate region 206 may have a radius R1 that is equal to the radius R2 of both the proximal region 208 and the distal region 208, as shown in FIG. 24A. In various embodiments, the delivery catheter 220 is typically engaged to the proximal neck 116 or proximal region 208 of the expandable body.

In other embodiments, one or more portions of the expandable body wall 102 may be thicker than the remaining portions of the wall. By way of example and not limitation, the wall in the middle of the main body or the intermediate region of the expandable body may be thicker or thinner than the wall in the proximal and distal regions or portions of the expandable body, or the wall of a neck may be thicker or thinner than the main body of the expandable body. In various embodiments, the wall thickness 120, as shown in FIGS. 16A-D, may be scaled relative to the overall diameter of the expandable body to avoid undesired increases in wall stress with increases in diameter. In various embodiments of the expandable body 100, 140, 150, or 170A-G, a balance can be made between a wall thickness 120 that is thin enough to enable the various small compressed forms of the delivery configuration and to permit expansion of the expandable body at lower pressures, and a wall thickness that is thick enough to maintain structure integrity and resist compression after delivery and detachment. Therefore, the average wall thickness 120 is preferably in a range between about 10 µm and about 50 µm. By way of example and not limitation, the wall thickness 120 for an expandable body 100, 140, 150, or 170A-G having an expanded diameter of about 4 mm may be about 10 µm, while the wall thickness for an expandable body having an expanded diameter of about 10 mm may be about 25 µm.

As shown in FIG. 24A, the expandable body 140 may have a generally cylindrical shape with rounded or hemispherical ends (where the longitudinal axis of the cylindrical shape is aligned with a longitudinal axis of the neck 116), such that the total length L1 of the main body of the expandable body parallel to the first axis is greater than the total width of the expandable body parallel to the second axis (i.e. twice the radial distance R1). In other embodiments, the expandable body 140 may have a generally cylindrical shape with flattened or flat ends as shown in FIGS. 16G and 16K, such that the total length of the main body of the expandable body along the central axis 212 is less than the total width of the expandable body perpendicular to the central axis. The expandable body 140 is in the form of a single-lobed metallic expandable body.

In various embodiments, the expandable body 140 has an expanded diameter (both along the center axis 212 and perpendicular to the center axis) ranging from about 2 mm to about 30 mm. Assuming no change in wall thickness 120, the stress in the wall of expandable body 140 will increase, as the radius R1 (see FIG. 24A) of the intermediate region 206 increases. Therefore, in some embodiments, the diameter of the expandable body 140 is limited by the ultimate tensile strength of the material (e.g. gold) used to form the expandable body and by the pressure required to expand the compressed expandable body. As can be understood from FIG. 24A, the expandable body 140 may have an expanded length L1 of between about 2 mm to about 120 mm, such length L1 comprising the proximal region, intermediate region, and distal region. Preferably, the length is between about 5 mm to about 60 mm, and in a particular embodiment the expanded length L1 is approximately 40±0.03 mm and the length L2 of the intermediate region 206 may be approximately 24±0.03 mm, such length L2 comprising only the intermediate region.

The concentration of stress between the neck 116 and the proximal region or end 208 of the expandable body 100, 140, 150, or 170A-G may be reduced or offset by increasing the radius R4 between the neck and the proximal region, as shown in FIGS. 24B-C. For example, the stress experienced by the wall 102 in FIG. 24B having a radius of R4 is greater than the stress experienced by the wall in FIG. 24C having a radius of R4', where R4' is greater than R4. In addition, stress may be concentrated at the point where the neck 116 transitions to the wall of the proximal region 208 of the expandable body 100, 140, 150, or 170A-G due to a metallic ring incorporated into the neck 116 during formation of the expandable body. This stress concentration may be mitigated by reducing the overall wall thickness N4 of the neck 116. By way of example and not limitation, the neck 116 shown in FIG. 24B may have a wall thickness N4 of approximately 25 μm, while the neck shown in FIG. 24C may have a wall thickness N4' of approximately 12.5 μm.

Expansion of the Expandable Body

The central void or space 108 of the expandable body 100, 140, 150, or 170A-G can be filled with fluids, gels, solids, or combinations thereof to expand or inflate the expandable body 100, 140, 150, or 170A-G. The terms expand, inflate, and forms thereof may be used interchangeable to refer to the action of changing the expandable body from the delivery or deliverable configuration to an expanded or at least partially expanded configuration. A fluid medium is a substance having particles that easily move and change their relative position without a separation of the mass. Fluid media that may be used to expand the expandable body 100, 140, 150, or 170A-G include liquids, gases, gels, and combinations thereof. By way of example and not limitation, the fluid medium may be water, a saline solution, a radiographic contrast solution, or a mixture thereof. In one embodiment, the fluid medium may further include a solution or suspension of a drug, pharmacologically active molecules, or a pharmaceutical preparation.

In various embodiments, the shape and construction, including multi-layer constructions, of the expandable body 100, 140, 150, or 170A-G permits the expandable body to remain in an inflated or expanded configuration without the use of any support structures not derived from the patient. For example, the fluid medium used to inflate the expandable body 100, 140, 150, or 170A-G, and optionally blood from the patient, will fill the interior void 108 and cause the ballstent, blockstent, or the expandable body to remain in an expanded configuration. In addition, support structures derived from the patient, including but not limited to blood clots and tissue ingrowths, may support and maintain the structural integrity of the expandable body 100, 140, 150, or 170A-G, when expanded.

Figure 17A:
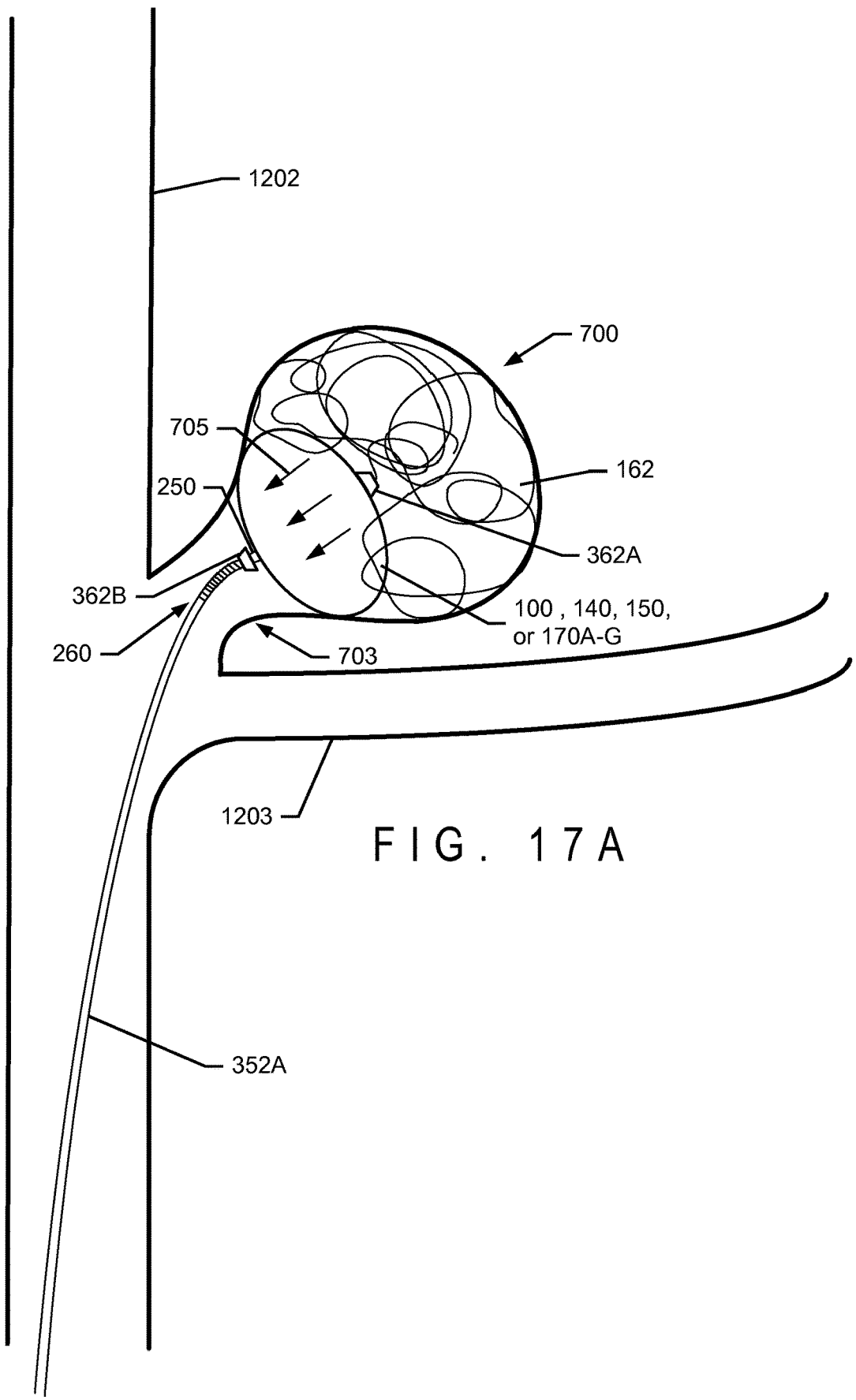
FIGS. 17A-B are views of the expandable body deployed in a bifurcation aneurysm with an accessory coil according to one embodiment.
Figure 17B:
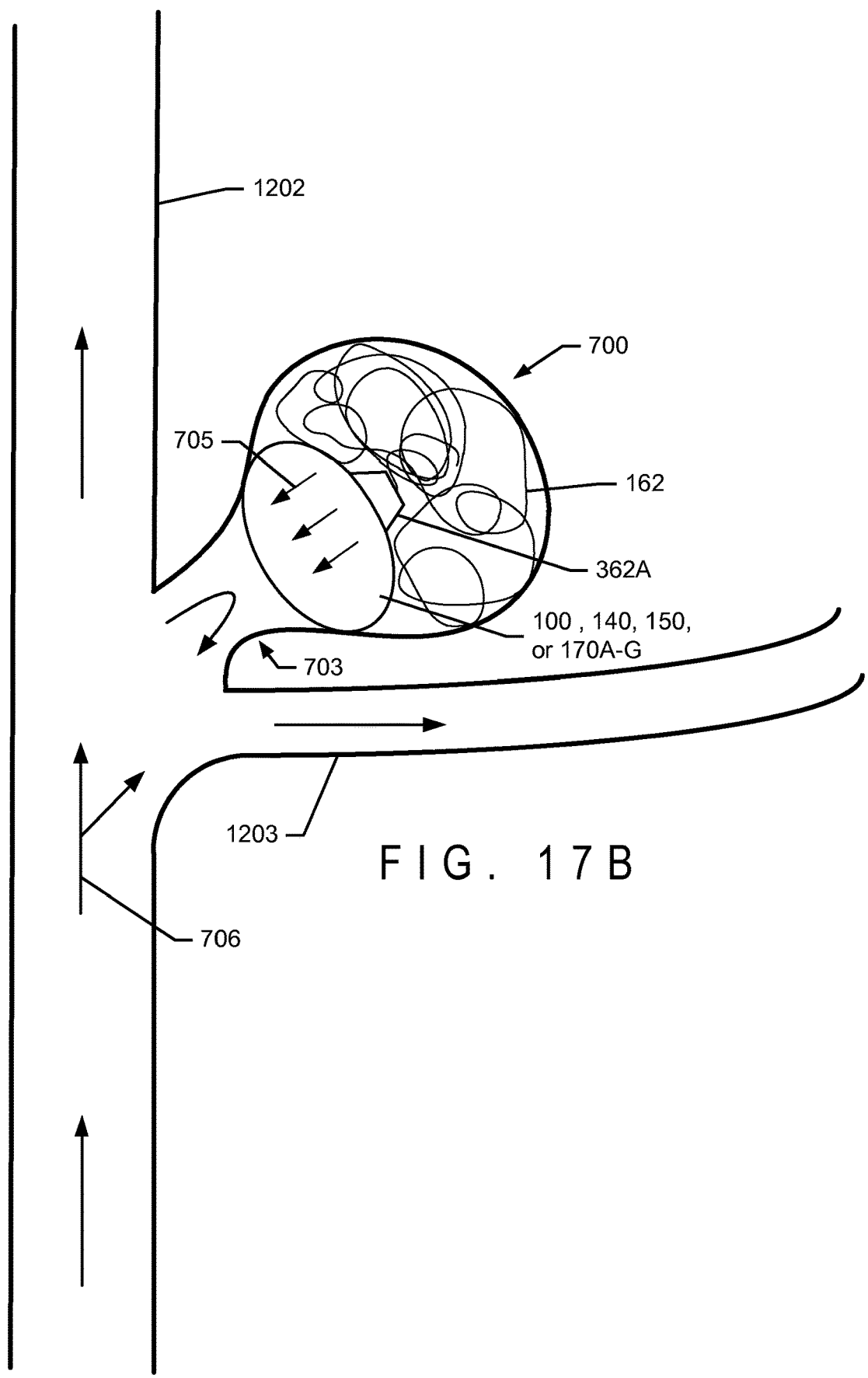

In one embodiment, as shown in FIGS. 17A-B, the expandable body 100, 140, 150, or 170A-G may be used to seal a saccular aneurysm 700 located near the junction of blood vessels 1202 and 1203. As shown, the expandable body 100, 140, 150, or 170A-G may be positioned and inflated by the delivery catheter 352A to seal the opening 703 of a saccular aneurysm 700 with the aid of a coil or accessory coil 162 that is introduced into the aneurysm by passage through the delivery catheter 352A and through the expanded expandable body. The coil or accessory coil 162 contacts the wall of the aneurysm 700 (including the wall opposite the opening from the parent vessels 1202 and 1203 to the aneurysm 703) as well as the exterior of the expandable body 100, 140, 150, or 170A-G, where the coil 162 exerts a force, as indicated by 705 upon the expandable body towards the opening 703 to press the expandable body against the opening. As a result, the expandable body 100, 140, 150, or 170A-G prevents the flow of blood, as indicated by 706, from entering the aneurysm. In one aspect, the expandable body 100, 140, 150, or 170A-G may be fully expanded before introducing the accessory coil 162. In another aspect, the accessory coil 162 may be introduced, at least partially, before inflation of the expandable body 100, 140, 150, or 170A-G. In yet another aspect, the expansion of the expandable body 100, 140, 150, or 170A-G and the introduction of the accessory coil 162 may occur simultaneously or in an alternating incremental fashion. In certain embodiments, after inflation or expansion of the expandable body 100, 140, 150, or 170A-G and insertion of the coil or accessory coil 162, the expandable body 100, 140, 150, or 170A-G is detached from the delivery catheter 352A by electrolysis that corrodes a portion of the proximal neck 250, including a ring-shaped region of exposed stainless steel.

Figure 17C:
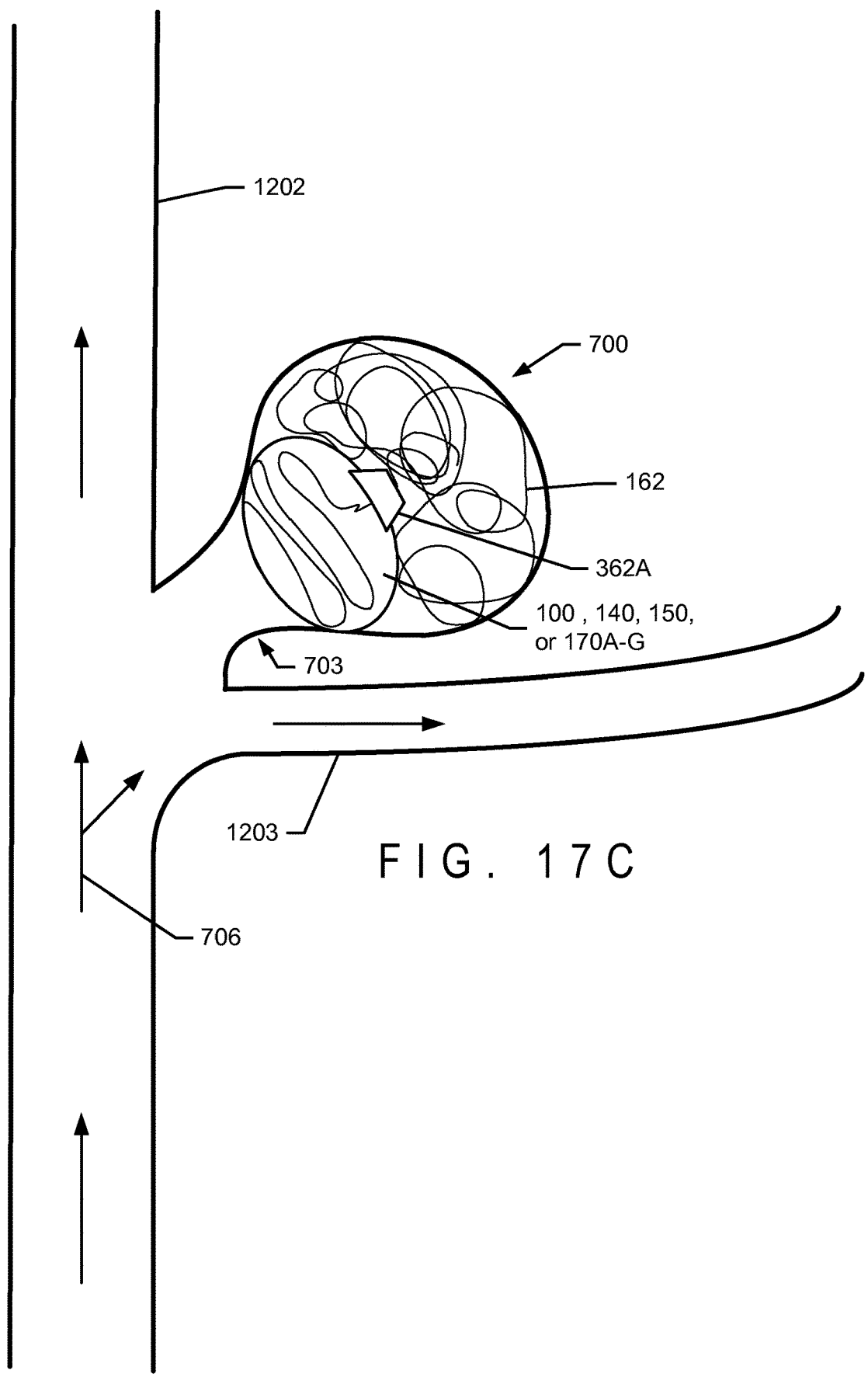
FIG. 17C is a plan view of the expandable body deployed in a bifurcation aneurysm after the insertion of an accessory coil that is positioned both within the expandable body and the void of the biological space.

In one embodiment, multiple coils or accessory coil(s) 162 may be deployed within the aneurysm 700. In one embodiment, as shown in FIG. 17C, a portion of one or more coil or accessory coil 162 is deployed within the lumen, void, or cavity of the aneurysm while another portion of the coil is deployed within the void of the expandable body 100, 140, 150, or 170A-G. For example, after inflating or expanding the expandable body, an accessory coil delivery catheter 352B may be fully inserted through delivery catheter 352A, through the expandable body 100, 140, 150, or 170A-G, and into the lumen of the aneurysm 700 and the accessory coil 162 may be inserted into the unfilled portion of the aneurysm 700. The coil delivery catheter 352B is then retracted so that its distal end is located within the expandable body 100, 140, 150, or 170A-G and the remainder of the accessory coil 162 or another accessory coil is deployed with the expandable body. The deployment of the accessory coil 162 both within and external to the expandable body 100, 140, 150, or 170A-G may serve to stabilize and maintain the position of the expandable body within the aneurysm 700.

Figure 17D:
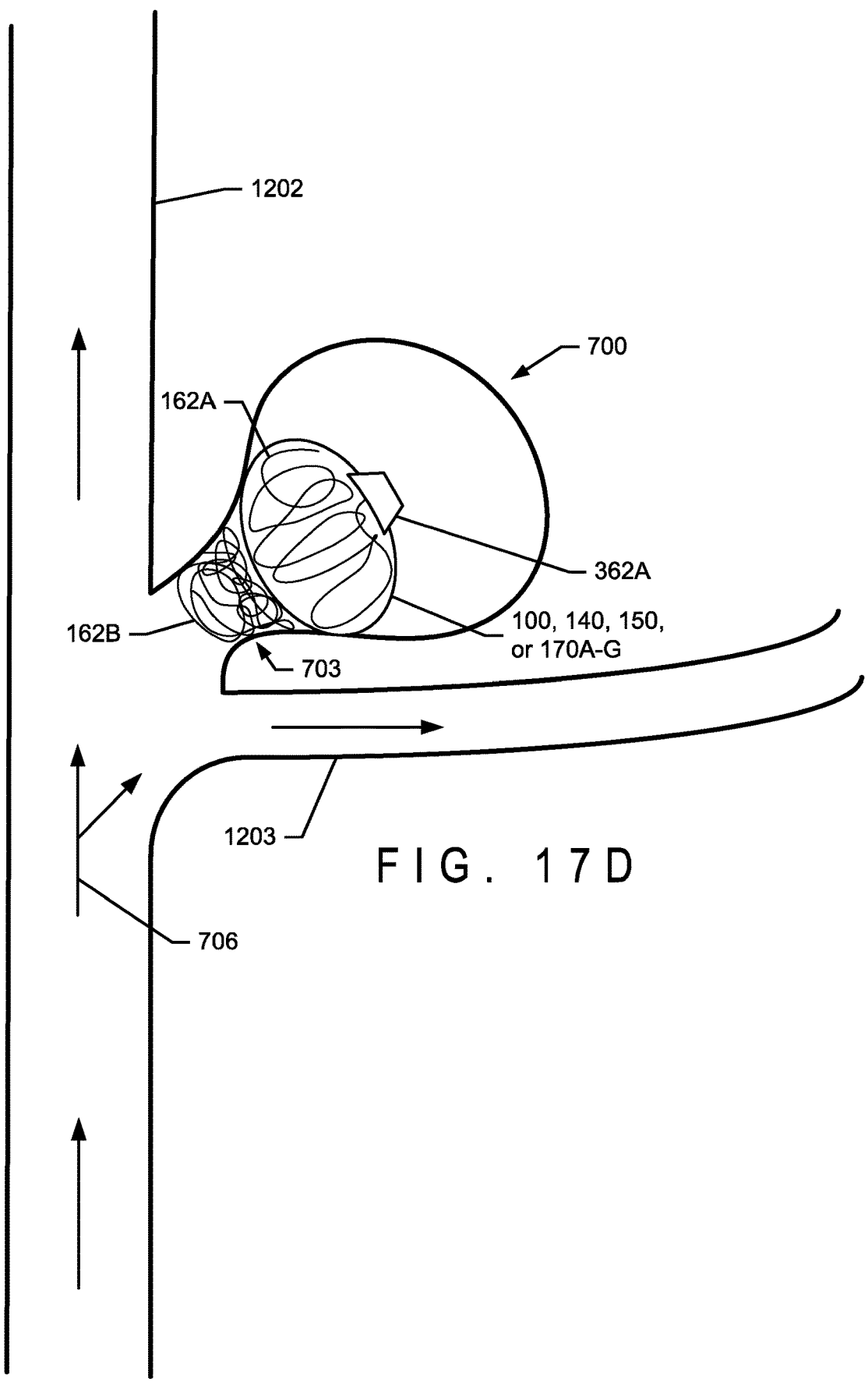
FIG. 17D is a plan view of the expandable body deployed in a bifurcation aneurysm after the insertion of a magnetic internal support structure and an external magnetic coil.

In another embodiment, the accessory coil 162 may be magnetic, such that multiple accessory coils may be deployed to stabilize the expandable body 100, 140, 150, or 170A-G within an aneurysm through the magnetic attraction of the coils. For example, as shown in FIG. 17D, a first magnetic accessory coil 162A may be deployed within an inflated expandable body 100, 140, 150, 170A-G, as previously described. One or more other magnetic accessory coils 162B are then deployed within the neck or opening 703 of the aneurysm 700. The accessory coil 162B fills and occludes any residual space in the neck or opening 703 after deploying the expandable body 100, 140, 150, or 170A-G. In one aspect, the accessory coils 162A-B are attracted to and contact the exterior surface of the expandable body 100, 140, 150, or 170A-G. In another aspect, the accessory coils 162A-B are attracted to one another through the wall of the expandable body 100, 140, 150, or 170A-G.

Figure 17E:
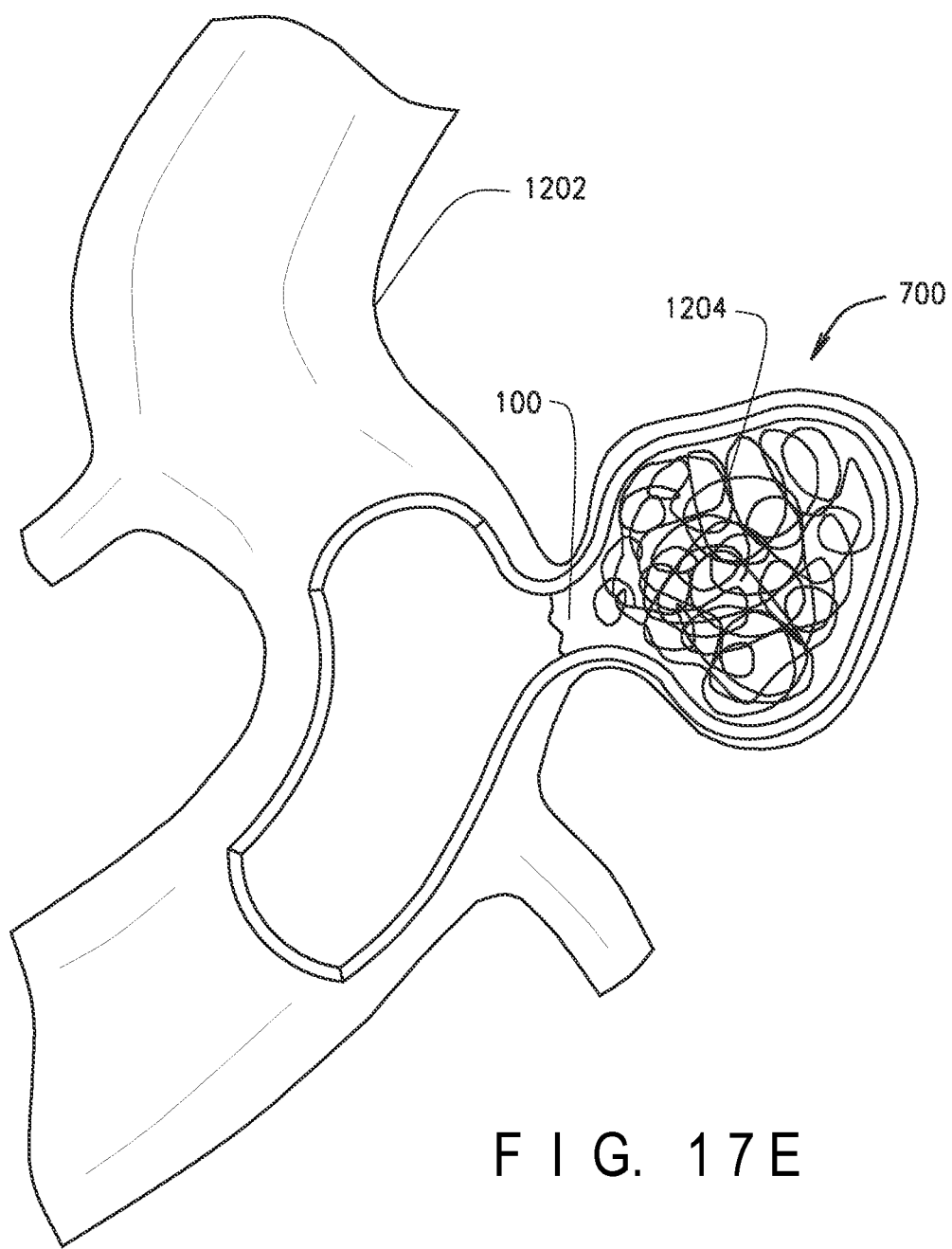
FIG. 17E is a plan view of the expandable body after the insertion of an internal support structure.

In various other embodiments, the shape of an expanded expandable body 100, 140, 150, or 170A-G is maintained by placing solid material or support structures into the central void or space 108. Examples of this solid material include metal or polymeric coils or wires, metal or polymeric solid support structures, bioresorbable materials, radially expansile materials, beads, particles, granules, spheres, microspheres, or sponges. In certain embodiments, these solid materials can also be used to help expand the expandable body 100, 140, 150, or 170A-G. In other embodiments, these solid materials are added after expansion. In one embodiment, as shown in FIG. 17E, the aneurysm 700 within the parent blood vessel 1202 is filled with a ballstent 100 containing at least one coil or expansile wire 1204. In one aspect, the expandable body 100, 140, 150, or 170A-G may be expanded by the coil or expansile wire 1204 only. In other aspects, the expandable body 100, 140, 150, or 170A-G may be expanded by a fluid medium, and the solid materials may be added later to provide support to maintain the expanded shape of the expandable body, or vice versa. Other suitable biocompatible solid materials may also be used. The solid fill members can function as a lattice to insure the structural integrity of the expandable body 100, 140, 150, or 170A-G. For example, the coil 1204 can promote the structural integrity of the expandable body 100, 140, 150, or 170A-G and reduce compression of the expandable body. In one embodiment, solid material may be designed and manufactured to match an expandable body 100, 140, 150, or 170A-G of a particular size or shape, and may be packaged as part of the medical device for use with the packaged expandable body.

In the event that the expandable body 100, 140, 150, or 170A-G is not appropriately sized or positioned for the desired treatment, the expandable body may be intentionally collapsed and recaptured. In one embodiment, where the expandable body 100, 140, 150, or 170A-G is still attached to the delivery catheter, a negative pressure can be generated within the delivery catheter to assist in the collapse of the expandable body. In this embodiment, the expandable body 100, 140, 150, or 170A-G may re-collapse due to the vacuum pressure alone.

In other embodiments, additional efforts are necessary to collapse the expandable body 100, 140, 150, or 170A-G after deployment due to the inherently stable geometry of expandable body. Additionally, structural features may be incorporated into the expandable body 100, 140, 150, or 170A-G to facilitate an intentional collapse. For example, a series of vertical grooves may be created in expandable body 100, 140, 150, or 170A-G during the electroforming process to create geometric stress concentrations that encourage collapse under sufficient vacuum pressure. In another embodiment, the exterior surface of the expandable body 100, 140, 150, or 170A-G is coated with a polymer (including a thick polymer) and then the polymer coating is etched (including by laser etching) to leave a series of "ribs", channels or grooves along exterior surface 110 of the expandable body. The grooves may be formed laterally or longitudinally around the expandable body 100, 140, 150, or 170A-G.

In other embodiments, one or more tools designed to collapse the expandable body 100, 140, 150, or 170A-G may be used. In one example, an elongated tubular collapsing tool having a number of outwardly biased or splayed "fingers" may be used. The fingers are collapsed inward when the collapsing tool is inserted into patient. When the collapsing tool is actuated, the fingers spring out radially and encircle the expanded expandable body 100, 140, 150, or 170A-G. The collapsing tool is then retracted such that the fingers engage and compress and deflate the expanded expandable body 100, 140, 150, or 170A-G. A vacuum may also be applied throughout the process to encourage collapse of the expandable body 100, 140, 150, or 170A-G.

The Expandable Body in Use

Figure 17F:
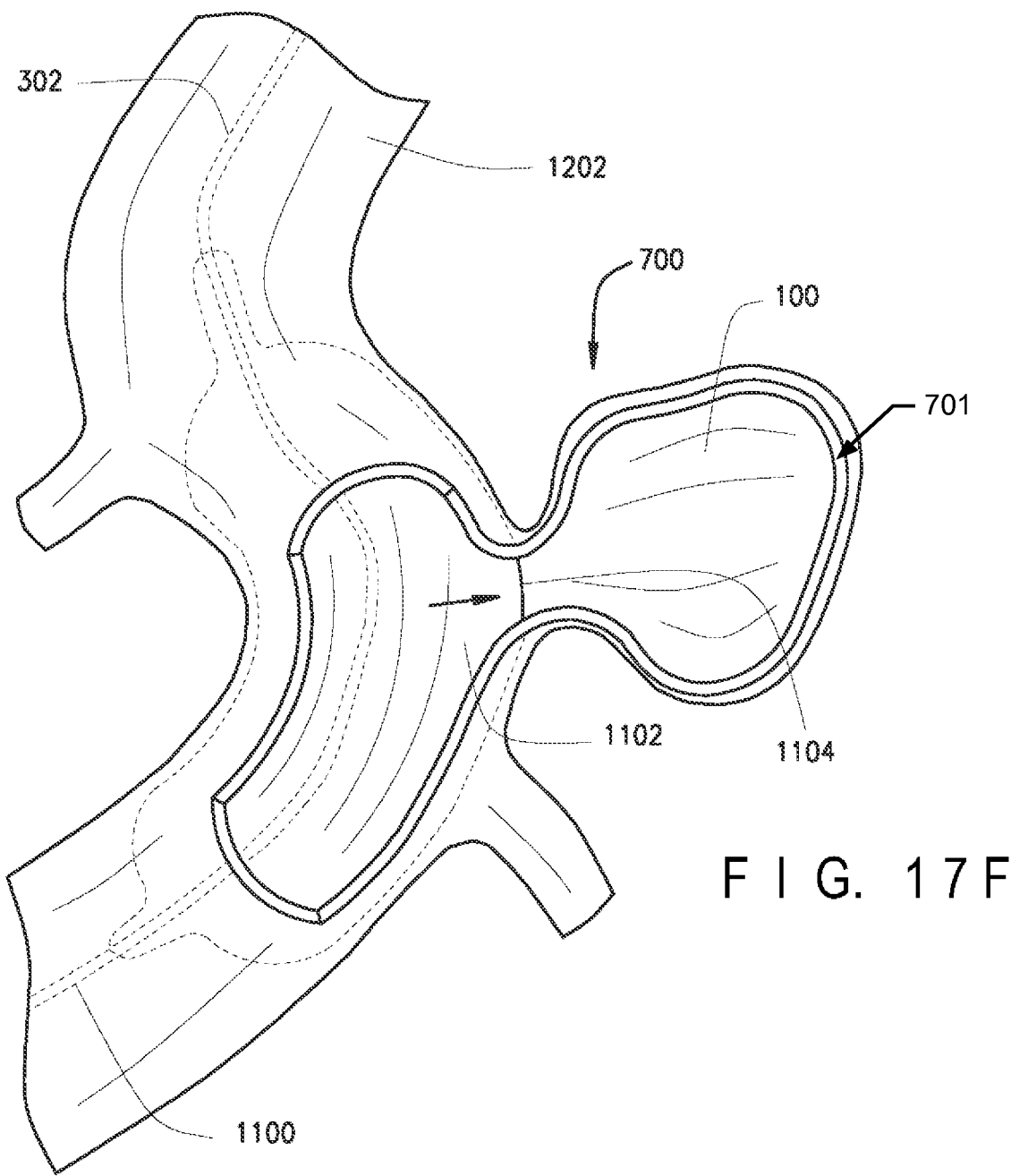
FIG. 17F is a plan view of an embodiment of the expandable body, wherein the shape of the expanded body is being changed by applying an external force using a balloon catheter.

Advantageously, as illustrated in FIG. 17F, the ballstent 100 can be delivered into the lumen, cavity, or dome 701 of a saccular aneurysm 700, expanded, and then separated from the delivery catheter 300, such that the delivery catheter can be removed while the expanded ballstent remains in place filling a portion, substantially all, or all of the lumen of the aneurysm in an expanded state. The expanded ballstent 100 will typically conform to the shape of the saccular aneurysm cavity 701 in which it is placed. The expanded ballstent 100 can also be shaped with external force, such as a physical force applied by the inflated balloon portion 1102 of an adjacent balloon catheter 1100, as shown in FIG. 17F. With precise placement and shaping, the ballstent 100 can be positioned such that the saccular aneurysm cavity 701 is completely or substantially filled and sealed, and further with none of the ballstent, or a minimal amount of the ballstent, extending into the lumen of the parent vessel 1202 from which the saccular aneurysm has formed.

When treating saccular aneurysms of various shapes, a host of expanded ballstent shapes are acceptable, including circular, oblong, and irregular, so long as the shape is generally rounded and the expanded ballstent includes a single lobe. Regardless of the formed shape, when a ballstent is expanded in the cavity 701 of an aneurysm sac 700, in one embodiment, the ballstent is designed to conform, at least partially, to the shape of the cavity.

Figure 8G:
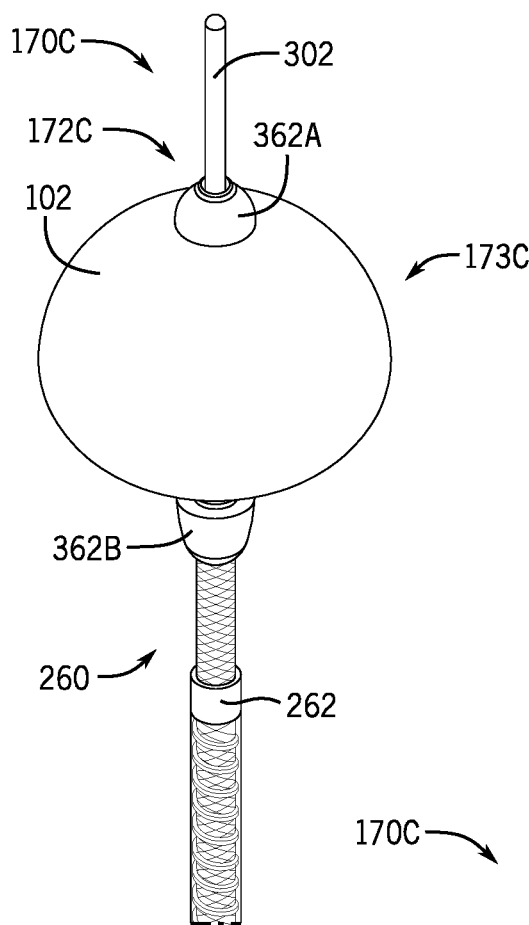
FIGS. 8G-V are views of various configurations for embodiments of an expandable body.
Figure 8H:
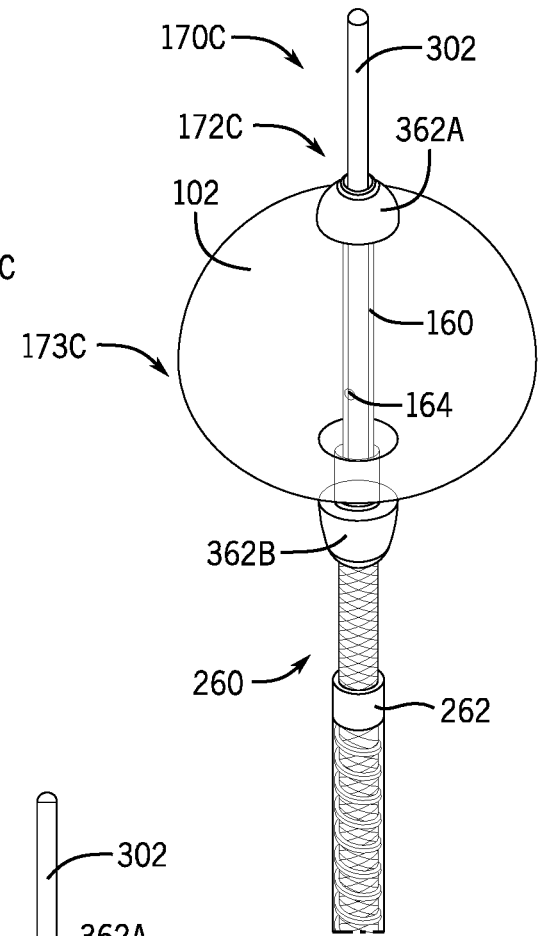
FIGS. 8A-F are planar views of various configurations for embodiments of an expandable body.
Figure 8I:
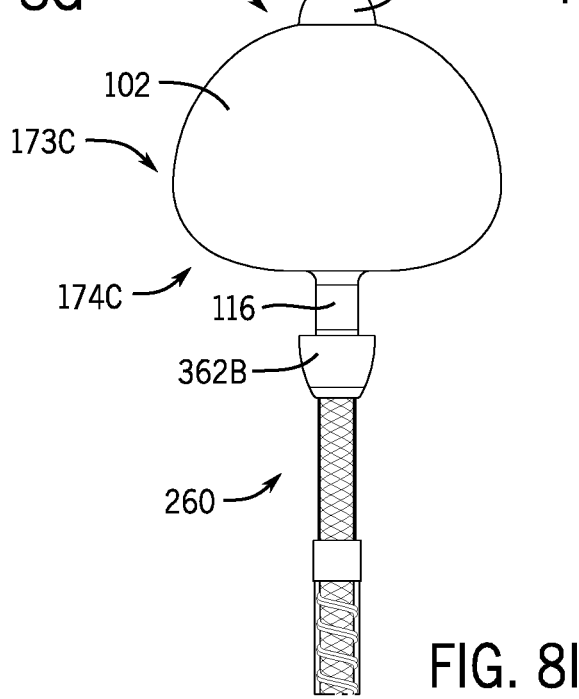
Figure 8J:
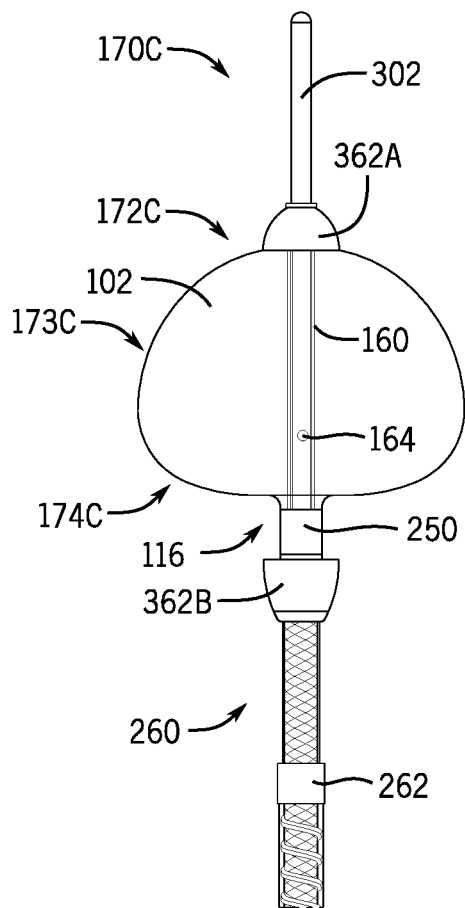
Figure 8K:
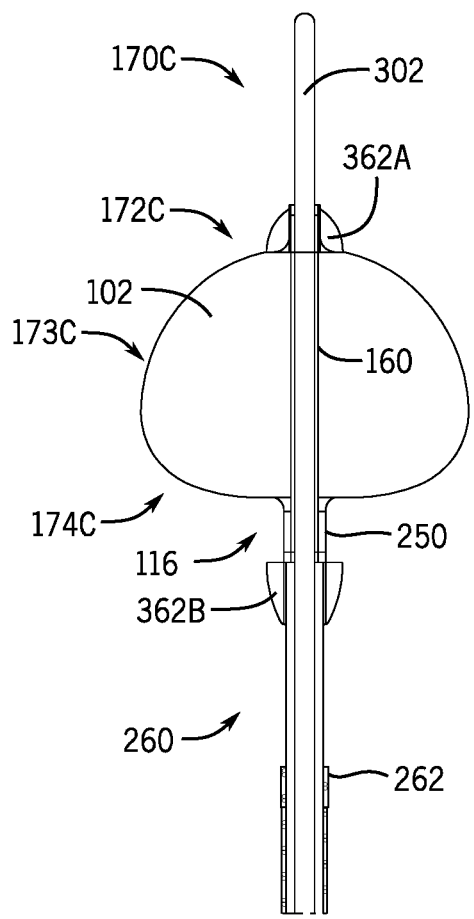
Figure 8L:
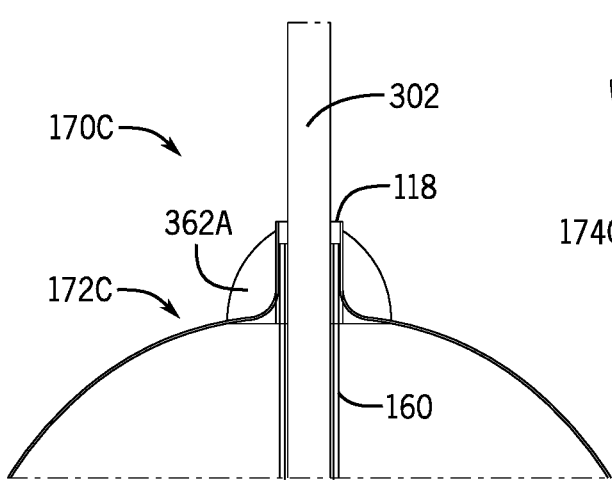
Figure 8M:
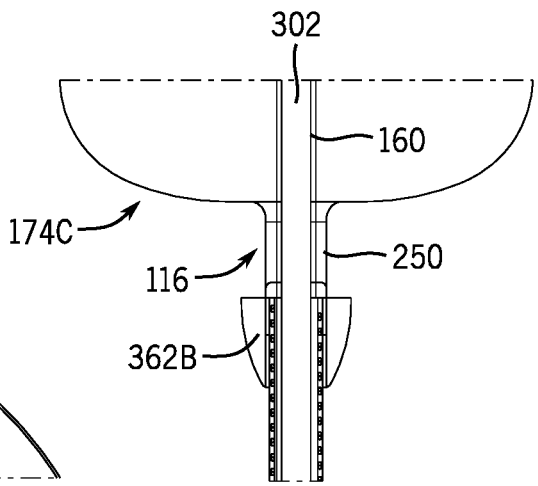
Figure 8N:
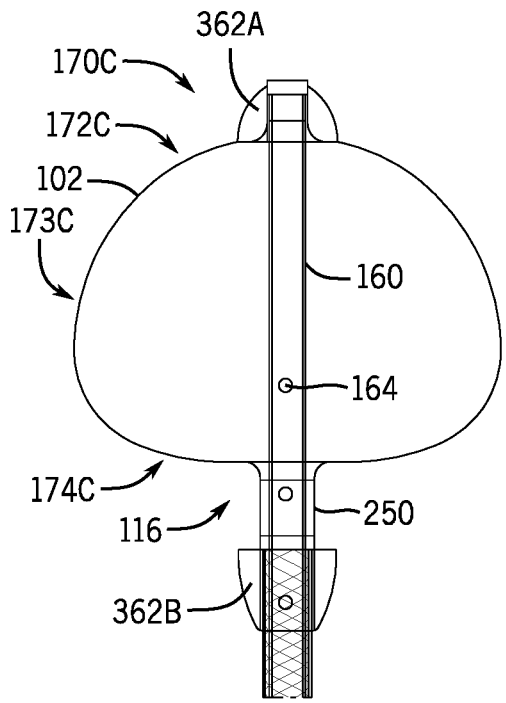
Figure 8O:
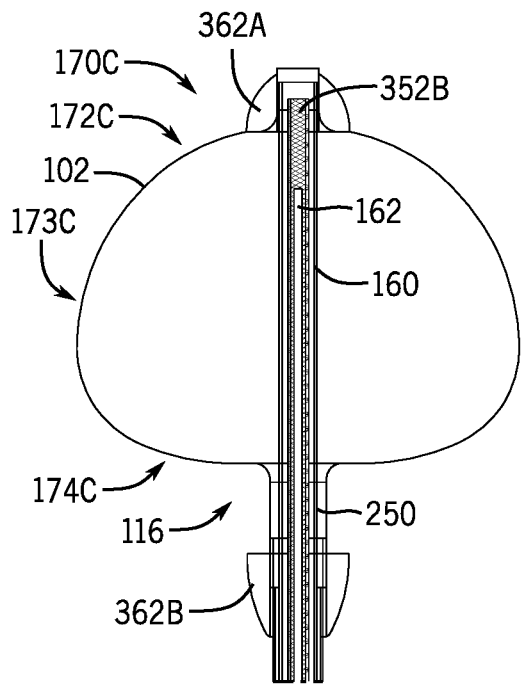
Figure 8P:
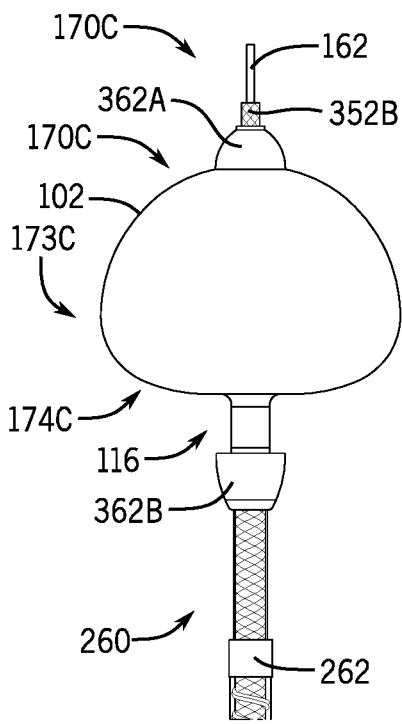
Figure 8Q:
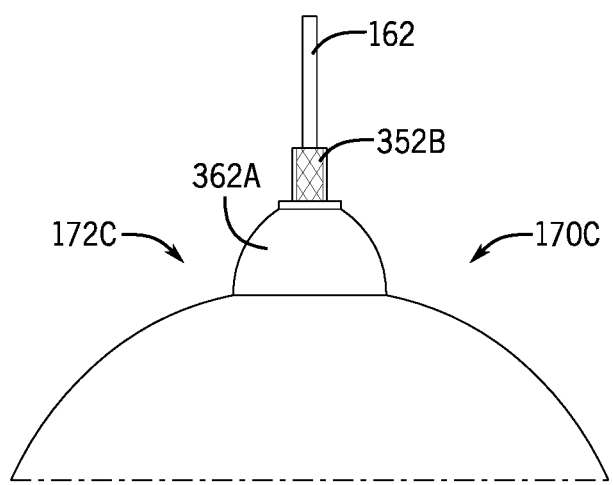
Figure 8R:
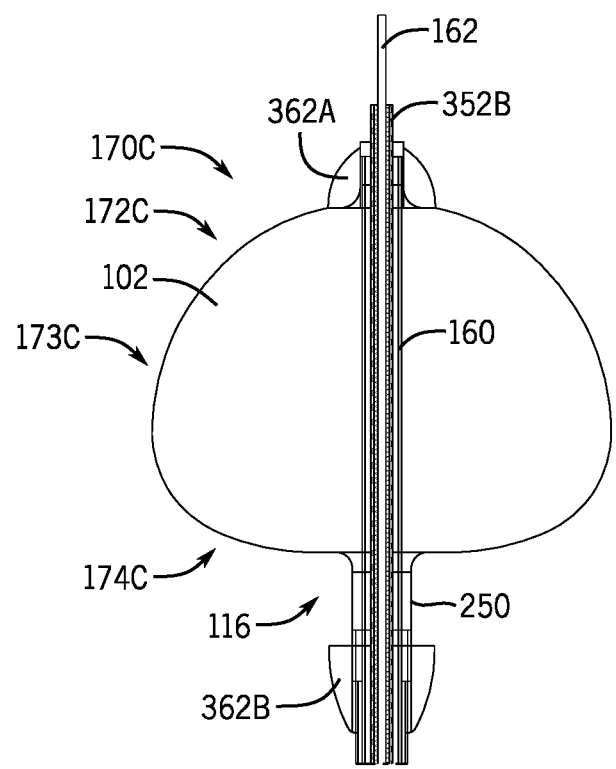
Figure 8S:
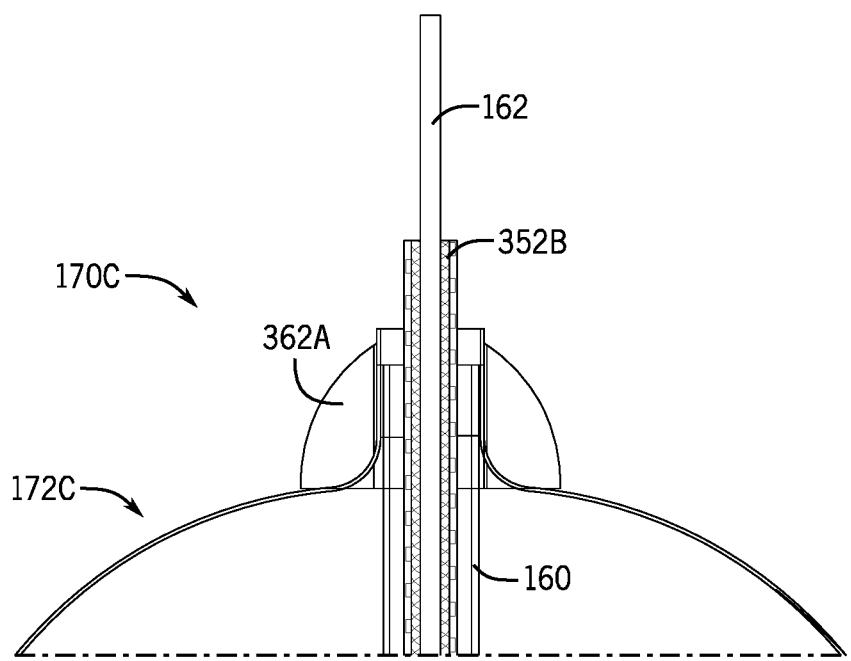
Figure 8T:
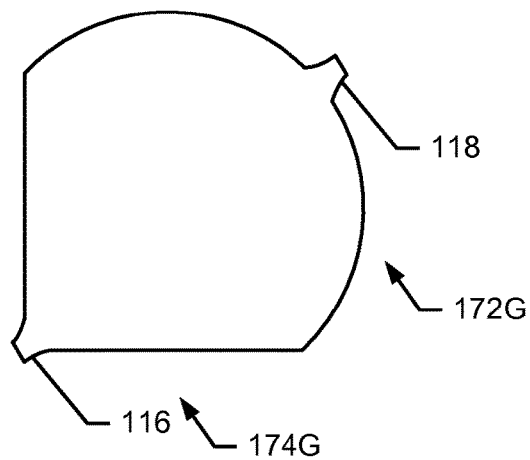
Figure 8U:
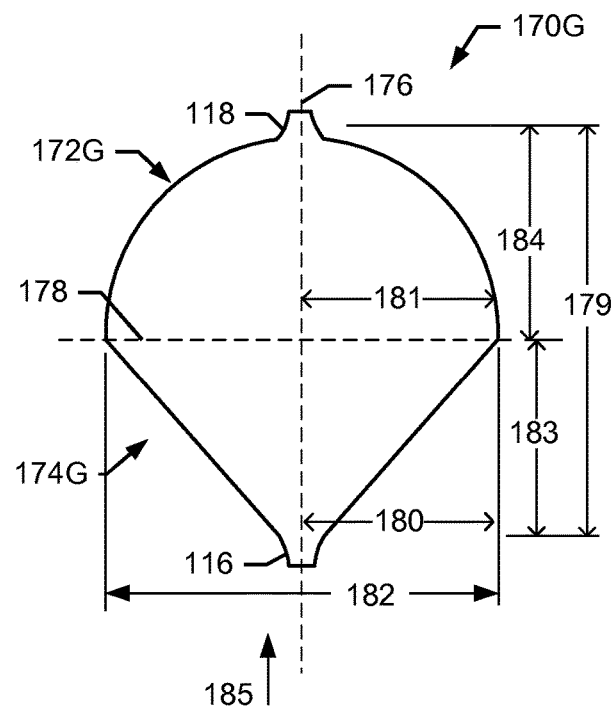
Figure 8V:
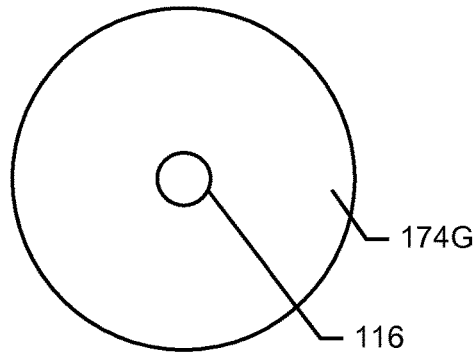
Figure 17G:
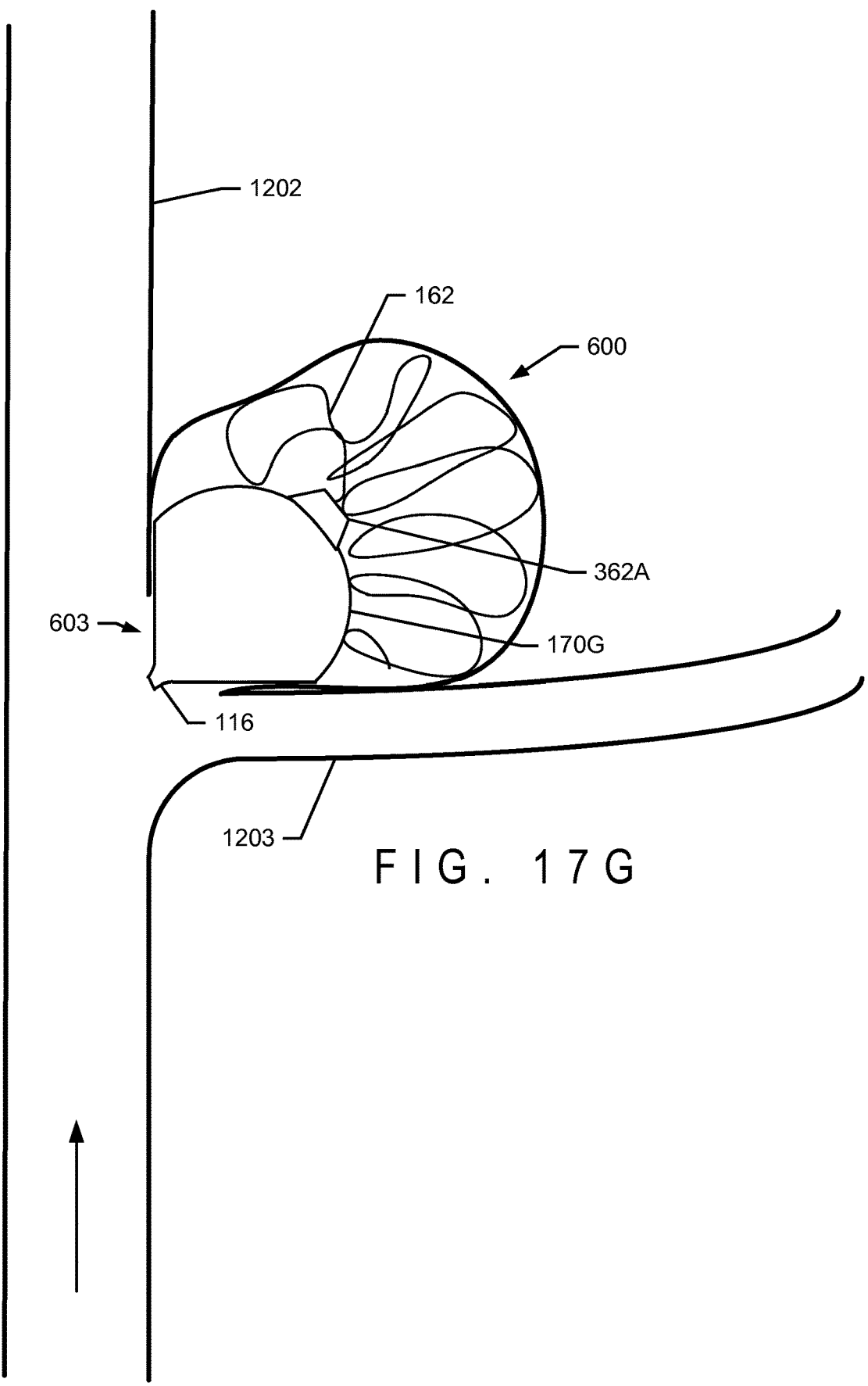
FIG. 17G is a plan view of the expandable body after insertion in a bifurcation aneurysm.

In one embodiment, the expandable body may be used to treat a bifurcation aneurysm that is located at the intersection of two or more blood vessels. As shown in FIG. 17G, a bifurcation aneurysm 600 has a neck or opening 603 that forms an approximate right angle to the blood vessels 1202 and 1203. In one aspect, the bifurcation aneurysm 600 may be treated by an expandable body 170G as shown in FIGS. 8T-V, where FIG. 8V is a view of the expandable body when the proximal region 174G is viewed along the first axis 176, as indicated by 185. The expandable body 170G includes a proximal region 174G that has generally frustoconical in configuration and a distal region 172G that has a configuration similar to any one of the distal regions 172A-G of the expandable bodies 170A-G, shown in FIGS. 8A-F and 8U. The expandable body 170G also includes proximal and distal necks 116 and 118, respectively. As shown in FIG. 17G, the frustoconical configuration of the expandable body 170G permits the expandable body to make contact and seal the perpendicular surfaces of the blood vessels 1202 and 1203 at the opening 603 of the bifurcation aneurysm 600. The deployment of coils or accessory coil(s) 162 within and/or external to the expandable body 170G may further serve to stabilize and maintain the position of the expandable body 170G within the bifurcation aneurysm 600.

Research suggests that the presence of an intact endothelium correlates with expansion of the lumen of blood vessels and aneurysms in certain clinical situations. In these settings, endothelial cells sense changes in the lumen of blood vessels or aneurysms and stimulate biological processes that lead to an increase in cellular and enzyme activity in the wall of blood vessel segments or aneurysms associated with changes in the extracellular and cellular components of the wall and expansion or enlargement of the lumen. Research has also shown that endothelial cells require flowing blood on their luminal surface to remain healthy and viable. Therefore, a medical device, system, or method that could reduce or eliminate flowing blood over the luminal surface of endothelial cells lining an aneurysm or blood vessel segment could thereby reduce endothelial cell viability, reduce biochemical signaling from endothelial cells, and cellular, and reduce enzymatic activity associated with blood vessel or aneurysm expansion or enlargement, which is an important goal in preventing or treating aneurysms. Given this, in certain embodiments, the ballstent 100 is fully expanded to treat a saccular aneurysm. In addition to the physical nature of the filling and blocking effect of the expanded ballstent in the aneurysm sac, this treatment also reduces endothelial viability in the aneurysm sac. In other embodiments, the ballstent 100 need not be fully expanded to treat a saccular aneurysm, but may successfully seal the aneurysm or reduce endothelial cell viability while partially expanded. In all embodiments, the ballstent remains in an expanded state (partially or completely) after detachment from the delivery catheter. An expanded state refers to the at least partial distention of the ballstent 100, such as at least 20%, 50%, 75%, or 90% and up to 100% of the maximum ballstent volume. In various aspects, the size of the biological space may be determined by any suitable method. The size and configuration of the expandable body 100, 140, 150, and 170A-G is then selected to best fill the space or the desired portion of the space.

In various embodiments as explained below with reference to FIGS. 11A-F and 15A-F, the expandable body 100 or 140 is positioned within the saccular aneurysm and inflated to an expanded state. In this embodiment, the expandable body 100 or 140 is dimensioned to have an expanded width or diameter (as measured transverse to the axis extending from the proximal nose cone 362B to the distal nose cone 362A) that is greater than the width of the opening 703 of the aneurysm from the parent vessel 1202. After inflation or expansion, the expandable body 100 or 140 is retracted towards the opening 703 of the aneurysm, and a coil or accessory coil 162, as shown in FIGS. 11E and 15E, is delivered through the delivery catheter and also through the expandable body 100 or 140 and positioned within the aneurysm 700 in the region of the dome 701 via the distal neck 118. The accessory coil 162 contacts both the inner surface 704 of the wall of the aneurysm 700, as shown in FIGS. 11E and 15E, and the external surface of the expandable body 100 or 140, including the distal surface of the expandable body. The accessory coil 162 exerts a force against the expandable body 100 or 140 to push the expandable body against the opening 703 of the aneurysm 700. In one embodiment, the accessory coil may be slightly magnetic such that it is attracted to and stays in contact with the expandable body 100 or 140, without undesirable biological or physiological effects.

As shown in FIGS. 11F, and 17B, the expandable body 100, in conjunction with the accessory coil 162, function similar to a poppet valve to seal the aneurysm opening 703. In particular, the expandable body functions like a plug that covers the aneurysm opening 703, while the accessory coil 162 functions as a spring to apply constant force on the expandable body 100.

In various embodiments, the accessory coil 162 is composed of nitinol. In one aspect, the accessory coil 162 may be formed from wires having a diameter in the range of approximately 0.05 mm to approximately 0.20 mm. The nitinol wires may further be coated with a polymer 161, including but not limited to PTFE, as shown in FIG. 3B. In one aspect, the coated nitinol wires or fibers of the accessory coil 162 may include an end-cap 163, including a polymeric end-cap, as shown in FIG. 3A, to minimize the potential for injury to aneurysm surface or other vessels traversed by the coil. The coating and the end caps may also reduce friction when inserting the coil with an accessory coil delivery catheter 352B, as shown in FIG. 7. In various embodiments, the accessory coil 162 may have a diameter in a range between approximately 0.002 and 0.012 inches. Preferably, the accessory coil 162 has a diameter between approximately 0.004 and 0.008 inches. Similarly, the polymer coating 161 on the accessory coil 162 may have a thickness in a range between approximately 0.001 and 0.003 inches. Preferably, the polymer coating has a thickness between approximately 0.0015 and 0.002 inches. The coil delivery catheter 352B may have an outer diameter in a range between approximately 0.014 and 0.022 inches, and preferably, an outer diameter between approximately 0.016 and 0.020 inches. Similarly, the coil delivery catheter 352B may have an inner diameter in a range between approximately 0.008 and 0.016 inches, and preferably, an inner diameter between approximately 0.010 and 0.014 inches.

Figure 12A:
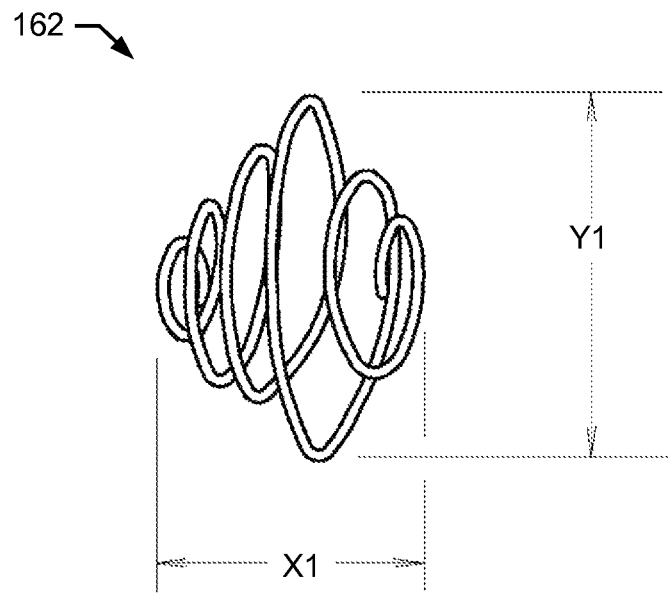
FIGS. 12A-B are perspective views of an embodiment of an accessory coil.
Figure 12B:
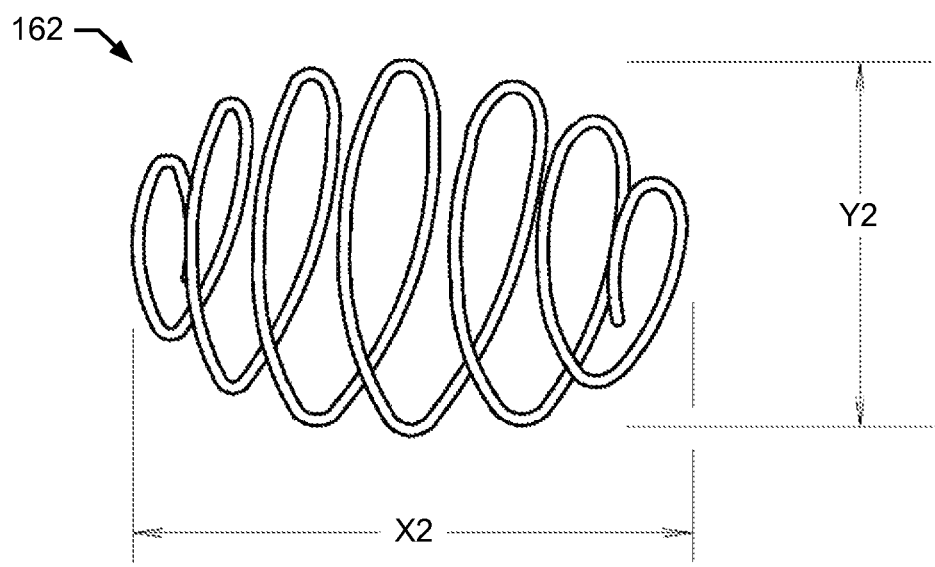

In one embodiment, the accessory coil is delivered into the aneurysm and allowed to fill the void in the aneurysm not occupied by the expandable body. In another embodiment, the accessory coil is pre-formed into a spherical shape having dimensions X1×Y1 as shown in FIG. 12A or is pre-formed into an oval shape having dimensions X1×Y1 or X2×Y2, as shown in FIG. 12B. By way of example, the accessory coil 162 may be formed into an approximately 8 mm diameter ball or an approximately 8 mm×4 mm spheroid. In other examples, the accessory coil may be configured into three-dimensional construct having a volume between approximately 50 mm³ and 300 mm³.

Forming the Expandable Body

In an exemplary method of forming the expandable body 100, 140, 150, or 170A-G, the central layer 122 of the wall 102 may be formed by vapor deposition, wherein vapors from one or more polymers, pure metals, metal alloys, or layers thereof, are condensed upon a substrate or mold (e.g., mandrel). The mold may be removed to provide a hollow shell formed of the pure metal or metal alloy.

In a preferred embodiment, the central layer 122 of the wall 102 is formed by electroforming or electroplating a metallic shell over a removable form or mold (e.g., mandrel). For example, as shown in FIGS. 25A-C, a multi-part mandrel 3200 for electroforming the expandable body 100, 140, 150, or 170A-G is shown in partial cross-section. The mandrel 3200 includes a steel base 3202 and form member 3204 that is removable from the base. Preferably, the form member 3204 is composed of a rigid material, including but not limited to aluminum or stainless steel. Although shown as a sphere, other embodiments of the form member 3204 may be other shapes, including but not limited to the shape of a partially pleated or partially folded body 3204 that results in an expandable body 100, 140, 150, or 170A-G having a configuration intermediate to the deliverable (i.e., fully collapsed or pleated and folded) configuration and the fully expanded configuration, such a partially pleated mandrel 3204 being depicted in FIG. 26. In addition, the protrusions 1800, as shown in FIGS. 18G-H, may be fashioned onto the form member 3204, such that the protrusions 1800 are formed during the electroforming or electroplating process. The form member 3204 may be spherical as shown in FIGS. 25A-B and 27 to form a spherical expandable body 100, or 150. Similarly, the form member 3204 may be oblong, a cylindrical body having hemispherical ends, or any other shape to form the expandable bodies 140 and 170A-G. In various embodiments, the mandrel 3200 or at least the removable form 3204 is sacrificial, such that it is consumed during the process of forming the expandable body 100, 140, 150, or 170A-G.

To form a metal expandable body, the form member 3204 is removed from the base 3202. A portion of the form member 3204 may be threaded so that it can engage a threaded spindle 3206 extending from the base 3202. After the form member 3204 is detached from the base 3202, a metallic ring 3208 is positioned on the threaded spindle 3206. In one embodiment shown in FIG. 27, the threaded spindle 3206 includes a shoulder 3212 that has a diameter greater than that of the threaded spindle 3206, such that the metallic ring 3208 can be seated in a desired position.

The metallic ring 3208 is a non-sacrificial component of the mandrel 3200. In one embodiment, the metallic ring 3208 is any biocompatible metal that is reactive to electrolysis. For example, the metallic ring 3208 may be composed of gold, 316L stainless steel, or 304 stainless steel. Preferably, the metallic ring comprises 304 stainless steel, as 304 stainless steel has lower nickel content than 316L stainless steel and will minimize the risk of cytotoxicity during electrolysis. In some embodiments, 304 stainless steel is preferred as it has a pitting potential (approximately 0.18 V-0.38 V relative to a reference electrode) that is lower than the hydrolysis potential of water (approximately 0.82 V). Therefore, electrolysis with 304 stainless steel may be performed under more controlled conditions with more repeatable results than electrolysis performed with 316L stainless steel or gold, whose pitting potentials (approximately 0.98 V-1.18 V and approximately 0.7 V-0.9 V, respectively) exceed the hydrolysis potential of water.

In various embodiments, the metallic ring 3208 is between approximately 0.025 inches and approximately 0.150 inches in length, with a wall that is between approximately 25.4 μm and approximately 254 μm thick. In one embodiment, the metallic ring 3208 is 0.05 inches in length. A gold plating or coating may optionally be applied to at least a portion 3210 of the metallic ring 3208 to encourage the deposition of gold that will be used to form a gold expandable body. Similarly, a plating or coating composed of another metal, including but not limited to platinum, may be used to encourage the deposit of the other metal. As such, the metallic ring 3208 will be integrated into the expandable body 100, 140, 150, or 170A-G and form all or a portion of the neck 116 or 118 of the expandable body. A non-conductive polymer joint may be placed between the neck 116 or 118 and the rounded body portion of the expandable body 100. This joint will provide additional flexibility to the expandable body 100, as well as further insulating the expandable body from the electrolysis current used to detach various embodiments of the expandable body.

Once the metallic ring 3208 and the form member 3204 are positioned on the threaded spindle 3206, the mandrel 3200 is placed in an electrolyte bath (not shown) containing metallic ions, such as gold, where the gold ions are deposited on the form member and at least a portion of the metallic ring 3208. In particular, the mandrel 3200 is positioned such that the expandable body 100, 140, 150, or 170A-G is electroformed over the form member 3204 and the portion of the metallic ring 3208 having the gold flash, thereby bonding the metallic ring to the expandable body. In some embodiments, a portion of the metallic ring 3208 is not coated by gold, including methods that use masking before electroforming.

In various embodiments and as can be understood from FIGS. 16A-D, the thickness 120 of the ballstent wall 102 can be controlled by varying the electroforming process. For example, by adjusting the duration of the electroforming process, walls of greater or lesser thickness may be formed. Similarly, the wall thickness 120 may be varied in certain locations by applying one or more masks to the mandrel 3200. In addition, the location of the mandrel 3200 relative to the anode in the solution bath will also affect the thickness of the wall. For example, an internal feature at the neck of the expandable body 100, 140, 150, or 170A-G may have a thinner wall than the rounded spherical portion of the expandable body. The expandable body 100, 140, 150, or 170A-G may be formed intentionally with a thinner, and therefore weaker, neck region that can be severed to separate the expandable body from the neck 116, including a neck that includes the metallic ring 3208. Alternatively or additionally, a stress concentration ring in the form of a line or strip may be defined in the neck or in the proximal portion 208 of the expandable body 100, 140, 150, or 170A-G, more specifically, a ring-shaped region of exposed metal (e.g., stainless steel portion of the ring 3208 or a gold portion of the neck 116) to help facilitate separation of the delivery device or catheter from the expanded expandable body at the ring-shaped region of the exposed metal. Such a stress concentration line may be formed into the ring-shaped region of the exposed metal by various methods including by laser etching, by various mechanical operations such as sawing or grinding, or by electrolysis.

After formation, the expandable body 100, 140, 150, or 170A-G and the form member 3204 are removed from the mandrel base 3202, where the form member is removed to leave only the metallic ring 3208, which may form all or a portion of a the proximal neck and the remainder of the expandable body, which may include the main body and optionally a distal neck, as shown in a partial cross-section in FIG. 28. In one embodiment, the aluminum form member 3204 is removed though the neck 116 by chemical and/or thermal leaching or etching. In another embodiment, a hole is drilled into the aluminum form member 3204 though the neck 116 by mechanical operations, such as, but not limited to, drilling with an auger bit. The hole may be used to accelerate and regulate the chemical etching process to remove the aluminum form member 3204 from the expandable body 100, 140, 150, or 170A-G. Preferably, combinations of mechanical, chemical, and thermal methods are used to ensure that all of the constituents of the form member 3204 are removed. It is desirable to completely remove the form member 3204 from the expandable body 100, 140, 150, or 170A-G to ensure sufficient plasticity or malleability of the expandable body and to minimize any toxic effects after implantation, such as may be the case specifically when the expandable body comprises residual aluminum.

To reduce the presence of stress concentrations regions or surface variations of the expandable body 100, 140, 150, or 170A-G and to eliminate the transfer of concentric machine marks from the form member 3204, the mandrel 3200 and in particular the form member may be polished or lapped before electroforming the expandable body. An unpolished form member 3204 and a resulting gold expandable body 100, 140, 150, or 170A-G are shown in FIGS. 29A and 29B, respectively. Conversely, a polished form member 3204 having a lapped finish and the resulting gold expandable body 100, 140, 150, or 170A-G are shown in FIGS. 29C and 29D, respectively. In one embodiment, polishing the form member 3204 reduces the distance between the highest and lowest points of surface imperfections or features to approximately 0.1 µm or less.

Once the form member 3204 has been removed from the expandable body 100, 140, 150, or 170A-G, the expandable body may undergo an annealing process to improve the pliability of the expandable body. In one embodiment, the expandable body is heated to approximately 300° C. for approximately 1 hour and then immediately quenched in a bath of distilled water at room temperature. In other embodiments, the expandable body 100, 140, 150, or 170A-G is folded or otherwise deformed after a first annealing process and then subjected to one or more additional annealing processes. In further embodiments, the expandable body 100, 140, 150, or 170A-G is coated on the external surface, including coating with a polymer such as Parylene, and then subjected to one or more annealing processes.

The interior and exterior surfaces of the expandable body 100, 140, 150, or 170A-G may be cleaned to remove any contaminants remaining from manufacture. For example, in one embodiment, the expandable body 100, 140, 150, or 170A-G is placed in an ultrasonic cleaner that contains an isopropyl alcohol bath for approximately 10 minutes. The expandable body 100, 140, 150, or 170A-G is then removed from the bath and injected with distilled water to remove any contaminants remaining in the interior of the expandable body. Optionally, the expandable body 100, 140, 150, or 170A-G may be dried in a vacuum oven held at approximately 90° C. In various embodiments, the exterior surface, and optionally the interior surface, of the expandable body may be plated with platinum to reduce the potential for undesired reactivity with a patient during deployment, including to reduce the potential for electrolysis on the surface of the main body or distal neck of the expanded expandable body.

Figure 30A:
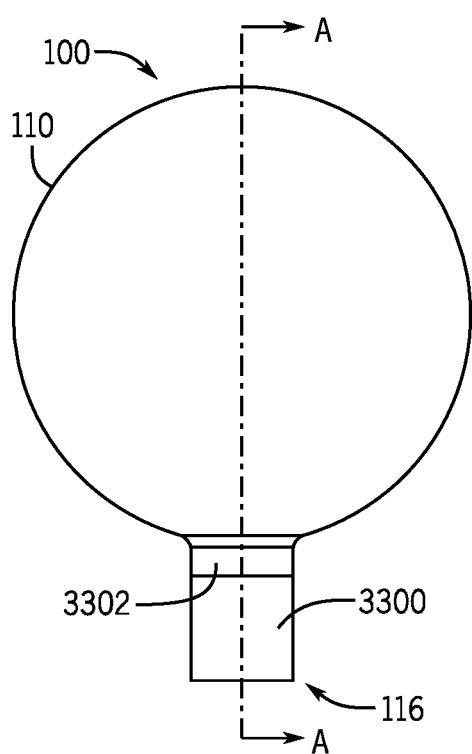
FIGS. 30A-B respectively depict coatings on an exterior surface and an interior surface of a spherical embodiment of an expandable body.
Figure 30B:
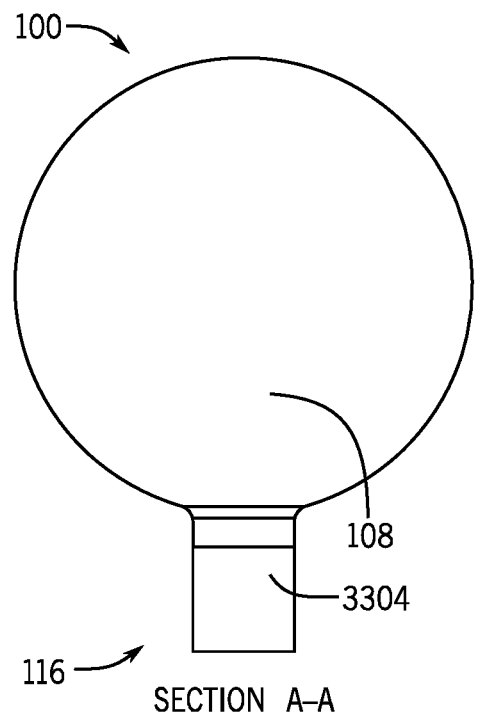

As shown in FIGS. 16D, 30A, and 30B, the exterior surface 110 of the ballstent 100, the interior surface 106, or both can be coated with a polymer such as Parylene or an acrylic polymer. The polymer can be added by incorporating a pre-formed material into the desired orientation, by vapor deposition, or other methods. In some embodiments, at least a portion of the neck 116 or the interior surface 3304 of the metallic ring 3208 is not coated. In one embodiment, the ballstent 100 may be annealed, as previously described, at least once after the application of the non-metallic coating.

In embodiments of the expandable body 100, 140, 150, or 170A-G where the wall 102 is composed of a material that his highly non-reactive during electrolysis, such as platinum, the interior and exterior of the neck 116 or 118 may be coated, while the remaining surfaces are not coated. Similarly, in some embodiments where the expandable body 100, 140, 150, or 170A-G will be detached by an operation other than electrolysis, only the interior surface 106 may be coated with the non-metallic coating.

In some embodiments, after coating, a portion of the polymer coating is removed from the exterior surface 3300 to expose the metal surface in a strip or ring configuration, as shown in FIGS. 30C-F. In other embodiments, the exposed metal surface may be formed by masking this region before coating, and then removing the masking material. Electrolysis can be used to separate the expanded expandable body from the remainder of the neck 3300 and the delivery catheter at the region comprising the exposed metal surface. The width W of the detachment site (i.e. the exposed metal surface in a strip or ring configuration) 3302 may be in a range between about 0.1 mm and about 0.4 mm. The detachment site W may be located anywhere along the length N1 of the neck 116. In some embodiments W may be located in the region of the neck formed by the metallic ring 3208. In one particular embodiment, the exposed strip of the detachment site 3302 has a width W of 0.25 mm±0.03 mm and is located at a length N5 of approximately 0.51 mm±0.03 mm from the end of the neck 116. The metallic strip may be exposed by any suitable method, including but not limited to laser etching or laser ablation. In other embodiments, the metallic strip of the detachment site 3302 may be exposed before or after the folding or compression of the expandable body 100, 140, 150, or 170A-G. By way of example and not limitation, in one embodiment, the exposed metal in the region 3302 is gold, while in other embodiments the exposed metal is stainless steel.

In various embodiments, the wall 102 of the expandable body 100, 140, 150, or 170A-G is perforated to create a plurality of microperforations 1300, as shown in FIG. 16B. By way of example and not limitation, the microperforations 1300 may be created by laser perforating the wall 102. The microperforations 1300 or pores may range from approximately 1 µm to approximately 500 µm in diameter and may extend completely through the thickness of the wall 1022 from the interior void 108 to the exterior surface 110. Alternatively, a microperforated expandable body 100, 140, 150, or 170A-G may be formed during the electroforming process, such as with the use of a masking pattern.

After perforating, the expandable body surfaces 110 and 106 may be coated with a polymer that does not completely cover the microperforations 1300, thereby leaving channels between the inner and outer surfaces. Alternately, the expandable body 100, 140, 150, or 170A-G may be laser perforated after coating. The microperforations 1300 permit the exchange of fluid between the interior void 108 of the expandable body 100, 140, 150, or 170A-G and the environment exterior to the expandable body.

In various embodiments, as shown in FIGS. 16C-D, the exterior layer 104 may be formed on the outside of the central layer 122 of the expandable body 100, 140, 150, or 170A-G by additional electroplating or electroforming, by vapor deposition, or by sputter deposition, wherein material is eroded from a target (e.g., a metal or metal alloy) and is then deposited onto a substrate (e.g., a mandrel or mold) forming a thin layer on the substrate. Similarly, an interior layer 214 may be formed on the inside of the central layer 122 of the expandable body 100, 140, 150, or 170A-G by additional electroplating or electroforming, or by vapor deposition, or by sputter deposition.

In various embodiments, an additional polymer coating is applied to the expandable body 100, 140, 150, or 170A-G to modify the strength and flexibility characteristics of the wall 102. For example, polymer may be applied via dip, spin, or spray coating, or through deposition processes specialized for the specific polymer to provide additional strength or flexibility to the wall. The additional coating may be Parylene, biocompatible polyurethanes, PTFE, and silicone, among others. In one embodiment, this coating can be limited to the neck 116 or 118 of the expandable body 100, 140, 150, or 170A-G by using a mechanical or chemical template. In various embodiments, detailed geometries and designs can be laser etched into the reinforcement coating to further optimize the wall properties with the folding geometry. Further, the removal of the reinforcement coating in regions where it is not needed would also remove unnecessary material from the final diameter of the collapsed and wrapped expandable body 100, 140, 150, or 170A-G.

The wall 102 of the main body of the expandable body 100, 140, 150, or 170A-G may be formed by different methods than the neck 116. As shown in FIGS. 16C-D, the central layer 122 of the expandable body 100, 140, 150, or 170A-G may be formed by different methods than the exterior layer or coating 104 or the interior layer or coating 214. In various other embodiments, the expandable body 100, 140, 150, or 170A-G may be formed by manipulating and securing one or more sheets of metal in the desired configuration to form the wall 102 and/or the exterior layer 104. These two-dimensional sheets may further comprise rubber, plastic, polymer, woven or knitted fiber materials, or other materials, or combinations thereof. By way of example and not limitation, one or more two-dimensional sheets of a metal may be folded into an expandable body shape and welded, soldered, glued, or bonded together. Similarly, two-dimensional sheets of material may be manipulated and secured to form the exterior layer 104 or the interior layer 214.

In another embodiment, a stainless steel (SST) ring 250, as shown in FIGS. 2A, 2B, 5A, and 5B is attached to the proximal neck 116 via welding after the formation of the expandable body 100, 140, 150, or 170A-G. In other embodiments, the entire neck 116 may be stainless steel and may be incorporated during the formation of the expandable body or subsequently welded to the body. The SST ring 250 or the SST neck 116 may be composed of any biocompatible stainless steel alloy, including but not limited to 300 series stainless steel or 400 series stainless steel and preferably 304, 316, 316L, or 316LVM stainless steel.

The SST ring 250 may be subjected to one or more heat-treating processes to make the SST ring more sensitive to the galvanic corrosion caused by electrolysis. Therefore, the heat-treating processes allow the SST ring 250 to be severed more easily thereby decreasing the time necessary to detach the expandable body from the delivery catheter. In one aspect, the SST ring is heated by laser etching the surface of the SST ring. The SST ring 250 is also heated by the welding process to attach the ring to the proximal neck 116. It is believed that the heating processes of welding or laser etching can sensitize the SST ring 250 to the galvanic corrosion of electrolysis.

In one embodiment, the SST ring 250 may be included in an elongated electrolysis segment 260, as shown in FIGS. 2A-B, 2D-I, 2K-N, 2P-Q, 6A-D, 8G-K, 8P, 10B, and 14B. In this embodiment, the electrolysis segment 260 is a coil segment, similar to a catheter or guide wire that is attached to the distal portion of a delivery catheter 400 that has been modified to include a cathode ring 262 and at least a portion of the SST ring 250 that serves as the anode for electrolysis. Similar to the thermoset polymer segment 1020, described below with reference to FIGS. 23H-I, the electrolysis segment 260 includes an insulating coating 264 that separates a ring cathode electrode 262 and the SST ring anode 250. In another embodiment, the electrolysis segment 260 may be fabricated independently and then affixed to the delivery catheter 400 using any suitable method. By way of example and not limitation, the methods to affix the electrolysis segment 260 to the delivery catheter 400 may include welds, solder, or an adhesive.

The Delivery Device

The expandable body 100, 140, 150, or 170A-G is advanced and positioned within human body by an elongated portion of the medical device known as the "delivery device" or "delivery catheter", with delivery catheter used particularly when the elongated portion of the medical device is flexible. In one embodiment, a delivery device is an elongated medical device that defines at least one lumen, or potential lumen. The delivery device has a proximal and a distal end and is dimensioned to deliver a fluid medium from a fluid medium source at the proximal end of the device into the central void or space 108 of the expandable body 100, 140, 150, or 170A-G, which is attached or coupled to the distal end of the delivery device. Further, any medical device or component of a medical device that can position the expandable body 100, 140, 150, or 170A-G at a desired location in the vascular system, such as the lumen of a saccular aneurysm or lumen of a target blood vessel, facilitate the expansion of the expandable body, and then facilitate the separation of the expandable body from the delivery device is generally acceptable as a delivery device. Typically, the delivery device is a flexible catheter (a "delivery catheter"). Preferably, the delivery catheter may be any flexible catheter, hollow wire, removable core wire, or combinations thereof, suitable for accessing locations with the vascular system including the delivery catheters 300, 352A-B, and 400, shown in FIGS. 7, 9, and 13. The delivery device may also be any other type of catheter, hollow wire, or removable core wire, or alternatively a needle or trochar, a stylet, or combinations thereof, suitable for accessing locations within the vascular system or in other biological conduits. In various embodiments, the delivery device is a catheter 300, 352A-B, or 400 that can carry an attached compressed expandable body 100, 140, 150, or 170A-G to the lumen of a saccular aneurysm or the lumen of a target artery or vein, or other form of biological conduit.

Figure 10A:
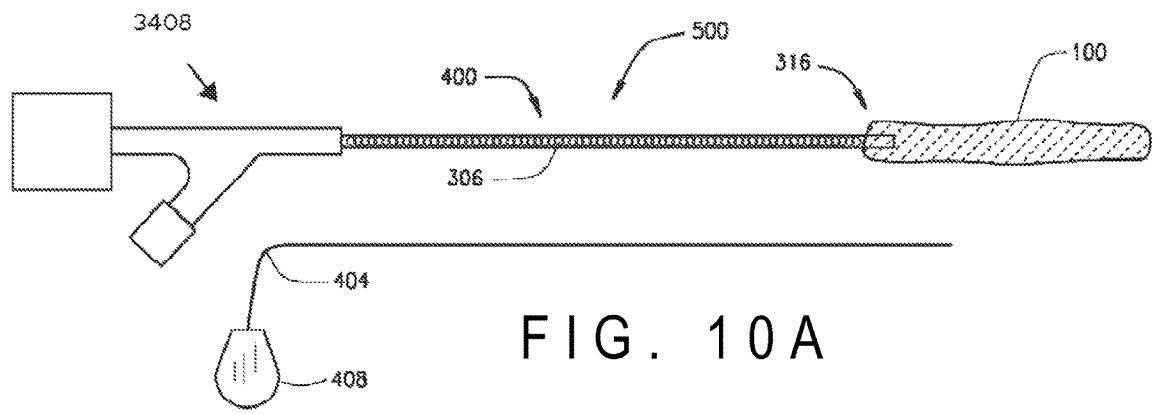
FIGS. 10A-B are plan views of an embodiment of a medical device.

A catheter is a flexible, tubular, elongate medical device configured for insertion into bodily compartments, including blood vessels, to permit the injection or the withdrawal of fluids, amongst other functions. Catheters are often formed of polymers or plastics and optionally further include metal, such as in a coil or braid configuration for reinforcement. Catheters can be configured to enable attachment to expandable bodies 100, 140, 150, or 170A-G, facilitate the delivery of compressed expandable bodies to the lumen of an aneurysm sac or lumen of a target blood vessel or other biological conduit, facilitate the inflation or expansion of compressed expandable bodies, and separate from expanded expandable bodies. In some embodiments, the delivery catheter 300, 352A-B, or 400 can be configured to pass through the vascular system with the attached expandable body 100, 140, 150, or 170A-G in a compressed form, as shown in FIGS. 10A and 17A. After expansion, the expandable body 100, 140, 150, or 170A-G is separated from the delivery catheter 300, 352A-B, or 400, thereby allowing the expanded expandable body to remain in place while the delivery catheter is removed from the body. In this way, delivery catheters are similar to angioplasty balloon catheters, which are configured to enable attachment to traditional rigid tubular stents, to facilitate the delivery of attached compressed traditional tubular stents to the lumen of a specific segment of a blood vessel or other biological conduit, enable expansion of compressed traditional tubular stents, and separate from expanded traditional tubular stents.

The delivery catheter 300, 352A-B, or 400 is composed of a biocompatible material. By way of example and not limitation, the delivery catheter 300, 352A-B, or 400 and various components thereof may be formed of silicone rubber, natural rubber, polyvinyl chlorides, polyurethane, copolyester polymers, thermoplastic rubbers, silicone-polycarbonate copolymers, polyethylene ethyl-vinyl-acetate copolymers, woven polyester fibers, or combinations thereof. In one embodiment, the wall of the delivery catheter 300, 352A-B, or 400 may be reinforced with a metal, such as coiled or braided stainless steel or nitinol, to enhance control and reduce kinking of the delivery catheter during use. Metals suitable for delivery catheter reinforcement include stainless steel and nitinol.

As shown in FIGS. 7, 9, 10A-B, 13, 14A-B and 23A-B, the delivery catheters 300, 352A-B, or 400 will have a hollow, or potentially hollow, cylindrical member that defines a lumen to allow for passage of a fluid medium from the proximal end of the delivery catheter to the distal end of the delivery catheter and into the central void 108 of the expandable body. The delivery catheter, 352A-B, or is designed and dimensioned such that it can be inserted in the body to deliver the compressed expandable body 100, 140, 150, or 170A-G to a desired location, facilitate the inflation or expansion of the expandable body, and facilitate the separation of the expanded expandable body from the delivery catheter. When a single lumen delivery catheter 300, 352A-B, or 400 is used, the compressed expandable body may be positioned in the lumen of a saccular aneurysm or lumen of the target blood vessel after being advanced through a separate larger catheter, guide catheter, or guide sheath that is positioned with its distal end within or near the aneurysm or target location within the target blood vessel. Once in the lumen of the aneurysm sac or lumen of the target blood vessel and out of the guide catheter, the compressed expandable body 100, 140, 150, or 170A-G can be expanded, and then the expanded expandable body and the delivery catheter 300, 352A-B, or 400 can be separated, and the delivery catheter and the guide catheter can be removed from the body, while the expanded expandable body remains in place. The hollow, or potentially hollow, cylindrical member 306 of delivery catheter 300, 352A-B, or 400 has a wall thickness ranging from about 0.05 mm to about 0.25 mm. Preferably, wall thickness of the hollow cylindrical member 306 ranges from about 0.1 mm to about 0.2 mm. The lumen 312 defined by the hollow cylindrical member 306 for the purpose of enabling the passage of a fluid medium into the central void or space of the expandable body 108 has a diameter ranging from about 0.4 mm to about 1 mm. The proximal end of the hollow cylindrical member 306 includes a port or hub 3408 to communicate with a pressurized fluid medium source, such as a syringe 314 or a pump (not shown) containing, for example, water, saline or a radiographic contrast solution. The fluid media for expanding the expandable body are received into the delivery catheter 300, 352A-B, or 400 through the hub or port 3408.

Single Lumen Catheters

Figure 9:
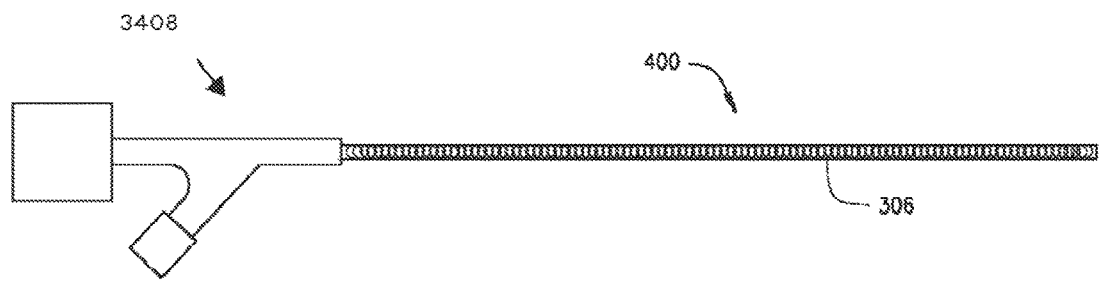
FIG. 9 is a plan view of an embodiment of a medical device.

FIG. 9 depicts a longitudinal view of a single lumen embodiment of the delivery catheter portion 400 of the medical device 500, and FIG. 20A depicts a transverse cross-section of the single lumen catheter. As shown in FIGS. 11A-F, for the single lumen embodiment, the delivery catheter 400 moves through the lumen of a guide catheter 800 to deliver the compressed ballstent 100 to the lumen 701 of a saccular aneurysm 700. For this single lumen embodiment, the delivery catheter 400 does not include a hollow cylindrical member that defines a lumen that is dimensioned to allow for the passage of a guidance member, or guide wire.

The dimensions of the delivery catheter 300, 352A-B, or 400 are a matter of design choice depending upon the size of aneurysm to be treated and the location of the aneurysm in the vascular system. The distance between the aneurysm to be treated and the site of insertion of the medical device into the vascular system, will determine, in part, the length of the delivery catheter 300, 352A-B, or 400. Delivery catheter lengths range between about 5 cm and about 300 cm, with preferable ranges between about 75 cm and about 225 cm. The smallest diameter blood vessel segment in the path between the site of insertion of the medical device into the vascular system and the aneurysm to be treated will determine, in part, the diameter of the delivery catheter 300, 352A-B, or 400. Delivery catheter diameters range between 2 Fr and 7 Fr, with preferable ranges between 2 Fr and 5 Fr.

Figure 10B:
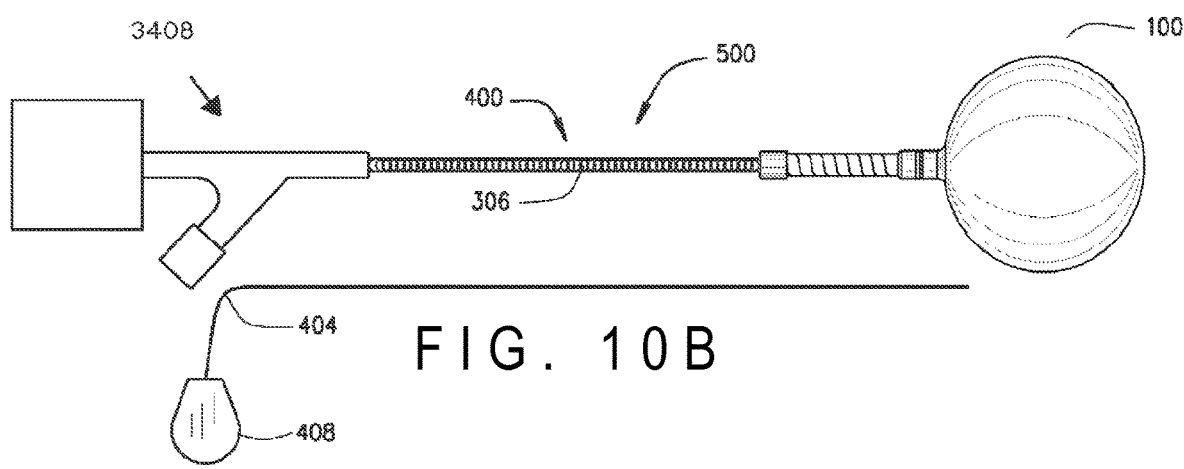

FIGS. 10A-B depict longitudinal views of a single lumen embodiment of the delivery catheter 400 portion of a medical device 500. FIG. 10A depicts a longitudinal view of a single lumen embodiment of the medical device 500 with the ballstent 100 in a compressed form. FIG. 10B depicts a longitudinal view of a single lumen embodiment of the medical device 500 with the ballstent 100 in an expanded form.

Figure 22:
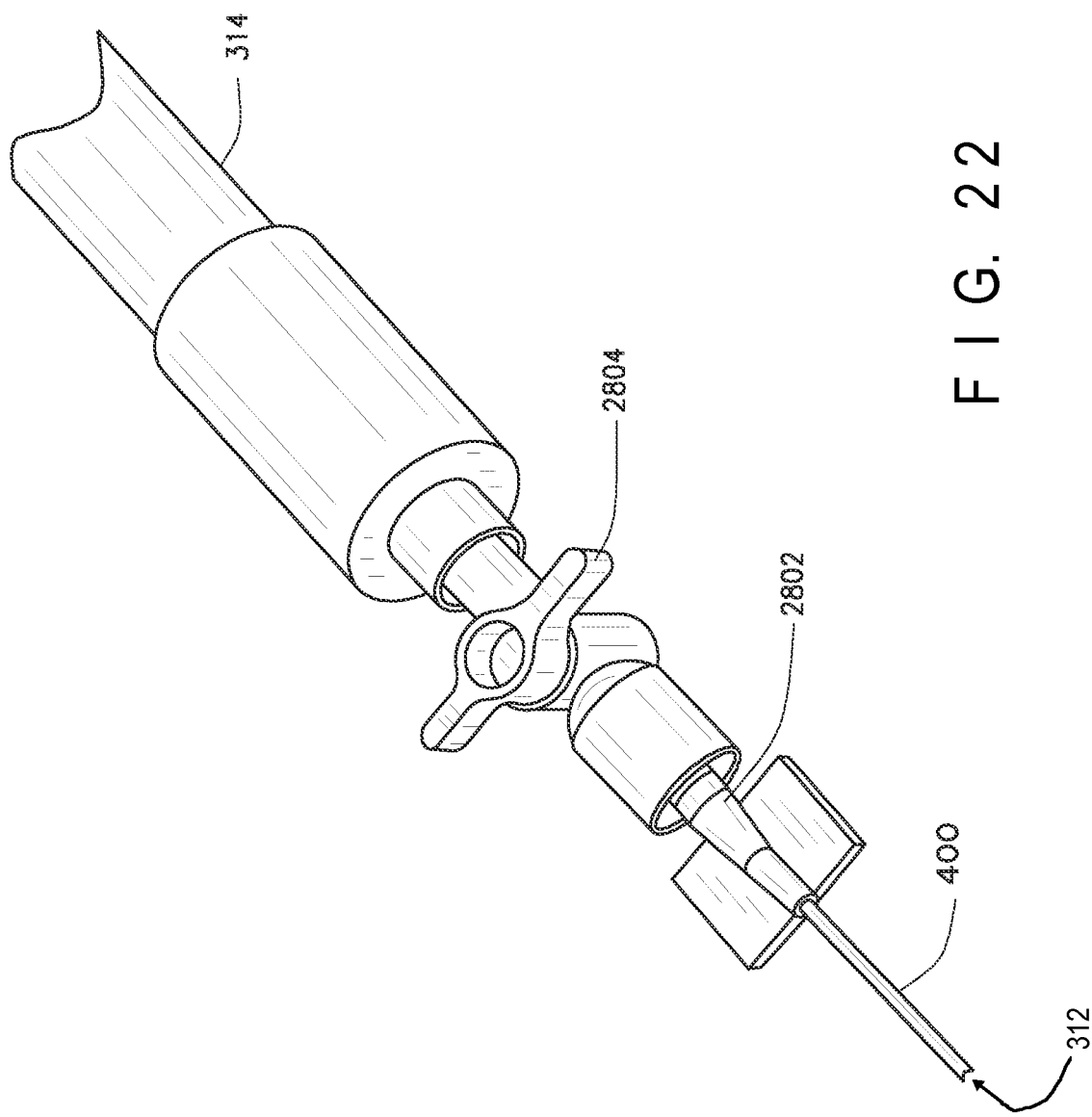
FIG. 22 is a perspective view of an arrangement for inflating or deflating an expandable body.

In some embodiments, as shown in FIGS. 10A-B, the proximal end of the delivery catheter 400 is configured with a hub 3408 that may facilitate a Luer-Lok or Luer-Slip type connection for connecting a fluid medium source, such as a syringe 314, to the lumen 312 of a hollow cylindrical member configured to transmit the fluid medium from the proximal end of the delivery catheter to the central void or space of the expandable body 100, 140, 150, or 170A-G. As shown, in FIG. 22, the lumen 312 of a delivery catheter 400 is connected to a fluid medium source, such as the syringe 314, through a female Luer fitting 2802. A stopcock 2804 or flow switch may be positioned between the fluid medium source and the delivery catheter 400 to enable greater control over the movement of the fluid medium into and out of the delivery catheter.

As shown in FIG. 17E, in one embodiment single lumen delivery catheter can be used to place a ballstent 100 in the lumen 701 of the aneurysm sac 700, For this embodiment, an optional removable wire or obturator 404 is removed from the delivery catheter. The removable wire or obturator 404 may include a handle 408 or other device to facilitate insertion and removal. Then, a fluid medium source, such as the syringe 314 can be connected to the hub 3408 and a fluid medium can be moved from the syringe 314 into the central void or space 108 of the ballstent 100 under pressure, resulting in inflation or expansion of the ballstent within the lumen 701 of the aneurysm sac 700 and filling substantially all or a portion of the aneurysm sac. Fluid media such as water (including deionized water), saline, solutions of radiographic contrast agents, or solutions of drugs, such as thrombin, can be used to expand the compressed ballstent 100. As shown in FIG. 17E, after inflation or expansion of the ballstent 100, a coil, accessory coil, expansile wire, or expansile structure 1204 can be placed into the central void of the ballstent 100.

A variety of methods and devices can be used to separate the delivery catheter 400 from the ballstent, blockstent, or expandable body. In one embodiment as indicated in FIGS. 9, 10A-B, and 23A, the delivery catheter 300 or 400 comprises one or more electrolysis wire(s) 320 or insulated conductor wire(s). For this embodiment, after the ballstent 100 is expanded, an electrical current is applied to the electrolysis wire(s) 320 or the insulated conductor wire(s) to dissolve a portion of the proximal neck of the ballstent 100 by electrolysis (including a stainless steel portion). In alternative embodiments, the electrical current may be applied to dissolve a portion of a stainless steel ring 250 between the ballstent 100 and the delivery catheter 300 or 400 or to dissolve a portion of the proximal region of the ballstent 100 by electrolysis. A direct current (DC) may be used for any of these embodiments. Once a portion of the proximal neck, stainless steel ring 250, or proximal region of the ballstent 100 is dissolved or corroded, the delivery catheter 300 or 400 is separated from the expanded ballstent and the delivery catheter and the guide catheter 800 are removed.

Figure 23B:
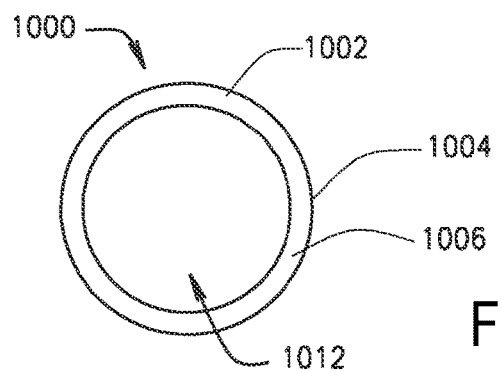
FIGS. 23B-F are transverse cross-sectional and plan views of various delivery catheters.
Figure 23C:
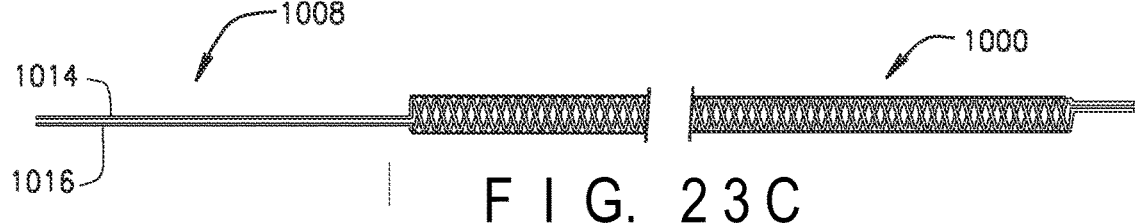
Figure 23D:
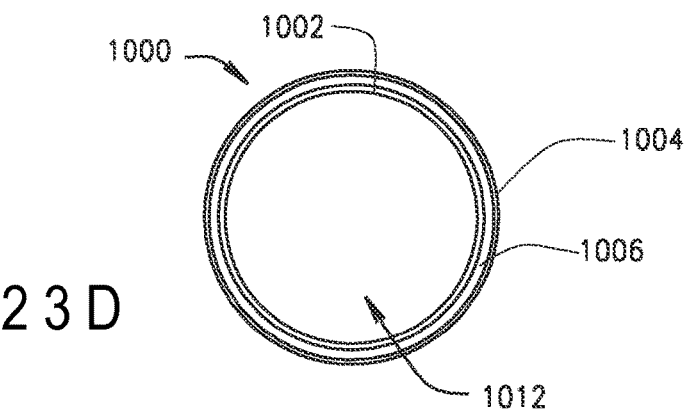

In various embodiment as illustrated in FIGS. 23B-C, a single lumen catheter 1000 has a coil-reinforced wall 1002 consisting of one, two, or three electrical conductor (e.g., wires or cables) to provide conductive path(s) for performing electrolysis, as explained more fully below. In one embodiment, the external surface 1004 of the wall 1002 is composed of polyimide and has a hydrophilic or lubricious coating, while the conductive path(s) includes 0.001 inch× 0.003 inch flat stainless steel coils 1006. The conductor coil(s) 1006 can be configured in a one, two, or three conductor arrangement 1008 as shown in FIGS. 23B-F, as discussed below with regard to performing electrolysis. The conductors of the coil 1006 and any other conductors may be straight, braided, or coiled. The conductive path defined by the conductor coils 1006 can be coated in an insulating polymer such as Parylene, while the interior lumen 1012 can be lined with PTFE, including a PTFE composite.

In certain embodiments, a modified infusion wire having a removable core can be used as a single lumen delivery catheter. An infusion wire is a modified guide wire wherein the solid metal core can be removed to leave a lumen that can be used to inject the fluid media. An infusion wire with a removable core can be modified such that an expandable body 100, 140, 150, or 170A-G can be attached to the distal end and expanded through the wire lumen, after the removal of the core wire.

In some embodiments all or a portion of the interior and exterior surfaces of the delivery device can be further coated with a hydrophilic or lubricious coating. In other embodiments, all or a portion of the expandable body 100, 140, 150, or 170A-G can also be coated with a hydrophilic or lubricious coating.

Dual Lumen Catheters

Figure 13:
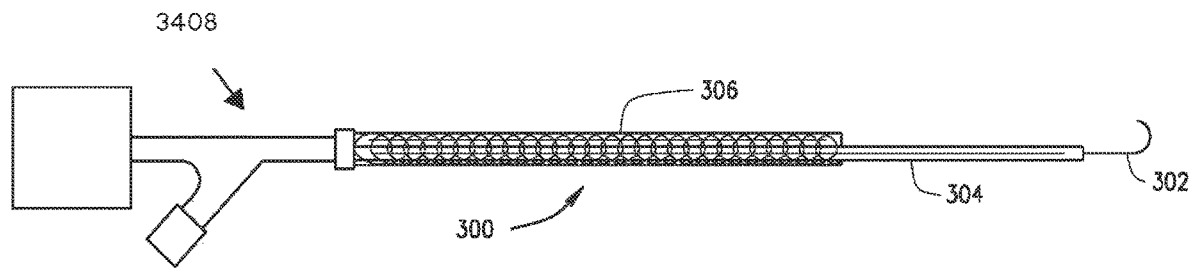
FIG. 13 is a plan view of an embodiment of a medical device.

As shown in FIG. 13 and FIG. 20B, the delivery catheter 300 may include an additional hollow cylindrical member that defines a second lumen 324 to receive a guidance member, such as a guide wire 302, to assist in the guidance of the ballstent 100 component of the medical device to the desired location, as can be understood from FIGS. 14A-B and 15A-F. This second lumen 324 is generally adjacent and parallel to the first lumen 312. As shown in FIGS. 13 and 20B, the delivery catheter 300 may be a double lumen catheter, with one lumen 312 configured to enable the passage of the fluid medium from a fluid medium source at the proximal end of the delivery catheter to the central void or space 108 of the ballstent at the distal end of the delivery catheter, and the other lumen 324 configured to accept a guidance member, such as a guide wire 302, to facilitate advancement and positioning of the medical device in the vascular system. In certain embodiments, the distal end of the lumen 324 configured to accept a guidance member may be defined by a bridging catheter, similar to the bridging catheter 160 as shown in FIGS. 2B-C, 2E, 2G, 2L-N, 20-P, 8H, 8J-O, and 8R-S, either as a part of the delivery catheter that passes from the proximal hub to the distal end of the delivery catheter, or as a distinct element coupled or bonded to the distal end of the delivery catheter. As described previously, this guidance catheter can pass through the proximal neck, through the void of the expandable body, and operatively couple to the distal neck, such that a guide wire, guidance member, coil, accessory coil, or accessory coil catheter can be passed through the hub of the delivery catheter and out the distal end of the medical device, including for positioning of a guide wire or guidance member in an artery, vein or other biological conduit and also including for placement of a coil or accessory coil in the lumen of a saccular aneurysm.

As shown in FIG. 20B, the delivery catheter 300 includes two hollow cylindrical members, each with a lumen, wherein the hollow cylindrical members 304 or 306 have a wall thickness ranging from about 0.05 mm to about 0.25 mm. Preferably, the hollow cylindrical member 304 or 306 wall thickness ranges from about 0.1 mm to about 0.2 mm. The lumen defined by the hollow cylindrical member 304 for the accepting a guide wire 302 has a diameter ranging from about 0.25 mm to about 0.5 mm. The diameter of the lumen for the passage of the fluid medium into the ballstent 100 and the diameter of the lumen for accepting a guidance member 324 may be similarly dimensioned. Alternatively, the diameter of the lumen for the passage of the fluid medium into the ballstent, blockstent, or expandable member may be larger or smaller than the diameter of the lumen for accepting a guidance member, such as the guide wire 302 or for accepting a coil, accessory coil, or accessory coil catheter.

For a delivery catheter with two lumens, the first and second hollow cylindrical members may be similarly dimensioned. Alternatively, the second hollow cylindrical member may have a larger diameter to accept the guide wire, guidance member, coil, accessory coil, or accessory coil catheter, or a smaller diameter. The proximal end of the second hollow cylindrical member 304 is engaged to the hub 3408. The hub 3408 facilitates the insertion of the guide wire 302, guidance member, coil, accessory coil, or accessory coil catheter into the second hollow cylindrical member 304. As can be understood from FIGS. 13, 14A-B, 15A-F, and 20B, in some embodiments the guide wire 302, guidance member, coil, accessory coil, or accessory coil catheter can be fed through the second hollow cylindrical member 304 and extended out of the distal end of the delivery catheter 300, and also out the distal end of the medical device. In other embodiments, including those embodiments lacking a bridging catheter component, the coil, accessory coil, or accessory coil catheter can be fed through the second hollow cylindrical member 304 and placed in the central void of the ballstent, blockstent, or expandable body. In some of the embodiments with a double lumen delivery catheter, the delivery catheter 300 is advanced over the guide wire 302 until the compressed ballstent 140 is positioned in the lumen of a saccular aneurysm. Once the compressed ballstent 140 is in the desired position, the ballstent 140 is expanded by the fluid medium provided to the first hollow cylindrical member 306 by the syringe 314 connected to the ballstent expansion hub 3408. Fluid media such as water, saline, solutions of radiographic contrast agents, or solutions of drugs, such as thrombin, can be used to expand the compressed ballstent. The guide wire 302 is preferably an angiographic wire of sufficient length for the distal tip of the guide wire to reach the aneurysm, and a proximal end extending out and away from the point of entry into the vascular system. In some embodiments, the guide wire 302 has a straight or angled distal tip, while in other embodiments, the guide wire 302 has a curved J-shaped distal tip, typically constructed from a shape-memory alloy or a braided metal that causes the tip to return to the J-shape after any applied stress is removed. The materials and dimensions of the guide wire 302 may be selected based upon the diameter, length, and tortuosity of the blood vessels being traversed. Typically, the guide wire 302 may be composed of any suitable biocompatible materials and have an outer diameter ranging between about 0.3 mm to about 0.95 mm.

Figure 14A:
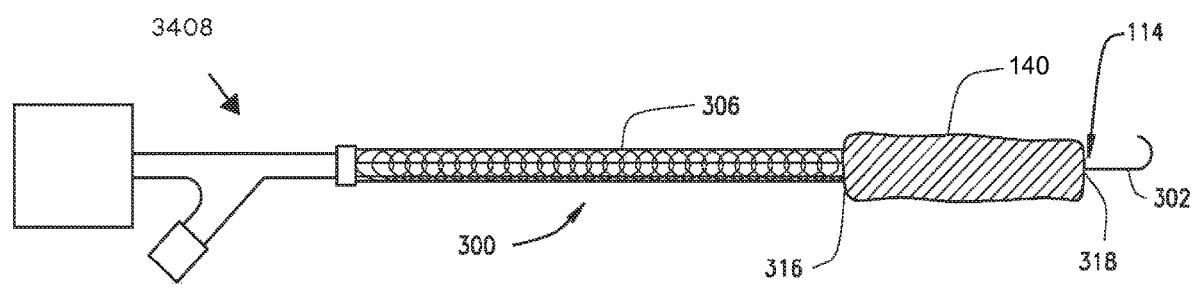
FIGS. 14A-B are plan views of an embodiment of a medical device.
Figure 14B:
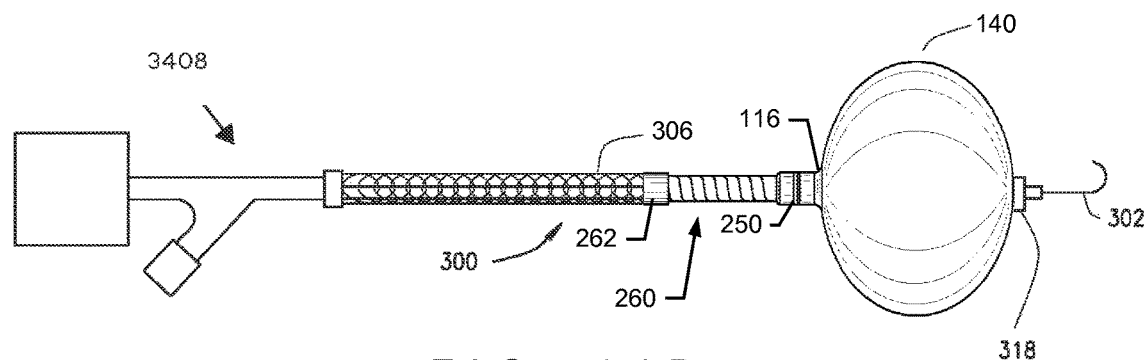

FIGS. 14A-B depict longitudinal views of a double lumen embodiment of the delivery catheter portion 300 of the medical device 500. FIG. 14A depicts a longitudinal view of a double lumen embodiment of the medical device 500 with the expandable body 140 in a compressed form, while FIG. 14B depicts a longitudinal view of a double lumen embodiment of the medical device 500 with the ballstent 140 in an expanded form. The delivery catheter 300 is used to advance the ballstent 140 over a guide wire 302 and into the lumen of the aneurysm sac. The delivery catheter 300 is also used to deliver a fluid, liquid, gas, solid, or a combination thereof, to expand the ballstent 140 in the lumen 701 of the aneurysm sac 700. In some embodiments, the delivery catheter 300 or 400 comprises one or more electrolysis wire(s) 320 or insulated conductor wire(s). For these embodiments, after the ballstent 100 is expanded, an electrical current is applied to the electrolysis wire(s) 320 or the insulated conductor wire(s) to dissolve a portion of the proximal neck of the ballstent 100 by electrolysis (including a stainless steel portion. In alternative embodiments, the electrical current may be applied to dissolve a portion of a stainless steel ring 250 between the ballstent 100 and the delivery catheter 300 or 400 or to dissolve a portion of the proximal region of the ballstent 100 by electrolysis. A direct current (DC) may be used for any of these embodiments. Once a portion of the proximal neck, stainless steel ring 250, or proximal region of the ballstent 100 is dissolved or corroded, the delivery catheter 300 or 400 is separated from the expanded ballstent and the delivery catheter and the guide catheter 800 are removed.

In one embodiment, an electrolysis wire 320 or an insulated conductor wire is connected or electrically coupled to a portion of the proximal neck of the ballstent, including at an exposed metal surface 3302. In another embodiment, an electrolysis wire 320 or an insulated conductor wire is connected or electrically coupled to a weld, solder, or other form of bonding between the ballstent and the delivery catheter, including an adhesive. In another embodiment, an electrolysis wire 320 or an insulated conductor wire is connected or electrically coupled to another portion of the ballstent 140, also including at an exposed metal surface 3302.

As shown in FIGS. 10A-B, 13, 14A-B, and 15A-F, in one embodiment of the medical device 500, the delivery catheter 300 or 400 advances the attached compressed ballstent 100 or 140 over a guide wire 302 and into the lumen or cavity 701 of the aneurysm sac 700. Once the compressed ballstent 100 or 140 has been placed in the lumen 701 of the aneurysm sac 700, the guide wire 302 is removed. Then, a fluid medium source, such as the syringe 314 is connected to the hub 3408 and a fluid medium is moved from the syringe 314 into the central void or space 108 of the ballstent 100 or 140 resulting in expansion of the ballstent until it fills at least a portion of the lumen of the aneurysm sac 701. After inflation or expansion, the delivery catheter 300 or 400 is pulled to back in the aneurysm sac 700 to pull the expanded expandable body 100 or 140 towards the opening 703 between the parent vessel and the aneurysm, including toward the neck or mouth, as indicated as 702 in FIG. 15D. This in turn, brings the expanded expandable body 100 or 140 into contact with the aneurysm wall 704 in, near, or adjacent to the neck or mouth 703 of the aneurysm. The coil or accessory coil 162 is then fed through the catheter 300 or 400, through the interior of the expandable body 100 or 140 and delivered into the aneurysm lumen 701, as shown in FIG. 15E, including passing the coil or accessory coil through the guide wire lumen. The accessory coil 162 is inserted until the accessory coil contacts both the aneurysm wall 704 opposite the mouth 703 and the external surface of the expandable body 100 or 140, where the accessory coil exerts a continuous force on the expandable body causing the expandable body to seal the mouth of the aneurysm 700. As shown in FIG. 15F, after the expandable body 100 or 140 is expanded and the coil or accessory coil has been placed, the delivery catheter 300 or 400 and the expandable body 100 or 140 are detached or separated and the delivery catheter is removed while leaving the expanded body in the lumen 701 of the aneurysm where it seals the mouth 703 of the aneurysm, and the accessory coil in place in the lumen of the aneurysm behind the expanded body where it acts to hold the expanded ballstent in place.

A variety of methods and devices can be used to separate the delivery catheter 400 from the ballstent, blockstent, or expandable body. In one embodiment as indicated in FIGS. 9, 10A-B, and 23A, the delivery catheter 300 or 400 comprises one or more electrolysis wire(s) 320 or insulated conductor wire(s). For this embodiment, after the ballstent 100 is expanded, an electrical current is applied to the electrolysis wire(s) 320 or the insulated conductor wire(s) to dissolve a portion of the proximal neck of the ballstent 100 by electrolysis (including a stainless steel portion). In alternative embodiments, the electrical current may be applied to dissolve a portion of a stainless steel ring 250 between the ballstent 100 and the delivery catheter 300 or 400 or to dissolve a portion of the proximal region of the ballstent 100 by electrolysis. A direct current (DC) may be used for any of these embodiments. Once a portion of the proximal neck, stainless steel ring 250, or proximal region of the ballstent 100 is dissolved or corroded, the delivery catheter 300 or 400 is separated from the expanded ballstent and the delivery catheter and the guide catheter 800 are removed.

In various embodiment, a double lumen catheter has a coil-reinforced wall consisting of one, two, or three electrical conductor (e.g., wires or cables) to provide conductive path(s) for performing electrolysis, as explained more fully below. In one embodiment, the external surface of the wall is composed of polyimide and has a hydrophilic or lubricious coating, while the conductive path(s) includes 0.001 inch×0.003 inch flat stainless steel or copper coils. The conductor coils 1006 can be configured in a one, two, or three conductor arrangement, as discussed below with regard to performing electrolysis. The conductors of the coil and any other conductors may be straight, braided, or coiled. The conductive path defined by the conductor coils can be coated in an insulating polymer such as Parylene, while the interior lumen can be lined with PTFE, including a PTFE composite.

In some embodiments all or a portion of the interior and exterior surfaces of the delivery device or catheter can be further coated with a hydrophilic or lubricious coating. In other embodiments, all or a portion of the expandable body 100, 140, 150, or 170A-G can also be coated with a hydrophilic or lubricious coating.

Guidance Members

As shown in FIGS. 15A-F, for an embodiment using a double lumen catheter, the delivery catheter 300 moves over a guidance member or guide wire 302 to deliver the compressed ballstent 140 to the lumen 701 of a saccular aneurysm 700. Examples of a guidance member include a flexible guide wire. The guide wire 302 can comprise metal in the form of a flexible thread, coil, or slender rod. For example, the basic angiography guide wire consists of a fixed solid metal core covered by a metal spring coil. In other situations, a delivery catheter is advanced over a needle or trochar. The guide wire 302 occupies a lumen in the delivery catheter, with such lumen defined by the tubular portion of the delivery catheter. Once located in place, the guide wire 302 can be removed in order to allow the injection or withdrawal of a fluid medium.

As shown in FIGS. 21A-B, in another embodiment, the delivery catheter of the medical device can be configured with a lumen that can accept a guide catheter 800 as a guidance member. With this configuration, the medical device can be advanced in a tri-axial configuration, with the medical device 500 advanced over a guide catheter 800, which is advanced over a guide wire. In certain embodiments, the proximal hub on the guide catheter can be removed to allow the lumen of the hollow cylindrical member 304 of delivery catheter 300 of the medical device 500 to accept the guide catheter 800. In certain instances, this embodiment of the medical device can result in better control over the delivery of the compressed expandable body to the aneurysm or target blood vessel lumen and better trackability of the compressed expandable body 100, 140, 150, or 170A-G as it is advanced to the desired location. As shown, in one aspect, the hollow cylindrical member 304 of delivery catheter 300 may be annular shaped and fully encircle the guidance catheter 800, while in other aspects, the delivery catheter may engage 60%, 70%, 80%, 90%, or more of the circumference of the guidance catheter.

Exemplary Ballstent Catheter and Expandable Body Catheter Medical Devices

Figure 31A:
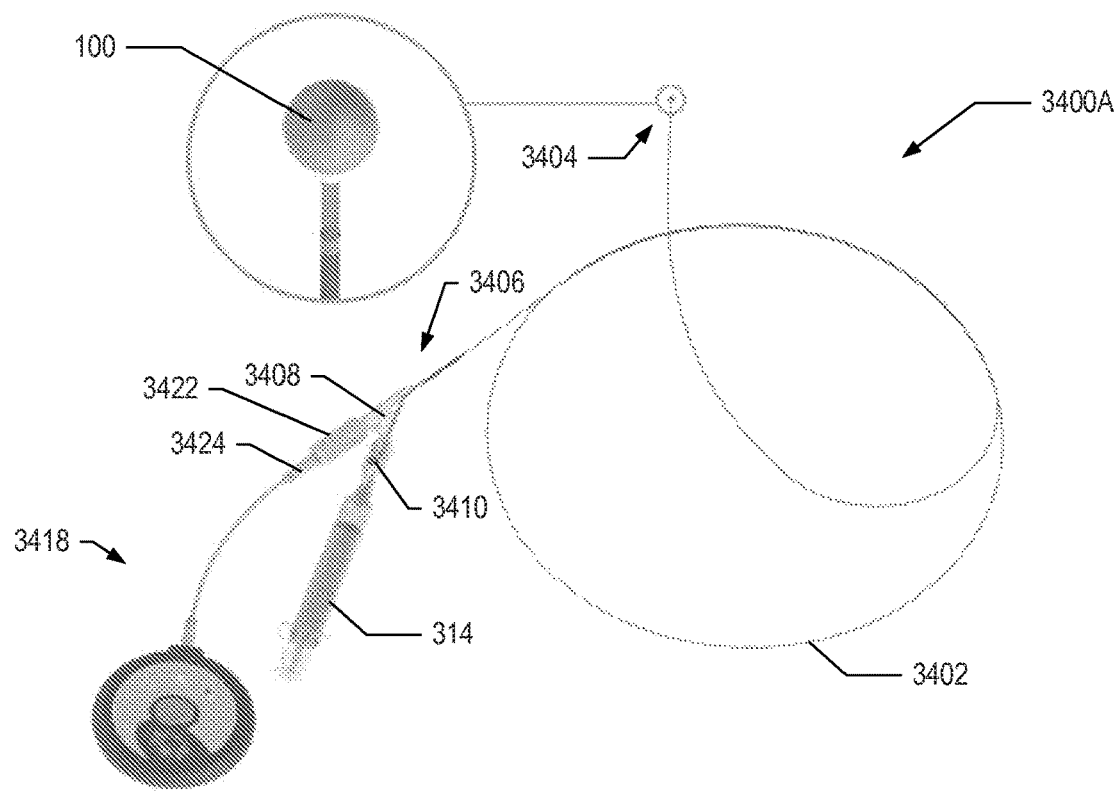
FIGS. 31A-B are plan views of embodiments of the medical devices for delivering various embodiments of the expandable body.

FIG. 31A depicts an embodiment of an expandable body medical device that can be used as a ballstent catheter 3400A. As shown, the ballstent catheter medical device 3400A includes a delivery catheter 3402 configured at a distal end 3404 for engaging the ballstent 100. The proximal end 3406 of the delivery catheter 3402 is engaged to a hub 3408 that permits electrical and fluid communication with the ballstent 100 through the catheter. A syringe 314 may be used to deliver a fluid medium to the ballstent 100. The device 3400A also includes an electrical connector or port 3422 for establishing electrical communication from a handheld controller 3418 to the ballstent 100, including through electrolysis wires or conductors present in the wall of the delivery catheter.

Figure 31B:
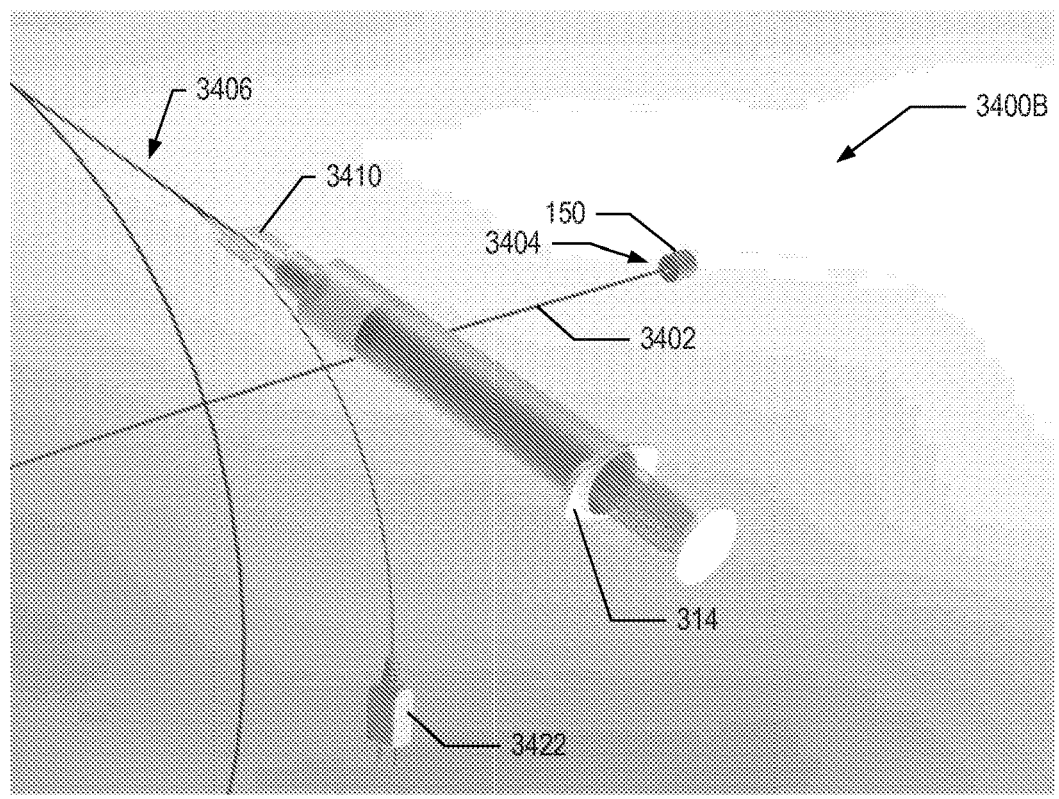

FIG. 31B depicts an embodiment of an expandable body medical device that can be used as a blockstent medical device 3400B. As shown, the medical device 3400B includes a delivery catheter 3402 configured at the distal end 3404 for engaging the expandable body 100. The proximal end 3406 of the delivery catheter 3402 is engaged to a hub that permits electrical and fluid communication with the expandable body 150 through the catheter. A syringe 314 may be used to deliver a fluid medium to the expandable body 150. The device 3400B also includes an electrical connector or port 3422 for establishing electrical communication from a power source (not shown) to the expandable body 150, including through electrolysis wires or conductors present in the wall of the delivery catheter.

Figure 32A:
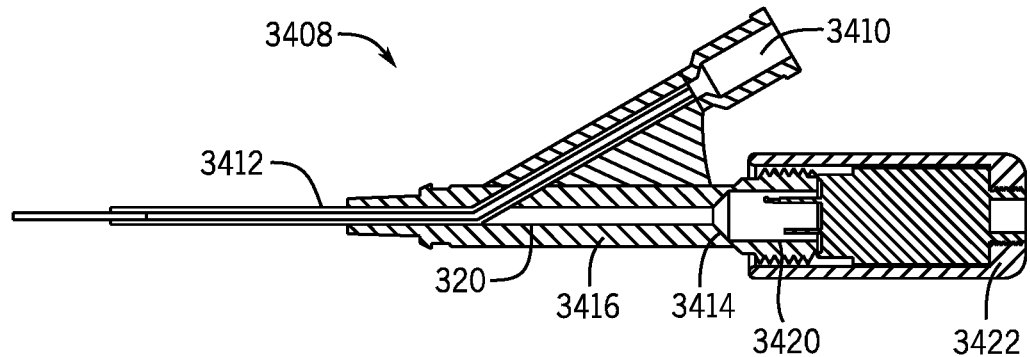
FIG. 32A is a cross-sectional view of a hub for use with a medical device wherein electrolytic detachment of the expanded body is performed by passing an electrical current into the medical device.

A cross-sectional view of a hub 3408 for a medical device with a single lumen delivery catheter wherein the primary method of detachment is electrolysis is shown in FIG. 32A. The hub 3408 includes a first connection port 3410 that is configured with a Luer hub or taper that may facilitate a Luer-Lok or Luer-Slip type connection for connecting a fluid medium source, such as a syringe 314, to the lumen 312 of a hollow cylindrical member of the delivery catheter 3402 configured to transmit the fluid medium from the proximal end of the delivery catheter to the central void or space 108 of the expandable body 100, 140, 150, or 170A-G. Optionally, the first connection port 3410 may also accept a guide wire or guidance member. The hub 3408 is also configured with a second connection port 3422 is configured to allow for electrical communication with the catheter 3402. For example, one or more electrolysis wire(s) 320 in electrical communication with electrodes mounted on the catheter 3402 and/or the ballstent, blockstent, or expandable member 100 may extend through a channel 3416 of the hub 3408 and into the second connection port 3422. Alternatively, one or more resistive wires may extend through the channel 3416 of the hub 3408 and into the second connection port 3422. A power source or source of electricity, such as a handheld controller 3418 shown in FIGS. 31A and 33, may communicate with the wire 320 to perform various functions including, but not limited to, electrolysis or heating a heat-sensitive material, such communication occurring through a coupling of the electrical connector portion 3424 of the handheld controller and the connection port 3422 of the hub 3408.

Figure 32B:
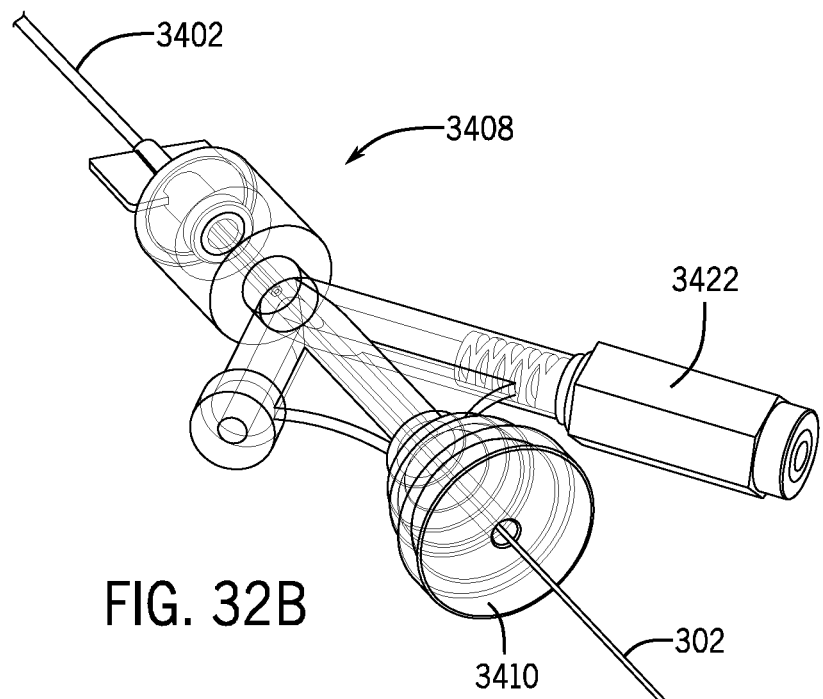
FIGS. 32B-C are partial see-through views of a hub for use with a medical device.

A view of a hub 3408 for a medical device with a double lumen delivery catheter wherein the primary method of detachment is electrolysis is shown in FIG. 32B. The hub 3408 includes a first connection port 3410 that is configured with a Luer hub or taper that may facilitate a Luer-Lok or Luer-Slip type connection for connecting a fluid medium source, such as a syringe 314, to the lumen 312 of a hollow cylindrical member of the delivery catheter 3402 configured to transmit the fluid medium from the proximal end of the delivery catheter to the central void or space 108 of the expandable body 100, 140, 150, or 170A-G. The hub 3408 is also configured with a second connection port 3422 is configured to allow for electrical communication with the catheter 3402. For example, one or more electrolysis wire(s) 320 in electrical communication with electrodes mounted on the catheter 3402 and/or the ballstent, blockstent, or expandable member 100 may extend through a channel 3416 of the hub 3408 and into the second connection port 3422. Alternatively, one or more resistive wires may extend through the channel 3416 of the hub 3408 and into the second connection port 3422. A power source or source of electricity, such as a handheld controller 3418 shown in FIGS. 31A and 33, may communicate with the wire 320 to perform various functions including, but not limited to, electrolysis or heating a heat-sensitive material, such communication occurring through a coupling of the electrical connector portion 3424 of the handheld controller 3418 and the connection port 3422 portion of the hub 3408. A third connection port 3410 is also configured to receive and engage a guide wire 302 or an obturator wire 404.

Figure 32C:
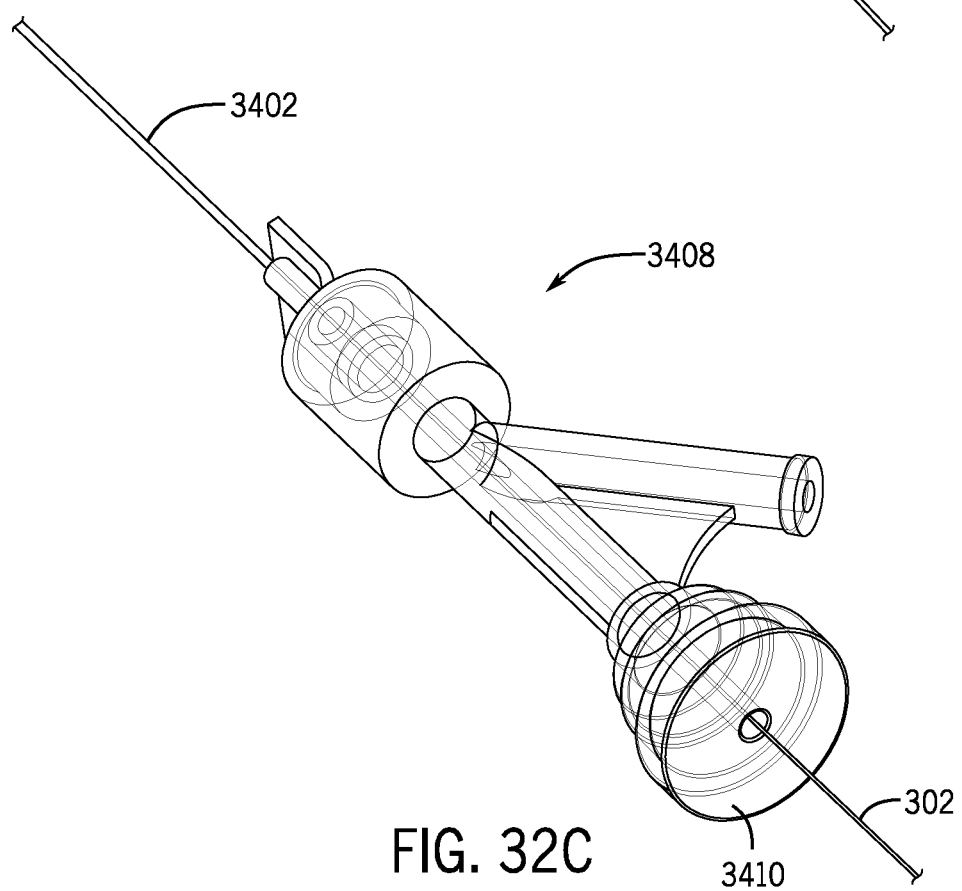

A view of a hub 3408 for a medical device with a double lumen delivery catheter wherein the primary method of detachment is mechanical is shown in FIG. 32C. The hub 3408 includes a first connection port 3410 that is configured with a Luer hub or taper that may facilitate a Luer-Lok or Luer-Slip type connection for connecting a fluid medium source, such as a syringe 314, to the lumen 312 of a hollow cylindrical member of the delivery catheter 3402 configured to transmit the fluid medium from the proximal end of the delivery catheter to the central void or space 108 of the expandable body 100, 140, 150, or 170A-G. A second connection port 3410 is also configured to receive and engage a guide wire 302 or an obturator wire 404.

As shown in FIG. 32A, in a preferred embodiment, the second connection port 3414 is bonded to a threaded nut 3420, such that an electrical terminal 3422 may be secured to the nut and the hub 3408. The electrical terminal 3422 is in electrical communication with the one or more conductive wires and configured to receive an electrical connector from an external power source, such as the handheld controller 3418. By way of example and not limitation, the electrical connector 3424 may be a 3.5 mm audio jack. Other electrical connectors may also be used.

Figure 23E:
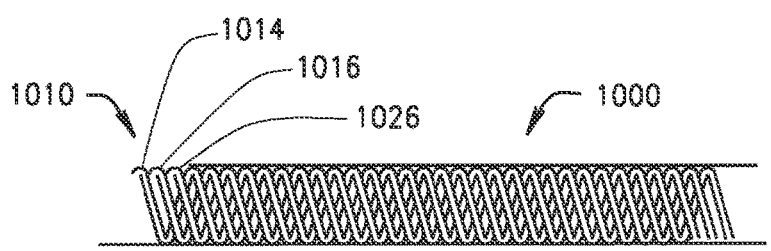
Figure 23F:
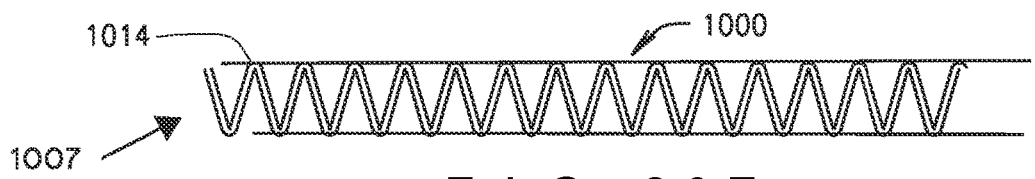
Figure 33:
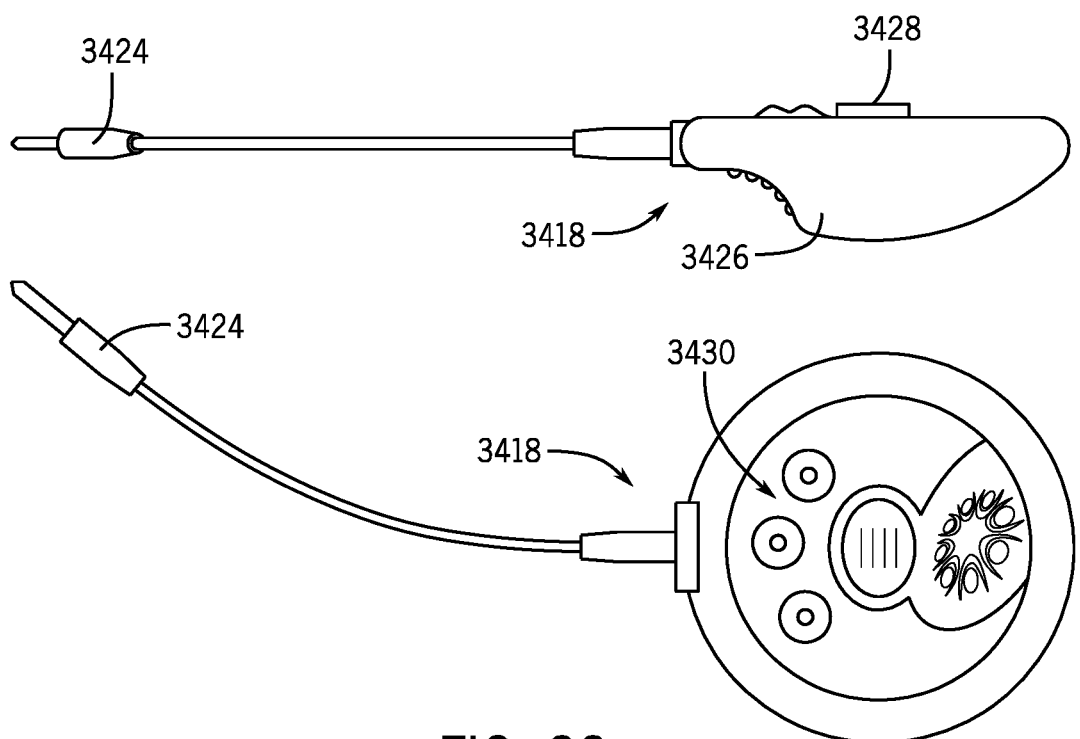
FIG. 33 is a top plan and side plan view of a handheld controller for use with a medical device wherein detachment of the expanded body is performed by passing an electrical current into the medical device.

As shown in FIG. 33, the handheld controller 3418 can be connected to the electrical terminal 3422 through a jack 3424 to deliver an electrical current through the catheter 3402 for detaching the expandable body 100, 140, 150, or 170A-G. For example, in one embodiment, the catheter 3402 includes a conductive coil 1006 that may be arranged in a one, two, or three conductor arrangement 1007, 1008, and 1010, respectively, as shown in FIGS. 23C and 23E and 23F. The various conductor arrangements 1008 and 1010 can provide both reinforcing strength and a conductive pathway along the length of the catheter 3402. The handheld controller 3418 provides a current or a voltage potential to the electrodes 1014, 1016, and optionally 1026, extending through the catheter 3402 to detach the expandable body 100, 140, 150, or 170A-G by electrolysis or thermal detachment, as explained below. In one embodiment, the handheld controller 3418 includes a body 3426, a power supply such as a battery, one or more actuation buttons 3428, and one or more indicators 3430 to indicate the status of the controller, the detachment of the expandable body 100, 140, 150, or 170A-G, and the status of the power source, such as the battery.

Folding the Expandable Body

In order to facilitate advancement of the expandable body through the vascular system, the expandable body 100, 140, 150, or 170A-G can be compressed into various shapes and dimensions. Optionally, this compression can include various forms and patterns of folding or pleating. For example, one or more pleats can be made in the expandable body 100, 140, 150, or 170A-G and then the pleats can be wrapped into a cylindrical shape. Alternatively, the expandable body 100, 140, 150, or 170A-G may be flattened into a planar shape and then rolled into a cylindrical shape. Alternatively, the expandable body 100, 140, 150, or 170A-G may be compressed into a compact spherical shape. Additionally, the portions of the expandable body 100, 140, 150, or 170A-G may be twisted during compression. In certain embodiments, the expandable body may be compressed around the delivery catheter 300, as in FIG. 14A. In other instances, the expandable body may be compressed around the obturator 404, as in FIG. 10A. In other embodiments, the expandable body may be compressed around a guidewire, including embodiments wherein the medical device has a delivery catheter with single lumen, where the single lumen is used both to deliver fluid to the central void of the expandable body for inflation or expansion and to accept a guide wire or guidance member. In other embodiments, the expandable body 100, 140, 150, or 170A-G may be compressed on itself, without a central catheter, obturator, or guidewire.

Figure 19A:
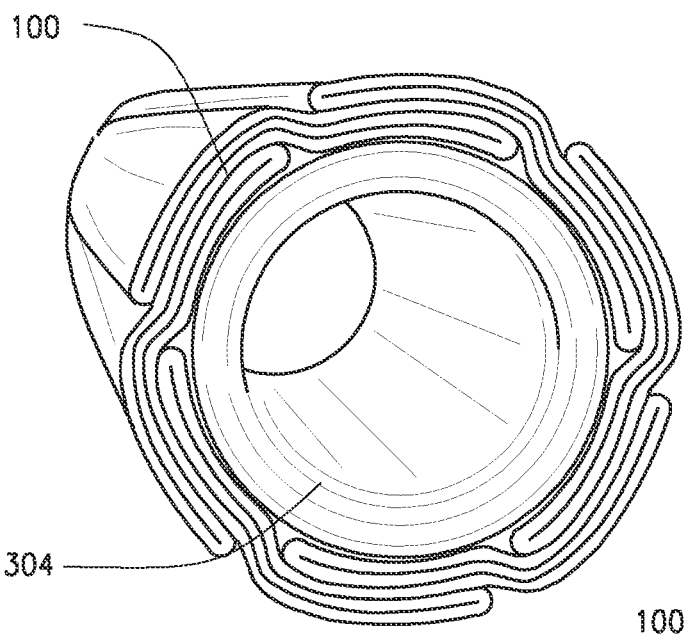
FIG. 19A is a perspective view of an embodiment of an expandable body as compressed against a delivery catheter.
Figure 19B:
FIG. 19B is an end view of an embodiment of a compressed expandable body.
Figure 19C:
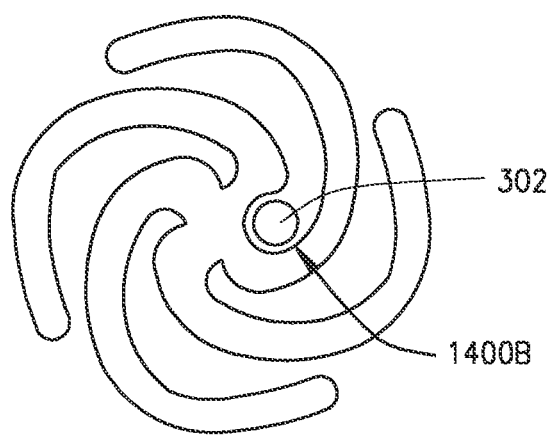
FIG. 19C is an end view of an embodiment of a compressed expandable body that defines an off-center channel.
Figure 19D:
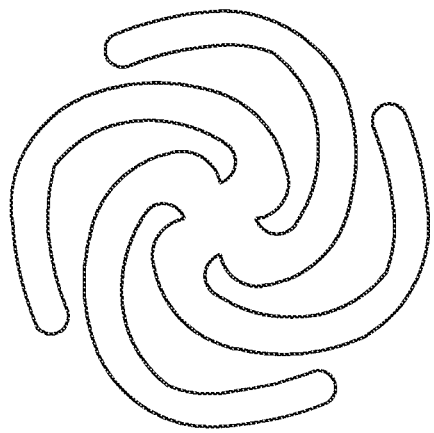
FIG. 19D is an end view of an embodiment of a compressed expandable body.

In FIG. 19A, the expandable body 100, 140, 150, or 170A-G has been pleated, folded, and wrapped around a hollow cylindrical member 304 of the delivery catheter 300, such hollow cylindrical member including a bridging catheter, similar to the bridging catheter 160. Such embodiment may also comprise compression of the folded and wrapped expandable against the delivery catheter. In FIG. 19B, the expandable body 100, 140, 150, or 170A-G is pleated and wrapped without being wrapped around a hollow cylindrical member or delivery catheter. In another embodiment, the expandable body 100, 140, 150, or 170A-G is folded into pleats, then the pleats of the folded expandable body are wrapped around an obturator, removable wire, guidewire, or guidance member 304, as shown in FIG. 19C. Such embodiment may also comprise compression of the folded and wrapped expandable against the obturator, removable wire, guidewire, or guidance member 304. In another embodiment, the expandable body 100, 140, 150, or 170A-G is folded into pleats, and then the pleated folds are rolled into a generally cylindrical shape without a removable wire, obturator, guidewire, guidance member or catheter acting as central fixation point, as shown in FIG. 19D.

In various embodiments, the expandable body 100, 140, 150, or 170A-G is attached to the delivery catheter 300, 400, then the pleats are formed, and then the pleated folds are wrapped and compressed onto the delivery catheter 300, obturator 404, or guidewire. In another embodiment, the expandable body 100, 140, 150, or 170A-G is first folded to form pleats, and then attached to the delivery catheter 300, 400, and then the pleated folds are wrapped and compressed onto the outer surface of the delivery catheter 300, obturator 404, or guidewire. In another embodiment, the expandable body 100, 140, 150, or 170A-G may be folded and compressed into a variety of shapes in a manner similar to Japanese origami.

The expandable body 100, 140, 150, or 170A-G may be folded to form one or more pleats, which may be further folded, rolled, and compressed, similar to the folding of non-compliant angioplasty expandable bodies. In various other embodiments, the pleated expandable body is folded and compressed to fit on the end of a flexible guide wire and travel within a hollow cylindrical member of a separate catheter. The expandable body 100, 140, 150, or 170A-G may be folded and compressed using any suitable arrangements and methods. It is desired that the surface of the expandable body 100, 140, 150, or 170A-G be smooth when in the delivery configuration. In certain embodiments, it is desired that the folding of the expandable body 100, 140, 150, or 170A-G result in even folds.

Detaching the Expandable Body

The expandable body 100, 140, 150, or 170A-G may be attached to, or engaged with, the delivery catheter in a variety of ways. For example, the expandable body 100, 140, 150, or 170A-G may be affixed to the delivery catheter by a friction fit, using an adhesive, or glue, by a weld or solder, by a junction or uniting of components, or by the application of a compressive force from a clamp, ring, elastomer sleeve or wrap, or compressive balloon. Various methods and devices may be used to separate the expanded expandable body from the delivery catheter. By way of example and not limitation, these methods and devices may be broadly categorized as physical or mechanical, electrical, thermal, chemical, hydraulic, and sonic.

Detachment by Electrolysis

The expandable body 100, 140, 150, or 170A-G may be detached or separated from the delivery catheter by electrolysis. When using electrolysis, a constant current, constant voltage, or square wave voltage potential may be used. Detachment of the expandable body 100, 140, 150, or 170A-G from the delivery catheter may be performed using a medical device or system with one, two, or three electrical conductors, as shown in FIGS. 23B-F. In one embodiment, a conductor arrangement 1010 includes three conductors incorporated into, or carried by, a delivery catheter 1000. In alternate embodiments of a three-conductor arrangement, two conductors are incorporated into, or carried by, a delivery catheter 1000 and a third conductor is configured to make electrical contact with patient in another manner, such as with an electrode patch or electrode needle. Similarly, one conductor may be is incorporated into, or carried by, a delivery catheter 1000 and two conductors that are configured to make electrical contact with patient in another manner, such as with an electrode patch or electrode needle, such as the patch 3106 shown in FIG. 23A. In a two conductor arrangement 1008, two conductors are incorporated into, or carried by, a delivery catheter 1000. Alternatively, one conductor may be incorporated into, or carried by, a delivery catheter 1000 and one conductor is configured to make electrical contact with patient in another manner, such as with an electrode patch 3106 or electrode needle, as shown in FIG. 23A. Another conductor arrangement 1007, as shown in FIG. 23F, includes a single conductor arrangement, where a single conductor is incorporated into, or carried by, a delivery catheter 1000.

The medical device or system may further comprise a terminus such as an electrode at the distal end of the conductor, including a terminus that is a tubular or ring shaped cathode ring 1028. In other embodiments, the terminus is a ring-shaped segment of exposed stainless steel in the proximal neck of the expandable body, such segment capable of functioning as an anode.

Figure 23G:
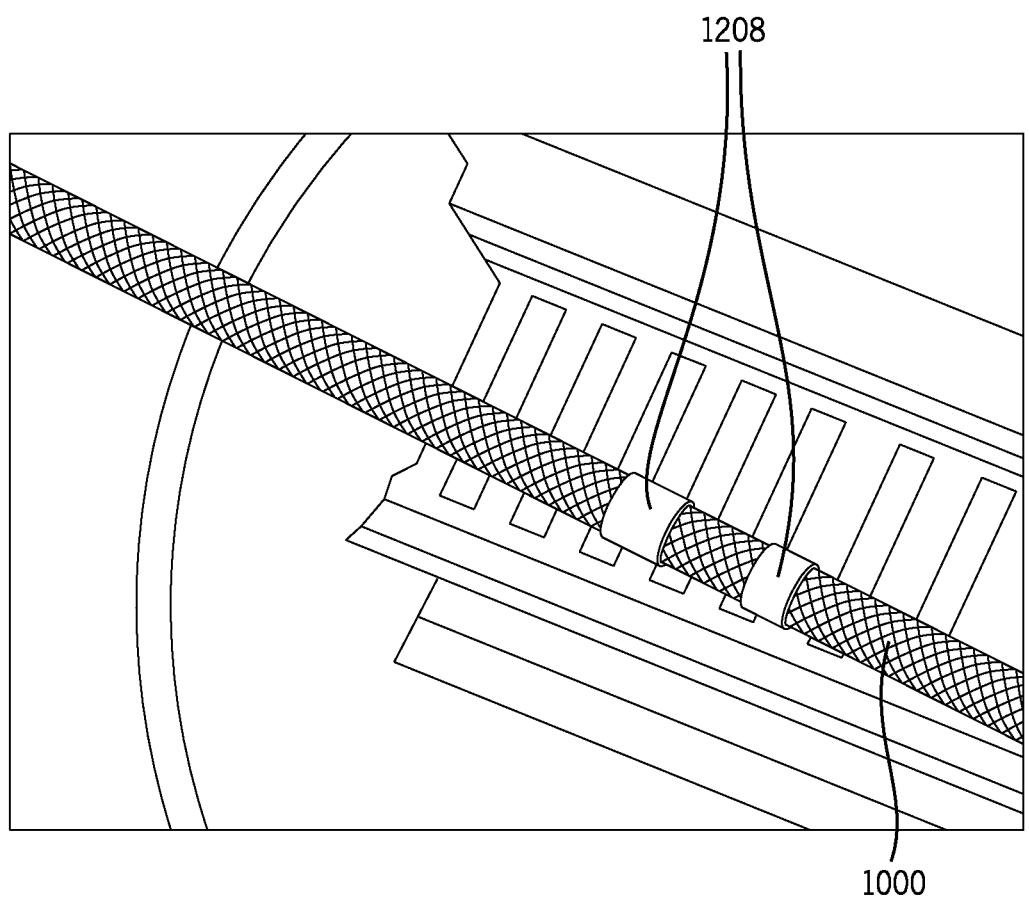
FIG. 23G is a plan view of a catheter supporting one or more electrode rings.

The two-conductor arrangement may be used to perform constant current electrolysis, wherein one conductor is electrically coupled to an anode and one conductor is electrically coupled to a cathode, as shown in FIG. 23G. The various three-conductor arrangements may be used to perform constant voltage electrolysis or electrolysis using a square-wave voltage potential, wherein one conductor is electrically coupled to an anode, one conductor is electrically coupled to a cathode, and a third conductor is electrically coupled to a reference electrode. In any of these arrangements, the electrical conductors or electrodes may be composed of any biocompatible conductive material including platinum, stainless steel, gold, or silver, and alloys thereof. In one example, the electrical conductors or electrodes may be comprised of a platinum-iridium alloy.

When using the two electrical conductor arrangement 1008 to perform constant current electrolysis, there is less control over the voltage potential in the anode or working electrode 1014. As such, the voltage potential at the working electrode 1014 and anode site or portion 3102, increases until the potential and current flowing to the working electrode, or anode, is sufficient to cause oxidation of ions in the bloodstream near the working electrode, or anode. For example, the electrical current may break down $H_2O$ molecules in the bloodstream to form $H^+$ ions and electronegative $O_2$ molecules. In one example, the $O_2$ molecules can then bond to exposed gold at the working electrode, or anode, of a gold expandable body 100, 140, 150, or 170A-G and dissolve the exposed gold strip, thereby enabling detachment of the expandable body and the delivery catheter. In one embodiment, a polymer coating on the expandable body 100, 140, 150, or 170A-G can be an electrical insulator or dielectric material that prevents or retards the $H^+$ ions and $O_2$ molecules from reacting with the coated portions of the expandable body. In another example, electrolysis can occur in a ring-shaped strip of exposed stainless steel at the anode site 3102, in the neck of expandable body wherein the main body comprises gold, resulting in dissolution of the exposed stainless steel, thereby enabling detachment of the expandable body and the delivery catheter. In one embodiment, a polymer coating on the expandable body 100, 140, 150, or 170A-G can be an electrical insulator or dielectric material that prevents or retards electrolysis the coated portions of the expandable body.

Figure 23H:
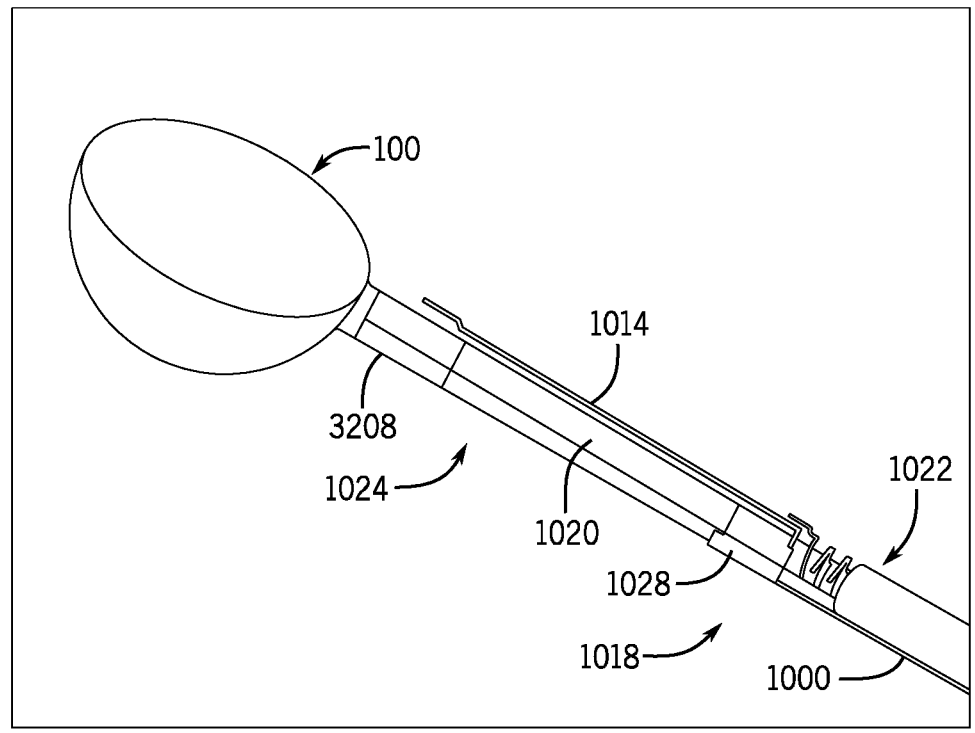
FIGS. 23H-I are partial cross-section and perspective views of an expandable body attached to a delivery device.
Figure 23I:
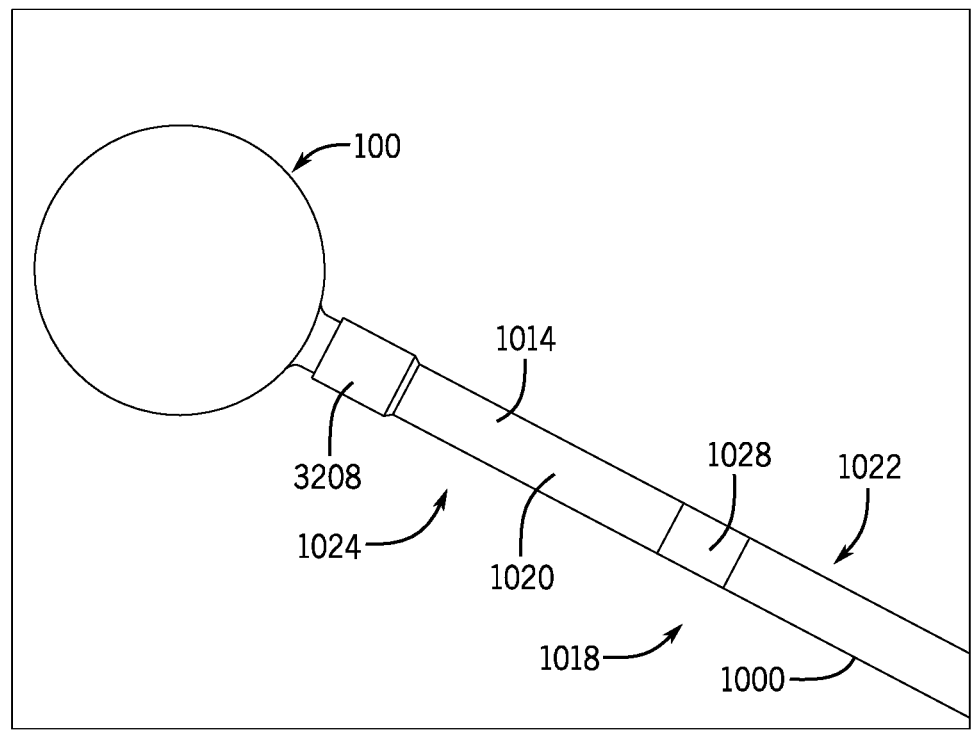

In one embodiment, approximately 0.01 to 5.0 mA of constant current is provided between the anode site 3102 or the working electrode and a cathode or ground electrode 3106 electrically engaged to an electrode patch 3106 on the patient's skin or a needle in the patient that functions as the cathode for the electrolysis system and process. In another embodiment, the cathode or ground electrode is mounted on the delivery catheter 300, as shown by 1028 on FIG. 23G, including in the form of a conductive cathode rings or tube. Another embodiment of the two electrical conductor arrangement is shown in FIGS. 23H-I. In this embodiment, the proximal end 1018 of a thermoset polymer segment 1020 is bonded to a distal end 1022 of the catheter 1000, while the distal end 1024 of the thermoset polymer segment is bonded to metallic ring 3208 formed in the neck 116 or 3208 of the expandable body 100, 140, 150, or 170A-G. An anode site 3102 is present in the neck 116 of the expandable body 100, 140, 150, or 170A-G. As shown in FIG. 23H, a conductor wire 1014 is embedded within the polymer segment 1020 and bonded to the neck 116 or 3208 of the expandable body 100, 140, 150, or 170A-G, resulting in an electrical connection to the ring-shaped anode site 3102, via the working electrode 1014. In one embodiment, the conductor wire may be bonded directly to the anode site 3102. In some embodiments, the conductor wire 1014 may be bonded to the neck 116 or 3208 of the expandable body 100, 140, 150, or 170A-G using a silver adhesive or any other suitable adhesive. In other embodiments, the conductor wire 1014 may be welded to the neck 116 or 3208 of the expandable body 100, 140, 150, or 170A-G, including by laser welding.

As shown in FIG. 23H, a cathode, or ground electrode 1028 is mounted on the delivery catheter 1000. Additionally, a conductor wire 1016 is embedded within the wall of the delivery catheter and bonded to the cathode, or ground electrode 1028, resulting in an electrical connection to the cathode, or ground electrode 1028, which is ring-shaped. In one embodiment, the conductor wire may be bonded directly to the cathode ring 1028. In some embodiments, the conductor wire 1016 may be bonded to the cathode ring 1028 using a silver adhesive or any other suitable adhesive. In other embodiments, the conductor wire 1016 may be welded to the cathode ring 1028, including by laser welding.

In another embodiment, the three electrical conductor arrangements may be used to provide more control and selectivity in the voltage potential of the anode site 3102. In addition to the working electrode 1014 and the ground electrode 1016, the three electrical conductor arrangement includes a reference electrode and a potentiostat (not shown) that are used to monitor and control the voltage potential of the and, or working electrode, relative to the reference electrode. In various embodiments, the reference electrode is preferably made of platinum, silver, or silver chloride. By way of example and not limitation, the three electrical conductor arrangement can be used to detach the expandable body 100, 140, 150, or 170A-G using a constant current, a constant voltage or an alternating square wave-potential voltage. The working electrode 1014 is modulated based on a comparison between the voltage of the anode site 3102 via the working electrode 1014 and the voltage of the reference electrode, which in some embodiment can be supported on the delivery catheter and in other embodiments can be configured to make electrical contact with patient in another manner, such as with an electrode patch or electrode needle. In one embodiment, the potentiostat is configured to provide a voltage in the range between approximately +0.5 V and +1.5 V at the working electrode 1014 relative to the reference electrode.

In various embodiments, the electrical current travels from the cathode ring 1028 that is supported on the delivery catheter 1000 to a location outside the body of the patient by a conductive wire 1016 embedded in the wall of the delivery catheter. The conductive wire 1016 can also simultaneously provide structural reinforcement for the wall of the delivery catheter 1000.

In another embodiment, the expandable body 100, 140, 150, or 170A-G and the delivery catheter 300 may be joined by one or more non-insulated welds 316, solder, or an adhesive 318, as shown in FIG. 23A, including embodiments wherein the joining is between the proximal neck 116 and the distal end of the delivery catheter 304 or 306. An electrical conductor 320, which may be in the form of a wire, or cable that relies on the surrounding electrical insulating material of the catheter wall and/or a dedicated electrical insulating jacket of the electrical conductor itself for electrical insulation, extends along the length of the delivery catheter from the proximal end of the delivery catheter 300 to the distal end of the delivery catheter. The proximal end of the electrical conductor 320 is electrically coupled to a power source or source of electrical current 3100 outside the patient's body. The power source 3100 is also in electrical communication with a needle or electrode patch 3106 on the patient's skin that functions as the cathode for the electrolysis process. The distal end of the electrical conductor 320 is coupled to the proximal portion of the expandable body 100, 140, 150, or 170A-G, which is also coupled to the distal portion of the delivery catheter. In this embodiment, a portion of the neck expandable body 100, 140, 150, or 170A-G is functioning as the anode site 3102 for electrolysis. In this embodiment, the electrolysis electrical conductor 320 is in electrical communication with the portion 3102 of the expandable body that is not electrically insulated and that is not bonded to the delivery catheter (i.e., the anode site). In various embodiments, the electrolysis electrical conductor 320 can lie within the wall of the delivery catheter 300 as shown in FIG. 23A, along the exterior surface of the delivery catheter, or within a lumen of the delivery catheter.

In some embodiments, as shown in FIG. 23A, the electrical conductor 320 is insulated, wherein a proximal anode portion 3102 of the expandable body 100, 140, 150, or 170A-G is not insulated, including a portion of the proximal neck, which is similar to detachment site 3302, as shown in 30A-F. In some embodiments, the electrical conductor 320 and the remainder of the expandable body 100, 140, 150, or 170A-G and 116, including the remainder of the necks, are insulated; while a proximal anode portion 3102 of the expandable body is not insulated, including a portion of the proximal neck in some embodiments. In some embodiments, the neck 116 of the expandable body 100, 140, 150, or 170A-G is comprised of metal that can readily undergo electrolysis (such as stainless steel) wherein the remainder of the expandable body is comprised of a metal that does not as readily undergo electrolysis, such as gold or platinum. For this embodiment, the gold or platinum portion of the expandable body 100, 140, 150, or 170A-G may not need to be insulated. An electrical current or charge is applied to the electrical conductor 320 after the expandable body 100, 140, 150, or 170A-G is expanded. The current is applied in an amount and for a time sufficient to dissolve at least a portion of the non-insulated anode portion 3102 of the expandable body 100, 140, 150, or 170A-G, enabling the separation of the delivery catheter from the expandable body, wherein the expanded expandable body remains in place at the desired position while the delivery catheter 300 is removed.

In another embodiment, an electrical current is applied to the electrical conductor 320 after the expandable body 100, 140, 150, or 170A-G is expanded. The current is applied in an amount and for a time sufficient to dissolve at least a portion of a weld or solder between the expandable body 100, 140, 150, or 170A-G and the delivery catheter 300, enabling the separation of the delivery catheter from the expandable body, wherein the expanded expandable body remains in place at the desired position while the delivery catheter 300 is removed. In another embodiment, the current is applied in an amount and for a time sufficient to dissolve at least a portion of the main body of the expandable body enabling the separation of the delivery catheter from the expandable body, wherein the expanded expandable body remains in place at the desired position while the delivery catheter 300 is removed. In one embodiment the current is a direct current (DC) while in another embodiment, the current is an alternating current (AC).

Typically, during constant current electrolysis, gas bubbles formed as a byproduct of the electrolysis tend to form an insulating barrier at the detachment site. The gas bubble barrier in combination with an aggregation of non-ionic blood constitutes (fats, proteins, and amino acids, among others) at the detachment site tends to increase impedance at the detachment site and increase the time necessary for detachment, as the rate of electrolysis is decreased. Similarly, blood may begin to clot at the detachment site 3302 further impeding the detachment processes.

Electrolysis is preferably performed when the expandable body 100, 140, 150, or 170A-G is positioned such that the detachment site 3302 shown in FIGS. 30A-F is within a constant stream of ionic blood constituents. For example, when the ballstent 100 is positioned to fill an aneurysm, the detachment site 3302 can be positioned such that the detachment site 3302 protrudes into the adjacent parent blood vessel or near the adjacent parent blood vessel. While in or near the adjacent parent blood vessel, the detachment site 3302 is exposed to a constant stream of ionic blood constituents that aid in the electrolysis process to detach the ballstent 100. The constant stream of blood also minimizes the incidence of blood coagulation at the detachment site 3302 during electrolysis, thereby potentially reducing the time required to separate the expanded expandable body 100, 140, 150, or 170A-G and the delivery catheter, and reducing the risk of embolism of thrombus and stroke, when cerebral aneurysms are treated.

In another embodiment, voltage controlled electrolysis is performed using an alternating square wave potential voltage. By way of example and not limitation, the potential at the anode site 3102 or working electrode 1014, as shown in FIGS. 23H-I, alternates between approximately +0.5 V and approximately +0.8 V, relative to the reference electrode, at a frequency in a range between 0.1 Hz and 10 Hz. In one aspect, the rate at which the voltage potential of the anode site 3102 or working electrode 1014 varies may be configured to allow for removal of oxides that form on the surface of the anode or working electrode and any aggregation of protein that may form. In this embodiment, oxides are removed during the "depassivation" period of lower voltage while aggregated proteins are removed during the "passivation or hydrolysis" period of higher voltage. The removal of both oxides and aggregated proteins is promoted by the voltage cycling. Therefore, the use of an alternating square wave potential voltage or the use of square wave voltage pulses may allow for a shorter and more consistent detachment times.

In various embodiments, the voltage ranges used to perform voltage-controlled electrolysis may vary in response to the composition of the material at the detachment site 3302 (e.g., anode portion 3102) and the reference electrode. For example, if the detachment site 3302 is composed of gold and the reference electrode 1026 is composed of platinum then the voltage at the gold anode may alternate between approximately +0.6 V and approximately +1.4 V relative to the reference electrode at approximately 1 Hz. Conversely, the voltage potential at a detachment site 3302 composed of 304 stainless steel may alternate between approximately +0.1 V and approximately +0.4 V relative to the platinum reference electrode at approximately 1 Hz. In one embodiment, the detachment site 3302, functioning as an anode site 3102, is 316L stainless steel. In this embodiment, electrolysis is performed such that the potential at the 316L stainless steel anode alternates between approximately +0.7 V and approximately +1.2 V relative to the platinum reference electrode at approximately 1 Hz. In various embodiments, it is desirable for the lower voltage of the alternating square wave voltage potential to be below the hydrolysis potential of water.

Sealing the Detached Expandable Body

In one embodiment, the opening 112 and or 114 of the expanded expandable body 100, 140, 150, or 170A-G is left open at the end of the procedure, including the opening in a proximal neck or a distal neck. In other embodiments, the openings 112 and/or 114 of the expanded expandable body 100, 140, 150, or 170A-G is closed prior to the end of the procedure. By way of example and not limitation, the opening 112 may be sealed by applying an external force with the inflation of the balloon portion 1102 of a balloon catheter 1100 adjacent to the expanded expandable body 100, 140, 150, or 170A-G, as shown in FIG. 17E. Alternatively, an opening may be sealed by snugging a loop of flexible material around the external surface of the neck of the expandable body 100, 140, 150, or 170A-G prior to separation of the expanded expandable body and the delivery catheter. In this method, the loop of material may comprise a wire, polymer strand, filament, string, thread, or snare.

In various embodiments, one or both necks 116 and 118 of the expandable body 100, 140, 150, or 170A-G are plugged or otherwise sealed after inflation. For example, the necks 116 and 118 may be plugged by the insertion of a solid structure dimensioned to fit securely within the necks. This material may be a sponge, a coil, or a metallic cap that is placed over or within the necks 116 and 118.

Radiopaque Marking of the Expandable Body

According to any of the methods where the expandable body 100, 140, 150, or 170A-G is detached or separated from delivery catheter, one or more radiopaque markers may be incorporated into the appropriate portions of the expandable body or delivery catheter, in addition to the nose cones 360 or 362A-B, to assist in the positioning of the expandable body, expansion of the expanded expandable body, detachment or separation of the expanded expandable body from the delivery catheter, and removal of the delivery catheter after detachment or separation. For example, a radiopaque marker band or spot may be incorporated into the medical device to identify the location where separation is intended or designed to occur. In addition, radiopaque material may be incorporated into the expandable bodies 100, 140, 150, or 170 A-G. In addition, a radiopaque spot or marker band may be incorporated into distal end of the delivery catheter so that the tip of the delivery catheter can be visualized under fluoroscopy while pulling the delivery catheter away from the expanded expandable body 100, 140, 150, or 170A-G. A radiopaque spot or marker band may also be placed onto the detachment components, as need be. The radiopaque marker may comprise various radiodense materials, including but not limited to a metal band, a metal spot or line, or spot or a line of barium.

In various embodiments, a saccular aneurysm 700 or a blood vessel may be visualized by using a radiopaque dye. The radiopaque dye may be injected prior to introducing the expandable body 100, 140, 150, or 170A-G and can be used to confirm the appropriate size and position for the compressed or expanded body.

Expandable Body Medical Kit

In various embodiments, a medical kit may be provided for treating a patient with the medical device. The medical kit may include the medical device 500, a guide wire 302, one or more guide catheters 800, one or more expandable body support structures, one or more accessory coils, and instructions for methods for separating the expanded expandable body 100, 140, 150, or 170A-G from the delivery catheter 300 or 400. In various embodiments, the medical kit may including medical devices comprising accessory coils or delivery catheters for accessory coils, and separate medical devices for separation, such as a power source and controller for performing electrolysis or heating a thermally-sensitive binding structure that joins the expandable member 100, 140, 150, or 170A-G and the delivery device. The medical kit may further include instructions for use. The instructions for use may be provided on the packaging of the medical kit in the form of a label. The instructions for use may be provided in any tangible medium (e.g., paper, CD, or DVD) either separate from the medical kit or contained within the packaging of the medical kit. The instructions for use may be provided via an electronic data feed or via instructions posted on the Internet.

The medical device 3400A can be used as part of various systems, methods, and medical kits. These systems, methods, and medical kits can be used to treat saccular arterial aneurysms, such as a saccular cerebral aneurysm. Alternatively, these systems, methods, and medical kits can be used to treat a variety of medical conditions. In one embodiment, the systems, methods, and medical kits can be used to occlude biological conduits in patients in need thereof, the biological conduits including arteries, veins, vascular structures, ducts, airways, bile ducts, pancreatic ducts, enterocutaneous fistulas, ureters, fallopian tubes, and urethras, among others. The medical kit includes the medical device and instructions for use. The medical kit may also contain additional components for carrying out a variety of treatments using the medical device 500.

Example Methods for Manufacturing a Medical Kit

FIGS. 34-36 are flowcharts of methods to manufacture the expandable body 100, 140, 150, or 170A-G, a delivery catheter 1000, and a medical kit. In one embodiment, a method 4000 for making the expandable body 100, 140, 150, or 170A-G includes forming the expandable body on a mandrel at step 4002 and coating the expandable body at step 4004. At step 4006, the detachment site and the sites where the conductive wires are bonded to the expandable body 100, 140, 150, or 170A-G are exposed. The expandable body 100, 140, 150, or 170A-G is then annealed, folded, wrapped, and annealed again at steps 4008-4012.

A method 4100 to manufacture or otherwise prepare an existing delivery catheter is provided. At step 4102, a coil-reinforced catheter 3402, with electrically conductive coils is obtained and the outer coating is removed from the catheter to expose a portion of the electrical conductors of the coil at step 4104. At step 4106 a portion of the exposed electrical conductors are unwrapped, a cathode ring 1028 is bonded to the catheter 1000 and an electrical conductor thereof at step 4108, and the exposed electrical conductors are then covered with an insulating material at step 4110. The bonding sites on the catheter 3402 are masked, and the catheter is coated with a hydrophilic or lubricious coating at steps 4112 and 4114. One end of the catheter 3402 is configured for engagement to a fluid source and optionally a source of electrical current. By way example and not limitation, the catheter 1000 may be bonded to a hub that may further include a Luer fitting, an electrical jack, or a port for passage of a guide wire.

The electrical conductors 1014 and 1016 are bonded to the anode and cathode, respectively, and then the electrical conductors are extended from the delivery catheter and covered in insulating jackets at steps 4118 and 4120. At steps 4122 and 4124, the extension electrical conductors are soldered to electrical plugs, such as the electric terminal 3422, and the soldered joints are insulated.

As shown in FIG. 36, the method 4200 to assemble the medical device 3400A and a medical kit includes bonding the expandable body 100, 140, 150, or 170A-G to the catheter 3402 at step 4202. At step 4204, the electrical conductor 1014 is bonded to the expandable body 100, 140, 150, or 170A-G to form an anode and the exposed conductive surfaces are further insulated at step 4206. Once assembled, the device 3400A is tested at step 4208 and packaged in a medical kit at step 4210.

Example Methods of Using the Expandable Body

A typical method for using the medical device 3400A to treat a saccular aneurysm includes accessing the vascular system of a human with a needle, passing a guidance member, or guide wire, 302 into the vessel, optionally placing a vascular sheath, advancing the medical device comprising a compressed ballstent 100 and a delivery catheter 300 or 400 and advancing it until the compressed ballstent is located in the lumen 701 of an aneurysm sac 700, such ballstent configured to occupy only a portion of the lumen or cavity of the saccular aneurysm. Then the ballstent 100 is expanded by passing a fluid, liquid, gas, or solid material, or combinations thereof, through the delivery catheter and into the central void or space 108 of the ballstent. The guidewire is removed and a coil delivery catheter with a pre-loaded accessory coil is passed through the guide wire until its tip has exited the distal end of the medical device, including exiting from an expandable body, the neck of an expandable body or a nose cone affixed to an expandable body. The accessory coil is then expelled from the coil delivery catheter and into the unfilled portion of the lumen of the aneurysm such that the accessory coil makes contact with the wall of the aneurysm opposite the opening from the parent vessel into the aneurysm lumen and simultaneously makes contact with the exterior surface of the wall of the expanded expandable body. Optionally, one or more additional accessory coils can be placed, as needed. The delivery catheter is then separated from the expanded ballstent 100 are then the delivery catheter is removed from the body, while the expanded ballstent and the accessory coil(s) remain in place within the lumen 701 of the aneurysm sac 700. The position of the ballstent 100 and accessory coil(s) during and after the procedure may be monitored by any suitable methods, including fluoroscopy, computed tomography, MRI, and ultrasound, including intravascular ultrasound. The degree of occlusion of the aneurysm can be evaluated using angiography before and after detachment of the expanded ballstent 100 from the delivery catheter.

In various embodiments of the ballstent 100, the shape of a ballstent that has been expanded in the lumen of a saccular aneurysm is determined, in part, by the formed shape of the ballstent. For example, in some embodiments, the ballstent 100 is manufactured into a round, oblong, irregular, or non-spherical orientation to match at least a portion of the contours of the cavity for a particular saccular aneurysm 700, including the diameter of the opening into the saccular aneurysm from the adjacent parent vessel from which it arose. The expanded shape is also determined by the size and shape of the lumen of the saccular aneurysm. The expanded shape can also be determined by the application of an external force, such as by inflating the balloon portion of a balloon catheter adjacent to the expanded ballstent 100. In certain embodiments of the methods, the balloon portion 1102 of a balloon catheter 1100 is inflated in the lumen of the parent blood vessel 1202 adjacent to the expanded ballstent 100 in the lumen of the aneurysm sac, thereby pushing the wall 1104 of the ballstent 100 toward the aneurysm, as shown in FIG. 17E. In other embodiments, the ballstent 100 is manufactured into a non-spherical orientation to match the contours of the cavity for a particular saccular aneurysm 700.

In all embodiments, the expanded shape of the ballstent 100 is determined by the following factors: 1) the manufactured shape of the ballstent 100; 2) the degree of ballstent expansion; 3) the size and shape of the aneurysm 700; and 4) the effect of any applied external force on the ballstent after expansion. By way of example and not limitation, the manufactured size and shape of the ballstent 100 may be determined by making measurements of the aneurysm 700. The measurements can be made by using medical images, including two-dimensional and three-dimensional reconstructions, and standard distance reference markers. Other methods of measuring the aneurysm may also be used.

In another embodiment, the position, size, and shape of the expanded ballstent 100 can be manipulated while positioned within the aneurysm 700. In this embodiment, it is not necessary to determine the precise contours of the aneurysm 700 prior to inserting the ballstent 100. The ballstent 100 is shaped by the degree of expansion of the ballstent and the application of external forces. For example, an external force may be applied by inflating the balloon portion of a balloon catheter adjacent to the expanded ballstent 100, or by tools inserted through or around the delivery catheter 400 or guide catheter 800. In other embodiments, the ballstent 100 may be shaped in a step prior to or after the step of separating the expanded ballstent from the delivery catheter 400.

In various embodiments, the ballstent 100 is designed so that the exterior surface 110 or 124 of the expanded ballstent 100 makes contact with a substantial portion of the inner surface 704 of the aneurysm 700, as shown in FIGS. 11A-F and 15A-F. In some embodiment, the exterior surface 110 or 124 of the ballstent 100 and 140 makes contact with at least 50%, 75%, 90% or more of the inner surface 704 of the aneurysm 700, including up to 100%. In embodiments, the expanded ballstent 100 and 140 is designed to completely or nearly completely fill the lumen 701 of the aneurysm 700, including up to 100%. In some embodiments, the expanded ballstent 100 and 140 fills at least 50%, 75%, 90% or more of the volume of the lumen 701 of the aneurysm 700.

In various embodiments of the expandable body 100, 140, 150, or 170A-G, the shape of the expandable body that has been expanded in the lumen of a blood vessel segment is determined, in part, by the formed shape of the expandable body. For example, in some embodiments, the expandable body 100, 140, 150, or 170A-G is manufactured into a cylindrical, oblong, irregular, or non-spherical orientation to match the contours of the lumen, void, or cavity for a particular blood vessel segment or biological conduit segment. The expanded shape is also determined by the size and shape of the lumen, void, or cavity of the blood vessel segment, or biological conduit segment. The expanded shape can also be determined by the application of an external force, such as by inflating the balloon portion of a balloon catheter adjacent to the expanded ballstent 100, 140, 150, or 170A-G. In other embodiments, the expandable body 100, 140, 150, or 170A-G is manufactured into a non-spherical orientation to match the contours of the lumen, void, or cavity for a particular blood vessel segment, or biological conduit segment.

In all embodiments, the expanded shape of the expandable body 100, 140, 150, or 170A-G is determined by the following factors: 1) the manufactured shape of the expandable body; 2) the degree of expandable body expansion; 3) the size and shape of the lumen, void, or cavity of the blood vessel segment, or biological conduit segment; and 4) the effect of any applied external force on the expandable body after expansion. By way of example and not limitation, the manufactured size and shape of the expandable body 100, 140, 150, or 170A-G may be determined by making measurements of lumen, void, or cavity to be filled. The measurements can be made by using medical images, including two-dimensional and three-dimensional reconstructions, and standard distance reference markers. Other methods of measuring the lumen, void, or cavity may also be used.

In another embodiment, the position, size, and shape of the expanded expandable body 100, 140, 150, or 170A-G can be manipulated and configured or changed in vivo or even in situ while positioned within the blood vessel segment or biological conduit. In this embodiment, it is not necessary to determine the precise contours of the lumen, void, or cavity to be filled prior to inserting the expandable body 100, 140, 150, or 170A-G. The expandable body 100, 140, 150, or 170A-G is shaped by the degree of expansion of the expandable body and the application of internal and/or external forces. For example, an external force may be applied by inflating the balloon portion of a balloon catheter adjacent to the expanded expandable body, or by tools inserted through or around the delivery catheter 400 or guide catheter 800. In other embodiments, the expandable body 100, 140, 150, or 170A-G may be shaped in a step prior to or after the step of separating the expanded expandable body from the delivery catheter 400.

In all embodiments, the expandable bodies 100, 140, 150, or 170A-G are configured to maintain their expanded shapes. As such, the expanded bodies are not designed for or intended for flattening into disc-like structures before or after separation from the delivery catheter.

An Example Method of Treatment Using the Expandable Body

By way of example and not limitation, as can be understood from FIGS. 9, 10A-B, and 11A-F, a first method of using the device 500 or 3400A to treat a patient may include the steps of examining a patient and collecting diagnostic medical images to identify a saccular aneurysm. The vascular system may be accessed using any suitable method including accessing an artery using the Seldinger technique. A guide wire 302 is then inserted into the vascular system. Then a guide catheter 800 is inserted into the vascular system and advanced into or near the lumen of the saccular aneurysm. The position and luminal dimensions of the saccular aneurysm are then visualized by an intra-arterial injection of radiographic contrast solution under fluoroscopy. The guide wire 302 is removed and the medical device 500 or 3400A is then inserted through the guide catheter 800 until the compressed ballstent 100 is advanced into the lumen 701 of the aneurysm 700. The ballstent 100 is then expanded in the lumen 701 of the aneurysm 700. A radiographic contrast solution may be injected into the parent vessel 1202 of the aneurysm 700 to confirm that the size of the expanded ballstent 100 is appropriate and that it is properly positioned in the aneurysm. Once proper placement and sizing of the expanded ballstent 100 has been confirmed, the expanded ballstent is separated from the delivery catheter 400 by any of the methods disclosed herein, and the delivery catheter is removed. The expanded ballstent 100 is left in the patient, where subsequent examination may be conducted to determine if additional treatment is necessary. The expanded ballstent 100 is left in the patient functions to reduce the flow of blood into the aneurysm, reduce the risk of bleeding of the aneurysm, or reduce the risk of expansion of the aneurysm, and as such it alleviates current medical problems the patient is experiencing or reduces the risk of future medical problems the patient might experience had the aneurysm 700 not been treated.

By way of example and not limitation, as can be understood from FIGS. 13, 14A-B, and 15A-F, a second method of using the device 500 or 3400A to treat a patient may include the steps of examining a patient and collecting diagnostic medical images to identify a saccular aneurysm. The vascular system may be accessed using any suitable method including accessing an artery using the Seldinger technique. A guide wire 302 is then inserted into the vascular system. Then a guide catheter 800 is inserted into the vascular system and advanced with the guide wire 302 until the guide wire 302 is positioned in or near the lumen of the saccular aneurysm. The position and luminal dimensions of the saccular aneurysm are then visualized by an intra-arterial injection of radiographic contrast solution under fluoroscopy. The guide catheter 800 is removed and the medical device 500 or 3400A is then inserted over the guide wire 302 until the compressed ballstent 140 is advanced into the lumen 701 of the aneurysm 700. The guide wire 302 is removed. The ballstent 140 is expanded in the lumen 701 of the aneurysm 700. A radiographic contrast solution may be injected into the parent vessel 1202 of the aneurysm 700 to confirm that the size of the ballstent 140 is appropriate and that it is properly positioned in aneurysm. Once proper placement and sizing of the expanded ballstent 140 has been confirmed, the expanded ballstent is separated from the delivery catheter 300 by any of the methods disclosed herein and the delivery catheter is removed. The expanded ballstent 100 left in the patient functions to reduce the flow of blood into the aneurysm, reduce the risk of bleeding of the aneurysm, or reduce the risk of expansion of the aneurysm, and as such it alleviates current medical problems the patient is experiencing or reduces the risk of future medical problems the patient might experience had the aneurysm 700 not been treated.

In another embodiment, the expandable bodies 100, 140, 150, or 170A-G may be rapidly deployed during an emergency. In particular, the expandable bodies 100, 140, 150, or 170A-G may be deployed rapidly to treat a ruptured cerebral aneurysm, to immediately reduce bleeding from the aneurysm.

An Exemplary Method of Treating a Patient Having a Cerebral Aneurysm

A hypothetical method for using the medical device 500 or 3400A to treat a patient having a saccular cerebral aneurysm may begin with one or more pre-surgical consultations, where a number of tests may be performed. The tests may include blood tests, urine tests, an electrocardiogram, and imaging tests including a head CT, a head MRI, and a cerebral angiogram, among others. From the diagnostic imaging tests, images, and measurements of the aneurysm may be obtained demonstrating the position, size, and shape of the aneurysm. The consultations may occur several days before, or on the same day, that the procedure is performed.

On the day of the procedure, the patient is prepared for the procedure and typically given local anesthesia. The patient's groin is then prepped and draped in an aseptic manner. Then a physician accesses a femoral artery in the patient with a micropuncture set. A soft tip guide wire 302 is inserted in a retrograde fashion into the femoral artery. A vascular sheath is placed. A diagnostic catheter is advanced over the guide wire until the tip of the diagnostic catheter is in the lumen of the saccular cerebral aneurysm, and the tip of the guidewire is placed in the aneurysm, while the diagnostic catheter is removed. While the physician is positioning guide wire, a surgical assistant prepares the ballstent portion 100 of the medical device by wetting the porous exterior layer 104 of the ballstent with a solution containing thrombin. The medical device 500 or 3400A is advanced over the guide wire and positioned in the lumen 701 of the aneurysm sac 700. After the compressed ballstent 100 is in the desired position, the compressed ballstent is expanded by injecting a saline solution through the lumen 312 of the delivery catheter 300 or 400 and into the central void 108 of the ballstent until the ballstent expands to fill at least a portion of the aneurysm. The physician obtains an angiogram of the aneurysm 700 and the parent artery 1202 by injection of radiographic contrast material in order to confirm that the expanded ballstent 100 is positioned properly within the lumen 701 of the saccular aneurysm 700 and fills the aneurysm adequately. The guidewire is removed and a coil delivery catheter with a pre-loaded accessory coil is passed through the guide wire until its tip has exited the distal end of the medical device, including exiting from an expandable body, the neck of an expandable body or a nose cone affixed to an expandable body. The accessory coil is then expelled from the coil delivery catheter and into the unfilled portion of the lumen of the aneurysm such that the accessory coil makes contact with the wall of the aneurysm opposite the opening from the parent vessel into the aneurysm lumen and simultaneously makes contact with the exterior surface of the wall of the expanded expandable body. Optionally, one or more additional accessory coils can be placed, as needed.

The physician then connects the proximal end of an electrolysis wire 320 or the insulated conductor wire to a DC power source and applies a current to the electrolysis wire or insulated conductor wire which is electrically coupled to the neck 116 of the ballstent 100 in an amount, and for a time sufficient, to result in the dissolution of a portion of the neck or proximal body 208 of the ballstent that is uncoated and without insulation, resulting in separation of the expanded ballstent and the delivery catheter. The physician obtains another angiogram of the aneurysm 700 and the parent artery 1202 in order to confirm that the expanded, released ballstent 100 is positioned properly within the lumen of the saccular aneurysm and fills the aneurysm adequately. The physician removes the delivery catheter 400. The physician advances a balloon catheter 1100 over the guide wire 302 until the balloon 1102 is adjacent to the expanded ballstent 100. The balloon portion 1102 of the balloon catheter 1100 is then inflated with a saline solution until it fills the lumen of the parent artery 1202 and flattens and pushes the wall 1104 of the expanded ballstent 100 toward the aneurysm 700. The physician obtains another angiogram of the aneurysm 700 and the parent artery 1202 in order to confirm that the expanded, released ballstent 100 is positioned properly within the lumen of saccular aneurysm, fills the aneurysm adequately, and that the lumen of the parent artery 1202 is free of obstruction. The physician withdraws the balloon catheter 1100, the guide wire 302, and the sheath and achieves hemostasis of the femoral artery puncture with compression. The patient is then transported to a recovery room. During and after recovery, the physician periodically monitors the patient as well as the position of the ballstent 100 and the completeness of the sealing of the aneurysm 700.

Clinical Examples of Use

Ballstent Treatment

Using a canine model of a large, terminal, carotid artery, venous pouch aneurysm, a comparison was made between treatment with the ballstent (n=2) and treatment with standard coils (n=1).

Methods

Figure 37A:
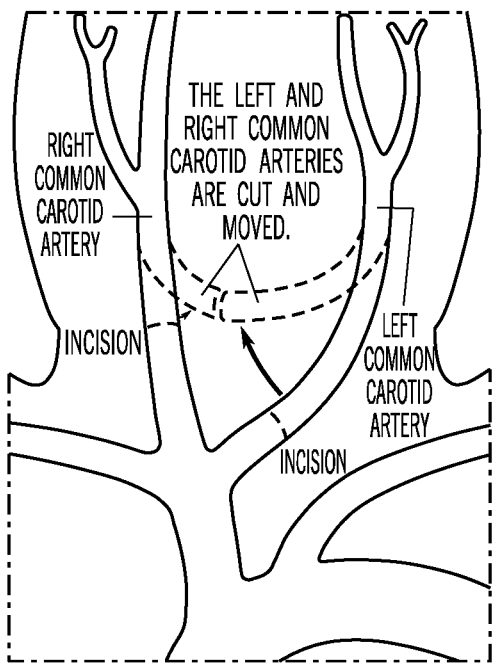
FIGS. 37A-D are illustrations of a process for surgically constructing a saccular aneurysm on a newly created carotid artery terminal bifurcation as performed during clinical testing of an embodiment of the expandable body.
Figure 37B:
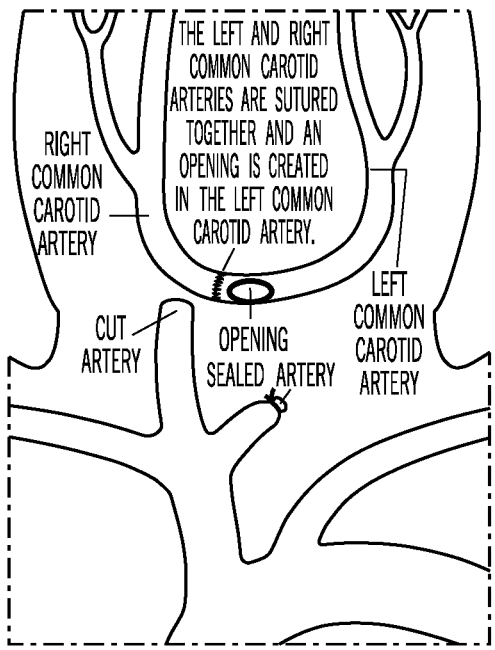
Figure 37C:
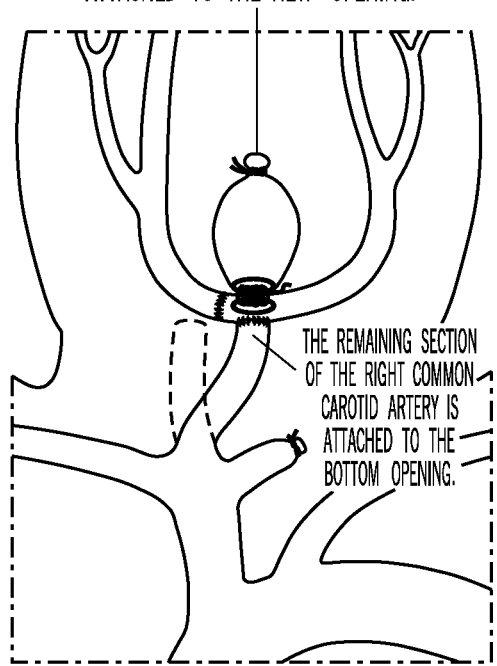
Figure 37D:
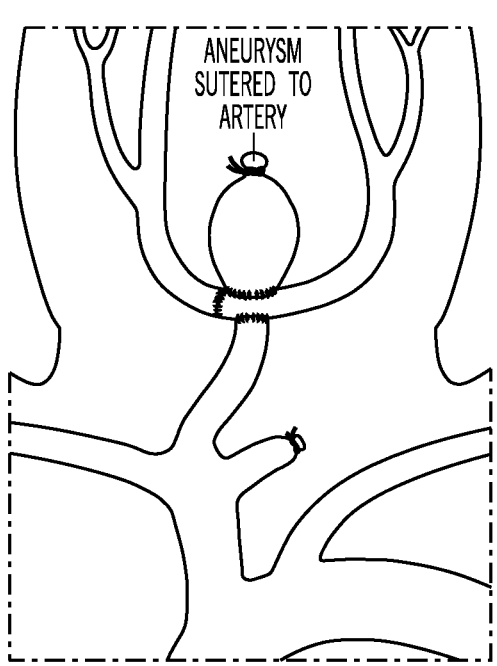

The experimental model used *Canis lupus familiaris* hound cross dogs weighing about 16 kg. In each dog, a single saccular aneurysm was surgically constructed on a newly created carotid artery terminal bifurcation according to FIGS. 37A-D, which illustrates transection of the carotid arteries (FIG. 37A), construction of the terminal bifurcation (FIG. 37B), addition of the saccular aneurysm (FIG. 37C), and the final configuration of the aneurysm fashioned from a transplanted segment of excised jugular vein (FIG. 37D). Contrast angiography was performed after aneurysm creation to verify integrity of the aneurysm.

Approximately 3 weeks after aneurysm creation, an appropriately sized sheath was placed in a femoral artery via surgical cut-down of the vessel. Heparin was administered to achieve a target activated clotting time (ACT)≥300 seconds. Under fluoroscopic guidance, a guide sheath (6 Fr×90 cm long) was advanced into the proximal right common carotid artery caudal to the aneurysm. Contrast angiography was then performed to visualize the lumen of the aneurysm and the parent vessels. A 0.018" guide wire was then placed into the lumen of the aneurysm and the guide sheath was advanced toward the aneurysm.

Figure 38:
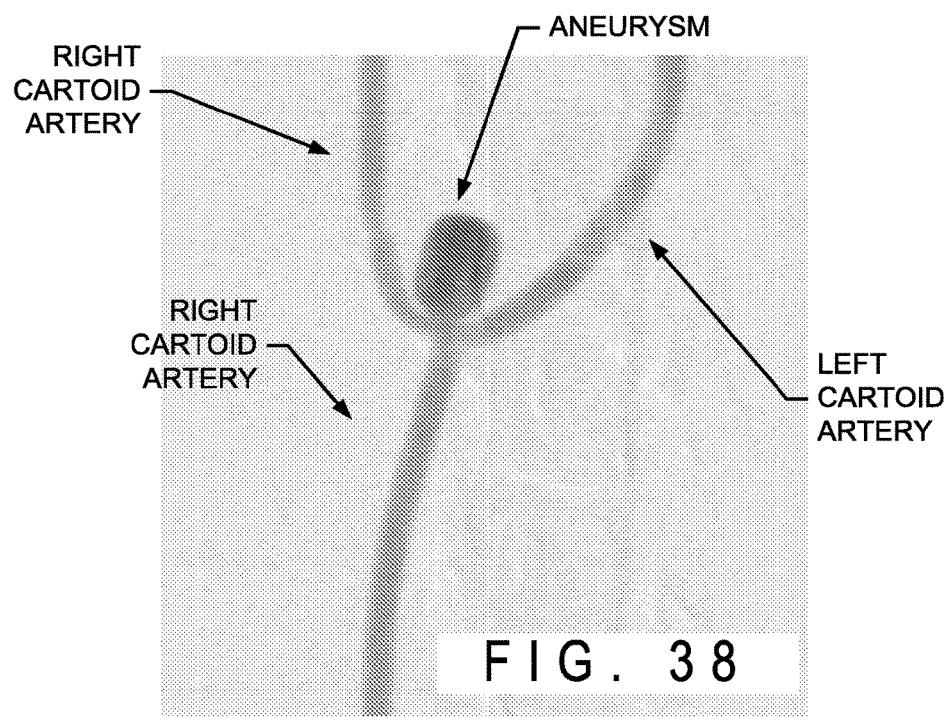
FIG. 38 is an angiogram of a saccular aneurysm acquired during clinical testing of an embodiment of the expandable body.

For the ballstent test group, at the time of treatment the aneurysm is the first animal measured about 12 mm×9 mm×6 mm (FIG. 38), while the aneurysm in the second animal measured about 15 mm×9 mm×10 mm. The aneurysm in each dog was treated with a system including: a first medical device further comprising a ballstent expandable body and one or more second medical device(s) comprising an accessory coil pre-loaded into an accessory coil delivery catheter. The expanded form of the ballstent was spherical. The main body and distal neck of the ballstent comprised gold while the proximal neck comprised stainless steel with a gold coating or plating. The main body of the ballstent measured 8 mm in diameter (in both the first and second axis) and was formed from a single layer of gold measuring 20 microns in thickness. A polymeric nose cone was attached to the proximal neck and also to the distal end of the delivery catheter. The delivery catheter had an outer diameter of 3.5 Fr and comprised two hollow cylindrical bodies or lumens, the first lumen configured for the passage of an 0.018" guide wire or an accessory coil or accessory coil catheter, and the second lumen configured for the injection of fluid from the proximal hub of the delivery catheter into the central void of the ballstent, in order to cause inflation or expansion of the ballstent from the delivery configuration. The distal portion of the first lumen was defined by a bridging catheter. The wall of the delivery catheter was formed of polyimide with a PTFE lining of the lumens, and was reinforced with braided wire. Also embedded in the wall of the delivery catheter were two insulated conductive wires. One conductive wire was electrically connected to the stainless steel portion of the proximal neck of the ballstent and was therefore electrically connected to a ring-shaped region of the proximal neck wherein the exterior surface of this region was comprised of exposed, non-insulated stainless steel, of the 304 series, further wherein the exposed region was formed by laser etching, to form an anode. A second conductive wire was electrically connected to a non-insulated ring-shaped electrode comprising platinum that was mounted on the delivery catheter, to form a cathode. Both conductive wires were connected to an electrical jack incorporated into the proximal hub of the delivery catheter. The proximal neck of the ballstent was coupled to the delivery catheter and held by adhesive, folded into pleats, and the pleats were wrapped around the distal end of the delivery catheter and the bridging catheter, and then compressed onto the delivery catheter.

The compressed ballstent and delivery catheter was advanced over a 0.018" guide wire, positioned in the aneurysm sac, and then inflated or expanded. The expanded ballstent was then pulled back to occlude the opening from the parent vessels into the lumen of the aneurysm sac, including the neck. Expansion of the ballstent was achieved using saline infused through into a port on the hub and through the delivery catheter into the central void of the ballstent with an inflation device, while measuring inflation pressure. The guide wire was then removed and an accessory coil catheter with a pre-loaded 8 mm diameter accessory coil comprising nitinol was advanced through the guide wire lumen until the tip of the accessory coil catheter had passed through the expanded ballstent, through the distal neck, and was in the lumen of an unfilled portion of the aneurysm between the expanded ballstent and the inner lining of a wall of the aneurysm generally opposite the opening from the parent vessels into the aneurysm lumen. The accessory coil was then expelled from the accessory coil catheter using a nitinol wire as a pusher. After placement, the accessory coil made contact with both the exterior surface of the expanded ballstent and the inner lining of a wall of the aneurysm generally opposite the opening from the parent vessels into the aneurysm lumen, and exerted a force on the expanded ballstent toward the opening from the parent vessels into the aneurysm lumen. In the first animal one accessory coil was placed. In the second animal three accessory coils were placed. To help induce thrombosis, a small amount of thrombin was injected through an empty coil delivery catheter and into the unfilled portion of the aneurysm lumen between the expanded ballstent and the inner lining of a wall of the aneurysm generally opposite the opening from the parent vessels into the aneurysm lumen. After this, the accessory coil delivery catheter was removed and angiography performed to evaluate the degree of aneurysm occlusion by injection of contrast through the guide catheter. The ballstent was detached by electrolysis with 2 mA of DC current provided to an electrical jack incorporated into a port on the hub of the delivery catheter, using a galvanostat system. Angiography was performed to evaluate the degree of aneurysm occlusion after detachment of the expanded ballstent and the delivery catheter by injection of contrast through the guide catheter. The guide catheter and sheath were then removed and the animal recovered.

For the coil test group, the lumen of aneurysm was partially filled with multiple coils of various sizes (Axium™, Covidien PLC, Dublin, Ireland) sufficient to reduce the flow of blood into the aneurysm sac, using standard microcatheters and guide wires, and standard coiling techniques. The position of the coils and the degree of occlusion of the experimental aneurysm were evaluated with angiography by injection of contrast through the guide catheter, including a final angiogram. For both test groups, contrast angiography was performed immediately after device deployment. Treatment time, device number and cost, and degree of occlusion at the end of the procedure were measured. The guide catheter and sheath were then removed and the animal recovered.

At 4 weeks, an appropriately sized sheath was placed in a femoral artery via surgical cut-down to the vessel. Heparin was administered to achieve a target ACT≥300 sec. Under fluoroscopic guidance, a catheter was advanced into the proximal right common carotid artery caudal to the aneurysm. Contrast angiography was then performed to visualize the aneurysm. The animal was then euthanized with an overdose of pentobarbital and tissue samples collected for histopathology, including the aneurysm and adjacent portions of the parent vessels.

Results

Figure 39A:
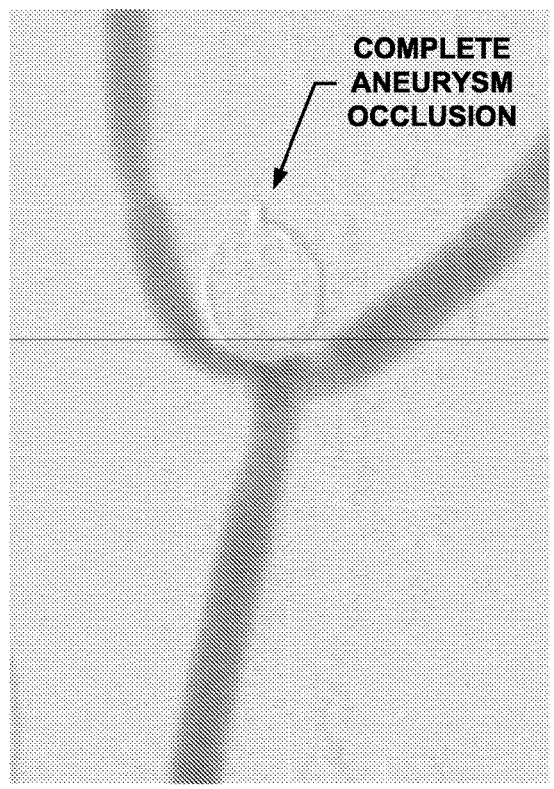
FIGS. 39A-B are angiograms of occluded saccular aneurysms acquired during clinical testing of an embodiment of the expandable body.
Figure 39B:
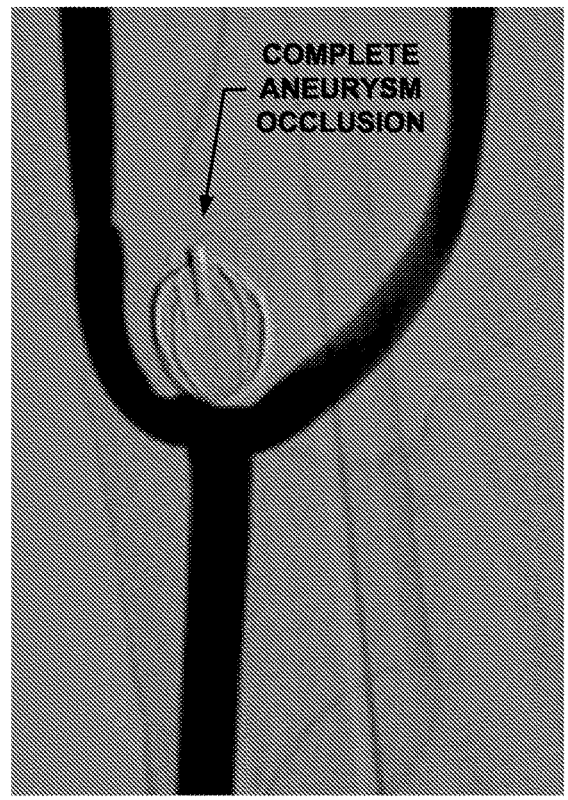
Figure 40:
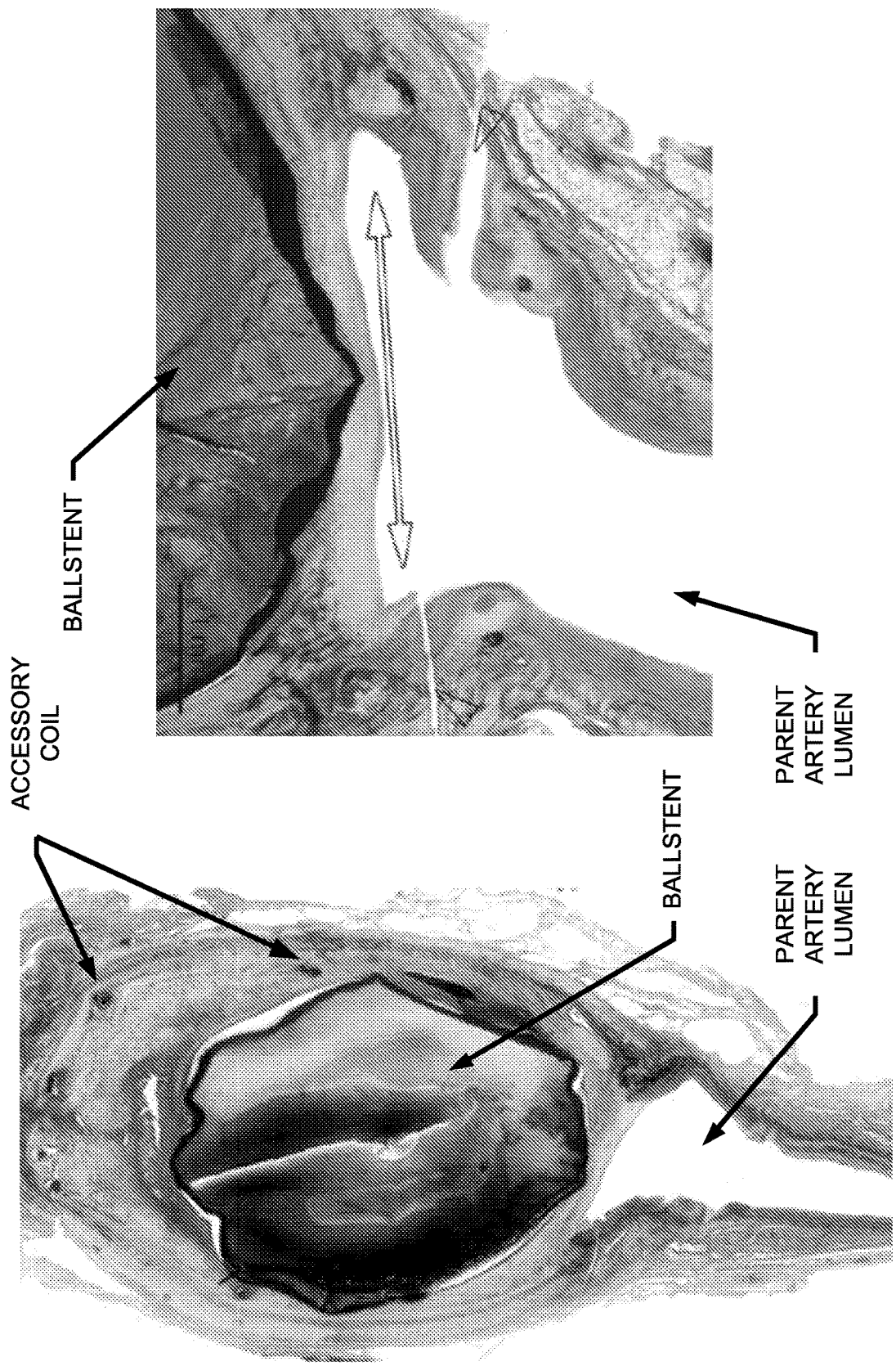
FIG. 40 depicts a tissue samples collected during clinical testing of an embodiment of the expandable body.

For the first animal in the ballstent test group, one ballstent and one accessory coil were placed over a 30-minute treatment period at an estimated cost of $11,750. The degree of acute occlusion with this ballstent treatment was estimated at 100% by angiography (FIG. 39A). Four weeks after treatment, the ballstent showed sustained occlusion of the aneurysm (FIG. 39B) with well organized, mature, and fully endothelialized neointima covering the entire aneurysm neck seen on histopathology (FIG. 40).

For the animal in the coil test group, 18 coils were placed over a 60-minute treatment period at a list price cost of $31,500. The degree of acute occlusion at the end of the coil treatment was estimated at 85-99% by angiography. Histopathology is pending for this animal.

Blockstent Treatment

Using a canine subclavian artery occlusion model, a comparison was made between treatment with the blockstent (n=3) and treatment with the Amplatzer® Vascular Plug II (AVP2, n=3).

Methods

The experimental model used *Canis lupus familiaris* hound cross dogs weighing about 20 kg each. The study involved the use of a medical device to place a 6 mm diameter blockstent expandable body in the subclavian/axillary artery on one side while a guide catheter was used to place a 6 mm AVP2 in the contralateral subclavian/axillary artery. An appropriately sized sheath was placed in a femoral artery via surgical cut-down of the vessel. Heparin was administered to achieve a target activated clotting time (ACT) of 250-300 sec. Under fluoroscopic guidance, a 0.018" guide wire was advanced beyond the intended occlusion site in the subclavian/axillary artery. A guide sheath (6 Fr×90 cm long) was advanced over the guide wire into the subclavian/axillary artery. Contrast angiography was then performed to visualize the subclavian/axillary artery and its side branches.

The blockstent medical device includes a blockstent form of an expandable body. The expanded form of the blockstent was cylindrical, with rounded ends. The blockstent had a proximal neck and a distal neck and comprised gold. The main body of the blockstent measured 8 mm in diameter and was formed from a single layer of gold measuring 20 microns in thickness. A polymeric nosecone was attached to the distal neck. The blockstent medical device further comprised a delivery catheter with an outer diameter of 3.25 Fr that comprised two hollow cylindrical bodies or lumens, the first lumen for the passage of an 0.018" guide wire and the second lumen for the injection of fluid from the proximal hub into the central void of the blockstent to cause inflation or expansion. The wall of the delivery catheter was formed of polyimide with a PTFE lining and was reinforced with braided wire. The proximal neck of the blockstent was coupled to the delivery catheter, folded into pleats, wrapped around the distal end of the delivery catheter and an obturator wire, and compressed. The proximal neck of the blockstent was held to the distal end of the delivery catheter by an elastomeric outer sleeve that gripped the neck of the blockstent and formed a friction fit.

After placement of a guide sheath or guide catheter in the proximal subclavian artery, and the placement of the 0.018" guide wire, the compressed blockstent and the delivery catheter were advanced over the guide wire positioned in the axillary/subclavian artery and then inflated or expanded. Angiography performed to evaluate the degree of artery occlusion by injection of contrast through the guide sheath or guide catheter. The tip of the guide sheath or guide catheter was advanced forward until it was touching the proximal end of the expanded blockstent. The delivery catheter was pulled back, resulting in mechanical detachment of the expanded ballstent from the delivery catheter by disengaging the proximal neck of the expanded blockstent from the elastic sleeve on the distal end of the delivery catheter. The position of the expanded, detached blockstent and the occlusion of the target vessel were confirmed with angiography and the guide wire removed.

For the AVP2 treatments, the guide wire was removed and exchanged for the AVP2, with care taken not to twist the device's delivery wire. The distal end of the AVP2 was positioned at the distal edge of the intended occlusion site. The guide sheath or guide catheter was then pulled back to expose the AVP2, resulting in expansion. The position of the expanded device was confirmed with angiography. The AVP2 was then detached by unscrewing its delivery wire. The position of the expanded, detached AVP2 was confirmed with angiography and the guide sheath removed along with the delivery wire.

For both treatments, contrast angiography was performed immediately after device deployment. The treated vessel segment was monitored with serial angiography every 2.5 minutes for the first 30 minutes or until occlusion was observed.

At 29 days, an appropriately sized sheath was placed in a femoral artery via surgical cut-down to the vessel. Heparin was administered to achieve a target ACT 300 sec. Under fluoroscopic guidance, a guide sheath (6 Fr×90 cm long) was advanced into the subclavian artery. Contrast angiography was then performed to visualize the artery and its side branches. This process was then repeated on the contralateral side. The animal was then euthanized with an overdose of pentobarbital and tissue samples collected for histopathology, including the aneurysm, the implanted ballstents, accessory coils, and Axium coils, and adjacent portions of the parent vessels.

Results

Figure 41:
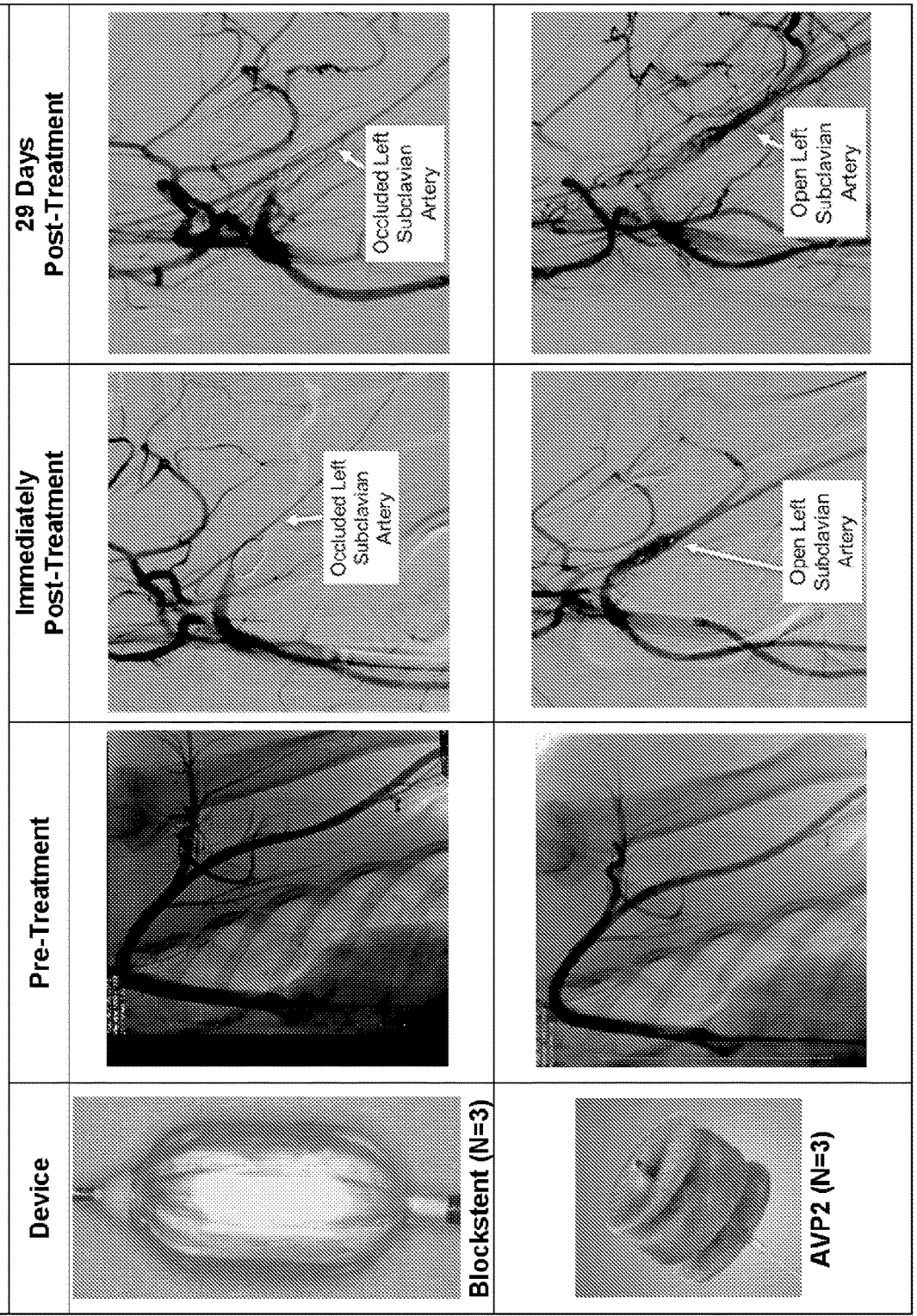
FIG. 41 depicts results of angiography performed during clinical testing of an embodiment of the expandable body.

A summary of the angiography results for each device is provided in FIG. 41. The blockstent demonstrated excellent fluoroscopic visibility, good trackability, low pressure (1-3 atm) expansion, and reliable detachment. Rapid occlusion achieved in 3/3 arteries with the blockstent and 3/3 arteries. All animals survived to the scheduled Day 29 termination. Complete occlusion was maintained at 29 days in 3 of 3 arteries with the blockstent (100%) and 0 of 3 arteries with the AVP2 (0%). All of the blockstent-treated arteries were also fully occluded by histopathology, with little inflammatory response or device-related damage to the vessel wall, as shown in FIG. 42. Partial blockstent deformation occurred over time, possibly caused either by issue ingrowth or compression between dog's forelimb and chest wall, but this deformation had no effect on the blockstent's ability to completely and permanently occlude the target artery segment. None of the AVP2 treated arteries were fully occluded at 29 days by histopathology.

It will be appreciated that the devices and methods of the present invention are capable of being incorporated in the form of a variety of embodiments, only a few of which have been illustrated and described above. The disclosures herein may be embodied in other specific forms without departing from its spirit or essential characteristics. The described embodiments are to be considered in all respects only as illustrative and not restrictive and the scope of the present invention is, therefore indicated by the appended claims rather than by the foregoing description. All changes that come within the meaning and range of equivalency of the claims are to be embraced within their scope.

What is claimed is:

1. A method of treating a saccular aneurysm using two expandable medical devices, the method comprising:
   inserting a portion of the first medical device into a lumen of an artery, the medical device comprising:
      a catheter comprising a longitudinally extending body comprising:
         a proximal end and a distal end generally opposite the proximal end;
         a hollow cylindrical member that defines a lumen configured to accept a guidance member;
      a first expandable body of the first medical device operably coupled with the catheter, the first expandable body defined by a non-porous wall, wherein:
         the wall of the first expandable body, when expanded, defines an interior surface and an exterior surface of the wall, the interior surface of the wall defining a central void of the first expandable body, and
         the wall of the first expandable body, when expanded, has a generally rounded single-lobed shape with a first axis and a second axis transverse to the first axis, the first axis extending generally parallel to a plane of an opening from a parent vessel into an aneurysm; and
   wherein, the first expandable body is initially configured in a compressed shape and the compressed first expandable body is operably coupled with the distal end of the catheter;
   advancing the compressed first expandable body of the first medical device using the operably coupled catheter until the compressed first expandable body is within a lumen of the aneurysm;

expanding the compressed first expandable body of the first medical device such that when the first expandable body is expanded in the lumen of the aneurysm adjacent to the opening from the parent vessel into the lumen of the aneurysm, filling a portion of the aneurysm while an unfilled area remains between the first expanded expandable body and an inner wall surface of the aneurysm opposite the opening from the parent vessel into the lumen of the aneurysm;

advancing a second expandable medical device through the hollow cylindrical member of the catheter of the first expandable medical device and through the expanded expandable body of the first expandable medical device until an expandable portion of the second medical device is within the lumen of the aneurysm adjacent to the expanded body of the first medical device and positioned wherein the expanded portion of the second medical device contacts the exterior surface of a distal portion of the expanded first expandable body and the inner wall surface of the aneurysm opposite the opening to the lumen of the aneurysm; and detaching the catheter of the first medical device from the expanded first expandable body of the first medical device and removing the catheter from the artery while leaving the expanded expandable body of the first medical device and the expanded portion of the second medical device in the aneurysm.

2. The method of claim 1, wherein the expanded first expandable body is positioned to reduce the flow of blood into the aneurysm.

3. The method of claim 1, wherein, when expanded, the first expandable body has a largest diameter as measured parallel to the first axis that is greater than the largest diameter as measured parallel to the second axis.

4. The method of claim 1, wherein, when expanded, the first expandable body has a largest diameter as measured parallel to the second axis that is equal to the largest diameter as measured parallel to the first axis.

5. The method of claim 1, wherein, when expanded, the first expandable body has a largest diameter as measured parallel to the second axis that is less than the largest diameter as measured parallel to the first axis.

6. The method of claim 1, wherein, when expanded, a maximum diameter of the first expandable body, as measured parallel to the first axis, ranges between 2 millimeters and 30 millimeters.

7. The method of claim 1, wherein, the guidance member is a guide wire.

8. The method of claim 1, wherein the wall of the first expandable body comprises at least one metal layer.

9. The method of claim 8, wherein the metal layer of the first expandable body comprises gold.

10. The method of claim 8, wherein the metal layer of the first expandable body has a thickness ranging between approximately 3 microns and 50 microns.

11. The method of claim 1, wherein the exterior surface of the first expandable body comprises a granular surface structure with surface protrusions having a surface height of 0.01 to 10 microns.

12. The method of claim 1, wherein an electrolysis system is connected with the first expandable body, such that the electrolysis system is configured to deliver electrical current to at least a portion of the first expandable body, such portion lacking electrical insulation, in a manner that causes galvanic corrosion of at least a portion of the uninsulated portion of the first expandable body and enabling detachment of the expanded first expandable body and the catheter.

13. The method of claim 12, wherein the electrolysis system is configured to deliver constant voltage to the first expandable body.

14. The method of claim 13, wherein the electrolysis system is configured to deliver constant voltage to the first expandable body of 2 mA.

15. The method of claim 1, wherein the second expandable body comprises a wire.

16. The method of claim 15, wherein the second expandable body, when expanded, comprises a coil.

17. The method of claim 15, wherein the second expandable body comprises nitinol, platinum, stainless steel, or gold.

18. The method of claim 15, wherein the wire has a diameter between 0.002 inches and 0.018 inches.

19. The method of claim 15, wherein the wire is coated with PTFE.

20. The method of claim 15, wherein the wire comprises a radiopaque marker.

21. The method of claim 15, wherein the second medical device further comprises a catheter with a hollow cylindrical member comprising a lumen that contains the wire located within that lumen.

22. The method of claim 21, further comprising:
advancing the second medical device through the lumen of the first medical device until the distal tip of the catheter of the second medical device is located within the lumen of the aneurysm;
expelling the wire from the catheter of the second medical device into the lumen of the aneurysm; and,
removing the catheter of the second medical device from the aneurysm.

23. The method of claim 22, wherein the catheter of the second medical device has an outer diameter of 0.014 inches to 0.022 inches.

24. The method of claim 22, wherein the catheter of the second medical device has an inner diameter of 0.008 inches to 0.016 inches.

25. The method of claim 22 wherein the expandable portion of the second medical device is expelled from the catheter of the second medical device using the wire advanced forward in the lumen of the catheter of the second medical device.

26. The method of claim 22, wherein the distal end of the catheter of the second medical device comprises a marker band.

27. The method of claim 26, further comprising using fluoroscopy to monitor the placement and position of the catheter of the second medical device in the aneurysm.

28. The method of claim 1 further comprising using fluoroscopy to monitor the placement and position of the second medical device in the aneurysm.

29. The method of claim 1, wherein two or more of the second expandable medical devices are placed in the lumen of the aneurysm.

30. The method of claim 1, further comprising pulling the expanded first expandable body towards the opening from the parent vessel to the lumen of the aneurysm prior to detaching the catheter of the first medical device from the first expanded expandable body such that the expanded first expandable body reduces the flow of blood into the aneurysm.

31. The method of claim 30, wherein the expanded first expandable body is pulled towards the opening from the parent vessel to the lumen of the aneurysm, prior to placing the expandable portion of the second medical device into the lumen of the aneurysm.

32. The method of claim 30, wherein the pulling of the expanded first expandable body causes the exterior surface of the first expanded expandable body to contact an aneurysm wall near or adjacent to the neck of the aneurysm.

33. The method of claim 1, wherein the expanded first expandable body is pulled towards the opening from the parent vessel to the lumen of the aneurysm after placing the expandable portion of the second medical device into the lumen of the aneurysm.

34. The method of claim 1, wherein after placement in the aneurysm, the the expandable portion of the second medical device exerts a force on the expanded first expandable body in a direction towards the opening from the parent vessel to the lumen of the aneurysm.

35. The method of claim 1, wherein a distal portion of the the expandable portion of the second medical device is placed in the aneurysm lumen between the expanded first expandable body and a wall of the aneurysm, and a proximal portion of the expanded second expandable body is placed in the central void of the first expanded expandable body.

36. The method of claim 1 wherein the expandable portion of the second medical device contacts a thrombus within the lumen of the aneurysm.

* * * * *